(12) United States Patent
Lo et al.

(10) Patent No.: US 6,610,506 B1
(45) Date of Patent: *Aug. 26, 2003

(54) **TRANSFERRIN BINDING PROTEINS OF *PASTEURELLA HAEMOLYTICA* AND VACCINES CONTAINING SAME**

(75) Inventors: Reggie Y. C. Lo, Guelph (CA); Anthony Bernard Schryvers, Calgary (CA); Andrew Allan Potter, Saskatoon (CA)

(73) Assignees: University Technologies International, Inc., Calgary; University of Guelph, Guelph; University of Saskatchewan, Saskatoon ( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/753,750

(22) Filed: Nov. 29, 1996

Related U.S. Application Data

(60) Provisional application No. 60/008,569, filed on Dec. 1, 1995.

(51) Int. Cl.$^7$ .......................... C12P 21/06; C12N 15/00; C12N 15/09; C12N 15/63
(52) U.S. Cl. ................ 435/69.1; 435/240.2; 435/252.3; 435/320.1; 536/1; 536/18.7; 536/22.1; 536/23.1; 536/23.5; 536/23.7; 536/24.1; 424/255.1
(58) Field of Search ............................... 536/23.1, 24.1, 536/1, 18.7, 22.1, 23.5, 23.7; 435/69.1, 240.2, 252.3, 320.1; 424/255.1

(56) References Cited

U.S. PATENT DOCUMENTS

| | | | | |
|---|---|---|---|---|
| 4,879,213 A | * | 11/1989 | Fox et al. | |
| 5,141,743 A | * | 8/1992 | Schryvers | |
| 5,417,971 A | | 5/1995 | Potter | |
| 5,922,562 A | * | 7/1999 | Loosmore et al. | |

FOREIGN PATENT DOCUMENTS

| | | |
|---|---|---|
| CA | 2098448 | 6/1993 |
| WO | WO 90/12591 | 11/1990 |
| WO | WO 92/03467 | 3/1992 |
| WO | WO 95/13370 | 5/1995 |
| WO | WO 95/25742 | 9/1995 |

OTHER PUBLICATIONS

Nucleic acid and amino acid databases, Sequences 3, 7 and 8 of U.S. Patent #5,922,562.*
Introduction for *Qiagen Genomic DNA Handbook* (Sep. 1997) pp. 8–9.
Pettijohn, David E., "The Nucleoid", *Cellular and Mol. Biol.*, 2nd Edition, F.C. Neidhardt, Editor–in–Chief, AS Press (1996) pp. 158–166.
Donachie, et al., Vet. Immunol. Immunopathol., 11:265–279, 1986.
Donachie and Gilmour, N.J.L., FEMS Microbiol. Lett., 56:271–276, 1988.
Gorringe et al., Vaccine, 13:1207–1212, 1995.
Legrain et al., Gene, 130:73–80, 1993.
Lissolo et al., Infect. Immun., 63:884–890, 1995.
Oggunnariwo, J. & Schryvers, A., Infect. Immun., 58:2091–2097, 1990.
Rossi–Campos, et al, Vaccine, 10:512–518, 1992.
Smith, Vaccine, 12/6:1515–1519, 1994.*
Ellis, New Technologies for Making Vaccines pp. 568–575, 1999.*
Ulmer et al Methods in Molecular Medicine ed: Robinson et al pp 289–300, 1996.*
Murphy et al. J. Clin. Microbiol. Sep. 1993, 31(9), 2303–2308.*
Lazar et al. Mol. Cell Biol 8:1247–52 1988.*
Burgess et al. J. Cell Biol. 111:2129–38 1990.*

* cited by examiner

*Primary Examiner*—Nita Minnifield
*Assistant Examiner*—Alana M. Harris
(74) *Attorney, Agent, or Firm*—Baker Botts L.L.P.

(57) ABSTRACT

Novel transferrin binding proteins from *Pasteurella haemolytica*, and nucleic acid molecules encoding the novel proteins are disclosed. Antibodies against the novel proteins are disclosed. The invention also relates to vaccines containing the novel proteins of the invention. The invention also provides methods for identifying substances which affect the binding of transferrin to the proteins and methods for screening for agonists or antagonists of the binding of the proteins and transferrin.

18 Claims, 36 Drawing Sheets

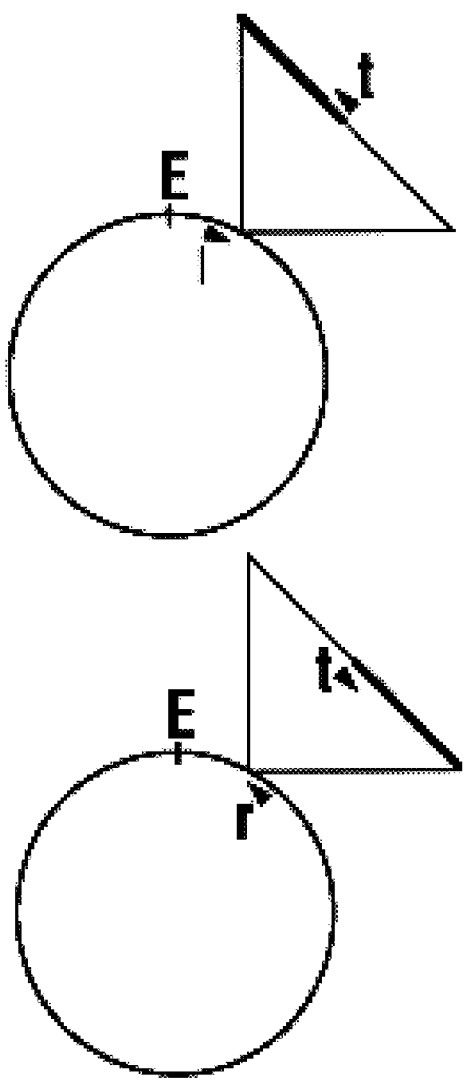 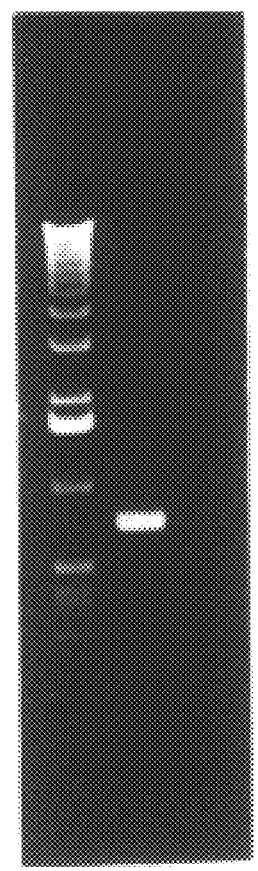
FIGURE 1A  FIGURE 1B

FIGURE 2
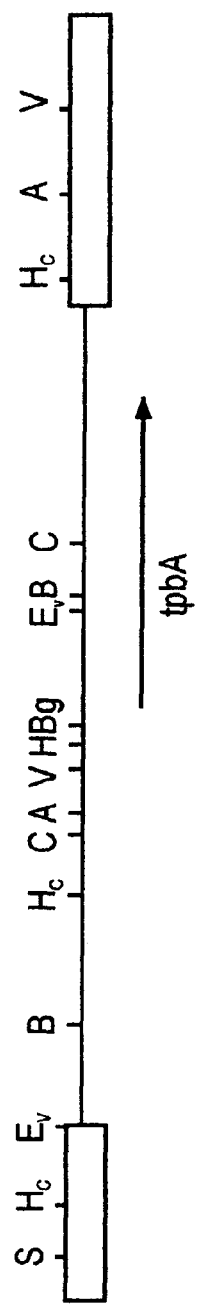
Plasmid 9
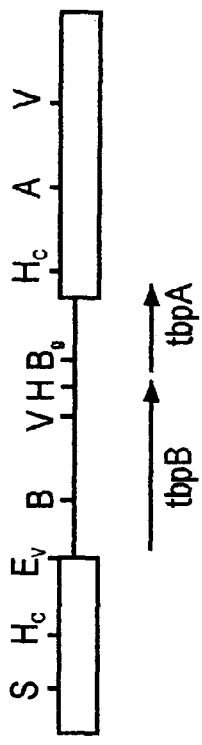
Plasmid 10
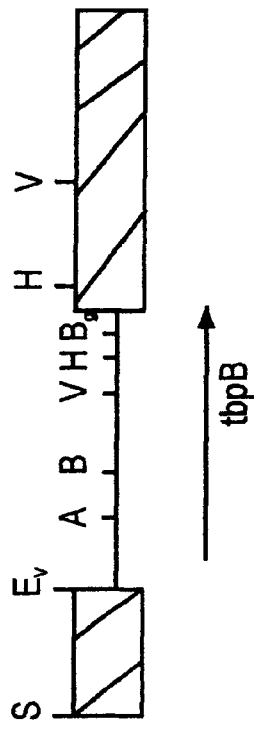
Plasmid 482

FIGURE 3A

*tbpB*

```
              10         20         30         40         50
               |          |          |          |          |
   1 CGCTTGCAGA TTTGTAAAAA ATTTAGCTAA AATCAGACCT GGCTTGTATT
  51 TTAGGGTTAT TATGGAACAG ACAACGGAAC AAATAGATTA TAAATTATTA
 101 AAGCATCGTT TTCGTGGCTA TTTACCGCTT GTGATTGATG TGGAACAGAG
 151 GCTTAAATGC CCAAACTGTG CCTTATTGGA ATTGGCCGGA ATTACTTTAA
 201 AATTGGACGA GCCAAGGTTA TCTTATTGCC GGATTCAACA ATGCCAATTT
 251 CCAATTTGCG GCCATTGGAG GGGGCGATTT TCAAGGGCCG AATATTTACC
 301 CTCAGTCATT AAAATTCAAC GGCATTCATA TTCACAACCC TCTAGAGGAA
 351 GCGGTTTAGA GAATATTGCC CAATTCCCGG AAATGTTCAA AATGGTTCGC
 401 AAAGCAATGA AGGAAGCAAG GCTGCCAACG GGCGGTGATT GTTGCCCCAC
 451 AATGCCAGCG TTCGATCAGG GCTTTTTTAC AGGGCTGCGA TTAAACGGAA
 501 TGCCAAGCGA GAGATCCCTT TCACCCTTTT GGCGATGTTT GACTACCGCC
 551 GCCACCCTTT GCAGGTTTTA TGTTATGGGC AAACCGTGTT CGTTAAAAGC
 601 CTGCCAGTGC AAAATCCGTT CACGTAGCAG CACTATAGGG CGAATTGGGT
 651 ACCGGGCCCC CCTCGAGGTC GACGGTATCG ATAAAGCTTC ATATCGAATT
 701 CCTGCAGCCC GGGGGATCCG ATGCGCCTTG CGGCTCAAGT TATTAGTGGC
 751 ATCGGTTTTT TGGGTGATGG TGTCATTTTG CATAAGAAAA ATGATGCGAT
 801 TTCAGGTTTA CCCACTGCGG CGATTATTTG GGCTTCTGCG GGGATCGGTA
 851 TTGCTGCAGG GGAGGGTTTC GTGTTTCATG CGGTCATCGC CACTGTCATT
 901 ATTTGGTGT CTATTCGATT ATGTCCGTTG GTTCAACGTT GGGTTCATCG
 951 TAAATCACAA CGTCGTCGAC GAAATATTCT TGTCAATGAT GCGGAAAGCA
1001 TACGGAAAGT TACCCAATTG TTATTCAATA ATCAGTATCG TATTGAACAT
1051 ATACAAGTCA AAGATCAAAG TAGTGGAGAA GTTGCCGGTT ACAAATTCGT
```

FIGURE 3B

```
1101 ATTGATTCCA CAATGTTCAA AGATGCGTAT GCTTTACTTA AAGCAGAAGA
1151 TGGCGAATAC TGTTCAAGTA GATATCATGA AAAAGAGTGC TTATATTCAA
1201 TTTTTTATTT TTTATTTAAT TTCTTTCCAC AAAAGATCAT TTTCAATTAT
1251 ATATACTGGA ATTTTGCCTT ACGCTATCTG TCATTTATTA TGCTATTCAA
1301 GCACAACAAA CTATGGAACA ACAATCAAAA TGTACGCTTA TCGGCTGCCG
1351 ATGATTTCGA TAATGATCGA TGTGCAGAAA TATTTGAACT TACGATTTTC
1401 ACTGAGCAGT CAAAGCACGT TCGCGAGTAT CGACTCTACT TTATTTATCG
1451 TTTGTGCACT ATGTATAATC CACCTAATTC CGTGCCTTGG CCATAAAAGC
1501 CCCCTTCAAA TTGTATTTAT ATCAGCTACC GTGCCACCAT TCGTACTTTT
1551 CGGATCAAGA TTAAAACAGA ATCCTGCAT GCACAGCGAA ATCAGCTGCG
1601 GTATGCGAAA CGCCGCAGGA GCGCAGTACG CGAAGTGTAC CGTCACTATC
1651 AGTGCTAGAT TTGTCAATAA AAAATTAGTG ACCAAGCTTG GGTGCATAAT
1701 GATGGTGATG AAAGAACGCT CAATGCTTGA CACGTTGCAG GCTATCTGTA
1751 AGGGTATGGT AGTTACAGGC ACAGCCCAAA CGGCCAATTG CTGGTTTTTT
1801 ATCCTTGATC CGAACAGTAC GAATGGTGGT CACGGTAGTG CATATACATA
1851 CTCAATTGAA GGGGGCTTTT ATGGCCCTAA GGCGACGGAA TTAGGTGGTA
1901 TTGTACATAG TGCAGAAACG GATAAAGATA GAGTCAGTAT TACATTCGGC
1951 GGAAAACGTC AAATAGAAAA ATAATCATAA TTCCCCTTTG CTGGTTGTAG
2001 ATAGCAGCGG GCAATTTTTT ATAAAAATTT GCAAAATTTA AATAA
```

FIGURE 3C tbpA

```
              10         20         30         40         50
               |          |          |          |          |
   1 AGACCCTATC TAATGATAAT GAAATATCAT CATTTTCGCT ATTCACCTGT
  51 TGCCTTAACA GTGTTATTTG CTCTTTCTCA TTCATACGGT GCTGCGACTG
 101 AAAATAAAAA AATCGAAGAA AATAACGATC TAGCTGTTCT GGATGAAGTT
 151 ATTGTGACAG AGAGCCATTA TGCTCACGAA CGTCAAAACG AAGTAACTGG
 201 CTTGGGGAAA GTAGTGAAAA ATTATCACGA AATGAGTAAA AATCAAATTC
 251 TTGGTATTCG TGATTTAACT CGCTATGACC CTGGTATTTC GGTGGTGGAA
 301 CAAGGTCGCG GTGCAAGTAG TGGCTATGCC ATTCGAGGTG TAGATAAAAA
 351 CCGTGTCAGC TTACTTGTTG ATGGGCTACC ACCAGCGCAC AGTTATCATA
 401 CGCTGGTTCA GATGCTAATG GTGGTGCAAT TAATGAGATT GAGTATGAAA
 451 ACATTCGTTC AATTGAGTTA AGCAAAGGAG CAAGTTCTGC GGAATATGGC
 501 TCTGGTGCGC ATGGTGGTGC TATTGGTTTT CGTACTAAAG ATCGCCAGGA
 551 TATTATTAAA GAGGGGCAGC ATTGGGGCTT ACATAGTAAG ACCTCTTATG
 601 CCAGCAAAAA TAGCCATTTT TACAGTCTAT CGCAGCGGCT GGTCAGGCGG
 651 GTGGTTTTCA AGCACTTGTT ATTGCAACTC ACCGACACGG TAAAGAGACC
 701 AAAATTCATT CCGAGGCAAA TCAATTACAT ATTATTCGGC GTATAACCGG
 751 CTTTCAAAAT CGCTACGACT TTACCCAATT CCGCACAGAA TGCCTCCTGG
 801 AGGATCTTTT TTTATTGTGG AAGATACTTG CCCAACATTA GATTGTACTC
 851 CTCGTGCAAG GGTTAAGTTG AACGCGATAA TTTCCCAGTC AGAACATTTC
 901 CGAATATACG CCTGGAAGAG GCGAAACAGC TTGAGATTCC TTATCGCACT
 951 GAGCTCTCAG CCCAAAGAAT ARACCGGTAA AGATCGCATT GCACCAAACC
1001 CTTTAGATTA CAAGAGTAAT TCTGTTTTTA TGAAGTTTGG CTATCACTTT
1051 ACCTCGTCTC ATTATCTTGG CGCATCTCAC AAGATGATAC AAAACAACGC
1101 ACGATATCCG TCATSTGCAA ACGCCAGCTT ACTATACAAA AGACGATATT
1151 TACTTATCAC TTTGGAACTA TGTTTATCAA GGGGATATTA TTTAGATGGC
1201 TTAGTGTTCA AGCCAAGGAT CCCTTATGGG TTGCGCATAT GCCATGTGAA
```

FIGURE 3D

```
1251 CGTCACCACA AACGTCGTTT AGGATTCACC TATAAATATA AACCAGAGAA
1301 TAATCGCTGG TTGGATAGCA TTAACTCGTG CGTACGTGCT TTGCGCTCTC
1351 GCTGCTGTGC TCTGAGTAAA CAAGATATTG AACTATATAG CCGGCTACAT
1401 CGCTTGCATT GTAGCGATTA TCCTGTGGTA GATAAAAATT GCGGCCCGAC
1451 TTTGGATAAA TCTGGTCTAT GTATCGAACT GAGCGTAATA ATTACCAAGA
1501 AAAGCATCGT GTCATTCATT TAGAATTTGA TAAAGCGCTA AATGCTGGTC
1551 AAGGCGTATT TAAGCAAACC CACAAACTGA ATTTAGGCTT GGGCTTTGAA
1601 TCGATTAATC GCTTATGATC ATGGGGATAT GACTGCCCAA TATACCAAAG
1651 GCCGGTTATA CCAGCTACCG CGGAGAGGGG CTTTAGATAA TCCATATATT
1701 TATCGCCGCG ATCCACGCAG TATTGAAACG GTATCTTTGT GTAATAATAC
1751 AGCGGCGACA CTTAACTGTG ACGCGTTAAA TAAAGGCATA CGTTTGTACC
1801 TCCGCTGCAC TTAGGAACTA TAGTTTATGA AGGGGATAAT ATTTAGATGG
1851 CTTAGTGTTC AAGCAAGCAA GGATCCCTTA TGGGTTGCGC GATATGCCAT
1901 GTGAAGTTTT TGATGAACGT CACCACAAAC GTCGTTTAGG ATTCACACCT
1951 ATAAATATAT AAACCAGAGA ATAATCGCTG GTTGGATAGC ATTAACTCGT
2001 GCGTACGTGC TTTGCGCTCT CGCTGCTGTG CTGTGAGTTA AACAAGATAT
2051 TGAAACTTAT AGCCGGCTAC ATCGCTTGCA TTGTGAGCGA TTATCCTGTG
2101 GTAGTAGTAA AAATTGCGGC CGACTTTGG ATAAATCTTG GTCTATGTAT
2151 CGAACTGAGC GTAATAATTA CCAAGAAAAG CATCGTGTCA TTCATTTAGA
2201 ATTTGATAAA GCGCTAAATG CTGGTCAAGG CGTATTTAAG CAAACCCACA
2251 AACTGAATTT AGGATTGGGC TTTGAATCGA TTAATTCGCT TATGGATCAT
2301 GGGGATATGA CTGCCCAATA TACCAAAGGC CGGTTATACC AGCTAACCGC
2351 GAGAGGGCGT TTAGATAATC CATATTTATC GCCGCGATCC ACGCAGTATT
2401 GAAACGGTAT CTTTGTGTAA TAATACACGC GCGACACTAA CTGTGACGCG
2451 TTAAATAAAG GCATACGTTT GTACCTCCGC TGCTGCCTAA TAAATCAAAA
2501 GAATAACCGA GATACGGTTC AGTGTTGTTC CAACCAGTTG CGATGGCCCA
```

FIGURE 3E

```
2551 CTACGTGAAC CATCACCCTA ATCAAGTTTT TTGGGGTCGA GGTGCCGTAA
2601 AGCACTTAAC CCTTCTGTCG TCTCCCGTGG ATGCTTAAAT TCGCAGCTAG

2651 TGGCAGGCAG GCACGTCACT CCTCTCGGTG ATTTCAGGTG CAACTGACCG
2701 GTTCTTGGTA CCACCCTTGA TATTAACCGG AGTCAATTAT AAAAACGAGT
2751 TACGTGGAGC GCAATTTATA ATGTCGATGT CAGATACTGT AAAACTCTAT
2801 ATTACCGTGG GCAGCAATTA GGTGACAGGG CCACGGGGCA AGCGAAACCA
2851 GACGGGTACC AATTACACCG ATTTGCCGCC CCCGGGAGAG AAATTTCAGT
2901 TACCATTCAA AGAAGTTTAG AGCCGGCCAA AAGAAAATAC AAAAAACGCT
2951 GAAAGTATAT TCAGCGCGTT TTTGTTGCTC TAACGGATTA CATACGAATT
3001 CAAAATGTTT TAACGGTCGG TTA
```

FIGURE 4

```
         ******************
CGCTTGCAGATTGTAAAAATTTAGCTAAAAATCAGACCCTGGCTTGTATTTAGGGTTATTAATG      PHTBPB
     |---|                          |---|           |--|
      -35                            -10             MET

********************
    TTTAAAAATAAATAAAAATAATAATCCTTATCATTCTTTAATTGAATCGGGTTTGTTATG        NGTBPB
        |---|                      |---|              |--|
         -35                        -10                MET

*********************
GTATTTGCAAATTGTTAAAAATAATAATCCTTATCATTCTTTAAT TGAATTGGGTTTATATG        NMTBPB
  |-----|                         |---|            |--|
    -35                             -10              MET
```

FIGURE 8
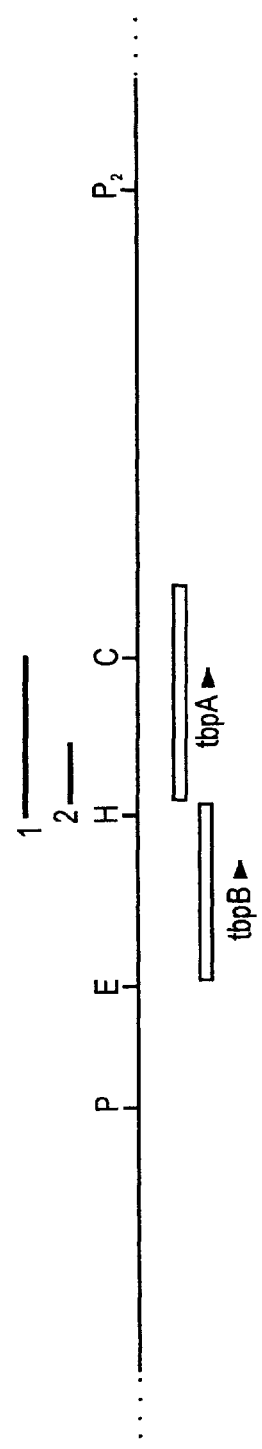
P. haemolyitca A1
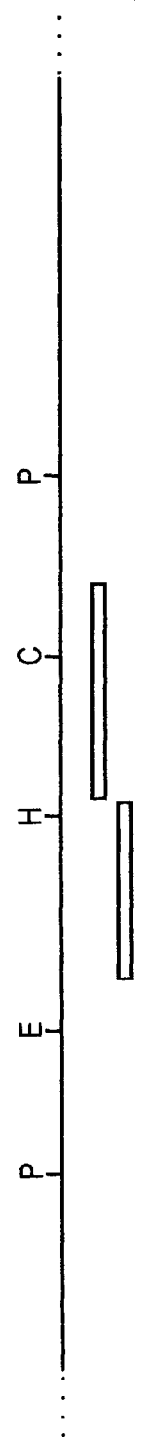
A. suis 3714
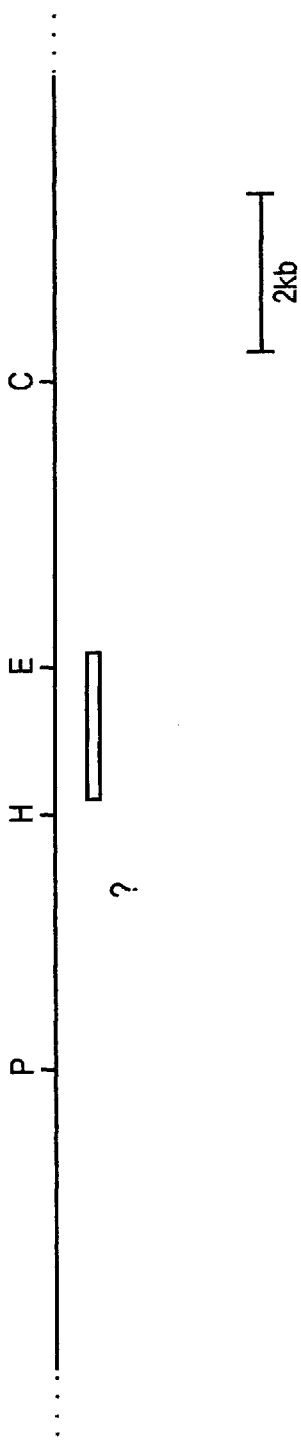
A.pleuropneumoniae CM5, Shope 4074

FIGURE 9A

```
PHTBP    MIMKYHHFRYSTVALTVLFALSHSYGAATENKKIEENNDLAVLDEVIVTE        50
NGTBP1   MQQQ-HLFRLNILCLSLMTALP-AYAENVQAGQAQEKQ----LDTIQVKA        44
NM1      MQQQ-HLFRLNILCLSLMTALP-VYAENVQAEQAQEKQ----LDTIQVKA        44
          * . * **  ... *... **. *........ .*..    **.. *..

PHTBP    SHYAHERQNEVTGLGKVVKNYHEMSKNQILGIRDLTRYDPGISVVEQGRG       100
NGTBP1   KKQKTRRDNEVTGLGKLVKTADTLSKEQVLDIRDLTRYDPGIAVVEQGRG        94
NM1      KKQKTRRDNEVTGLGKLVKSSDTLSKEQVLNIRDLTRYDPGIAVVEQGRG        94
          ..   *.********.**. ...**.*.*.*********.*******

PHTBP    ASSGYAIRGVDKNRVSLLVDGLPQAHSYHT---LSGD---ANGGAINEIE       144
NGTBP1   ASSGYSIRGMDKNRVSLTVDGLAQIQSYTAQAALGGTRTAGSSGAINEIE       144
NM1      ASSGYSIRGMDKNRVSLTVDGVSQIQSYTAQAALGGTRTAGSSGAINEIE       144
          *****.***.******  ***..* .**  .   *.*.   ...*******

PHTBP    YENIRSIELSKGASSAEYGSGAHGGAIGFRTKDAQDIIKEGQHWGLDSKT       194
NGTBP1   YENVKAVEISKGSNSVEQGSGALAGSVAFQTKTADDVIGEGRQWGIQSKT       194
NM1      YENVKAVEISKGSNSSEYGNGALAGSVAFQTKTAADIIGEGKQWGIQSKT       194
          ***....*.***..* * *.**  .*...*.**.*.*.* **..**..***

PHTBP    SYASKNSHFLQ-IAAAGEAGGFEALVIATHRHGKETKIHSEANKLKHNIR       243
NGTBP1   AYSGKNRGLTQSIALAGRIGGAEALLIRTGRHAGEIRAHEAAGRGVQSFN       244
NM1      AYSGKDHALTQSLALAGRSGGAEALLIYTKRRGREIHAHKDAGKGVQSFN       244
          .*...*.  . * .* ** ** ***.* * *.. *.. *...*..  ....

PHTBP    RITGFENRYDFTQIPHRMPPGGS---FFIVEDTCPTLDCTPRARVKLNRD       290
NGTBP1   RLAPVDD--------------GSKYAYFIVEEECKNGGHE-KCKANPKKD       279
NM1      RLVLDEDKKE----------GGSQYRYFIVEEECHNG-YA-ACKNKLKED       282
          *..  ..              **   .****..*  .    .... *

PHTBP    NFPVRTFPEYTPEERNAEQIPYRTEQLSAQEKTGKDRIAPNPLDYKSNSV       340
NGTBP1   VV--------GEDKRQT---------VSTRDYTGPNRFLADPLSYESRSW       312
NM1      AS--------VKDERKT---------VSTQDYTGSNRLLANPLEYGSQSW       315
                    ..*..          .*... **  .*.  ..**.*  *.*

PHTBP    FMKFGYHFNSS-HYLGAILEDTKQR-TISVICKRQLTIQKTILTYHLGTM       388
NGTBP1   LFRPGFRFENKRHYIGGILERTQQTFDTRDMTVPAFLTKAVFDANQKQAG       362
NM1      LFRPGWHLDN-RHYVGAVLERTQQTFDTRDMTVPAYFTSEDYVP-----G       359
          ... *......   **.*..** *.*     ... ..  . .

PHTBP    FMKGIIFRWLSVQAK-DPLWVAHMPCEV----------DERHHKRRLGF       426
NGTBP1   SLRGNGNHKYAGNHKYGGLFTSGENNAPVGAEYGTGVFYDETHTKSRYGL       412
NM1      SLKGLG--KYSGDNKAERLFVQGEGSTLQGIGYGTGVFYDERHTKNRYGV       407
          ..*       .. *.*..                   ** * *.* *
```

FIGURE 9B

```
PHTBP    TYKY-KPENNRWLDSINSCVRALRSRCCALSKQDIELYSRLHRLHCSDYP              475
NGTBP1   EYVYTNADKDTWAD----YARL------SYDRQGIGLDNHFQQTHCSA-D              451
NM1      EYVYHNADKDTWAD----YARL------SYDRQGIDLDNRLQQTHCSH-D              446
          .*  *.....  * *    ..*        . ..*.*.* .....  ***

PHTBP    VVDKNCGPTLDKSWSMYRTERNNYQEKHRVIHLEFDLALNAGQGVFLQTH              525
NGTBP1   GSDKYCRPSADKPFSYYKSDRVIYGESHKLLQAAFKKSFDTAK----IRH              497
NM1      GSDKNCRPDGNKPYSFYKSDRMIYEESRNLFQAVFKKAFDTAK----IRH              492
          ** * *. .*..* *...*  * *.......*.  .......        *

PHTBP    KLNLGLGFESINSLMDHGDMTAQYTLGRLYQL---PRRDPRSIWTVSLCN              572
NGTBP1   NLSVNLGYDRFGSNLRHQDYYYQSAN-RAYSLKTPPQNNGKKTSPNGREK              546
NM1      NLSINLGYDRFKSQLSHSDYYLQNAV-QAYDLITPK----KPPFPNGSKD              537
          .*...**.... * . * *    * . . * *              .  ...  .

PHTBP    NT------RATLNCDAL-NLGIRLYLRCCLINQLNNPRYGSVLFQFGTRV              615
NGTBP1   NPYWVSIGRGNVVTRQICLFGNNTYTDCTPRSINGKSYYAAV--RDNVRL              594
NM1      NPYRVSIGKTTVNTSPICRFGNNTYTDCTPRNIGGNGYYAAV--QDNVRL              585
          *.           ....  ..* *  *  *       . .. *...*    ...*.

PHTBP    HRTWTPTSLGELPSIRAMAHYVNHHPNQVFWGRGAVKHLT------LLSS              659
NGTBP1   GR-WADVGAG----LRY--DYRSTHSDDGSVSTGTHRTLSWNAGIVLKPA              637
NM1      GR-WADVGAG----IRY--DYRSTHSEDKSVSTGTHRNLSWNAGVVLKPF              628
          * *...  *     .*  .* . *... *... *.   *  .

PHTBP    PWM-LKFAASG--RHVTLSVISG-ATDRFLVPPLILTGVNYKNES---YV              702
NGTBP1   DWLDLTYRTSTGFRLPSFAEMYGWRSGDKIKAVKIDPEKSFNKEAGIVFK              687
NM1      TWMDLTYRASTGFRLPSFAEMYGWRAGESLKTLDLKPEKSFNREAGIVFK              678
          *. *...*. *   ... *    ..  . . ... ....*.  .

PHTBP    SAIYNVDVRYCKTLY-------YRGQQLGDRATGQAKPDGY---QLHRFA              742
NGTBP1   GDFGNLEASWFNNAYRDLIVRGYEAQIKDGKEQVKGNP-AYLNAQSARIT              736
NM1      GDFGNLEASYFNNAYRDLIAFGYETRTQNGQTSASGDP-GYRNAQNARIA              727
          ... *..... .. *       *   ..  ....  ..* .*  *  *..

PHTBP    APG------------------RNFSYHSKKFRPAK---ENTKNAESIFS              770
NGTBP1   GINILGKIDWNGVWDKLPEGWYSTFAYNRVRVRDIKKRADRTDIQSHLFD              786
NM1      GINILGKIDWHGVWGGLPDGLYSTLAYNRIKVKDADIRADRTFVTSYLFD              777
          . .                  ....*.. . .    ..*   . .*.

PHTBP    A-----FFVGSNGLHTNSKSCFNGRLHEPIPYFFNFLRNVPRFNEYHCCC              815
NGTBP1   AIQPSRYVVGSYDQPEGKWGVNGMLT------YSKAKEITELLGSR---              827
NM1      AVQPSRYVLGLGYDHPDGIWGINTMFT------YSKAKSVDELLGSQ---              818
          *    . .* *  ....    *...       .. ... .  .
```

FIGURE 9C

```
PHTBP    TSLIAASILLHHIYHWVFDFRYYYFV--YFCWILHHLIHINSFLMLLSHY        863
NGTBP1   -ALLNGNSRNTKATARRTRPWYIVDVSGYYTVKKHFTLRAGVYNLLNHRY        876
NM1      -ALLNGNANAKKAASRRTRPWYVTDVSGYYNIKKHLTLRAGVYNLLNYRY        867
          .*....    .   .   .*    *   *.    *    .. . . .*  .*

PHTBP    --REVVYLTCCACAFNIVTVNGF----CVGCCSNILAEMKF        898
NGTBP1   VTWENVRQTAAGAVNQHKNVGVYNRYAAPGRNYTFSLEMKF        917
NM1      VTWENVRQTAGGAVNQHKNVGVYNRYAAPGRNYTFSLEMKF        908
          .*  *  *    . . . .*. .      *    ..  ****
```

FIGURE 10A

```
PHTBP1   MIMKYHHFRYSTVALTVLFALSHSYGAATENKKIEENNDLAVLDEVIVTE              50
APL      MHFKLNPY---ALAFTSLFLVACSGGKGSFD----------LEDVRPNQ              36
APL7     MHFKLNPY---ALAFTSLFLVACSGGKGSFD----------LEDVRPNK              36
         * .*  ...    ..*.* **  . *  * ...  .           *..*    ..

PHTBP1   SHYAHERQNEVTGLGKVVKNYHEMSK--NQILG--IRDLTRYDPGISVVE              96
APL      TAKAEKATTSYQDEETKKKTKEELDKLMEPALGYETQILRRNKAPKTETG              86
APL7     TTGVSKEE--YKDVETAKKEKEQLGELMEPALGYVVKV------PVSSFE              78
         . .  .    . ..     .  *. .....   .. **   ..           .

PHTBP1   QGRGASSGYAIRGVDKNRVSLLVDGLPQAHSYHTLSGDANGGAINEI-EY             145
APL      EKRNER----VVELSEDKITKLYQESVEIIPH--LDELNGKTTSNDVYHS             130
APL7     NKK--------VDISD----------IEVITNGNLDDVPYKANSSK-YNY             109
            . .        ....          .  .     *..     .. ..    .

PHTBP1   ENIRSIELSKGASSAEYGSGAHGGAIGFRTKDAQ-DIIKEG---------             185
APL      HDSKRLDKNRDLKYVRSGYVYDGSFNEIRRNDSGFHVFKQGIDGYVYYLG             180
APL7     PDIK--TKDSSLQYVRSGYVIDGEHSGSNEK-----------GYVYYKG             145
           .  .   . ...   .   *   .*.   . .

PHTBP1   ----QHWGLDSKTSYASKNSHFLQIAAAGEAGGFEALVIATHRH------             225
APL      VTPSKELPKGKVISYKGTWDFVSNINLEREIDGFDTSGDKNVSATSITE             230
APL7     NSPAKELPVNQLLTYTGSWDFTSNANLNNE------EGRPNYLNDDYYTK             189
              ..  .  .*  ... .  . .  *         .

PHTBP1   --GKETKI-HSEANKLKHNIRRITGFENRYDFTQIPHRMPPGGSFFIVED             272
APL      TVNRDHKVGEKLGDNEVKGVAHSSEFAVDFDNKKLTGSLYRNG--YINRN             278
APL7     FIGK--RVGLVSGDAKPAKHKYTSQFEVDFATKKMTGKL---------SD             228
          ..   ..    ..       .      . *.  .. ...  ..            .

PHTBP1   TCPTLDCTPRARVKLNRDNFPVRTFPEYTPEERNAEQIPYRTEQ--LSAQ             320
APL      KAQEVTKRYSIEADIAGNRFRG------KAKAEKAGDPIFT-DSNYLEGG             321
APL7     KEKTI---YTVNADIRGNRFTGAATASDKNKGKGESYNFFSADSQSLEGG             275
            .  ..  ... ..*       ...  ..  .  . *..

PHTBP1   EKTGKDRIAPNPLDYKSNSVFMKFGYHFNSSHYLGAILEDTKQRTISVIC             370
APL      FYGPKAEEMAGKFFTNNKSLFAVFAAKSENGETTTERIIDATKIDLTQFN             371
APL7     FYGPKAEEMAGKFVANDKSLFAVFSAKHNGSNVNTVRIIDASKIDLTNFS             325
         . *.   .  ...  ...*.*  *. ....  .     *...  ..   .

PHTBP1   KRQLTI--QKTILTYHLGTMFMKGIIFRWLSVQAKDPLWVAHMPCEVDER             418
APL      AKELNNFGDASVLIIDGQKIDLAGVNFKNSKTVEINGKTMVAVACCSNLE             421
APL7     ISELNNFGDASVLIIDGKKIKLAGSGFTNKHTIEINGKTMVAVACCSNLE             375
          ..*.     . ...*. .   ..   *   *    . .  ..   ..*   .
```

FIGURE 10B

```
PHTBP1    HHKRRLGFTYKYKPENNRWLDSINSCVRALRSRCCALSKQDIELY-----    463
APL       YMK----FGQLWQKEGKQQVKDNSLFLQGERTATDKMPAGGNYKYVGTWD    467
APL7      YMK----FGQLWQQAEGGKPENNSLFLQGERTATDKMPKGGNYKYIGTWD    421
          . *    *.   .. ..    .. ..  ... *.  .. .   *

PHTBP1    ---SRLHRLHCSDYPVVDKNCGPTLDKSWSMYRTERNNYQEKATCHSFCI    510
APL       ALVSKGTNWIAEADNNRESGYRTEFDVNFSDKKVNGKLFDKGGVNPVFTV    517
APL7      AQVSKENNWVATADDDRKAGYRTEFDVDFGNKNLSGKLFDKNGVNPVFTV    471
             *.  .  ..     . .. ...*  ...  . .. ... .. . *  .

PHTBP1    LKALNAGQGVFKQTHKLNLGLGFESNLIRLTIIGIILPNIPKAGYTSYRG    560
APL       DATIN-GNGFIGSAKTSDSGFALDAGSSQHGNAVFSDIKVNGGFYGP--T    564
APL7      DAKID-GNGFTGKAKTSDEGFALDSGSSRYENVKFNDVAVSGGFYGP--T    518
          .. *.*     ...  *......   . .    .   . *..  .

PHTBP1    RGRLDNPYIYRRDPRSIETVSLCNNTRATLLLLRVNKGIRLLLR    604
APL       AGELGGQFHHKSDNGSVGAV------------FGAKRQIE---K    593
APL7      AAELGGQFHHKSENGSVGAV------------FGAKQQVK---K    547
          . *....   ....    *...*              . .... .
```

FIGURE 12

```
       1              TonB box
PHTBP1          DEVIVTE                              22
CIRP            ETMVVTA                              12
FEPAP           DTIVVTA                              17
FHUAP           DTITVTA                              13
FECAP           FTLSVDA                              30
                . . *.

2
PHTBP1          YAIRGVD---KNRVSLLVDG                121
CIRP            VSIRGLDSS---YTLILVDG                105
FEPAP           IDIRGMGPE---NTLILIDG                102
FHUAP           LIIRGFAAEGQSQNNYL-NG                141
FECAP           FGIRGLNPRLTSRSTVLMDG                199
                ***  .           *  *

3
PHTBP1          IELSKGASSAEYGSGAHGGAIGFRTKD         177
CIRP            IEVVRGPMSSLYGSDALGGVVNIITKK         159
FEPAP           IEVLRGPARARYGNGAAGGVVNIITKK         180
FHUAP           AEIMRGPVSVLYGKSSPGGLLNMVSKR         188
FECAP           IDVVRGGGAVRYGPQSVGGVVNFVTRA         251
                .. .*      **  . **  ...  ..

4
PHTBP1          FKQTHKLNLGLGF                       533
CIRP            PETSESWELGLYY                       461
FEPAP           AETSINKEIGLEF                       447
FECAP           PSKGKQYEVGVKY                       560
FECAP           PEKARTWELGTRY                       578
                . .  ..*  .
```

FIGURE 16

|       | HRP–bTf | HRP–oTf | HRP–cTf | HRP–eTf |
|-------|---------|---------|---------|---------|
| h173– | ●       | ●       | ●       |         |
| h174– | ●       | ●       | ●       |         |
| h175– | ●       | ●       | ●       |         |
| h176– | ●       | ●       | ●       |         |
| h44–  | ●       | ●       | ●       |         |
| h50–  |         |         |         | ●       | i) h44 i) h173 i) h175

| FIGURE 19A | FIGURE 19B | FIGURE 19C |
|---|---|---|
| HRP-bTf | Anti-Tbp1 | Anti-Tbp2 |

| | HRP-bTf | Anti-Tbp1 | Anti-Tbp2 |
|---|---|---|---|
| h98 | ● | ● | ● |
| h99 | ● | ● | ○ |
| h100 | · | · | ◌ |
| h105 | · | ● | ● |
| h106 | ● | ● | ● |

FIGURE 20A

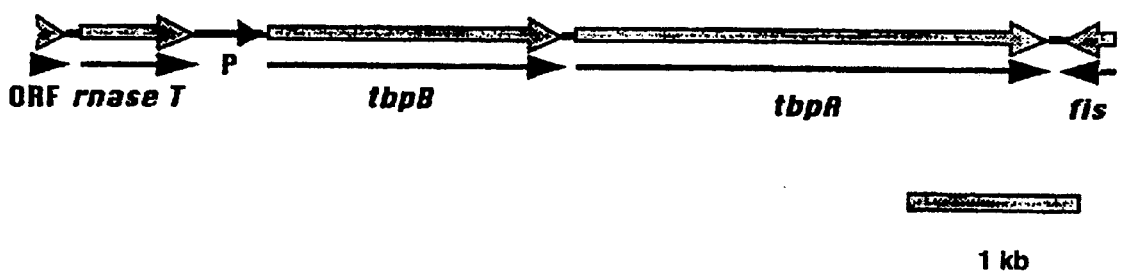

1 kb

1168
ATTTTTTATCTAATCTAAAAACAAGCGTTTCCACCTTGGAAATGATTAACATGATC

CTGAAACTAATAAAGTTCAAACCTTTACATTAAGTTTATATTATAAATTATAATGA
                                    -35                                       -10

TTATTATTTTATAAATTAAAGGAGACATTATGTTTAAACTTAAAAGTAGTTTTGTA
        SD           Met$_{1309}$

CTG........tbpB.....GAAAAATAATCATAATTCCCCTTTGCTGGTTGTAG
                        SC$_{3063}$
ATAGCAAGCGGGCAATTTTTTATAAAAATTTGCAAAATTTAAATAAAGGAGACCCT
                                             SD
ATCTAATGATAATGAAATATCATCATTTTCGC......tbpA.........AGAAA
Met$_{3151}$
TTTCAGTTTAGCATTTGAAATGAAGTTTTAG.
                         SC$_{5943}$

```
ATGATAATGAAATATCATCATTTTCGCTATTCACCTGTTGCCTTAACAGTGTTATTTGCTC
TTTCTCATTCATACGGTGCTGCGACTGAAAATAAAAAATCGAAGAAAATAACGATCTAGC
TGTTCTGGATGAAGTTATTGTGACAGAGAGCCATTATGCTCACGAACGTCAAAACGAAGTA
ACTGGCTTGGGGAAAGTAGTGAAAATTATCACGAAATGAGTAAAAATCAAATTCTTGGTA
TTCGTGATTTAACTCGCTATGACCCTGGTATTTCGGTGGTGGAACAAGGTCGCGGTGCAAG
TAGTGGCTATGCCATTCGAGGTGTAGATAAAAACCGTGTCAGCTTACTTGTTGATGGGCTA
CCACAAGCGCACAGTTATCATACGCTAGGTTCAGATGCTAATGGTGGTGCAATTAATGAGA
TTGAGTATGAAAACATTCGTTCAATTGAGTTAAGCAAAGGAGCAAGTTCTGCGGAATATGG
CTCTGGTGCGCATGGTGGTGCTATTGGTTTTCGTACTAAAGATGCGCAGGATATTATTAAA
GAGGGGCAGCATTGGGGCTTAGATAGTAAGACCTCTTATGCCAGCAAAAATAGCCATTTTT
TACAGTCTATCGCAGCGGCTGGTGAGGCGGGTGGTTTTGAAGCACTTGTTATTGCAACTCA
CCGACACGGTAAAGAGACCAAAATTCATTCCGAGGCAAATAAATTAAAACATAATATTCGG
CGTATAACCGGCTTTGAAAATCGCTACGACTTTACCCAAATTCCGCACAGAATGCTCCTGG
AGGATCTCCTTTTAATTGTGGAAGATACTTGCCCAACATTAGATTGTACTCCTCGTGCAAG
GGTTAAGTTGAACCGCGATAATTTCCCAGTGAGAACATTTCCGGAATATACGCCTGAAGAG
CGCAAACAGCTTGAGCAGATTCCTTATCGCACTGAGCAGCTCTCAGCCCAAGAATATACCG
GTAAAGATCGCATTGCACCAAACCCTTTAGATTACAAGAGTAATTCTGTTTTTATGAAGTT
TGGCTATCACTTCAACTCGTCTCATTATCTTGGCGCAATCTTAGAAGATACAAAACACGC
TACGATATCCGTGATATGCAAACGCCAGCTTACTATACAAAAGACGATATTAACTTATCAC
TTAGGAACTATGTTTATGAAGGGGATAATATTTAGATGGCTTAGTGTTCAAGCCAAGGAT
CCCTTATGGGTTGCGCTATAGCCATGTGAAGTTTTTGATGAACGTCACCACAAACGTCGT
TTAGGATTCACCTATAAATATAAACCAGAGAATAATCGCTGGTTGGATAGCATTAAACTCA
GTGCGGATAAACAAGATATTGAACTATATAGCCGGCTACATCGCTTGCATTGTAGCGATTA
TCCTGTGGTAGATAAAAATTGCCGCCCGACTTTGGATAAATCTTGGTCTATGTATCGAACT
GAGCGTAATAATTACCAAGAAAAGCATCGTGTCATTCATTTAGAATTTGATAAAGCGCTAA
ATGCTGGTCAAGGCGTATTTAACCAAACCCACAAACTGAATTTAGGGTTGGGCTTTGATCG
ATTTAATTCGCTTATGGATCATGGGGATATGACTGCCCAATATACCAAAGGCGGTTATACC
AGCTACCGCGGTAGAGGGCGTTTAGATAATCCATATATTTATCGCCGCGATCCACGCAGTA
TTGAAACGGTATCTTTGTGTAATAATACACGCGGCGACATCTTAAACTGTGAACCGCGTAA
AATTAAAGGCGATAGCCATTTTGTTAGCTTCCGCGATCTAGTGATAAGCGAGTATGTGGAT
TTGGGATTAGGGGTGCGTTTTGATCAACATCGATTTAAATCTGATGATCCGTGGACACTTA
GCCGAACTTATCGAAATTGGTCTTGGAATGGTGGGATTACGCTTAAACCAACAGAGTTTGT
ATCGCTTTCTTATCGCATTTCAAACGGTTTTAGAGTGCCTGCATTCTATGAACTTTATGGT
AAACGTGATCATATTGGGCTTAAAGATAACGAATATGTGCAACGCGCGCAACGTAGCCACC
AGTTAGAGCCAGAAAAATCGACTAATCATGAGATTGGAGTTAGCTTTAAAGGTCAATTTGG
TTACCTTGATGTGAGCTATTTCCGTAATAACTATAAAAATATGATTGCGACAGCATGTAAA
AGAATAATACAAAATCACACTGTTTCTATAACTACCATAATATTCAAGATGTAGCACTAA
ACGGGATAAATTTAGTCGCTAAATTTGACTTACACGGTATTTTATCTATGCTGCCAGATGG
TTTTTATTCATCAGTTGCTTATAACCGTGTAAAAGTAAAAGAGCGGAAACTAACCGACTCA
AGACTCGATAGCGTAAACGATCCTATTCTAGATGCGATTCAGCCAGCACGCTATGTGCTTG
GATTCGGCTACGATCACCCAGAAGAAAATGGGGAATTGGCATTACTACCACCTATTCTAA
AGCCAAAAACGCCGATGAGGTGGCAGGCACACGTCATCACGGNATACATCGCGTTGATTTA
GGTGGCAAACTGACCGGTTCTTGGTACACCCATGATATTACCGGTTACATCAATTATAAA
ACTACACCTTACGTGGAGGAATTTATAATGTGACTAATCGTAAATATTCCACTTGGGAATC
AGTGCGCCAATCCGGTGTGAATGCAGTAAACCAAGACCGGGGTAGCAATTACACTCGATTT
GGCGCTCCGGGGAGAAATTTCAGTTTAGCATTTGAAATGAAGTTTTAG
```

```
ATGTTTAAACTTAAAAGTAGTTTTGTACTGCTTAATGCGGCGCTACTTGCTGCTTGTTCCT
CAAATGGTGGAAGCTTTGATGTTCAATCTGCCAAAGTTGAATCTCAAACGCAAACTACCCC
CAAAAAGCCAAGTTTACAAGATGATAATAGTAACGCAAGACGTACAGTAAGCGCTTCTGAA
ACTGAAGCTTTATTGCAGCCGGGGTTTGGTTTTTCAGCCAAAATTCCGCGTCGTAATCTCC
TTCCGCAGGGGAAGGAAGATGTAGCCCCTATTGGTGATATAAAAGAGATTACTGGAGATCT
GCCAAAAATTCCGTATGAAGAAGAGGTTAAAGCGTGCGGTAGTAGTGCTGATGGATTTAGC
CATACTCATGATAGAAATCATAAGTTGTATACAAGAGATTTTAATTTTGTTCGTTCCGGCT
ATGTTGTGCATTCTGGTCCAAAACCTGAAATAAAGCCTAAAGAAATTTTGAGAACAGGTGC
ACATGGGTATGTTTACTATTTAGGTATAGAGCCGCCCAAAGCAATACCTACCCAAAAACTA
ACTTATAAAGGATATTGGGATTTTACTACCTATGCGGCTAAGGGGAGAGATAGTAATATTT
TTCTAATTCCCGCAGGCATCAATAGTGGCGCCATACCGGAAAATAGTCACGATATTAATGT
TGATGATTCTGAAAAACCAATGGGGCATACAGGAGAATTTACGGCTGATTTTGCTAATAAA
ACTTTAACTGGAACATTGGTTCGTAATGGGTATGTTAGTCGTAGCAAAGAGCAAAAAATTA
CAACAATTTACGATATTGATGCGAAAATTAAAGGTAATCGCTTTTCTGGTAAAGCAAACCC
AAAAAAACCGATGATCCTTATTTTTGGGAAAAGCTCCACGACACTTGAAGGTGGATTTTTT
GGTGGGGAGGCTCAAGAACTTGCCGGTAAATTCTTAGCTGATGATAAGTCGGTATTTGTTG
TTTTTGCTGGCACACGAGATGCTAAAAAAGATGATAGTGAATCTGCCTTTGATGCTTTCCC
AATTAAACTTAAAGATTTAAATAAATCTGAGATGGATACTTTCGGGAATGCGACACATTTG
ATTATTAACAATAAGCAGATTCCACTTATTGCGGAAGCCACAAAAAGCTTTGCCGAGATGA
AATTTGATGATTTGGTTACCCGTACTATTGATGGAAAAACGTATCGAGTTTCAGTCTGCTG
TAATAATTTAGATTATGTCAAATTTGGGATTTATAGCGAGGGAAATAATAGTGATACTGCT
CTCCAAGAATATTTAGTAGGAGAACGTACAGCTCTGGCAGATTTGCCAACAGGGACAGTAA
AATATCGAGGTACTTGGGACGGGGTAATGTACAGTAAATCTGGCTCGGCAGGGGTTGAATC
GCCAAGTAACAGCGAAAGTGGTACTCGTTCACTATTCGATGTAGATTTTGTCAATAAAAAA
ATTAATGGCAAGCTGATTGCTAATGATGGTGTTGAAGAACGCCCAATGCTGACACTGGAAG
GCAATCTGAAAGGGAATGGTTTTGGAGGCACAGCCAAAACGGGCAATTCTGGTTTTAATCT
TGATCCCAAAAGTACGAATGGTGGCACGGTAGGGCATATAAATACTCAATTTGAAGGGGGC
TTTTATGGCCCTAAGGCGACGGAATTAGGTGGTATTGTACAAAATACAGAAACGGATAAAG
ATAGAGTCAGTATTACATTCGGCGGAAAACGTCAAATAGAAAAATAA
```

FIGURE 24

```
  1  MFKLKSSFVLLNAALLAACSSNGGSFDVQS
 31  AKVESQTQTTPKKPSLQDDNSNARRTVSAS
 61  ETEALLQPGFGFSAKIPRRNLLPQGKEDVA
 91  PIGDIKEITGDLPKIPYEEVKACGSSADG
121  FSHTHDRNHKLYTRDFNFVRSGYVVHSGPK
151  PEIKPKEILRTGAHGYVYYLGIEPPKAIPT
181  QKLTYKGYWDFTTYAAKGRDSNIFLIPAGI
211  NSGAIPENSHDINVDDSEKPMGHTGEFTAD
241  FANKTLTGTLVRNGYVSRSKEQKITTIYDI
271  DAKIKGNRFSGKANPKKPMILIFGKSSTTL
301  EGGFFGGEAQELAGKFLADDKSVFVYFAGT
331  RDAKKDDSESAFDAFPIKLKDLNKSEMDTF
361  GNATHLIINNKQIPLIAEATKSFAEMKFDD
391  LVTRTIDGKTYRVSVCCNNLDYVKFGIYSE
421  GNNSDTALQEYLVGERTALADLPTGTVKYR
451  GTWDGVMYSKSGSAGVESPSNSESGTRSLF
481  DVDFVNKKINGKLIANDGVEERPMLTLEGN
511  LKGNGFGGTAKTGNSGFNLDPKSTNGGTVG
541  HINTQFEGGFYGPKATELGGIVQNTETDKD
571  RVSITFGGKRQIEK
```

TRANSFERRIN BINDING PROTEINS OF PASTEURELLA HAEMOLYTICA AND VACCINES CONTAINING SAME

"This application claims priority from U.S. Provisional Application No. 60/008,569, filed Dec. 1, 1995."

FIELD OF THE INVENTION

The invention relates to novel transferrin binding proteins of *Pasteurella haemolytica*, truncations, analogs, homologs and isoforms thereof; nucleic acid molecules encoding the proteins and truncations, analogs, and homologs of the proteins; vaccines containing the proteins; antibodies against the proteins; and, uses of the proteins and nucleic acid molecules.

BACKGROUND OF THE INVENTION

Members of the genus Pasteurella comprise a group of related bacterial species that are important pathogens of ruminants. This group includes the species *Pasteurella haemolytica* which has been classified into two biotypes, A and T, on the basis of sugar utilization, and into 16 serotypes which are recognized on the basis of their somatic antigens (Biberstein, E. L. et al., 1960; Fraser et al., 1982). The T-type strains of *P. haemolytica*, characterized by utilization of trehalose, have been recently reclassified as a new species *P. trehalosi* (Sneath, P. H. A. et al., 1990).

Pneumonic pasteurellosis caused by *Pasteurella haemolytica* is a major economic problem to the cattle, sheep and goat industries world-wide. Shipping fever, a variation of this disease, is a major problem in the cattle industry in North America and is almost exclusively caused by type A1 strains of this species (Babiuk, L. A. and S. D. Acres, 1984). Serotype A2 is the most prevalent disease-causing type in sheep but other serotypes may be important in sheep and goats (Gilmour and Gilmour, 1991). The related species, *Pasteurella trehalosi* (formerly know as T-type *P. haemolytica*) is the causitive agent of septicemia in lambs, a problem plaguing the sheep industry particularly in the United Kingdom. Similarly, strains of the related species *Pasteurella multocida*, are responsible for haemorrhagic septicemia, a serious infection in cattle and water buffalo, which is particularly serious in South East Asia.

Vaccination is a desired method of control for pasteurellosis in ruminants but success has been limited by the lack of immunizing preparations that induce protection against all disease-causing serotypes, particularly if a vaccine effective for all ruminants is considered. Killed whole cell vaccines elicited inconsistent levels of protection and antibody response in calves (Wilkie, B. N., 1980). Homologous vaccines containing sodium salicylate extracts (SSEs) protected sheep against diseases due to serotypes A1, A6 and A9 (Gilmour et al., 1983) but not against the more epidemic serotype A2 (Fraser et al., 1982). An exotoxin produced by *P. haemolytica* which is specifically lethal to leucocytes and alveolar macrophages from ruminants (Benson et al., 1978) has shown a lot of promise as a vaccine candidate in protection experiments in calves and sheep (13,35) but there is limited protection against heterologous serotypes (33). The inclusion of proteins induced under iron-limited growth conditions into a vaccine for pasteurellosis in lambs has been implicated in enhanced protection (15).

Previous studies have established that the ability of pathogenic bacteria to acquire iron in vivo is a critical factor in their pathobiology (7,11). One mechanism of iron retrieval from the host iron-binding glycoprotein, transferrin, involves direct binding of transferrin by surface receptors on the bacteria and the removal of iron from transferrin and uptake into the cell (21). Schryvers (1992) describes the isolation of transferrin receptor proteins from various bacterial pathogens using affinity chromatography. The transferrin receptor has been shown to consist of two proteins, called transferrin binding protein 1 or A (Tbp1 or TbpA) and transferrin binding protein 2 or B (Tbp2 or TbpB). The receptor-mediated type of iron uptake has been demonstrated to operate in serotype A bovine strains of *P. haemolytica* (26). Cells of *P. haemolytica* growing in vitro under iron-limited conditions express a number of iron-repressible outer membrane proteins (IROMPs) identical to those produced by cells recovered in vivo from infected sites in animals with pasteurellosis (9,10). Especially prominent among these proteins were those of molecular sizes 100, 77, 70 and 60 Kda (9,10). The 100 Kda protein has been identified as one of the host specific transferrin receptors in bovine isolates (26) while some of the other IROMPs had been suggested as possibly associated with the 100 Kda protein in an iron acquisition receptor complex (26). The role of the IROMPs expressed by *P. haemolytica* from lambs (10) in iron acquisition has not been elucidated, neither is it known if similar proteins are expressed by goat isolates.

*P. haemolytica* acquires iron from bovine host transferrin by a receptor-mediated type of mechanism. The proposal that bacteria with this type of iron acquisition mechanism may be solely dependent upon their surface receptor for iron acquisition in vivo (29) implies that they can only cause disease in those hosts whose transferrin is recognized by their surface receptors. *P. haemolytica* has been reported to cause disease in cattle, sheep and goats and accordingly their surface receptors would be expected to recognize these hosts' transferrins. Therefore it is important to determine whether sheep and goat isolates also possessed transferrin receptors involved in iron acquisition, to evaluate their specificities for different ruminant transferrins and to determine if there is antigenic relatedness amongst the surface receptors from the different strains causing pneumonic pasteurellosis in cattle, sheep and goats.

SUMMARY OF THE INVENTION

Transferrin receptors were identified in a collection of *Pasteurella haemolytica* (and *P. trehalosi*) strains of various serotypes and biotypes (A and T) from cattle, sheep and goats. Growth studies, binding studies and affinity isolation experiments demonstrated that these receptors had identical specificities which recognized transferrins from cattle, sheep and goats. This indicates that there are conserved regions on the receptor proteins, involved in ligand binding, which are accessible at the cell surface.

Antisera prepared against the individual purified receptor proteins (TbpA and TbpB) from a serotype A1 strain of *P. haemolytica* demonstrated considerable crossreactivity against receptor proteins from a representative selection of strains. The cross-reactivity was also observed against intact cells indicating that there are conserved immunological epitopes at the cell surface which could serve as targets for the host's immune effector mechanisms.

The present inventors have cloned, sequenced and expressed tbpA and tbpB genes encoding the transferrin receptor proteins, TbpA and TbpB (also referred to herein as Tbp1 and Tbp2, respectively), from *Pasteurella haemolytica* A1. The genes were organized in an operon arrangement of tbpB- tbpA. The tbpB gene was preceded by putative promoter and regulatory sequences, and followed by a 96 base pair intergenic sequence in which no promoter regions were found, suggesting that the two genes are coordinately transcribed. The deduced amino acid sequences of the TbpA and TbpB proteins had regions of homology with the corresponding *Neisseria meningitidis*, *N. gonorrhoeae*, *Haemophilus influenzae* and *Actinobacillus pleuropneumoniae* Lbp and Tbp proteins. The intact tbpB gene was expressed in a T7 expression system and the resulting recombinant TbpB protein retained the functional bovine transferrin binding characteristics. The availability of the recombinant TbpB enabled the inventors to demonstrate its specificity for ruminant transferrin, its ability to bind both the C-and N-terminal lobes of bovine transferrin, and its preference for the iron-loaded form of this protein.

The present inventors also significantly found that vaccination with a formulation containing *P. haemolytica* TbpA and TbpB provided significant protection against experimental bovine pneumonic pasteurellosis. Immunization with two doses of TbpB also provides protection Broadly stated, the present invention provides a purified and isolated nucleic acid molecule comprising a sequence encoding a TbpA protein, or a purified and isolated nucleic acid molecule comprising a sequence encoding a TbpB protein. The TbpA and TbpB proteins bind ruminant transferrins and function in receptor-mediated iron acquisition by *P. haemolytica* in its ruminant hosts. The TbpA protein is approximately 100 kDa, and TbpB is approximately 60 kDa in size.

In an embodiment of the invention, the purified and isolated nucleic acid molecules comprise a sequence encoding a TbpA protein having the amino acid sequence as shown in FIG. 22 or SEQ.ID.NO:2, or a sequence encoding a TbpB protein having the amino acid sequence as shown in FIG. 24 or SEQ.ID.NO:4. In a preferred embodiment of the invention, the purified and isolated nucleic acid molecules comprise a sequence encoding a TbpA protein and having the nucleic acid sequence as shown in FIG. 21 or SEQ.ID.NO:1, or a sequence encoding a TbpB protein having the nucleic acid sequence as shown in FIG. 23 or SEQ.ID.NO:3.

The invention also contemplates (a) nucleic acid molecules comprising a sequence encoding a truncation of TbpA or TbpB which is unique to the protein, an analog or homolog of TbpA or TbpB or a truncation thereof, (herein collectively referred to as "TbpA related proteins" or "TbpB related proteins", respectively); (b) a nucleic acid molecule comprising a sequence which hybridizes under high stringency conditions to the full length nucleic acid encoding TbpA or TbpB having the amino acid sequences as shown in FIGS. 22 and 24 respectively, or to a TbpA or TbpB related protein; (c) a nucleic acid molecule comprising a sequence which hybridizes under high stringency conditions to the full length nucleic acid sequence of the tbpA or tbpB genes having the sequences as shown in FIGS. 21 or SEQ.ID.NO:1, or FIG. 23 or SEQ.ID.NO:3, respectively.

The invention further contemplates a purified and isolated double stranded nucleic acid molecule containing a nucleic acid molecule of the invention, hydrogen bonded to a complementary nucleic acid base sequence.

The nucleic acid molecules of the invention may be inserted into an appropriate expression vector, i.e. a vector which contains the necessary elements for the transcription and translation of the inserted coding sequence. Accordingly, recombinant expression vectors adapted for transformation of a host cell may be constructed which comprise a nucleic acid molecule of the invention and one or more transcription and translation elements operatively linked to the nucleic acid molecule.

The recombinant expression vector can be used to prepare transformed host cells expressing TbpA and/or TbpB, or a TbpA or a TbpB related protein. Therefore, the invention further provides host cells containing a recombinant molecule of the invention.

The invention further provides a method for preparing a novel TbpA or TbpB, and TbpA or TbpB related proteins, utilizing the purified and isolated nucleic acid molecules of the invention. In an embodiment a method for preparing TbpA or TbpB is provided comprising (a) transferring a recombinant expression vector of the invention into a host cell; (b) selecting transformed host cells from untransformed host cells; (c) culturing a selected transformed host cell under conditions which allow expression of TbpA or TbpB; and (d) isolating the recombinant TbpA or TbpB.

The invention further broadly contemplates a purified and isolated TbpA or TbpB which binds to ruminant transferrin, preferably obtained by culturing a host cell containing a recombinant expression vector of the invention. In an embodiment of the invention, a purified TbpA or TbpB is provided which has the amino acid sequence as shown in FIG. 22 or FIG. 24 respectively. The invention also includes truncations of the protein and analogs, homologs, and isoforms of the protein and truncations thereof (i.e., "TbpA or TbpB related proteins").

The TbpA and TbpB, or TbpA and TbpB related proteins of the invention may be conjugated with other molecules, such as proteins, to prepare fusion proteins. This may be accomplished, for example, by the synthesis of N-terminal or C-terminal fusion proteins.

The invention further contemplates antibodies having specificity against an epitope of TbpA or TbpB, or TbpA or TbpB related proteins of the invention. Antibodies may be labelled with a detectable substance and they may be used to detect the TbpA or TbpB, or TbpA or TbpB related proteins of the invention in samples.

The invention also permits the construction of nucleotide probes which are unique to the nucleic acid molecules of the invention and accordingly to TbpA or TbpB, or TbpA or TbpB related proteins of the invention. Thus, the invention also relates to a probe comprising a sequence encoding TbpA or TbpB, or TbpA or TbpB related proteins. The probe may be labelled, for example, with a detectable substance and it may be used to select from a mixture of nucleotide sequences a nudeotide sequence coding for a protein which displays one or more of the properties of TbpA or TbpB.

The invention still further provides a method for identifying a substance which is capable of binding to TbpA or TbpB, or TbpA or TbpB related proteins, or an activated form thereof, comprising reacting TbpA or TbpB, or TbpA or TbpB related proteins, or an activated form thereof, with at least one substance which potentially can bind with TbpA or TbpB, or TbpA or TbpB related proteins, or an activated form thereof, under conditions which permit the formation of complexes between the substance and TbpA or TbpB, or TbpA or TbpB related proteins, or an activated form thereof, and assaying for complexes, for free substance, for non-complexed TbpA or TbpB or a TbpA or TbpB related proteins, or an activated form thereof. Substances which potentially can bind TbpA or TbpB, or TbpA or TbpB related proteins, include transferrins, particularly ruminant transferring, analogs and derivatives of transferrins and antibodies against TbpA and TbpB, or TbpA or TbpB related proteins.

Still further, the invention provides a method for assaying a medium for the presence of an agonist or antagonist of the interaction of TbpA or TbpB, or TbpA or TbpB related proteins, and a substance which binds to TbpA or TbpB, or TbpA or TbpB related proteins or an activated form thereof. In an embodiment, the method comprises providing a known concentration of TbpA or TbpB, or TbpA or TbpB related proteins, with a substance which is capable of binding to TbpA or TbpB, or TbpA or TbpB related proteins and a suspected agonist or antagonist substance under conditions which permit the formation of complexes between the substance and TbpA or TbpB, or TbpA or TbpB related proteins, and assaying for complexes, for free substance, for non-complexed TbpA or TbpB, or TbpA or TbpB related proteins. In a preferred embodiment of the invention, the substance is a ruminant transferrin, analog, derivative or part thereof or an antibody against TbpA or TbpB, or TbpA or TbpB related proteins.

Substances which affect expression of TbpA or TbpB, or TbpA or TbpB related proteins, may also be identified using the methods of the invention by comparing the pattern and level of expression of TbpA or TbpB, or TbpA or TbpB related proteins of the invention, in cells in the presence, and in the absence of the substance.

The substances identified using the methods of the invention may be used in the treatment of animals, particularly ruminants infected with *P. haemolytica* and accordingly they may be formulated into pharmaceutical compositions for adminstration to ruminants, such as cattle, sheep and goats suffering from infection with *P. haemolytica* or exposed to infection by *P. haemolytica*.

The present inventors have demonstrated that the TbpA or TbpB, or TbpA or TbpB related proteins of the invention, are immunogenic. Therefore, the invention also relates to antibodies against the TbpA or TbpB, or TbpA or TbpB related proteins of the invention. In an embodiment, the antibodies are cross reactive against TbpA or TbpB or TbpA, or TbpB related proteins, from a wide range of serotypes of *P. haemolytica*. The antibodies may be used in the diagnosis and treatment of *P. haemloytica* infection and may be used, for example, in passive immunization to treat or prevent diseases in ruminants caused by *P. haemolytica*.

The invention further includes vaccine compositions comprising the TbpA or TbpB, or TbpA or TbpB related proteins of the invention, either alone, or in combination. The invention still further includes methods of immunizing a host, preferably a ruminant host against infection by *P. haemolytica* by administering therapeutically effective amounts of such vaccines. The present inventors have demonstrated that different strains of *P. haemolytica*, from a range of ruminants, are able to bind and utilize a range of ruminant transferrins. Thus it is contemplated that the vaccine compositions of the invention will be useful as broad spectrum vaccines suitable for immunizing a range of ruminants, such as sheep, cows and goats against infection with a wide range of *P. haemolytica* biotypes and serotypes.

The invention also contemplates the use of nucleic acid molecules of the invention encoding TbpA or TbpB, or TbpA or TbpB related proteins, in a recombinant viral vector vaccine for augmenting the immune response of a ruminant to *P. haemolytica* or for treating *P. haemolytica* infection. Recombinant viral vectors may be constructed using techniques known in the art.

Other objects, features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which:

FIGS. 1A–1B is a schematic diagram of the PCR procedure (*a*), and the 0.8 kb PCR product amplified by Tbp1 primer and primer left (*b*);

FIG. 2 is a restriction endonuclease map of tbp plasmids 9, 10, and 482;

FIGS. 3A–3E is a preliminary nucleotide sequence of *P haemolytica* tbpA and tpbB, FIGS. 3A–3B shows the sequence of tpbB and FIGS. 3C–3E shows the sequence of tpbA.;

FIG. 4 and SEQ ID NOS:7, 8, and 9 is the promoter region of *P haemolytica* tbpB (PHTBPB);

FIG. 8 are restriction maps of the tbpA, tbpB regions in *P. haemolytica* A1, *A. pleuropneumoniae* CM5, Shope 4074, and *A. suis* 3714;

FIGS. 9A–9C shows an alignment of the amino acid of Tbp1 of *P. haemolytica* A1, (PHTBP) and the Tbp1 of *N.gonorrhoeae* (NGTBP1) and *N. meningitidis* (NM1);

FIGS. 10A–10B shows an alignment of the amino acid of Tbp1 of *P. haemolytica* A1, (PHTBP) and the *A. pleuropneumoniae* serotype 1 and 7 TfbA proteins (APL, APL7);

FIG. 12 is a peptide alignment between *P. haemolytica* A1 Tbp1 and TonB-dependent outer membrane receptors of *E. coli* (SEQ ID NO:16–20, 53–67).

FIG. 16 is a blot showing the binding of labelled transferrins by iron-deficient bacterial membranes;

FIGS. 19A–19C are blots showing the binding of labelled transferrin and anti-receptor antibody by intact cells;

FIGS. 20A–20B is a map of the *P. haemolytica* tbp operon (Top) and *P. haemolytica* tbp operon (Top) and regulatory sequences (Bottom); tbpA and tbpB are the genes encoding for TbpA and TbpB, respectively; p, is the putative promoter region preceding tbpB and denoted as −35 and −10 sites at the bottom;

FIG. 21 and SEQ ID NO:1 show the DNA sequence of the tbpA gene from *P. haemolytica* strain h196;

FIG. 22 and SEQ ID NO:2 show the predicted amino acid sequence of the TbpA protein from *P. haemolytica* strain h196;

FIG. 23 and SEQ ID NO:3 show the DNA sequence of the tbpB gene from *P. haemolytica* strain h196;

FIG. 24 and SEQ ID NO:4 show the predicted amino acid sequence of the TbpB protein from *P. haemolytica* strain h196;

DETAILED DESCRIPTION OF THE INVENTION

Figure 5:
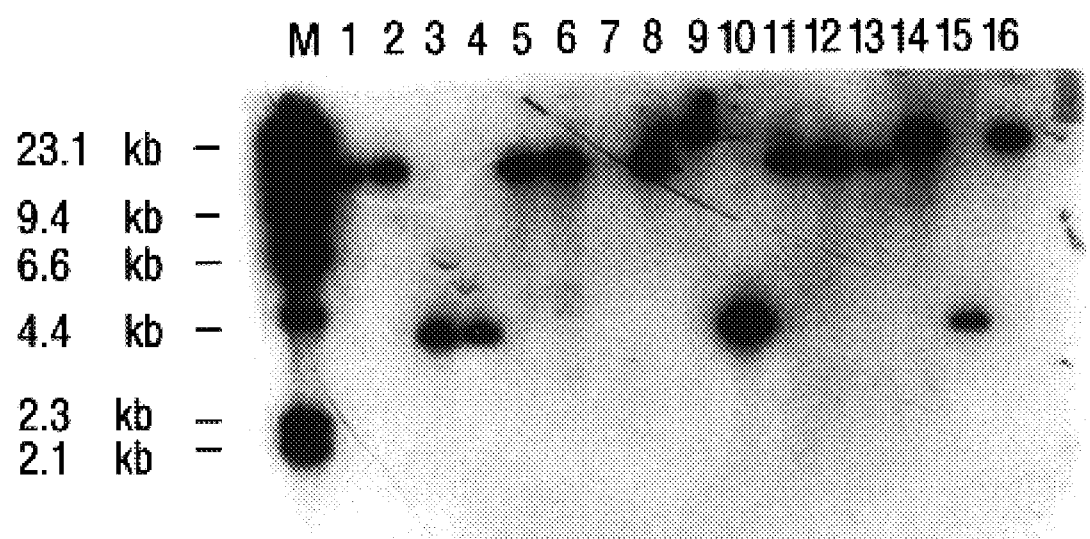
FIG. 5 is a blot of Southern hybridization of *P. haemolytica* genomic DNA digested with ClaI and probed with tbpA gene.

The following standard abbreviations for the amino acid residues are used throughout the specification: A, Ala—alanine; C, Cys—cysteine; D, Asp—aspartic acid; E, Glu—glutamic acid; F, Phe—phenylalanine; G, Gly—glycine; H, His—histidine; I, Ile—isoleucine; K, Lys—lysine; L, Leu—leucine; M, Met—methionine; N, Asn—asparagine; P, Pro—proline; Q, Gln—glutamine; R, Arg—arginine; S, Ser—serine; T, Thr—threonine; V, Val—valine; W, Trp—tryptophan; Y, Tyr—tyrosine; and p.Y., P.Tyr—phosphotyrosine.

I. Nucleic Acid Molecules of the Invention

As hereinbefore mentioned, the present invention provides a purified and isolated nucleic acid molecule comprising a sequence encoding a TbpA protein, or a purified and isolated nucleic acid molecule comprising a sequence encoding a TbpB protein. The term "isolated and purified" refers to a nucleic acid substantially free of cellular material or culture medium when produced by recombinant DNA techniques, or chemical precursors, or other chemicals when chemically synthesized. An "isolated and purified" nucleic acid is also free of sequences which naturally flank the nucleic acid (i.e., sequences located at the 5' and 3' ends of the nucleic acid) from which the nucleic acid is derived. The term "nucleic acid" is intended to include DNA and RNA and can be either double stranded or single stranded.

In an embodiment of the invention, a nucleic add molecule is provided which encodes TbpA having the amino acid sequence as shown in FIG. 22 or SEQ.ID.NO:2. In another embodiment, a nucleic acid molecule is provided which encodes TbpB having the amino add sequence as shown in FIG. 24 or SEQ.ID.NO:4. In preferred embodiments of the invention, the nucleic acid molecule is a DNA comprising the nucleotide sequence as shown in FIG. 21 or SEQ.ID.NO:1, or the nucleotide sequence as shown in FIG. 23 or SEQ.ID.NO:3.

The invention includes nucleic acid sequences complementary to the nucleic acid (a) encoding TbpA having the amino acid sequence as shown in FIG. 22 or SEQ.ID.NO:2; (b) encoding TbpB having the amino acid sequence as shown in FIG. 24 or SEQ.ID.NO:4; (c) having the sequence as shown in FIG. 21 or SEQ.ID.NO:1, or in FIG. 23 or SEQ.ID.NO:3. Preferably, the sequences are complementary to the full length nucleic acid sequences sequence shown in FIG. 21 or SEQ.ID.NO:1, or in FIG. 23 or SEQ.ID.NO:3.

The invention also includes nucleic acid molecules having substantial sequence identity or homology to the nucleic acid sequence as shown in FIG. 21 or SEQ.ID.NO:1 or FIG. 23 or SEQ.ID.NO:3; or encoding TbpA or TbpB proteins having substantial homology to the amino acid sequences shown in FIG. 22 or SEQ.ID.NO:2, or in FIG. 24 or SEQ.ID.NO:4, respectively. Homology refers to sequence similarity between sequences and can be determined by comparing a position in each sequence which may be aligned for purposes of comparison. When a position in the compared sequence is occupied by the same nucleotide base or amino acid, then the molecules are matching or have identical positions shared by the sequences.

Nucleic acid sequences having substantial homology include (a) nucleic acid sequences having at least 40–60%, preferably 60–80% most preferably 80–90% identity with the nucleic acid sequence as shown in FIG. 21 or SEQ.ID.NO:1; and (b) nucleic acid sequences having at least 40–60%, preferably 60–80% most preferably 80–90% identity with the nucleic acid sequence as shown in FIG. 23 or SEQ.ID.NO:3.

Another aspect of the invention provides a nucleic acid molecule, and fragments thereof having at least 15 nucleotide bases, which hybridizes to the nucleic acid molecules of the invention under hybridization conditions, preferably stringent hybridization conditions. Appropriate stringency conditions which promote DNA hybridization are known to those skilled in the art, or may be found in Current Protocols in Molecular Biology, John Wiley & Sons, N.Y. (1989), 6.3.1–6.3.6. For example, 6.0×sodium chloride/sodium citrate (SSC) at about 45° C., followed by a wash of 2.0×SSC at 50° C. may be employed. The stringency may be selected based on the conditions used in the wash step. By way of example, the salt concentration in the wash step can be selected from a high stringency of about 0.2×SSC at 50° C. In addition, the temperature in the wash step can be at high stringency conditions, at about 65° C.

Isolated and purified nucleic acid molecules encoding a protein having the activity of TbpA or TbpB, and having a sequence which differs from the nucleic acid sequence shown in FIG. 21 or SEQ.ID.NO:1, or in FIG. 23 or SEQ.ID.NO:3, respectively, due to degeneracy in the genetic code are also within the scope of the invention. Such nucleic acids should encode functionally equivalent TbpA or TbpB proteins but differ in sequence from the sequence in FIG. 21 or SEQ.ID.NO:1, or in FIG. 23 or SEQ.ID.NO:3, respectively, due to degeneracy in the genetic code.

An isolated and purified nucleic acid molecule of the invention which comprises DNA can be isolated by preparing a labelled nucleic acid probe based on all or part of the nucleic acid sequence shown in FIG. 21 or SEQ.ID.NO:1, or in FIG. 23 or SEQ.ID.NO:3, and using the labelled nucleic acid probe to screen an appropriate DNA library (e.g. a cDNA or genomic DNA library). Nucleic acids isolated by screening of a cDNA or genomic DNA library can be sequenced by standard techniques.

An isolated and purified nucleic acid molecule of the invention which is DNA can also be isolated by selectively amplifying a nucleic acid encoding TbpA or TbpB using the polymerase chain reaction (PCR) methods and cDNA or genomic DNA. It is possible to design synthetic oligonucleotide primers from the nucleotide sequence shown in FIG. 21 or SEQ.ID.NO:1, or in FIG. 23 or SEQ.ID.NO:3, for use in PCR. A nucleic acid can be amplified from cDNA or genomic DNA using these oligonucleotide primers and standard PCR amplification techniques. The nucleic acid so amplified can be cloned into an appropriate vector and characterized by DNA sequence analysis. It will be appreciated that cDNA may be prepared from mRNA, by isolating total cellular mRNA by a variety of techniques, for example, by using the guanidinium-thiocyanate extraction procedure of Chirgwin et al., Biochemistry, 18, 5294–5299 (1979). cDNA is then synthesized from the mRNA using reverse transcriptase (for example, Moloney MLV reverse transcriptase available from Gibco/BRL, Bethesda, Md., or AMV reverse transcriptase available from Seikagaku America, Inc., St. Petersburg, Fla.).

An isolated and purified nucleic acid molecule of the invention which is RNA can be isolated by cloning a cDNA encoding TbpA or TbpB into an appropriate vector which allows for transcription of the cDNA to produce an RNA molecule which encodes a protein which exhibits TbpA or TbpB activity.

A nucleic acid molecule of the invention may also be chemically synthesized using standard techniques. Various methods of chemically synthesizing polydeoxynucleotides are known, including solid-phase synthesis which, like peptide synthesis, has been fully automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373,071).

Determination of whether a particular nucleic acid molecule encodes a protein having TbpA or TbpB activity can be accomplished by expressing the DNA in an appropriate host cell by standard techniques, and testing the ability of the expressed protein to bind ruminant transferrins and/or mediate iron uptake. A cDNA having such activity can be sequenced by standard techniques, such as dideoxynucleotide chain termination or Maxam-Gilbert chemical sequencing, to determine the nucleic acid sequence and the predicted amino acid sequence of the encoded protein.

Regulatory elements of tbpA or tbpB can be identified using conventional techniques. The function of the elements can be confirmed by using these elements to express a reporter gene which is operatively linked to the elements. These constructs may be introduced into cultured cells using standard procedures.

The sequence of a nucleic acid molecule of the invention may be inverted relative to its normal presentation for transcription to produce an antisense nucleic acid molecule. An antisense nucleic acid molecule may be constructed using chemical synthesis and enzymatic ligation reactions using procedures known in the art.

II. Recombinant TbpA and TbpB

The invention also contemplates a purified and isolated TbpA or TbpB protein from *Pasteurella haemolytica* A1 which exhibits transferrin binding activity. In an embodiment of the invention, a purified TbpA protein is provided which has the amino acid sequence as shown in FIG. 22 or in SEQ. ID. NO:2. In another embodiment of the invention, a purified TbpB protein is provided which has the amino acid sequence as shown in FIG. 24 or in SEQ. ID. NO:4. Recombinant TbpB, unlike the native receptor complex, recognizes binding determinants on the N-lobe and C-lobe of transferrin.

In addition to the full length TbpA or TbpB amino acid sequences, the proteins of the present invention include truncations of TbpA or TbpB, and analogs, and homologs of TbpA or TbpB and truncations thereof as described herein. Truncated proteins may comprise peptides with at least 3 amino acid residues. The truncated proteins may have an amino group (—NH2), a hydrophobic group (for example, carbobenzoxyl, dansyl, or T-butyloxycarbonyl), an acetyl group, a 9-fluorenylmethoxy-carbonyl (PMOC) group, or a macromolecule including but not limited to lipid-fatty acid conjugates, polyethylene glycol, or carbohydrates at the amino terminal end. The truncated proteins may have a carboxyl group, an amido group, a T-butyloxycarbonyl group, or a macromolecule including but not limited to lipid-fatty acid conjugates, polyethylene glycol, or carbohydrates at the carboxy terminal end.

The proteins of the invention may also include analogs of TbpA or TbpB as shown in FIG. 22 or in SEQ. ID. NO:2, or in FIG. 24 or in SEQ. ID. NO:4, respectively, and/or truncations thereof as described herein, which may include, but are not limited to TbpA or TbpB (FIG. 22 or in SEQ. ID. NO:2, or in FIG. 24 or in SEQ. ID. NO:4), containing one or more amino acid substitutions, insertions, and/or deletions. Amino acid substitutions may be of a conserved or non-conserved nature. Conserved amino acid substitutions involve replacing one or more amino acids of the TbpA or TbpB amino acid sequence with amino acids of similar charge, size, and/or hydrophobicity characteristics. When only conserved substitutions are made the resulting analog should be functionally equivalent to TbpA or TbpB. Non-conserved substitutions involve replacing one or more amino acids of the TbpA or TbpB amino acid sequence with one or more amino acids which possess dissimilar charge, size, and/or hydrophobicity characteristics.

One or more amino acid insertions may be introduced into TbpA or TbpB (FIG. 22 or in SEQ. ID. NO:2, or in FIG. 24 or in SEQ. ID. NO:4). Amino acid insertions may consist of single amino acid residues or sequential amino acids ranging from 2 to 15 amino acids in length.

Deletions may consist of the removal of one or more amino acids, or discrete portions from the TbpA or TbpB (FIG. 22 or in SEQ. ID. NO:2, or in FIG. 24 or in SEQ. ID. NO:4), sequence. The deleted amino acids may or may not be contiguous. The lower limit length of the resulting analog with a deletion mutation is about 10 amino acids, preferably 100 amino acids.

The proteins of the invention also include homologs of TbpA or TbpB (FIG. 22 or in SEQ. ID. NO:2, or in FIG. 24 or in SEQ. ID. NO:4), and/or truncations thereof as described herein. Such TbpA or TbpB, homologs are proteins whose amino acid sequences are comprised of the amino acid sequences of TbpA or TbpB regions from other species that hybridize under stringent hybridization conditions (see discussion of stringent hybridization conditions herein) with a probe used to obtain TbpA or TbpB.

Protein sequences having substantial homology include protein sequences having at least 40–60%, preferably 60–80%, most preferably 80–90% identity with the amino acid sequence as shown in FIG. 22 (or SEQ. ID. NO:2) or FIG. 24 (SEQ. ID. NO:4).

The invention also contemplates isoforms of the proteins of the invention. An isoform contains the same number and kinds of amino acids as the protein of the invention, but the isoform has a different molecular structure. The isoforms contemplated by the present invention are those having the same properties as the protein of the invention as described herein.

The present invention also includes a TbpA, TbpB or a TbpA or TbpB related proteins conjugated with a selected protein, or a selectable marker protein (see below) to produce fusion proteins. Additionally, immunogenic portions of TbpA, TbpB or a TbpA or TbpB related proteins are within the scope of the invention.

TbpA, TbpB or a TbpA or TbpB related protein of the invention are prepared using recombinant DNA methods. Accordingly, the nucleic acid molecules of the present invention having a sequence which encodes TbpA, TbpB, or a TbpA or TbpB related protein of the invention may be incorporated in a known manner into an appropriate expression vector which ensures good expression of the protein. The expression vectors are "suitable for transformation of a host cell", means that the expression vectors contain a nucleic acid molecule of the invention and regulatory sequences selected on the basis of the host cells to be used for expression, which is operatively linked to the nucleic acid molecule. Operatively linked is intended to mean that the nucleic acid is linked to regulatory sequences in a manner which allows expression of the nucleic acid.

The invention therefore contemplates a recombinant expression vector of the invention containing a nucleic acid molecule of the invention, or a fragment thereof, and the necessary regulatory sequences for the transcription and translation of the inserted protein-sequence. Suitable regulatory sequences may be derived from a variety of sources, including bacterial, fungal, viral, mammalian, or insect genes. Selection of appropriate regulatory sequences is dependent on the host cell chosen as discussed below, and may be readily accomplished by one of ordinary skill in the art.

The recombinant expression vectors of the invention may also contain a selectable marker gene which facilitates the selection of host cells transformed or transfected with a recombinant molecule of the invention. Examples of selectable marker genes are genes encoding a protein which confers resistance to certain drugs, or β-galactosidase.

The recombinant expression vectors may also contain genes which encode a fusion moiety which provides increased expression of the recombinant protein; increased solubility of the recombinant protein; and aid in the purification of the target recombinant protein by acting as a ligand in affinity purification.

Recombinant expression vectors can be introduced into host cells to produce a transformant host cell. The term "transformant host cell" is intended to include prokaryotic and eukaryotic cells which have been transformed or transfected with a recombinant expression vector of the invention. The terms "transformed with", "transfected with", "transformation" and "transfection" are intended to encompass introduction of nucleic acid (e.g. a vector) into a cell by one of many possible techniques known in the art. Suitable methods for transforming and transfecting host cells can be found in Sambrook et al. (Molecular Cloning: A Laboratory Manual, 2nd Edition, Cold Spring Harbor Laboratory press (1989)), and other laboratory textbooks.

The proteins of the invention may also be prepared by chemical synthesis using techniques well known in the chemistry of proteins such as solid phase synthesis (Merrifield, 1964, J. Am. Chem. Assoc. 85:2149–2154) or synthesis in homogenous solution (Houbenweyl, 1987, Methods of Organic Chemistry, ed. E. Wansch, Vol. 15 I and II, Thieme, Stuttgart).

N-terminal or C-terminal fusion proteins comprising TbpA, TbpB, or a TbpA or TbpB related protein of the invention conjugated with other molecules, such as proteins, may be prepared by fusing, through recombinant techniques, the N-terminal or C-terminal of TbpA, TbpB or a TbpA or TbpB related protein, and the sequence of a selected protein or selectable marker protein with a desired biological function. The resultant fusion proteins contain TbpA, TbpB or a TbpA or TbpB related protein, fused to the selected protein or marker protein.

III. Applications of the Invention

The nucleic acid molecules of the invention allow those skilled in the art to construct nucleotide probes for use in the detection of nucleic acid sequences in samples. Suitable probes include nucleic acid molecules based on nucleic acid sequences encoding at least 6 sequential amino acids from regions of the TbpA or TbpB protein as shown in FIG. 22 and SEQ. ID. NO: 2, or in FIG. 24 and SEQ. ID. NO: 4, respectively. For example, a suitable probe may include nucleic acid molecules of TbpA selected from nucleotide nos. 1741 to 2784 of the sequence of TbpA shown in FIG. 21 and SEQ ID NO:1. A nucleotide probe may be labelled with a detectable substance such as a radioactive label which provides for an adequate signal and has sufficient half-life such as $^{32}P$, $^{3}H$, $^{14}C$ or the like. Other detectable substances which may be used include antigens that are recognized by a specific labelled antibody, fluorescent compounds, enzymes, antibodies specific for a labelled antigen, and luminescent compounds. An appropriate label may be selected having regard to the rate of hybridization and binding of the probe to the nucleotide to be detected and the amount of nucleotide available for hybridization. Labelled probes may be hybridized to nucleic acids on solid supports such as nitrocellulose filters or nylon membranes as generally described in Sambrook et al, 1989, Molecular Cloning, A Laboratory Manual (2nd ed.). The nucleic acid probes may be used to detect genes, preferably in human cells, that encode TbpA, TbpB, or TbpA or TbpB related proteins.

TbpA, TbpB, or TbpA or TbpB related proteins of the invention can be used to prepare antibodies specific for the proteins. Conventional methods can be used to prepare the antibodies. To produce polyclonal antibodies a mammal (such as a rabbit, mouse or rat) may be immunized with TbpA,TbpB, fragments of the proteins or a mixture of the two. The immunogenicity of the protein(s) may be enhanced by adding an adjuvant to the protein mixture or by coupling the protein to an immunogenic carrier. Examples of carriers include keyhole limpet hemocyanin(KLH) and bovine serum albumin(BSA).

To produce monoclonal antibodies, antibody producing cells (lymphocytes) can be harvested from an animal (immunized as described above) and fused with myeloma cells by standard somatic cell fusion procedures thus immortalizing these cells and yielding hybridoma cells. Such techniques are well known in the art, [e.g., the hybridoma technique originally developed by Kohler and Milstein (Nature 256, 495–497 (1975)) as well as other techniques such as the human B-cell hybridoma technique (Kozbor et al., Immunol. Today 4, 72 (1983)), the EBV-hybridoma technique to produce human monoclonal antibodies (Cole et al. Monoclonal Antibodies in Cancer Therapy (1985) Allen R. Bliss, Inc., pages 77–96), and screening of combinatorial antibody libraries (Huse et al., Science 246, 1275 (1989)]. Hybridoma cells can be screened immunochemically for production of antibodies specifically reactive with the peptide and the monoclonal antibodies can be isolated. Therefore, the invention also contemplates hybridoma cells secreting monoclonal antibodies with specificity for TbpA or TbpB, or TbpA or TbpB related proteins, as described herein.

The term "antibody" as used herein is intended to include fragments thereof which also specifically react with a protein, or peptide thereof, having the activity of TbpA or TbpB. Antibodies can be fragmented using conventional techniques and the fragments screened for utility in the same manner as described above. For example, F(ab')$_2$ fragments can be generated by treating antibody with pepsin. The resulting F(ab')$_2$ fragment can be treated to reduce disulfide bridges to produce Fab' fragments. Multivalent antibodies may be prepared by fusing two or more F(ab')$_2$ or Fab' fragments. For example, a multivalent antibody may contain one F(ab')2 fragment specific for TbpA and one F(ab')2 fragment specific for TbpB.

Chimeric antibody derivatives, i.e., antibody molecules that combine a non-ruminant animal variable region and a ruminant constant region are also contemplated within the scope of the invention. Chimeric antibody molecules can include, for example, the antigen binding domain from an antibody of a mouse, rat, or other species, with bovine constant regions. Conventional methods may be used to make chimeric antibodies containing the immunoglobulin variable region which recognizes the gene product of novel Tbp genes of the invention (See, for example, Morrison et al., Proc. Natl Acad. Sci. U.S.A. 81,6851 (1985); Takeda et al., Nature 314, 452 (1985), Cabilly et al., U.S. Pat. No. 4,816,567; Boss et al., U.S. Pat. No. 4,816,397; Tanaguchi et al., European Patent Publication EP171496; European Patent Publication 0173494.

Antibodies specifically reactive with TbpA, TbpB, or TbpA or TbpB related proteins, or derivatives thereof, such as enzyme conjugates or labeled derivatives, may be used as probes to detect TbpA, TbpB, or TbpA or TbpB related proteins in samples such as tissues and cells, for example they may be used in any known immunoassays which rely on the binding interaction between an antigenic determinant of TbpA, TbpB, or TbpA or TbpB related proteins and the antibodies. Examples of such assays are radioimmunoassays, enzyme immunoassays (e.g.ELISA), immunofluorescence, immunoprecipitation, latex agglutination, hemagglutination, and histochemical tests. Thus, the antibodies may be used to detect and quantify TbpA, TbpB, or TbpA or TbpB related proteins in a sample. In an embodiment, the antibodies are cross reactive against TbpA or TbpB or TbpA, or TbpB related proteins, from a wide range of serotypes of P. haemolytica. When used as probes the antibodies are usually labelled by techniques known in the art.

The antibodies of the present invention may also be used in the diagnosis and treatment of P. haemloytica infection. In one embodiment, the antibodies are used in passive immunization to treat or prevent diseases in ruminants caused by P. haemolytica. In such a case, a mixture of antibodies or a multivalent antibody may be used.

The invention still further provides a method for identifying a substance which is capable of binding to TbpA or TbpB, or TbpA or TbpB related proteins, or an activated form thereof, comprising reacting TbpA or TbpB, or TbpA or TbpB related proteins, or an activated form thereof, with at least one substance which potentially can bind with TbpA or TbpB, or TbpA or TbpB related proteins, or an activated form thereof, under conditions which permit the formation of complexes between the substance and TbpA or TbpB, or TbpA or TbpB related proteins, or an activated form thereof, and assaying for complexes, for free substance, for non-complexed TbpA or TbpB or a TbpA or TbpB related proteins or an activated form thereof. Substances which potentially can bind TbpA or TbpB, or TbpA or TbpB related proteins, include transferring, particularly ruminant transferring, analogs and derivatives of transferrins and antibodies against TbpA and TbpB, or TbpA or TbpB related proteins.

Still further, the invention provides a method for assaying a medium for the presence of an agonist or antagonist of the interaction of TbpA or TbpB, or TbpA or TbpB related proteins, and a substance which binds to TbpA or TbpB, or TbpA or TbpB related proteins or an activated form thereof. In an embodiment, the method comprises providing a known concentration of TbpA or TbpB, or TbpA or TbpB related proteins, with a substance which is capable of binding to TbpA or TbpB, or TbpA or TbpB related proteins and a suspected agonist or antagonist substance under conditions which permit the formation of complexes between the substance and TbpA or TbpB, or TbpA or TbpB related proteins, and assaying for complexes, for free substance, for non-complexed TbpA or TbpB, or TbpA or TbpB related proteins. In a preferred embodiment of the invention, the substance is a ruminant transferrin, analog, derivative or part thereof, or an antibody against TbpA or TbpB, or TbpA or TbpB related proteins.

Substances which affect expression of TbpA or TbpB, or TbpA or TbpB related proteins, may also be identified using the methods of the invention by comparing the pattern and level of expression of TbpA or TbpB, or TbpA or TbpB related proteins of the invention, in cells in the presence, and in the absence of the substance.

The substances identified using the methods of the invention may be used in the treatment of animals, particularly ruminants infected with P. haemolytica and accordingly they may be formulated into pharmaceutical compositions for adminstration to ruminants, such as cattle, sheep and goats suffering from infection with P. haemolytica, or exposed to infection by P. haemolytica.

The substances may be formulated into pharmaceutical compositions for adminstration to subjects in a biologically compatible form suitable for administration in vivo. By "biologically compatible form suitable for administration in vivo" is meant a form of the substance to be administered in which any toxic effects are outweighed by the therapeutic effects. The substances may be administered to living organisms including humans, and animals. Administration of a therapeutically active amount of the pharmaceutical compositions of the present invention is defined as an amount effective, at dosages and for periods of time necessary to achieve the desired result. For example, a therapeutically active amount of a substance may vary according to factors such as the disease state, age, sex, and weight of the individual, and the ability of antibody to elicit a desired response in the individual. Dosage regima may be adjusted to provide the optimum therapeutic response.

The active substance may be administered in a convenient manner such as by injection (subcutaneous, intravenous, etc.), oral administration, inhalation, transdermal application, or rectal administration. Depending on the route of administration, the active substance may be coated in a material to protect the compound from the action of enzymes, acids and other natural conditions which may inactivate the compound.

The compositions described herein can be prepared by per se known methods for the preparation of pharmaceutically acceptable compositions which can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). On this basis, the compositions include, albeit not exclusively, solutions of the substances in association with one or more pharmaceutically acceptable vehicles or diluents, and contained in buffered solutions with a suitable pH and iso-osmotic with the physiological fluids.

TbpA or TbpB, and/or TbpA or TbpB related proteins may be used as vaccines for the prophylaxis and treatment of various infectious diseases in animals. Infectious diseases contemplated by the invention include infections caused by *P. haemolytica*. such as bovine pneumoniae in cattle and systemic disease and pneumonia in sheep. In addition, vaccines according to the present invention may be used for the prophylaxis and treatment of infections caused by other Pasteurella spp. One example is the prophylaxis and treatment of *Pasteurella multocida* in cattle, swine and poultry including respiratory and systemic infections such as Hemorrhagic septicemia and bovine mastisis. The vaccines can be intended for administration to various animals, preferably ruminants, including cattle, sheep, and goats.

The present inventors have demonstrated that different strains of *P. haemolytica*, from a range of ruminants, are able to bind and utilize a range of ruminant transferring. Thus it is contemplated that the vaccine compositions of the invention will be useful as broad spectrum vaccines suitable for immunizing a range of ruminants, such as sheep, cows and goats against infection with a wide range of *P. haemolytica* biotypes and serotypes.

The vaccine compositions comprise the TbpA ,TbpB, and/or TbpA or TbpB related proteins, either alone, or in combination. The vaccine compositions may contain any combination of the described proteins or immunogenic fragments thereof. Further, the composition may contain Tbp proteins isolated from one or more biotypes or serotypes of *P. haemolytica* or other microorganisms. Recombinant proteins comprising TbpA, TbpB, and/or TbpA or TbpB related proteins are preferably employed in the vaccine compositions of the invention. In a preferred embodiment, one or more of recombinant TbpA or TbpB, and TbpA or TbpB related proteins of the invention, are used in the vaccine compositions. In another embodiment of the invention, the vaccine composition consists of purified and isolated TbpA and TbpB, preferably recombinant TbpA and TbpB.

The vaccine of the invention contains an immunologically effective amount of one or more of TpbA, TbpB, TbpA related protein, and TbpB related protein. The optimum amounts of the proteins depends on the nature of the infection against which protection is required, the characteristics of the animals to be protected, and other factors known to persons skilled in the art.

In addition to the TpbA, TbpB, TbpA related protein, and/or TbpB related protein, the vaccine may comprise an immunologically acceptable carrier such as aqueous diluelts, suspending aids, buffers, excipients, and one or more adjuvants known in the art. Suitable adjuvants include aluminum hydroxide, Freund's adjuvant (complete or incomplete), bacteria such as *Bordetella pertussis* or *E. coli* or bacterium derived matter, immune stimulating complex (iscom), oil, sapronin, oligopeptide, emulsified paraffin-Emulsigen™ (MVP Labs, Ralston, Nebr.), L80 adjuvant containing $AL(OH)_3$ (Reheis, N.J.), Quil A (Superphos), or other adjuvants known to the skilled artisan. Preferably, the adjuvant is L80 adjuvant containing $AL(OH)_3$ (Reheis, N.J.) and Quil A (Superphos). The vaccine can be incorporated into a liposome system which will allow the slow release of the TbpA and/or TbpB protein in the recipient. The vaccine may also contain preservatives such as sodium azide, thimersol, gentamicin, neomycin, and polymyxin.

The vaccine may be a multivalent vaccine and additionally contain other immunogens of *P. haemolytica* or immunogens related to other diseases in a prophylactically or therapeutically effective manner. For example, the vaccine composition of the invention may consist of *P. haemolytica* leukotoxin and TbpB.

The vaccines of the invention may be administered in a convenient manner, such as intravenously, intramuscularly, subcutaneously, intraperitoneally, intranatally or orally. Preferably the vaccine is administered intramuscularly or subcutaneously.

The dosage will depend on the nature of the infection, on the desired effect and on the chosen route of administration, and other factors known to persons skilled in the art.

The invention also contemplates the use of recombinant viral vector vaccines and recombinant bacterial vector vaccines containing nucleic acid molecules of the invention encoding TbpA, TbpB, TbpA related protein, and/or TbpB related protein, for the treatment and/or prophylaxis of *P. haemolytica* infection. In such systems, the TbpA or TbpB proteins are synthesized in vivo in the recipient from the exogenous nucleic acid molecules in the vaccine. The recombinant viral or bacterial vectors may be constructed using techniques known in the art, and as described herein. Examples of bacterial systems include *E.coli* and Salmonella spp. , The following non-limiting examples are illustrative of the present invention:

EXAMPLES

Example 1

The following materials and methods were used in the studies described in the example:

Materials and Methods
BACTERIAL STRAINS AND CLONING VECTORS

*P. haemolytica* strains were provided by Dr. P. Shewen, Department of Veterinary Microbiology and Immunology (VMI), University of Guelph, and were originally obtained from Dr. E. Biberstein, University of California, Davis, Dr. G. Frank, USDA, Ames, Iowa, and Dr. W. Donachie, Moredun Research Institute, Edinburgh, U.K. *Actinobacillus suis* strain 3714, *A. pleuropneumoniae* strains CM5 and Shope 4074 were provided by Dr. S. Rosendal, VMI. *E. coli* strains HB101 and TG-1 were provided by Dr. R. Lo, Department of Microbiology, University of Guelph, and were used as recipient strains for cloning experiments. *E. coli* strain JM109 (DE3) was provided by Dr. C. Whitfield, Department of Microbiology, University of Guelph.

Pasteurella and Actinobacillus strains were maintained on sheep's blood agar and cultured in brain heart infusion broth (BHIB), (Difco Labs, Detroit, Mich.). *E. coli* HB101 was grown on Luria-Bertaini plus thymidine (LT), supplemented with ampicillin (Sigma Chemical Co., St. Louis, Mo.) at 100 mg/L for selection of recombinant plasmids. Similarly, *E. coli* TG-1 and JM109 DE3) were grown on Davis minimal medium with ampicillin. Iron-depleted conditions were prepared by adding the iron chelator ethylenediamine-di(o-hydroxyphenylacetic) acid (EDDA) (Sigma) to a final concentration of 100 $\mu$M. Iron-depleted conditions were prepared by adding $FeCl_3$ to 1 mM.

The plasmid pBR322, bacteriophage vectors M13/mp18 and M13/mp19 were used as previously described (Lo and Cameron, 1986; Lo et al., 1985; and Lo et al., 1987). The pBluescript vector was obtained from Stratagene (La Jolla, Calif.). The recombinant Clone 482 was provided by Dr. A. Schryvers, Department of Microbiology, University of Calgary.

Enzymes, Chemicala and Antisera

Restriction endonucleases and DNA modifying enzymes were purchased from Bethesda Research Laboratories (BRL) (Burlington, Ontario) or Pharmacia Chemicals Incorporated (Dorval, Quebec) and were used as described by the manufacturers. Radioisotopes were purchased from ICN Biomedical (Montreal, Quebec) or Amersham Laboratories (Oakville, Ontario).

Goat anti-rabbit immunoglobulin G-alkaline phosphatase conjugate and immunodectection reagents were purchased from Bio-Rad Laboratories (Mississauga, Ontario). Goat anti-bovine immunoglobulin G-Alkaline phosphatase conjugate was purchased from Jackson lmmunoresearch (West Grove, PA). Rabbit anti-autologous antiserum and bovine anti-Presponse antisera were obtained from Dr. P. Shewen, Department of Veterinary Microbiology and immunology, University of Guelph. The rabbit "anti-autologous" antiserum was raised against the soluble antigens of *P. haemolytica* A1 cultured in RPMI 1640 supplemented with that rabbit's own serum. It is important to note that RMPI 1640 is an iron poor medium.

DNA Methods a) Chromosomal DNA Isolation

Chromosomal DNA was isolated from bacterial cells according to the method of Marmer (1961). Bacteria were inoculated into 250 ml of the appropriate medium and grown overnight at 37° C. with 150 rpm shaking. The following day, the cells were pelleted by centrifugation at 4,000×g in a GSA rotor in a Sorvall RC5-B refrigerated centrifuge (Dupont Instruments, Mississauga, Ontario) for 10 min. The pellet was suspended in 8 ml of a 0.6 M sorbitol, 0.05 mM Tris-HCI (pH 8.0), 0.05 M EDTA solution. Lysozyme (Sigma) was added to a final concentration of 3 mg/ml and the sample was incubated for 30 min on ice. Two ml of lytic solution (0.5% SDS, 0.05 M EDTA, 0.05 M Tris-Cl [pH 8.0]) and 3 mg/ml of proteinase K (Sigma) solution were added to the sample, which was then incubated for 4 h in a 37° C. water bath, followed by incubation at 56° C.

The suspension was extracted with an equal volume of phenol (Gibco/BRL) saturated with TE buffer (0.05 M Tris-HCl [pH 7.5], 0.001 M EDTA) and shaken at 30–50 rpm for 45 min. The phenol and aqueous phases were separated by centrifugation at 12,000×g at 5° C. for 10 min in a SS34 rotor. The supernatant was collected by a cut off wide mouth pasteur pipette and the DNA was precipitated with 2–3 volumes of ice-cold 95% ethanol. The strands of DNA were spooled onto a glass rod and dissolved in a small volume of 0.1×SSC (1×SSC contains 0.15 M NACl, 0.015 M sodium citrate).

The DNA was then treated with RNase to a final concentration of 10 $\mu$g/ml and incubated at 37° C. for 30 min. The DNA was again precipitated by 2–3 volumes of cold 95% ethanol, spooled onto a glass rod and dissolved in 1×SSC. Samples were stored at 4° C.

b) Restriction Endonuclease Digestion and Ligation

Plasmid and bacteriophage vectors were digested with the appropriate restriction endonucleases according to manufacturer's instructions. Vector and insert DNA were mixed to a final volume of 5 $\mu$l and were ligated with 0.5 units of T4 DNA ligase. Ligation mixtures were either incubated for 3–4 hours at room temperature, or overnight at 14° C. prior to tranformation into *E. coli* cells.

c) Preparation of Competent *E. coli* Cells

Transformation was used to introduce plasmid and bacteriophage DNA into competent *E. coli* cells (Mandel and Higa, 1970; Lederberg and Cohen et al., 1972). *E. coli* strains to be transformed were grown overnight in LT broth at 37° C. with 150 rpm shaking. The following day, a 1/40 subculture in 20 ml of the same medium was prepared and grown for an additional 60 min at 37° C. with 75 rpm shaking. The cells were collected by centrifugation at 3,000×g in an SS34 rotor and resuspended in 10 ml sterile ice-cold 50 mM $CaCl_2$. The suspension was incubated for 30 min. on ice, then the cells were collected by centrifugation and resuspended in 2 ml sterile icecold mM $CaCl_2$. The competent cells could then be stored at 4° C. and used for up to 3 days.

For transformation, 0.2 ml of the competent cells were mixed with the DNA sample and incubated for 30 min on ice. The cells were heat-shocked for 2 min at 42° C. and then 0.2 ml of LT broth was added. The cells were incubated at 37° C. for 15 min then plated onto LT plates containing appropriate antibiotics and incubated overnight at 37° C.

d) Large-scale Plasmid Isolation

Large-scale plasmid isolation was performed according to the procedure of Clewell and Helinski (1969) with modifications. *E. coli* carrying the plasmid was inoculated into 250 ml LT broth containing ampicillin and grown overnight at 37° C. with 150 rpm shaking. The following day, chloramphenicol (Sigma) was added to a final concentration of 25 mg/l and the culture was grown for a further 4–6 h. The cells were collected by centrifugation at 4,000×g for 10 min in a GSA rotor. The cell pellet was resuspended in 4 ml of an ice-cold solution containing 25% sucrose and 0.05 M Tris HCl (pH 8.0), then 1 ml of a fresh 10 mg/ml lysozyme (Sigma) solution was added. The mixture was incubated in a 37° C. waterbath for 30 min, placed on ice for 5 min and then 2 ml of 0.25 M EDTA (pH 8.0) was then added. After a further 5 min incubation on ice, 5 ml of a lytic solution (0.05 M Tris-HCl [pH 8.0], 0.0625 M EDTA and 2% Triton X-100) were added. The mixture was returned to the 37° C. waterbath for 5–15 min until cell lysis was complete. The mixture was then centrifuged for 30 min at 27,000×g and the dear lysate was transferred to a clean test tube, the lysate was mixed with solid CsCl (Boehringer Mannheim, Laval, Quebec) at 1 g/ml to a total of 4.5 ml. One hundred $\mu$l of ethidium bromide (10 mg/ml) were then added in 4.5 ml of the sample. The centrifuge tube was heat sealed and the sample was centrifuged at 240,000×g for a minimum of 9 h at 15° C. in a Beclanan VTi65 vertical rotor.

Plasmid DNA was recovered by puncturing the top and bottom of the centrifuge tube and collecting the lower of two bands in the tube. To extract the ethidium bromide from the sample, the plasmid DNA solution was mixed with an equal volume of Cs/Cl satured n-butanol. After allowing the phases to separate, the upper layer containing n-butanol and ethidium bromide was removed. This process was repeated three times. Following ethidium bromide extraction, the lower aqueous phase was dialyzed to remove the CsCl. Dialysis tubing (Fisher) with a molecular cutoff of 10 kDa was prepared by boiling 2×15 min in 0.1 M Na bicarbonate and 1×15 min in 0.25 M EDTA (pH 7.5) and was stored at 4° C. in 50% ethanol and 1mM EDTA. Prior to dialysis, the tubing was rinsed in $dH_2O$ and then filled with the plasmid DNA solution. The DNA was dialyzed for 24 h in 4×1L of dialysis buffer (0.01 M Tris-HCl [pH 7.5 at 4° C.], and 0.001 M EDTA) at 4° C. The sample was stored at −20° C.

Alternatively, the Flexi-prep kit from Pharmacia (Quebec City, Quebec) was used for small-scale plasmid preparation. This method involved a standard alkaline cell lysis, including RNase treatment and isopropanol precipitation (Birnboim and Doly, 1979; Isch-Horowicz and Burke, 1981). The plasmid DNA was purified and concentrated using a silica matrix (Sephaglas FP™) in guanidine hydrochloride.

e) Radiolabelling of DNA Probes by Random Priming

DNA fragments were labelled with [$\alpha$-$^{32}$P] dATP (3,000 Ci/mmol, ICN) using the random primer DNA labelling system of GIBCO/BRL. This labelling system is based on the method of Feinberg and Vogelstein (1983), with modifications (Feinberg and Vogelstein, 1984). The sample (25 ng of DNA in 10 µl of $H_2O$) was denatured by boiling for 5 min, then immediately cooled on ice. While still on ice, the following reagents were added: 2 µl of each of dCTP, dGTP and dTTP, 15 µl of random primer buffer, 4 µl [$\alpha$-$^{32}$P]dATP and $H_2O$ to 49 µl. The sample was mixed briefly and 3 units of Klenow Fragment was added. The reaction mixture was incubated for 1 h at 25° C. and terminated by the addition of 5 µl of stop buffer.

The radiolabelled DNA was separated from unincorporated radionucleotides by gel filtration through a mini Sephadex G-50 column. The column was prepared in a Pasteur pipette plugged with glass wool and was equilibrated with TE buffer prior to addition of the radiolabelled sample. The migration of DNA through the column was monitored using a Geiger counter (Mini-lnstruments Ltd., Essex, England). The first peak of radioactivity corresponded to the labelled DNA, while the second peak corresponded to the unincorporated [$^{32}$P]-dATP. The DNA probe was denatured by boiling for 5 min before being added to the hybridization solution.

f) Agarose Gel Electrophoresis and Southern Hybridization

Agarose gels were prepared by adding TAE buffer (40 mM Tris [pH 7.9], 1M EDTA) to electrophoresis grade agarose powder (regular or low-melting point; Sigma) to a final concentration of 0.7% to 1%. The agarose gel was electrophoresed in a horizontal flatbed gel apparatus (Tyler Research, Edmonton, Alberta).

DNA samples were mixed with ½ volume of tracking dye (50% glycerol, 0.1% ladder (Gibco/BRI), or lambda DNA (Pharmacia) digested with HindIII was used as a molecular standard. A running buffer of TAE supplemented with 1 µg/ml of ethidium bromide was used. Samples were initially electrophoresed at 100V for 5 min, then the voltage was reduced to 10–12V for overnight electrophoresis. After electrophoresis, the samples were viewed with a medium range ultraviolet transilluminator and photographed using Polaroid type 57 black and white film (Sharp et al., 1973; Hayward, 1972).

For Southern hybridization, the agarose gel was immersed in 0.25 M HCl for 15 min to depurinate the DNA. The gel was transferred to an alkaline solution consisting of 0.5 M NaOH and 1.5 M NaCl for 15 min, then neutralized in a solution of 0.5 M Tris-HCl (pH 7.5), 1.5 M NaCl for 30 min. The DNA was transferred to a nitrocellulose membrane (Schleicher and Shuell, Willowdale, Ontario) by electrophoretic transfer in a semi-dry blotting apparatus (Tyler Research) in 20×SSPE buffer (3.6 M NaCl, 0.2 M $Na_2PO_4$ [pH 7.0], 0.02 M $Na_2EDTA$, M NaOH) at a constant current of 150 mA for 30 minutes (Wahl et al., 1979; Southern, 1975).

After electrophorectic transfer, the nitrocellulose membrane was washed in 2×SSPE buffer for 10 min, and the DNA was cross-linked by a UV Cross-linker (Stratagene). The membrane was prehybridized in a sealed plastic bag containing a solution of 25% (low stringency) or 50% (high stringency) formamide (Gibco/BRL) in 0.1% glycine, 5×BFP (100×BFP contains 2% w/v bovine serum albumin, Ficoll and polyvinyl pyrrolidine-40), 5×SSPE buffer and 0.1 mg/ml sonicated, boiled salmon sperm carrier DNA. The sealed bags were placed in a 42° C. shaking waterbath where the membranes were allowed to prehybridize for at least an hour. The prehybridization buffer was then discarded and replaced with hybridization buffer (10% dextran sulphate, 5×SSPE, 5×BFP, 0.1% SDS, 0.1 mg/ml carrier DNA and 25% or 50% formarnmide) containing the boiled, radiolabelled DNA probe. The bags were placed in a 42° C. shaking waterbath where the membranes were hybridized overnight.

After hybridization, the nitrocellulose membrane was removed from the plastic bag and washed 4×10 min in either high stringency (5×SSPE, 0.1% SDS) or low stringency (2×SSPE, 0.1% SDS) wash buffer in a 42° C. shaking waterbath. The membrane was air-dried, placed on Whatman filter paper, covered with plastic wrap and exposed to X-ray film (Cronex, Willingmington, Del.) at −20° C. for 104 days until the desired exposure was obtained. The exposure time was determined by measuring the intensity of the radioactive signal using a Geiger counter. Autoradiographs were developed in Kodak GBX rapid developer (Eastman Kodak, Rochester, N.Y.) for 2 min. The developing reaction was stopped by immersing the film in 2.5% acetic acid for 1 min and fixed for 2 min in Kodak GBX fixer (Eastman Kodak).

g) Southern Colony Blot

A master template of bacterial colonies grown on LT plus ampicillin was grown overnight at 37° C. The colonies on the master plate were duplicated onto a nitrocellulose membrane overlaid on an LT plus ampicillin plate and grown for 2–3 h at 37° C. The membrane was then overlaid on Whatman filter paper soaked in a 0.5 M NaOH, 1.5 M NaCl solution and incubated at room temperature (RT) for 5 min to lyse the cells. The nitrocellulose membrane was then transferred to Whatman filter paper soaked in a 0.5 M Tris=HCl (pH 7.5), 1.5 M NaCl solution and incubated for 5 min at RT to neutralize the membrane. The membrane was transferred to Whatman filter paper soaked in 95% ethanol and sprayed with 95% ethanol to precipitate the DNA. The DNA on the membrane was cross-linked in a UV cross-linker (Stratagene), then prehybridized and hybridized as described above.

h) Polymerase Chain Reaction (PCR)

PCR reactions were carried out in thin-walled 500 µl GeneAmp microfuge tubes in a Perkin-Elmer Cetus 480 DNA Thermal Cycler, using the Perkin-Elmer Cetus PCR core reagent kit which included deoxynucleotides triphosphates, $MgCl_2$, reaction buffer and Ampli-Taq DNA polymerase (Perkin-Elmer Cetus). Amplification reactions were performed according to the method of Saiki et al. (1988), with modifications by Perkin-Elmer Cetus. PCR reactions were performed in 100 μl mixtures containing 1×reaction buffer (0.5 M KCl, 0.1 M Tris-HCl [pH 9.0]), 0.2 mM of each of dNTP, 0.4 pM primer, 5 μg of template, 15 mM $MgCl_2$ and 2.5 units of Ampli-Taq enzyme. The reaction mixture was heated at 95° C. for 2 minutes to denature the template DNA. Then 30 cycles of denaturation, annealing and extension followed with temperatures and times of 95° C. (1 min) 52° C. (1 min) and 72° C. (2 min) respectively. The fastest available transitions between temperatures (ramp time of 0.01s) were used. A negative control which did not contain template DNA was included in each PCR run.

After amplification, the PCR products were examined by agarose gel electrophoresis. PCR products were purified by electrophoretic separation through a low-melting point agarose gel followed by excision of required DNA fragments. The DNA products were purified from the agarose using a glass-bead matrix purification kit (GENECLEAN).

i) Purification of DNA Fragments from Agarose Gels

DNA fragments were purified from agarose gels using the GENECLEAN kit from Bio/Can Scientific (Mississauga, Ontario). The GENECLEAN purification process is based in the procedure by Vogelstein and Gillespie (1979). The gel slice containing the fragment was excised from the gel using a razor blade and placed in a 1.5 ml Eppendorf centrifuge tube. An equal volume of stock NaI solution was added and the sample was incubated for 5 min in a 55° C. waterbath until the agarose had completely melted.

GLASSMILK (Bio/Can Scientific) was added to the sample at a volume of 5 μl for 5 μg or less of DNA and the mixture was incubated on ice for 5 min. The silica matrix was then collected by centrifugation at 16,000×g for 10 sec and resuspended in 600 μl of NEW wash buffer (Bio/Can Scientific). The pellet was washed with NEW buffer a total of three times. After the final wash, the silica matrix was resuspended in 10 μl of TE buffer and incubated for 5 min at 55° C. The sample was then centrifuged and the TE recovered, avoiding the silica matrix pellet. Samples were stored at −20° C.

j) DNA Dideoxy Sequencing

DNA fragments were sequenced either by cloning into M13 mp18/mp19 bacteriophage vectors (single-stranded sequencing) or directly from recombinant plasmids (double-stranded sequencing) using the Pharmacia T7-sequencing kit as described by the manufacturer. The Pharmacia T7-sequencing kit procedure is based on the method outlined by Sanger et al. (1977).

For single stranded sequencing, DNA fragments were cloned into the M13 mp18/mp19 bacteriophage vector and transformed into competent $E.$ $coli$ TG-1 cells. Recombinant phage "plaques", which appeared white due to the loss of β-galactosidase production, were selected. Each plaque was inoculated into 10 ml of LT broth seeded with 0.1 ml overnight culture of $E.$ $coli$ TG-1 grown in Davis minimal medium and incubated 4–5 h at 37° C. with 75 rpm shaking. The sample was centrifuged at 12,000×g for 10 min to remove the $E.$ $coli$ cells. The phage were precipitated from the culture supernatant by the addition of ¼ volume of 20% polyethylene glycol (8,000 MW; Sigma), 2.5 M NaCl and incubated for 30 min on ice. Precipitated phage were recovered by centrifugation in a microfuge at 12,000×g for 10 min. The pellet was then resuspended in 0.6 ml of phage buffer (0.1 M Tris-HCl [pH 8.0], 0.001 M EDTA, 0.3 M NaCl).

The phage DNA was extracted with 0.5 ml of phenol (Gibco/BRL) saturated with TE buffer. The phenol and aqueous phases were separated by centrifugation at 14,000×g for 10 min. The aqueous phase was extracted with 1:1 phenol:chloroform and finally with chloroform. The phage DNA was then precipitated with 1/10 volume 3 M sodium acetate (pH 7.0) and 2 volumes of cold 95% ethanol and incubated at −20° C. overnight. Precipitated DNA was collected by centrifugation at 14,000×g for 10 min. The aqueous phase was extracted with 1:1 phenol:chloroform and finally with chloroform. The phage DNA was then precipitated with 1/10 volume 3 M sodium acetate (pH 7.0) and 2 volumes of cold 95% ethanol and incubated at −20° C. overnight. Precipitated DNA was collected by centrifugation at 14,000×g for 10 min in a 4° C. microfuge. The pellet was air-dried and resuspended in 50 μl of TE buffer and was used for sequencing. The DNA was annealed to either the universal M13 primer or specific primers in the presence of annealing buffer (Pharmacia T7 sequencing kit) by incubation at 65° C. for 10 min, then room temperature for 10 min prior to the sequencing reactions.

For double-stranded sequencing, the plasmid template was prepared using the procedure outlined in the Pharmacia T7 sequencing kit protocol, with modifications. Plasmid DNA was adjusted to 1.5–2.0 μg/32 μl and denatured by the addition of 12 μl of 2M NaOH for 1 min. Denaturation was terminated by the addition of 11 μl of 3 M sodium acetate (pH 5.0). The DNA was precipitated with 7 μl of $dH_2O$ and 120 μl of ice-cold absolute ethanol and incubated at −20° C. overnight.

The DNA was collected by centrifugation at 14,000×g in a 4° C. microfuge for 10 min. The pellet was washed with 100 μl of ice-cold 70% ethanol, centrifuged and dried under vacuum. The sample was resuspended in 5 μl of $dH_2O$ and mixed with 5 μl of primer and 2 μl of annealing buffer. The mixture was incubated at 65° C. for 5 min, 37° C. for 10 min and 5 min at RT prior to sequencing.

Either [$^{32}$P]dATP or [$^{35}$S]dATP (specific activity of 3000 Ci/mmol) were used in the sequencing reactions. For short autoradiography exposure time, [$^{32}$P]dATT was used. For superior resolution, [$^{35}$S]dATP was used. Oligonucleotide primers were synthesized on an Applied Biosystems International 391 PCR-Mate DNA synthesizer and purified according to the manufacturer's instructions. The primers were quantitated by measuring the optical density at 260 nm prior to use.

For [$^{32}$P]dATP sequencing, the sequencing gel consisted of 18 g of urea (ICN, Montreal, Quebec), 3.75 ml of 10×TBE buffer (1 M Tris [pH 8.3], 0.02 M EDTA, and 0.865 M boric acid) and 7.5 ml of 40% acrylamide (19:1 ratio of acrylamide:bisacrylamide, Bio-Rad) made up to 38 ml with $dH_2O$. The solution was stirred until the urea was dissolved and then 0.23 ml of 10% ammonium persulfate (Sigma) and 10 μl of TEMED (N, N, N'N'-Tetramethylethylenediamine; Sigma) (0.01% final concentration) were added for polymerization.

For [$^{35}$S]dATT sequencing the gel consisted of 16.8 g of urea (ICN), 4.8 ml of 10×TBE buffer and 4 ml of a modified acrylamide solution ("Long Ranger", J. T. Baker, Phillipsburg, N.J.). The solution was made up to 40 ml with $dH_2O$ and polymerized with 200 μl of ammonium persulfate (Sigma) and 20 μl of TEMED (Sigma).

The running buffer consisted of 1×TBE. The sequencing gel was run at 40 W/gel constant power for 2–6 hr. [$^{35}$S] dATP sequencing gels were transferred onto a sheet of Whatman filter paper and dried under vacuum at 80° C. for 45 min. Both types of sequencing gels were exposed to Cronex 4 X-ray film (Cronex for 18–48 h at −20° C.

IV. Protein Methods a) Isolation of Inner and Outer Membranes

Inner and outer membrane preparations were prepared from $E.$ $coli$ and $P.$ $haemolytica$ A1 by the procedure of Hancock and Carey (1979), with modifications (Lo et al., 1991). Bacteria were grown in 250 ml of the appropriate medium at 37° C. overnight. The cells were collected by centrifugation at 4,000×g, washed twice in 0.01 M Tris-HCl (pH 6.8) and resuspended in 7.5 ml of a cold Sucrose-Tris solution containing 20% sucrose, 0.01 M Tris-HCl (pH 6.8), lysozyme (1 mg/ml), DNase (50 µg/ml), and RNase (100 µg/ml). The cells were lysed by French pressure cell three times at 16,000–18,000 psi at 4° C. The sample was then centrifuged at 1,085×g for 5 min to remove unlysed cells.

The supernatant was layered onto a 70:52:sample:12% sucrose gradient which consisted of 14 ml of the 70 and 52% sucrose followed by 5 ml of the sample lysate and 4–5 ml of 12% sucrose. The gradient was centrifuged in a swinging bucket rotor at 80,000×g for 16–18 h at 4° C. The inner and outer membrane fractions were collected by aspiration. The inner membrane fraction was located between the 12% and 52% sucrose regions and had a yellowish-brown colour. The outer membrane fraction, which was white, was located near the 70% sucrose region. The collected fractions were loaded into centrifuge tubes, topped up with $dH_2O$ and centrifuged in a fixed-angle Ti80 rotor at 225,000×g for 1 h at 4° C. The pellet was then air-dried and resuspended in a Tris-HCl (pH 6.8), 0.001 M dithiothreitol buffer. Samples were stored at −20° C.

b) Bradford Determination of Protein Concentration

The protein concentrations of the inner and outer membrane fractions were determined using the method of Bradford (1976). Dilutions of each membrane fraction were prepared and $dH_2O$ was added to a final sample volume of 0.8 ml. The sample was then mixed with 0.2 ml of Bradford reagent (Biorad, Mississauga, Ontario) and incubated at room temperature for 5 min to allow colour development to occur. The optical density (OD) of each sample was measured in a spectrophotometer at a wavelength of 595 nm. A standard curve was plotted using bovine serum albumin (BSA; Sigma) in the 1–25 µg range. The protein concentration of each sample was extrapolated from the BSA standard curve.

c) Sodium Dodecyl Sulfate Polyacrylamide Gel Electrophoresis

Proteins were analyzed using sodium dodecyl sulphate polyacrylamide electrophoresis (SDS-PAGE) with 4% (w/v) stacking and 7.5% (w/v) separating gels (Laemelli, 1970). The gels were polymerized by the addition of 0.1% ammonium persulfate and TEMED to 0.01%. The samples were solubilized at 100° C. for five minutes in an equal volume of 2×sample buffer. A high molecular weight standard was also boiled and loaded onto the gel. A discontinuous buffer system was used (0.192 M glycine, 0.02 M Tris-HCl [pH 8.4], 0.1% SDS).

The gels were run at 100V until the samples entered the separating gel, when the voltage was increased to 150V. The samples were run until the dye front ran off the bottom of the gel. The stacking gel was removed and the separating gel was either stained with Coomassie Brilliant Blue or electrophoretically transferred to nitrocellulose for Western immunoblotting. Gels were stained in Coomassie Brilliant Blue R250 (0.05% in 40% methanol, 10% acetic acid) (Eastman Kodak) overnight and then destained in a methanol: acetic arid solution.

d) Western Immunoblot Analysis

The proteins on the acrylamide gel were transferred to a nitrocellulose membrane according to the method of Burnette (1981). The gel was soaked in blotting buffer (0.192 M glycine, 0.025 M Tris-Cl [pH 8.4], 20% methanol) for 10 minutes to remove the SDS. A piece of nitrocellulose membrane (Schleicher and Shuell, Willowdale, Ontario) cut to fit the gel was also soaked in blotting buffer. The proteins were transferred to the nitrocellulose membrane in a Bio-Rad Transblot apparatus at 450 mA for 3 h. A water-cooling system was used to prevent heating and breakdown of the blotting buffer.

After electrophorectic transfer, the nitrocellulose membrane was soaked in 3% gelatin in TTBS buffer (0.02 M Tris-Cl [pH 7.5], 0.5 M NaCl, 0.05% Tween-20) for 30 min to block the membrane. The nitrocellulose membrane was transferred to a 1/500 dilution of the first antibody in 1% gelatin and incubated overnight at room temperature with gentle shaking. The membrane was then washed twice in TTBS buffer (15 min per wash) and placed in the second antibody solution (1/2000 dilution) for an hour. The second antibody was goat anti-rabbit or goat anti-bovine IgG-alkaline phosphatase conjugate (Bio-Rad) in 1% gelatin. The membrane was washed twice in TTBS buffer (15 min per wash) and then twice (5 min per wash) in NBT buffer (0.1 M Tris-Cl [pH 9.5], 0.1 M NaCl, 50 mM $MgCl_2$). The membrane was then placed in the developing solution of 100 µl of each of the reagents 5-bromo-4-chloro-3-indolyl phosphate (BCIP, 25 mg/ml in dimethylformamide; Sigma) and nitro-blue-tetrazolium (NBT, 50 mg/ml in 70% dimethylformamide; Sigma). Colour development was allowed to proceed until the desired visibility of the bands was obtained. The colour reaction was stopped by rinsing the membrane in $H_2O$. The membrane was air-dried.

e) T7 Protein Expression

Proteins encoded by a recombinant plasmid were analyzed using the method of Tabor and Richardson (1985). The tbpA gene was cloned into the plasmid vector pBluescipt. The recombinant plasmid was transformed into *E. coli* JM109 (DE3), which is a strain of *E. coli* JM109 with the T7 RNA polymerase gene integrated into the chromosome and T7 polymerase gene under the control of the lac promoter (Yaninsch-Perron et al., 1985).

After transformation, the cells were grown overnight at 37° C. in Davis minimal medium containing 1.0% casamino acids, 0.4% glucose and the appropriate antibiotics. A 1/50 subculture into 20 ml of the same medium was prepared and incubated at 37° C. for an additional 3–4 h until the $OD_{550}$=0.6. The cells were collected by centrifugation at 14,000×g for 5 min and the pellet was resuspended in Davis minimal medium with 0.4% glucose. The sample was incubated for 90 min at 37° C., then 100 µl of 5 mM isopropyl-β-D-thiogalactopyranoside (IPTG) were added. After the cells were incubated at 37° C. for 20 min, rifampicin was added (final concentration of 400 µg/ml). The sample was incubated at 37° C. for 30 min and then labelled for 60 min with 5 µCi[$^{35}$S]-methionine ("Trans-Label", ICN Biomedical, Quebec). The cells were washed twice in ice-cold PBS and collected by centrifugation at 14,000×g for 5 min in a microfuge. The pellet was resuspended in 2×SDS-PAGE sample buffer.

The proteins were separated using SDS-PAGE and the gel was stained with Coomassie blue R250. The gel was then soaked in Amplify™ (Amersham, Oakville, Ontario) for 30 min and dried under vacuum. Autoradiographs were exposed 18–48 h.

RESULTS

I. Preliminary Cloning of PutativetbpA, tbpB Genes

The first stage in cloning the tbpA gene was to screen a *P. haemolytica* A1 gene library by polymerase chain reaction. An oligo primer specific for the N-terminal amino acid sequence of the Tbp1 protein was synthesized. A *P. haemolytica* A1 codon table (Lo, 1992) was used to optimize the primer sequence. The Tbp1 primer was used in conjuction with primers based on the junction sequences of the cloning vector pBR322 (Table 1) (see also SEQ. ID. NOS.22, 23, and 24). A 0.8 kbp PCR product was obtained (FIG. 1) and cloned into the M13 vector and sequenced. Sequence analysis of this PCR product demonstrated that the first twenty amino acids matched the sequence obtained by N-terminal amino acid sequencing of Tbp1.

be coordinately expressed. A Fur consensus sequence in the promoter region of tbpB suggests that the proteins may be regulated in a Fur-like manner. The Fur consensus sequence in *P. haemolytica* tbpB is similar to the consenses sequence found in *N. gonorrhoeae* and *N. meningitidis* tbpB (FIG. 4 or SEQ. ID. NOS.7, 8, and 9). The isoelectric point of Tbp1

TABLE 1

Oligonucleotide primers used in PCR.

| Primer | Primer Sequence | | Size |
|---|---|---|---|
| Tbp1 | thr-glu-asn-lys-lys-ile-glu-glu | (SEQ ID NO:68) | 32 |
| | 5'GG<u>AAGCTT</u>ACT-GAA-AAT-AAA-AAA-ATC-GAA-GAA* | (SEQ ID NO:22) | mer |
| primer left | 5' GG<u>AATTC</u>CCGTCCTGTGGATC** | (SEQ ID NO:23) | 22 mer |
| primer right | 5' GT<u>GAATTC</u>CGGCGTAGAGGATC** | (SEQ ID NO:24) | 22 mer |

*the underlined sequence is the HindIII site
**the underlined sequence is the EcoRI site The 0.8 kb PCR product was then radiolabelled and used as a specific probe to screen the *E. coli* clones containing *P. haemolytica* A1 gene library by Southern hybridization. Two recombinant clones, 9 and 10, hybridized strongly with the tbpA probe. The plasmid DNA from each recombinant clone was analyzed by restriction endonuclease mapping (FIG. 2). The insert of *P. haemolytica* A1 was determined to be approximately 8.7 kb and 2.3 kb for plasmids 9 and 10, respectively. Initial sequence analysis of the plasmids confirmed that the insert DNA from both plasmids share an overlapping region. Plasmid 9 contained the entire tbpA gene but the region directly uptstream of tbpA was different than the upstream region in plasmid 10. It is possible that the insert DNA in plasmid 9 was formed from two DNA fragments from separate regions of the genome. In plasmid 10, the region directly upstream of tbpA contained an additional open reading frame which corresponded to the tbpB gene. This plasmid, therefore, contained not only the 5' region of tbpA but also part of the tbpB gene, directly upstream from the tbpA gene.

A third recombinant clone, 482, contained the entire tbpB gene. This plasmid shares an overlapping region with plasmid 10 (FIG. 2). The insert DNA in plasmid 482 is a PCR product obtained from *P. haemolytica* A 1 genomic DNA using primers specific for the amino acid sequence of Tbp2 protein. This PCR product was then cloned into the vector PCRII.

The 3.0 kbp tbpA gene was sequenced from plasmid 9 (starting from the BglII site). The 2.1 kbp tbpB gene and the 91 bp sequence between tbpA and tbpB was sequenced from plasmids 482 and 10.

II. Sequence Analysis

The 5.2 kbp of DNA was sequenced and shown to contain two open reading frames arranged in tandem, with tbpB upstream of tbpA (FIG. 3 or SEQ. ID. NOS.5 and 6). This genetic organization is consistent with other iron uptake systems in other bacteria where the genes often arranged in an operon (Payne, 1988). Upon sequence analysis of the deduced Tbp1 protein, a putative 28 amino acid leader peptide was observed. A putative cleavage sequence for lipoproteins was observed in the deduced Tbp2 protein. The close proximity of tbpA and tbpB and the absence of a promoter region in tbpA suggests that the two proteins may and Tbp2 was calculated by PCGene (Chargpro) to be 9.16 and 9.71 respectively, making them basic proteins.

III. Predicted Protein Topology

The sequence analysis program Gene Runner (Hastings Software) was used to analyze the physical characteristics and to predict the secondary structure of the *P. haemolytica* Tbp1 and Tbp2 proteins. The hydropathy plot of Tbp1 and Tbp2 were generated using the method of Kyte and Doolittle (1982). The first 28 amino acids of Tbp1 form a hydrophobic region, which is characteristic of all signal sequences. There are six other hydrophobic regions in the protein, which may be transmembrane domains of the protein. Hydrophilic areas of the protein may be either exposed at the cell surface or in the periplasm. The hydropathy plot of *N. gonorrhoeae* was also generated. The *N. gonorrhoeae* Tbp1 protein seems to be less hydrophobic than *P. haemolytica* Tbp1 but the location of some of the hydrophobic regions are similar. For example, both proteins have hydrophobic regions around the 200, 400, and 780 amino acid residues. The similarity in hydrophobic regions suggests that the two proteins share a significant degree of homology and may have a similar structure.

The Kyte-Doolittle plot of *P. haemolytica* Tbp2 reveals several large hydrophobic regions in the centre of the protein and two smaller hydrophilic regions at each end. This is significantly different than the hydropathy plot of *N. gonorrhoeae* Tbp suggesting that the two proteins may have different structures.

Surface exposed regions of Tbp1 and Tbp2 were determined using the Emini surface probablility method (Emini et al., 1985). The peaks on the graph correspond to the regions with the highest probability of being exposed. Surface exposed regions of each protein may be involved in ligand binding and may be antigenic. The Emini plot of *P. haemolytica* Tbp1 suggests that the hydrophilic regions near amino acids 330, 410, 460, 560, 610 and 820 of the protein may be exposed at the cell surface. The Emini plot of *N. gonorrhoeae* Tbp1 showed a few common exposed regions with *P. haemolytica* Tbp1 (regions at 330, 580, 810).

The Emini plot of *P. haemolytica* Tbp2 suggests that the hydrophilic regions at amino acids 140, 160 and 620 have the greatest probability of being exposed. The Emini plot of *N. gonorrhoeae* Tbp2 shows that only the exposed regions at 160, 330 are similar to the surface regions of *P. haemolytica* Tbp2.

The secondary structure of both Tbp1 and Tbp2 were predicted using the method of Chou-Fasman (1978). The Chou-Fasman plot of P. haemolytica Tbp1 predicts that the protein is primarily a β-sheet and β-turn structure. The Chou-Fasman plot of N. gonorrhoeae Tbp1 predicts a similar structure. These predictions are consistent with other topology predictions of other iron-regulated outer membrane proteins, which are also composed of amphipathic β-sheets (Moeck et al., 1994). It is also interesting to note that the location of the β-sheets correspond to the location of the hydrophobic domains in the two Tbp1 Kyte-Doolittle graphs.

The Chou-Fasman plot of P. haemolytica Tbp2 indicates that it also consists primarily of β-Sheets and β-turns. The predicted pattern of B-sheets is different than N. gonorrhoeae Tbp2, which also has β-sheet regions. These results add to the evidence that the Tbp2 proteins have different structures.

IV. Distribution of tbpA in P. haemolytica and Related Species

Southern hybridization analysis was carried out to determine whether or not all sixteen serotypes of P. haemolytica carried the gene for the Tbp1 protein. Chromosomal DNA from each of the serotypes was disgested with restriction endonuclease and probed with the 5' end of the typA gene from P. haemolytica A1. Similar hybridization experiments were performed on digested chromosomal DNA from A. pleuropneumoniae CM% and shope 4074 and A. suis 3714.

Figure 6:
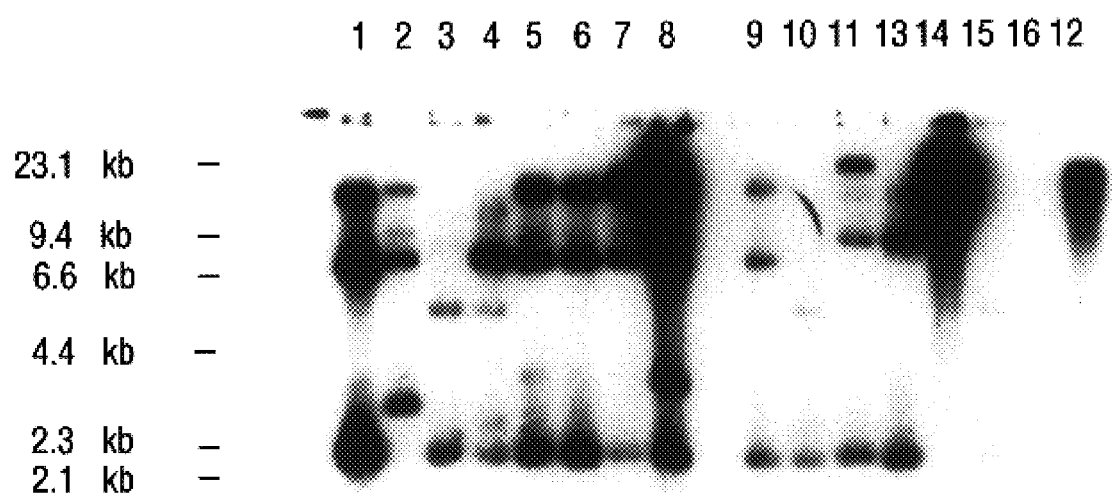
FIG. 6 is a blot of Southern hybridization of *P. haemolytica* genomic DNA digested with Hind III and BamHI and probed with the tpbA gene.

High-stringency Southern hybridization (50% formamide) with the P. haemolytica A1 tbpA probe demonstrated the presence of tbpA homologous sequences in all sixteen serotypes of P. haemolytica (FIGS. 5,6). In addition, there is a considerable difference in the size of fragments which hybridized with the probe between the A and T biotypes. It is important to note that in FIG. 5, there was a problem with the quality of the serotype 7 DNA, which did not give a reactive band with Southern hybridization. The reaction of this serotype should be identical to that of serotype 1. A similar problem is seen in FIG. 6, where serotypes 12 and 16 DNA was not properly digested. The reaction of these serotypes should be identical to that of serotype 1.

Figure 7:
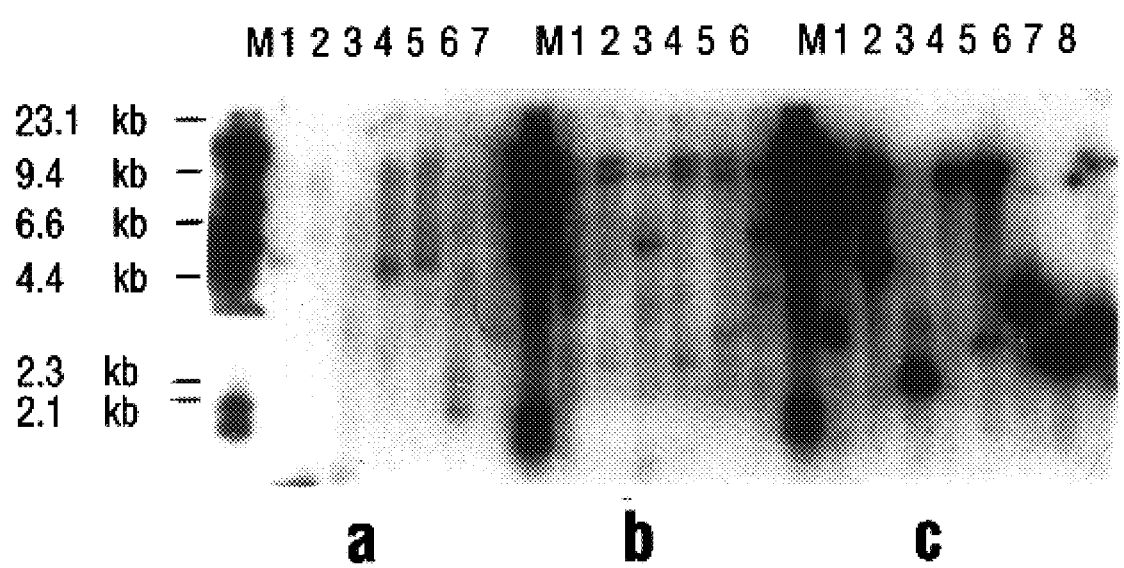
FIG. 7 is a blot of Southern hybridization of *A. suis* 37114, *A. pleuropneumoniae* CM5 and shope 4074 genomic DNA digested with various restriction endonucleases and probed with *P. haemolytica* tbpA.

Low-stringency Southern hybridization (25% formamide) with the tbpA probe indicated that A. suis 3714, A. pleuropneumoniae CM5 and Shope 4074 genomic DNA hybridized with the P. haemolytica tbpA probe (FIG. 7). The two strains of A. pleuropneumoniae both belong to serotype 1 and hybridized in the same fashion. A preliminary restriction map of the tbpA, tbpB regions in P. haemolytica A1, A. suis and A. pleuropneumoniae is shown in FIG. 8.

V. Homology Studies

The predicted amino acid sequence of P. haemolytica Tbp1 was compared with the predicted sequences for the Neisseria spp. and A. pleuropneumoniae transferrin binding proteins as well as for several E. coli TonB-dependent receptor proteins. All of the comparisons were performed according to the Higgins and Sharp algorithm (Higgins and Sharp, 1988).

The predicted amino acid sequence of P. haemolytica Tbp1 was found to have a high degree of homology with both the N. gonorrhoeae and N. meningitidis Tbp1 proteins (Cornelissen et al., 1992; Legrain et al., 1993) (FIG. 9 or SEQ. ID. NOS.10, 11, and 12). The homology, including identical and conserved amino acids, was found to be 41%.

This result agrees with the protein topology studies which suggested that the P. haemolytica and Neisseria spp. Tbp1 proteins share a similar structure. A homology comparison between P. haemolytica Tbp1 and A. pleuropneumoniae serotype 7 and serotype 1 TfbA proteins (Gerlach et al., 1992a; Gerlach et al., 1992b) reveals only a low degree (22%) of homology (FIG. 10 or SEQ. ID. NOS.13, 14, and 15). The degree of genetic relatedness among the Pasteurella, Neisseria, and Actinobacillus transferrin binding proteins is shown in the form of a dendrogram in FIG. 11. It is interesting to note that P. haemolytica Tbp1 is more closely related to Neisseria Tbp1 than to Actinobacillus transferrin binding proteins.

P. haemolytica Tbp1 also has localized regions of homology with E. coli TonB dependent outer membrane receptors (FIG. 12 or SEQ. ID. NOS.16, 17, 18, 19, and 20). Homology with these proteins implies the P. haemolytica Tbp1 is also a TonB dependent receptor protein. The first homologous domain includes the TonB box, which has been implicated in the direct interaction between TonB and the receptor protein (Bell et al., 1990). The significance of the other homologous domains is not known, however, it is possible that they are also involved in TonB interaction.

VI. T7 Expression of Tbp1

Figure 13:
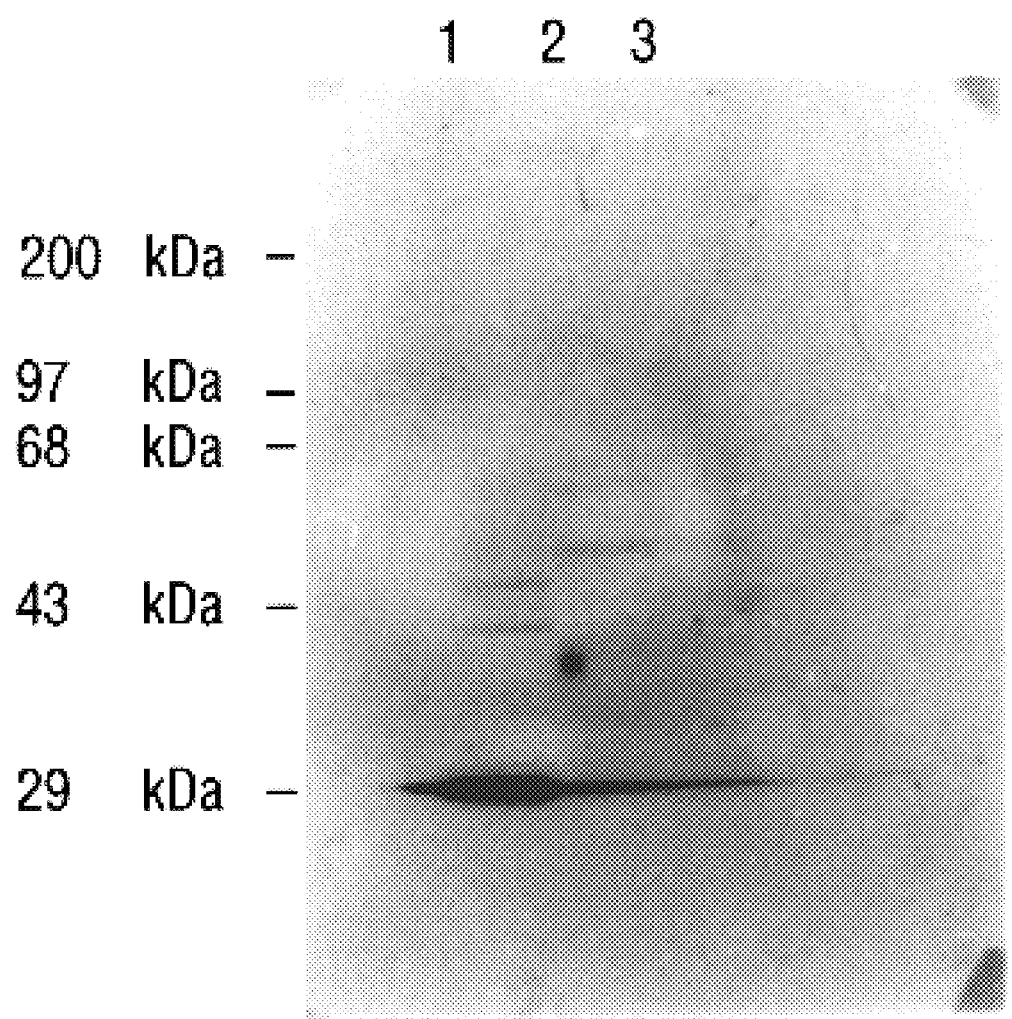
FIG. 13 is a blot showing T7 analysis of the *P.haemolytica* Tbp1 protein.

T7 expression was performed in order to express the protein encoded by tbpA (FIG. 13). An attempt to express tbpA by maxi-cell analysis of E. coli under iron-depleted and iron-repleted conditions was not successful (data not shown). The T7 expression did not produce any reactive band at 100 kDa. A 30 dDa positive control is shown in lane 1. There was no difference between the plasmid carrying tbpA and the pBluescript vector alone (FIG. 13, lanes 2 and 3).

VII. Western Immunoblot Analysis

Figure 14:
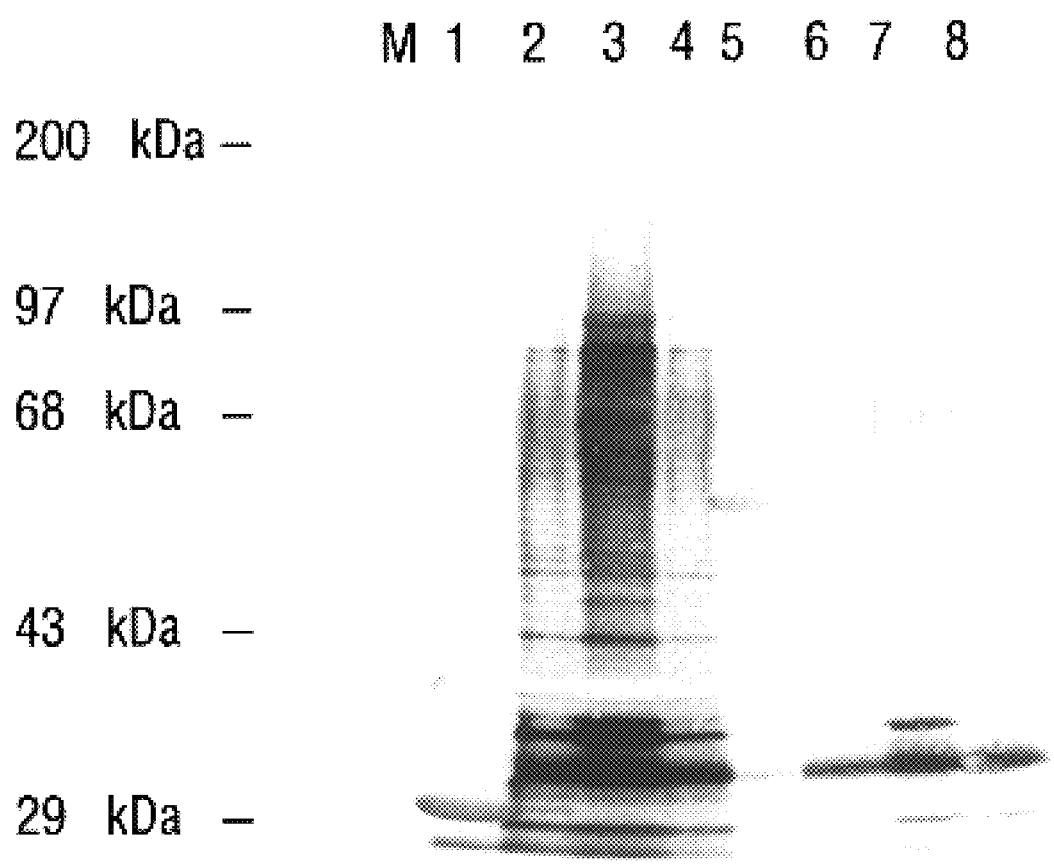
FIG. 14 is a Western immunoblot of inner and outer membranes from *P. haemolytica* A1 and *E.coli* HB101.

Inner and outer membrane fractions from P. haemolytica A1 and E. coli HB101 cells grown under iron-limiting and iron-sufficient conditions, were prepared and analyzed by Western immunoblotting. The purpose of these experiments was to determine whether or not the iron-regulated proteins would react antigenically with antiserum prepared against the soluble antigens of P. haemolytica. The inner and outer membrane fractions were immunoblotted with rabbit "anti-autologous" antiserum which was raised against the soluble antigens of P. haemolytica A1 cultured in RPMI 1640 that had been supplemented with the rabbit's own serum (to avoid inclusion of antibodies to serum proteins). The antiserum was preabsorbed with E. coli HB101 cells in order to minimize reactivity with E. coli antigens. Immunoreactive bands corresponding to the transferrin binding proteins were not observed in the outer membrane fraction from P. haemolytica A1 cells grown under iron-limiting conditions (FIG. 14, lane 3).

Figure 15:
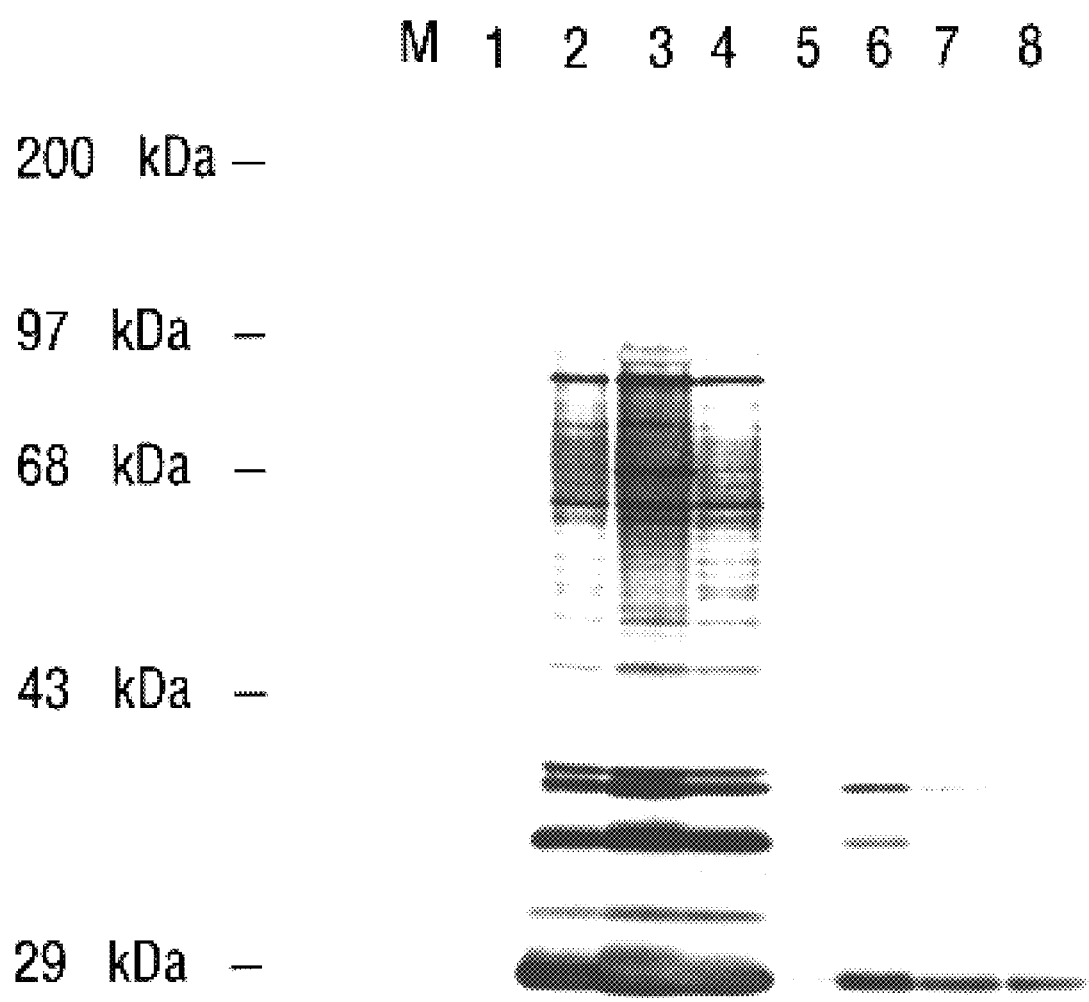
FIG. 15 is a Western immunoblot of inner and outer membranes from *P. haemolytica* A1 and *E.coli* HB101 using sera raised in calves to soluble antigens by vaccination with Presponse®.

The inner and outer membrane fractions were also immunoblotted with the serum from a calf vaccinated with Presponse® as a first antibody (FIG. 15). The antiserum was preabsorbed with E. coli HB101 cells to limit the number of E. coli immunoreactive. Bands of 71, 77 and 100 kDa were observed in the outer membranes of P. haemolytica cells which were grown under iron-limiting conditions (FIG. 15, lane 3). These protein bands correspond to the size of the P. haemolytica transferrin binding proteins. If these antigenic bands are the transferrin-binding proteins then this result suggests that these peptides are antigenic and also immunogenic in cattle.

Discussion

I. Preliminary Sequence Analysis

The preliminary nucleotide sequences of *P.haemolytica* tbpA and tbpB are shown in FIG. 3. The promoter region of *P. haemolytica* tpbB is shown in FIG. 4.

Upon preliminary sequence analysis of the cloned DNA, the two tbp genes were found in tandem with tbpB directly upstream of tbpA. This genetic organization is consistent with iron uptake systems in other bacteria such as Neisseria spp. where the genes where are arranged in an operon (Anderson at al., 1994). It is likely that the genes involved in *P. haemolytica* A1 iron uptake are also arranged in an operon. The tbpA gene has only a ribosomal binding sequence whereas the tbpB gene is preceded by a ribosomal binding site and has a Fur consensus sequence in its promoter region.

The presence of a putative Fur consensus sequence implies that the two genes could be coordinately regulated by iron concentrations and that a Fur homolog exists in *P. haemolytica* A1. Fur homologs have been cloned and sequenced in pathogenic Neisseria Spp. (Berish et al., 1993; Thomas and Sparling, 1994). If a *P. haemolytica* A1 Fur homolog exists, it may be involved in the regulation of other antigens such as the leukotoxin. Strathdee and Lo (1989) reported that under iron-limiting conditions, there was a decrease in the amount of leukotoxin produced. This is the opposite of the situation in the diptheria toxin (Boyd et al., 1990) where toxin production increases when the cells are grown under iron-limiting conditions. It is possible that Fur acts as a positive regulator in *P. haemolytica* leukotoxin production. This would be consistent with the earlier observation by Gentry et al. (1986) of increased toxin production in iron containing media. *N. meningitidis* also produces iron-regulated proteins which are related to the RTX family of exoproteins (Thompson et al., 1993).

The first 28 predicted amino acids in the tbpA sequence form a putative signal sequence. A signal sequence is essential for inserting the precursor protein into the membrane during the process of translocation across the membrane. The signal sequence also acts as a recognition site for the proteolytic cleavage of the precursor protein into its mature form (von Heijne, 1983; Benson and Silhavy, 1983). The presence of a signal sequence confirms that Tbp1 is located beyond the cytoplasmic membrane, but it does not contain any sorting information. The predicted amino acid sequence of Tbp1 has a terminal phenylalanine residue at the carboxyl-terminal of the protein. Phenylelanine is a hydrophobic aromatic amino acid which facilitates the partitioning of the hydrophobic environment in the membrane. The presence of a terminal phenylalanine residue has been shown to be important for outer membrane localization (Struve et al., 1991) and suggests that *P. haemolytica* Tbp1 is located in the outer membrane.

Sequence analysis of tbpB revealed a putative cleavage sequence for lipoproteins. Lipoproteins have a characteristic cleavage sequence of Leu-X-Y-Cys, where X and Y are small neutral amino acids (Wu, 1987). This suggests that Tbp2 is processed and lipid modified. It is interesting to note that Tbp2 lacks a terminal phenylalanine residue which is involved in outer membrane localization. Analogous transferrin binding lipoproteins have been found in *H. influenzae*, *N. gonorrohoeae* and *N. meningitidis* (Legain et al., 1993; Anderson et al., 1994) Griffiths et al. (1993) has demonstrated common antigenic domains among the Tbp2 proteins in *N. gonorrohoeae*, *N. meningitidis* and *H. influenzae* type b.

The isoelectric point (pI) of a protein is defined as the pH at which the peptide has a net charge of zero. The pI calculation assumes that there are no three-dimensional structures which interfere with the ionization states. Therefore, calculated pI values are only approximate values and may differ from experimental results. The pI of *P. haemolytica* Tbp1 and Tbp2 has been calculated to be 9.16 and 9.71, respectively. It has been suggested that cationic polypeptides enhance in vivo membrane interactions. It is possible that the basic nature of Tbp1 enhances interaction with the host transferrin proteins. The Neisserial Tbp1 (Cornelissen et al., 1992) and Fbp (Berish et al., 1990) proteins are also basic proteins. In Legionella pneumophilia, basic surface proteins act to inhibit phagolysosomal fusion (Cianociotto et al., 1989).

II. Preliminary Predicted Protein Topology

The hydropathy plots of Tbp1 and Tbp2 were generated using the method of Kyte and Doolittle (1982). In the hydropathy plot of *P. haemolytica* Tbp1, the first peak is located from the amino acids 1 to 30. This represents the hydrophobic core which is common to all signal sequences (Hayashi and Wu, 1990). The other hydrophobic regions may be transmembrane domains. Hydrophilic domains may be regions of the protein which are exposed to either the cell surface or to the periplasm. The location of the transmembrane regions in the *P. haemolytica* Tbp1 protein is similar to many transmembrane regions predicted in *N. gonorrhoeae* Tbp1. This suggests that the Tbp1 proteins may have a similar structure and that they share a certain degree of homology at the amino acid level. The *P. haemolytica* Tbp2 protein possesses a hydrophobic leader sequence as well as several large hydrophobic regions in the centre of the protein and it is significantly different than the hydropathy plot predicted for *N. gonorrhoeae* Tbp2. This implies that both proteins are structurally different.

Surface exposed regions of Tbp1 and Tbp2 were predicted using the Emini surface probability method. Regions of Tbp1 and Tbp2 which are exposed to the cell surface may be involved in ligand interaction and may be antigenic.

The Chou-Fasman method is commonly used in predicting the secondary structure of a protein. This method is based on the tendency each amino acid has for being in an α-helix, a β-sheet or a β-turn. The Chou-Fasman method predicts that *P. haemolytica* Tbp1 consists of many β-sheets and β-turns. It is possible that these β-sheets cross the outer membrane repeatedly and that the intervening sequences constitute surface or periplasm exposed loops. The Chou-Fasman method also predicts that *N. gonorrhoeae* Tbp1 also consists of β-sheets. This structure has already been proposed for *E. coli* outer membrane proteins such as FepA (Moeck et al., 1994). *P. haemolytica* and *N. gonorrhoeae* Tbp1 proteins share a common structure which implies that they may also have a similar mechanism of removing iron from the host transferrin molecule. The Chou-Fasman plot of *P. haemolytica* Tbp2 also predicts a predominantly β-sheet and β-turn structure which is significantly different than the prediction for *N. gonorrhoeae* Tbp2.

III. Distribution of tbpA in *P. haeinolytica* and Related Species

Southern hybridization of the genomic DNA of the sixteen *P. haemolytica* serotypes with the tbpA probe demonstrated that a highly homologous gene is present within the A biotype. The results also suggest that the genetic organization or the tbpA gene is significantly different in the T biotypes. This supports the observations by Murray et al. (1992) who demonstrated that iron-regulated proteins from the A and T biotypes were antigenically distinct. Previous work on *P. haemolytica* antigenic determinants demonstrated that the sialoglycoprotease, the serotype specific antigen, three lipoproteins and a LPS biosynthetic gene were either missing or had a different genetic organization in the T biotype (Burrows, PhD thesis, 1993). The A and T biotypes do share phenotypic and biochemical traits (Holt, 1977), but they are only distantly related based on DNA:DNA hybridization (Bingham et al., 1990). Sneath and Stevens (1990) proposed that the biotype T serotypes be renamed as the species *P. trehalosi.*

Diversity in the genetic organization of transferrin binding proteins has also been demonstrated in *A. pleuropneumoniae* TfbA (Gonzalez et al., 1990; Gerlach et al., 1992b) and *N. meningitidis* Tbp2 (Legrain et al., 1993; Rokbi, 1993). In *A. pleuropnuemoniae*, serotype 1 and serotype 7 TfbA proteins share only 55% homology at the amino acid level (Gerlach et al., 1992b). *N. meningitidis* Tbp2 proteins are divided into two classes based on their molecular weight, sequence similarity and antigenic heterogeneity (Robki et al., 1993). The diversity in transferrin binding proteins within a species may facilitate the binding of different serotypes to avoid the host immune response against heterologous strains (Gerlach et al., 1992b).

Southern hybridization experiments demonstrated that chromosomal DNA from *A. pleuropneumoniae* strains CM5 and Shope 4074 hybridized with the tbpA probe only under low-stringency conditions. This suggests that *P. haemolytica* and *A. pleuropneumoniae* transferrin binding proteins share only a low degree of homology. This result was confirmed by homology studies on the amino acid sequence from both *P. haemolytica* Tbp1 and *A. pleuropneumoniae* TfbA proteins.

The *A. suis* genomic DNA also hybridized with the tbpA probe, which suggests that it may have an analogous transferrin binding protein. The results also suggest that *A. suis* transferrin binding proteins may be more closely related to the Tbp1 and *P. haemolytica* than to *A. pleuropneumoniae* TfbA.

IV. Homology Studies

All of the protein sequences were aligned by PCGene (Clustal), which compares sequences according to the method of Higgins and Sharp (1988). The first step in this method is to calculate all pairwise sequences similarities. A dendrogram is then generated from the similarity matrix generated in the first step. The dendrogram in FIG. 11 was generated by a Higgins and Sharp alignment of the Pasteurella, Actinobacillus, and Neisseria transferrin binding proteins.
a) Neisseria spp.

The predicted amino acid sequence of *P. haemolytica* tbpA has regions of homology with the predicted amino acid sequence of tbpA in *N. gonorrhoeae*. This suggests that the transferrin binding proteins are structurally similar and agrees with the observations made in the protein topology studies. Ogunnariwo and Schryvers (1990) reported that *P. haemolytica* A1 Tbp1 was similar to *N. gonorrhoeae* Tbp1 proteins in size and properties. Both species produce 100 kDa receptor proteins which cannot bind transferrin after SDS-PAGE, which suggests that the conformation of the native protein is important in transferrin binding. However, the two proteins differ in their binding specificities: *N. gonorrhoeae* Tbp1 bound only human transferrin whereas *P. haemolytica* A1 Tbp1 bound only bovine transferrin. This suggests that differences between the two tbpA sequences may be regions which encode for specificity of iron source.
b) *A. pleuropnuemoniae*

The predicted amino acid sequence of *P. haemolytica* A1 Tbp1 has a low degree of homology with the sequence of *A. pleuropneumoniae* TfbA. This result is confirmed by the Southern hybridization experiments, which demonstrated that chromosomal DNA from *A. pleuropneumoniae* strains CM% and Shope 4074 hybridized with the tbpA probe only under low-stringency conditions. This is interesting because both bacteria belong to the family Pasteurella and would therefore be expected to have a similar transferrin binding protein. Previous work has suggested that the two proteins are functionally similar but structurally different. The TfbA protein in *A. pleuropneumoniae* has been shown to be a lipoprotein (Gonzalez et al., 1990), whereas the 100 kDa *P. haemolytica* A1 Tbp1 is not (Ogunnariwo and Schryvers, 1990). *A. pleuropneumoniae* is able to distinguish between iron-saturated and iron-depleted transferrin) (Gerlach et al., 1992a), whereas *N. meningitidis* cannot (Tsai et al., 1988). It is interesting to note that *A. pleuropneumoniae* TfbA has homology with *N. gonorrhoeae* Tbp2, which is also a lipoprotein. This suggests that the TfbA protein is analogous to Tbp2, and that Tbp1 of *A. pleuropneumoniae* has not yet been identified.
c) TonB Dependent-receptor Proteins The *P. haemolytica* Tbp1 sequence also has amino acids which are common to a group of *E. coli* TonB dependent receptor proteins. This finding suggests that *P. haemolytica* A1 belongs to this family and that a TonB homolog exists in Pasteurella species. The first homologous domain or "TonB box" has been implicated in direct interaction between the receptor protein and TonB (Bell et al., 1990, Brewer et al., 1990). The significance of the other homologous regions is not known, but they may be required for TonB interaction or may be necessary for outer membrane localization. *P. haemolytica* Tbp1, like many other TonB-dependent proteins, is a transmembrane protein which is iron-regulated and involved in iron utilization (Mietzner and Morse, 1994). It is possible that *P. haemolytica* Tbp1 functions as a gated channel as has been proposed for *E. coli* FepA (Rutz et al., 1992). Tbp1 from both *N. gonorrhoeae* (Cornelissen et al., 1992), and *H. influenzae* Garosik et al., 1994) also belong to the family of TonB-dependent receptor proteins.

V. Proposed Model for *P. haemolytica* Iron Uptake

The existence of many analogous proteins in Neisseria, Pasteurella and Haemophilus suggests that a common mechanism may be utilized for iron acquisition. A hypothetical model of iron acquisition has been proposed for Neisseria (Chen et al., 1993) which may be used as a model for *P. haemolytica* A1. Iron deprivation activates transcription of the iron-regulated proteins by a Fur-like regulatory system. Host transferrin binds to the bacterial cell surface via a specific iron receptor complex composed of two or more proteins. The iron is removed from the transferrin and transported across the outer membrane of the bacterium with the energy provided by TonB. In the periplasm, the iron is transiently complexed to a periplasmic component, Fbp, which transports it to a cytoplasmic membrane permease. The iron is transported across the cytoplasmic membrane by a periplasmic binding protein transport system. In the cytoplasmic the iron is reduced to $Fe^{2+}$ and assimilated by the cell.

One feature which may be unique to *P.haemolytica* A1 iron uptake is the presence of a third iron-regulated outer membrane protein (71 kDa) which may form part of the receptor complex (Ogunnariwo and Sryvers, 1990). In addition, *P. hemolytica* does not have a receptor protein which is capable of binding transferrin after SDS-PAGE and electroblotting, while *N. gonorrhoea* does (Schryvers and Morris, 1988). This suggests that the binding mechanism of *P. haemolytica* receptor complex may be slightly different than the receptor complex in *N. gonorrhoea*.

Proteins which are similar to *N. gonorrhoea* Fbp have been identified in the family Pasteurellacease. In *H. influenzae*, a 40 kDa periplasmic protein was identified and its N-terminal sequence was found to be 81% homologous to *N. gonorrhoea* Fbp (Harkness et al., 1992). In *P. haemolytica* A3, 35 kDa periplasmic iron-regulated protein has been described but no function has been found (Lainson et al., 1990). In addition, a 37 kDa iron regulated protein has been isolated by affinity procedure from *P. haemolytica* A1 (Ogunnariwo and Schryvers, 1990). Based on size and location similarities, it is possible that both of these proteins are analogous to *N. gonorrhoea* Fbp.

VI. T7 Protein Expression

T7 RNA polymerase-dependent production of a Tbp1 gene product in *E.coli* JM109 (DE3) was not successful (FIG. 13). One possible explanation may be that the ribosomal binding site of tbpA was inefficient. The gene could perhaps be cloned into a vector that carries a functional ribosome-binding site. Alternatively, the Tbp1 protein may be unstable and requires the presence of other proteins or factors in order to be correctly produced. Components of heterodimeric proteins are often unstable when they are synthesized singly.

VII. Western Immunoblot Analysis

Western immunoblots were performed on the inner and outer membrane fractions from *P. haemolytica* A1 cells which were grown under iron-sufficient or iron-limiting conditions (FIGS. 14 and 15). The iron-limiting conditions were simulated by adding the iron chelator EDDA, which is a common synthetic iron chelator used to limit the availability of iron in culture media. EDDA was chosen for these studies because of its specificity for iron and its lack of toxic side effects to bacteria (Neilands, 1981).

*P. haemolytica* A1 membrane fractions immunostained with rabbit antiserum to soluble antigens did not react with the iron-regulated proteins (FIG. 14). Neither the 100 kDa nor the 77 kDa iron-regulated proteins were observe in this immunoblot, possibly because the original *P. haemolytica* A1 culture (used in the hyperimmunization of the rabbit) was not grown under iron-restricted conditions. The medium used contained 7% serum to avoid the inclusion of antibodies of serum proteins. In contrast, peptides which may be the iron-regulated proteins reacted with antisea from calves vaccinated with the Presponse® (FIG. 15). Presponse® is produced from *P. haemolytica* A 1 cells which are grown to late log phase in serum-free RPMI medium 1640 (Shewen and Wilkie, 1987; Shewen et al., 1988). It is possible that the low iron concentration of this medium induced production of the transferrin binding proteins. It is also possible that the calf responded to transferrin binding proteins produced by *P. haemolytica* which are commensal organisms in the nasopharynx. The presence of antibodies to transferrin binding proteins suggests that these proteins are immunogenic.

Example 2

Bacterial strains. The bacterial strains used in this study are listed in Table 2. *P. haemolytica* strains h173, h174, h175 and h176 were field isolates from ruminants with pneumonic pasteurellosis and were provided by Dr. Frank Milward, Rhone Merieux, Lyon, France. *P. haemolytica* strains h44–h46 were bovine clinical type A1 isolates from bovine pneumonia obtained from S. Lundberg Veterinary Laboratory, Regional Agricultural Building, Airdrie, Alberta. h44 has been described previously (26). *P. haemolytica* strains h93–h97 were bovine clinical type A1 isolates from bovine pneumonia obtained from by Dr. A. Potter of the Veterinary and Infectious Diseases Organization (VIDO), Saskatoon. Strains h98–h107 are ATCC *P. haemolytica* strains (5) also obtained from Dr. A. Potter. *Actinobacillus* (Haemophilus) *equuli* strain h50 was obtained from Dr. Jane Pritchard, Veterinary Laboratory, Regional Agricultural Building, Airdrie, Alberta. new species, *P. trehalosi* (34).

TABLE 2

List of strains included in this study.

| Species | Strain | Serotype | Host Species | Source |
|---|---|---|---|---|
| P. haemolytica | h44 | A1 | cattle | S. Lunberg, Airdrie |
| P. haemolytica | h45 | A1 | cattle | S. Lunberg, Airdrie |
| P. haemolytica | h46 | A1 | cattle | S. Lunberg, Airdrie |
| P. haemolytica | h93 (ph21) | A1 | cattle | A. Potter, VIDO |
| P. haemolytica | h94 (ph24) | A1 | cattle | A. Potter, VIDO |
| P. haemolytica | h95 (ph27) | A1 | cattle | A. Potter, VIDO |
| P. haemolytica | h96 (ph45) | A1 | cattle | A. Potter, VIDO |
| P. haemolytica | h97 (ph46) | A1 | cattle | A. Potter, VIDO |
| P. haemolytica | h196 | A1 | cattle | R. Lo, U. of Guelph |
| P. haemolytica | h98 (ATCC33366) | A2 | sheep | A. Potter, VIDO |
| P. haemolytica* | h99 (ATCC33367) | T3 | sheep | A. Potter, VIDO |
| P. haemolytica* | h100 (ATCC33368) | T4 | sheep | A. Potter, VIDO |
| P. haemolytica | h101 (ATCC33370) | A6 | sheep | A. Potter, VIDO |
| P. haemolytica | h102 (ATCC33371) | A7 | sheep | A. Potter, VIDO |
| P. haemolytica | h103 (ATCC33372) | A8 | sheep | A. Potter, VIDO |
| P. haemolytica | h104 (ATCC33373) | A9 | sheep | A. Potter, VIDO |
| P. haemolytica | h105 (ATCC33369) | A5 | sheep | A. Potter, VIDO |
| P. haemolytica* | h106 (ATCC33374) | T10 | sheep | A. Potter, VIDO |
| P. haemolytica | h107 (ATCC33375) | A11 | goat | A. Potter, VIDO |
| P. haemolytica | h173 (77020-15184) | Untypable | goat | F. Milward, Rhone Merieux |
| P. haemolytica | h174 (90020-16266) | A7 | goat | F. Milward, Rhone Merieux |
| P. haemolytica | h175 (84020-15786) | A7 | sheep | F. Milward, Rhone Merieux |
| P. haemolytica | h176 (84020-15792) | A9 | sheep | F. Milward, Rhone Merieux |
| A. equuli | h50 | | horse | J. Pritchard, Airdrie |

*T-type strains are now considered as a new species, *P. trehalosi* (34).

Growth conditions. All bacterial strains were stored frozen at −70° C. in 30% glycerol. Isolates from the frozen stocks were streaked onto chocolate agar plates and incubated at 37° C. in a 5% $CO_2$ incubator. Iron-restricted growth was achieved by growing the bacteria in Brain Heart Infusion broth (BH1, Difco Laboratories) or O'Reilly Niven broth (25) supplemented with 2 $\mu$g/ml thiamine monophosphate and 3 $\mu$g/ml nicotinamide adenine dinucleotide (NAD) and containing the iron chelator ethylenediaminedihydroxyphenylacetic acid (EDDHA, Sigma) at a final concentration of 100 $\mu$M. Growth experiments for use of different transferrins as iron source was performed as previously described (26).

Preparation of transferins and derivatives. Bovine transferrin was obtained from Sigma. The preparation of equine (horse), ovine (sheep) and caprine (goat) transferrins (2), the iron loading of transferrins to 30% or 100% saturation (22) and conjugation of horse-radish peroxidase (HRP) to transferrin (37) was essentially as described previously. In the preparation of conjugates of bovine, ovine, caprine and equine transferrins (HRP-bTf, HRP-oTf, HRP-cTf and HRP-eTf), the mixture of HRP and transferrin were subjected to gel filtration after chemical conjugation. The fractions demonstrating maximal activity were pooled, dialyzed and aliquots frozen and stored at −70° C.

Solid-phase binding assays. The solid phase binding assay was essentially derived from methods described previously (32). Aliquots of intact cell suspensions or crude total membrane preparations were spotted onto nitrocellulose/cellulose acetate membranes (HA paper, Millipore Corporation, Bedford, Mass.) and after drying the HA paper was blocked with buffer containing 0.5% skim milk (blocking solution). For the transferrin binding assay, the paper was exposed to blocking solution containing 450 ng/ml of the HRP-conjugated transferrin, washed and developed with HRP substrate mixture essentially as previously described (32). For assessment of binding of anti-receptor antibody by intact cells a similar procedure was utilized except that the first binding solution contained a $1/1,000$ dilution of the anti-TbpA and anti-TbpB antisera and, after washing, the membrane was exposed to a second binding solution containing a $1/3,000$ dilution of a HRP-conjugated goat anti-rabbit antibody preparation.

Affinity isolation of transferrin binding proteins (TbpA and TbpB). Bovine, ovine, caprine and equine transferrins were individually coupled to CNBr-activated Sepharose 4B according to the manufacturers instructions using solutions containing 3.5 mg/ml of iron-saturated transferrin. Activated groups were blocked by addition of ethanolamine. Non-coupled transferrin was removed by washing with 10 to 20 column volumes of a 50 mM TrisHCl, 1 M NaCl, pH 8.0 buffer containing 6.0 M guanidine hydrochloride and after further washing the bound transferrin was reloaded with iron using a solution containing 5 $\mu$g/ml $FeCl_3$ in 0.1 M sodium citrate/0.1 M $NaHCO_3$ pH 8.6 buffer.

Iron-deficient total membrane (200 mg protein) from *P. haemolytica* or *A. equuli* prepared as previously described (32) was diluted to 2 mg/mi in 50 mM Tris pH 8.0 containing 1.0 M NaCl. The diluted membrane was solubilized by addition of EDTA and sarkosyl to a final concentration of 10 mM and 0.75%, respectively followed by incubation of the mixture at room temperature for 15–30 min with gentle rocking. The solution was centrifuged at 10,000 rpm for 10 min to remove insoluble debris. The supernatant containing the solubilized membrane was applied to a 1.5×10 cm transferrin-affinity column and then washed extensively (at least 10 bed volumes) with 50 mM Tris pH 8.0 containing 1.0 M NaCl, 10 mM EDTA, 0.75% Sarksosyl to remove non-specifically bound protein. In experiments using low salt washing conditions the washing buffer contained 100 mM NaCl in lieu of 1M NaCl. In some instances, additional washing with 2–3 bed volumes of washing buffer containing 0.2 M guanidine hydrochloride was necessary to remove contaminating proteins.

Coelution of both transferrin binding proteins (TbpA and TbpB) was achieved by application of 2–3 bed volumes of 2.0 M guanidine hydrochloride in 50 mM Tris pH 8.0, containing 1.0 M NaCl, 1 mM EDTA, 0.01% sarkosyl. The eluant was collected for immediate dialysis against 50 mM Tris pH 8.0. Further treatment with higher concentrations of guanidine hydrochloride usually did not result in any further yield of receptor protein. Individual isolation of TbpA and TbpB was attained by sequential elution with 2 bed-volumes of each buffer containing 0.2, 0.5, 0.75, 1.0, 1.5, 2.0 and 3.0 guanidine hydrochloride, respectively. The eluates were dialyzed against 3 changes of 3 litres 50 mM Tris pH 8.0 over an 18-hour period and concentrated by ultrafiltration. After SDS-PAGE analysis the fractions from the 0.5 and 0.75 M guanidine HCl elution buffers were pooled for a preparation of TbpB and fractions from the 1.5 and 2 M guanidine HCl elution buffers were pooled for a preparation of TbpA.

Analytical methods. Protein samples were analyzed by SDS-PAGE followed by silver staining as previously described (32). For Western blot analysis, about 1–2.m of purified receptor proteins or 40.m of outermembrane protein from iron-poor cells were separated on 10% polyacrylamide gels. Proteins were electrophoretically transferred to nitrocellulose (Millipore, Bedford, Mass.) overnight at 15V in 20 mM Tris, pH 7.5, 150 mM glycine, 20% methanol and 0.1% SDS. The filters were blocked with 0.5% skim milk in 20 mM Tris pH 7.5, 500 mM NaCl (TBS) for 30 minutes at room temperature. A $1/300$ dilution of the appropriate antibody in the blocking solution was applied to the paper for 1 hour at room temperature followed by two, 10-minute washes each with TBS. A $1/3000$ dilution of secondary antibody (goat anti-rabbit IgG-horse-radish peroxidase conjugate from BioRad) was allowed to bind for 1 hour at room temperature. The conjugate was removed by three, 10-minute washes in TBS and developed using the HRP-substrate mixture.

Comparison of Receptor Specificity

Prior studies had demonstrated differences in specificities towards different ruminant transferrins (i.e. cattle, sheep and goat) by transferrin receptors from various pathogenic bacterial species of ruminants (38). This probably reflects differences in the regions of the receptor proteins involved in ligand binding and thus suggests that these regions could not serve as the basis of a broad-spectrum transferrin receptor-based vaccine for ruminant pathogens. However, it does not preclude the possibility that a group of related ruminant pathogens, such as the various Pasteurella species, may have common ligand binding domains that could provide the basis for generation of a cross-protective response. Thus it was important to determine whether the transferrin receptors from a collection of representative Pasteurella isolates possessed the same specificity for ruminant pathogens.

As a preliminary analysis of receptor specificity, a collection of representative isolates were assessed for their ability to utilize various ruminant transferrins as a source of iron for growth (Table 2). A simple plate assay described in the methods section was utilized. The growth of all the representative ruminant isolates of *Pasteurella haemolytica* and *P. trehalosi* was stimulated by Fe-saturated transferrins from ruminant (bovine, caprine and ovine) but not from non-ruminant (equine) hosts. The stimulation of the growth of the equine pathogen, *Actinobacillus equuli* (strain h50), by equine transferrin indicated that the inability of the

*P. haemolytica* strains to use equine transferrin as iron source was not due to deficiencies in the preparation.

TABLE 3

Growth on different transferrins.

| Species | Strain | Serotype | Host | bTf | oTf | cTf | eTf |
|---|---|---|---|---|---|---|---|
| P. haemolytica | h44 | A1 | cattle | + | + | + | − |
| P. haemolytica | h173 | Untypable | goat | + | + | + | − |
| P. haemolytica | h174 | A7 | goat | + | + | + | − |
| P. haemolytica | h175 | A7 | sheep | + | + | + | − |
| P. haemolytica | h176 | A9 | sheep | + | + | + | − |
| P. haemolytica | h106 | T10 | sheep | + | + | + | − |
| A. equuli | h50 | | horse | − | − | − | + |

As a further assessment of the receptor specificity, binding of transferrin by intact cells or isolated membranes was assessed by a simple binding assay utilizing horse-radish peroxidase (HRP) conjugates of transferrin. Conjugates were prepared from bovine, ovine and caprine transferrin and then tested for their ability to bind to total membranes isolated from iron-deficient cells of several representative strains of *P. haemolytica* and *P. trehalosi*. The results illustrate that all the selected strains were capable of binding the three ruminant transferrins (bovine, caprine and ovine) but not equine transferrin (FIG. 16), which is consistent with the results of the growth studies (Table 3). To confirm that the observed binding by all three ruminant transferrins was due to the same receptor in the selected species, competitive binding assays were performed in which the ability of unlabelled ruminant transferrins were tested for their ability to block binding of the labelled transferrins. In these experiments reciprocal inhibition by the various ruminant transferrins was equally effective, indicating that they bound to the same receptor with similar affinities (data not shown).

The results of the growth and binding studies suggested that bovine, ovine and caprine transferrins were capable of interacting with the receptor components involved in iron acquisition in *P. haemolytica*. The affinity procedures described in the methods section were used to identify the proteins interacting with the ruminant transferrins by employing bovine, caprine or ovine transferrin-sepharose resins. As illustrated in FIG. 17, a predominant receptor protein of approximately 100,000 molecular weight was isolated with membrane preparations from the bovine isolate (h44), the caprine isolate (h173) or the ovine isolate (h175) when either bovine (lanes A and B), ovine (lane C) or caprine (lane D) transferrin affinity columns were used. This protein is analogous to receptor proteins of similar size that are found in other bacterial pathogens (18,27,30,31), which have conventionally been termed transferrin binding protein 1 (Tbp1). An alternate name, TbpA has been recommended (21)to be consistent with existing conventions of nomenclature.

A second protein of approximately 60,000 molecular weight was also evident in the samples isolated by affinity chromatography with the ruminant transferrins (lanes B, C and D) using membranes from the bovine isolate (h44). This protein is comparable to the lower molecular weight receptor protein, transferrin binding protein 2 (Tbp2), isolated from other pathogenic bacterial species (18,27,30,31). For reasons alluded to above, the alternate name, TbpB, has been recommended (21). A protein of this molecular weight is also detectable in most samples obtained with the caprine (h173) and ovine (h175) isolates but the presence and yield of this component was sensitive to the conditions of isolation. The characteristically low yield of TbpB (Tbp2) relative to TbpA (Tbp1) observed in these species is not a general property of the bacterial receptor proteins and may even reflect common properties of TbpB from related species.

Neither of the proteins were isolated when equine transferrin-Sepharose was used in the affinity isolation procedure (lane E) indicating that their isolation was specifically due to the presence of ruminant transferrin. When less stringent washing conditions were used during the affinity isolation procedure, additional proteins of approximately 38,000 and 70,000 molecular weight were retained by the affinity column (lane A) when membranes from the bovine (h44), caprine (h173) or ovine (h175) isolate were used. An additional protein of approximately 77,000 molecular weight was also evident in the sample obtained with membranes from the bovine isolate.

Comparison of the Immunological Properties of the Receptor Proteins

The observation that bovine, caprine and ovine transferrins compete for the saine receptors suggested that there is conservation at least in the binding domain of the receptors. In order to determine whether there was also a similarity with respect to presence of common immunological epitopes, antisera were prepared against purified receptor proteins from one strain to evaluate their crossreactivity with receptor proteins from other isolates. Affinity purified preparations of TbpA and TbpB were obtained from strain h44 (see methods section) and used for generation of monospecific antisera in rabbits. These antisera were then tested against receptor proteins isolated from representative strains of different serotypes including isolates obtained from cattle, sheep and goats. The results in FIG. 18, Panel A demonstrate that the anti-TbpB antisera reacted strongly with a protein of approximately 60,000 molecular weight (TbpB) that was affinity isolated with bTf-Sepharose from all of the representative strains. Similarly, the anti-TbpA antisera crossreacted with TbpA isolated from all seven representative strains (FIG. 18, Panel B). Extension of this analysis to the additional serotypes of ruminant isolates (Table 2) continued to show considerable cross-reactivity with both receptor proteins (data not shown). These data suggest that both receptor proteins are conserved amongst the different serotypes of *P. haemolytica* causing pneumonic pasteurellosis in cattle, sheep and goats.

Although the immunological cross-reactivity illustrated in FIG. 18 indicates that there are conserved epitopes in receptor proteins from different species, there is no indication whether any of these epitopes are exposed at the bacterial surface, where they could serve as effective targets for the host immune effector mechanisms. In order to address this issue, a solid-phase binding assay was used to assess the binding of antireceptor antibodies by intact cells. This assay demonstrated that there was strong binding by cells grown under iron-deficient, but not iron-sufficient conditions, when a selection of bovine type A1 isolates were tested (data not shown). When a selection of sheep isolates of varying serotypes were tested, there was a variable degree of reactivity (FIG. 19). Other serotypes of type A *P.haemolytica* strains (h98 and h105, FIG. 19) showed considerable reactivity against the anti-TbpA and anti-TbpB antisera. In contrast, the T-type strains (*P. trehalosi*, h99, h100 and h106) showed only very weak reactivity against both of the anti-receptor antisera. However, the fact that there was also weak binding by labelled bTf indicates that there was limited production of receptor proteins under the iron-deficient growth conditions used in this experiment.

Thus the lack of reactivity of the anti-receptor antisera cannot be attributed to a lack of surface-exposed, cross-reactive epitopes in the receptor proteins from these species.

Example 3

Cloning of the Transferrin Receptor Genes from a Type A1 Strain

The following materials and methods were used in the studies described in the example:

Materials and Methods

Bacterial, plasmids, phages and culture conditions. *P.haemolytica* and *E.coli* strains were from the inventors' laboratory collections. The plasmid clone bank of *P. haemolytica* A1 DNA in pBR322 has been described (Lo et al., 1985). The 1 clone bank containing *P. haemolytica* A1 DNA was obtained from G.Weinstock. *P. haemolytica* A1 strain H196 was from the Veterinary Infectious Diseases Organization (VIDO, Saskatoon, Saskatchewan, Canada). All bacterial strains were stored frozen at −70° C. in 30% glycerol. Isolates from the frozen stocks were streaked onto chocolate (*P. haemolytica*) or Luria-Bertani plus antibiotic (*E. coli*) agar plates and incubated at 37° C. in a 5% $CO_2$ incubator.

PCR amplification. The primers for PCR were synthesized in an Applied Biosystems Model 390E Synthesizer and purified according to manufacturer's instructions. PCR was carried out in thin-walled 500 ml tube in a Perkin-Elmer Cetus 480 Thermal Cycler using the PCR coreagents and Taq DNA polymerase as recommended. The PCR conditions consist of 95° C. for 2 min., followed by 30 cycles of denaturation, annealing and extension at 95°C. (1 min.), 52° C. (1 min.) and 72° C. (2min.) respectively. A negative control which did not contain template DNA was included in each PCR run.

Mapping of tbp region in the genome. Genomic DNA from *P. haemolytica* A1 were digested with a number of restriction enzymes, separated by agarose gel electrophoresis, blotted onto nitrocellulose membrane and hybridized with DNA probes specific for the different regions of tbpA or tbpB as described. The restriction maps were compared with that obtained from the recombinant plasmids as well as the sequenced regions to verify the correct positions of the tbp genes.

Preparation of transferrins and derivatives. Bovine transferrin (bTf) was obtained from Sigma. The apo-form of bTf was produced following a procedure described elsewhere (Mazurier and Spik, 1980). Briefly, bTf was dissolved to a concentration of 0.5–1.0% in 0.1 M Na acetate, 0.1 M Na phosphate, 25 mM EDTA, and adjusted to (pH 5.5) by adding drops of concentrated glacial acetic acid. The solution was equilibrated overnight at 4° C., and the iron removed using an acrylamide gel column equilibrated with the Na acetate/Na phosphate low pH buffer. The low pH buffer was exchanged using a acrylamide gel column equilibrated with 50 mM Tris-HCl (pH 7.5). Finally, the protein was concentrated using Amicon filter. The N-and C-terminal derivatives of bTf were produced as described (Yu and Schryvers, 1994). Briefly, 80 mg of ConA purified bTf were digested with 2 mg proteinase K in 40 ml 0.1 M Tris-HCl (pH 8.2), 25 mM $CaCl_2$ at room temperature for 20h. To stop the reaction, phenylmethylsulfonyl fluoride (PMSF) was added to 0.1 mg/ml. Five ml of concentrated preparation were applied to a Sephadex G-100 column equilibrated with 50 mM Tris-HCl (pH 8.0), the N-lobe and C-lobe fractions were dialyzed against 50 mM Na acetate (pH 6.9), 1 mM $CaCl_2$, 1 mM $MgCl_2$, 1 mM $MnCl_2$ and applied to a ConA-Sepharose column (which binds glycosylated C-lobe but not N-lobe of bTf).Eluants from the column washed with the buffer just described were retained as the N-lobe containing fraction. The C-lobe containing fraction was eluted by using the same buffer containing 0.2 M methyl-a-D-mannopyranoside. Both C-lobe and N-lobe fractions were dialyzed against 50 mM Tris-HCl (pH 8.0), concentrated by ultrafiltration, and frozen as aliquots at 70° C.

Expression of recombinant receptor protein. *E. coli* strains carrying the appropriate recombinant plasmid (DH5αF/pCRIIPHtbpB for TbpB and DH5αF/pCRIIPHtbpA for TbpA) were used to inoculate 50 ml LB-broth starter cultures containing 0.2% maltose and 150 mg/ml ampicillin. After growth at 37° C. for several hours the cultures were used to inoculate 1 liter of the same medium to a starting $OD_{600}$ of 0.05. Once the $OD_{600}$ reached 0.4, glucose was added to 4 mg/ml and grown until $OD_{600}$ reached 0.7–0.8. At that time $MgSO_4$ to 10 mM and 100 ml of a $10^{10}$ pfu/ml suspension of CE6 1 phage were added. The cell culture was incubated for an additional 2 hrs at 37° C. and then harvested by centrifugation. The cell pellet was resuspended in 5 ml of ice cold 50 mM Tris-HCl pH 8.0, 1 M NaCl for affinity isolation, SDS-PAGE, and Western Immunoblot analysis.

Affinity isolation of transferrin binding proteins and analytical methods. Bovine transferrin was coupled to CNBr-activated Sepharose 4B (Pharmacia) according to the manufacturer's instructions using solutions containing 3.5 mg/ml of iron-saturated bTf. Activated groups were blocked by addition of ethanolamine. Non-coupled transferrin was removed by washing with 10 to 20 column volumes of a 50 mM TrisHCl, 1 M NaCl, pH 8.0 buffer containing 6.0 M guanidine hydrochloride. After further washing with 50 mM Tris-HCl (pH 8.0) the bound transferrin was reloaded with iron using a solution containing 5 mg/ml $FeCl_3$ in 0.1 M sodium citrate/0.1 M $NaHCO_3$ (pH 8.6). After washing again with 50 mM Tris-HCl (pH 8.0), the bTf-Sepharose resin was pre-equilibrated with 50 mM Tris-HCl (pH 8.0), 1 M NaCl before it was used in affinity experiments *E. coli* cells containing recombinant plasmids resuspended in 50 mMTris-HCl (pH 8.0)/1 M NaCl were solubilized in 20 mM EDTA, 2% Sarkosyl and incubated for 2 h at room temperature. The mixture was centrifuged for 15 min at 8,000 rpm (4° C.) and the supernatant containing the solubilized receptor was carefully decanted. The supernatant was diluted 4 times with 50 mM HCl (pH 8.0), 1 M NaCl buffer and pre-incubated for 30 min at room temperature with an excess (1 mg/ml) of each of the following transferrins diluted in the same buffer: iron-loaded bTf, goat or caprine transferrin (cTf), sheep or ovine transferrin (oTf), and human transferrin (hTf); apo-bTf; C-lobe bTf; and N-lobe bTf. Only the buffer was added to the positive control experiment. After pre-incubation the supernatants were applied to a bTf-Sepharose column previously equilibrated with 50 mM Tris-HCl (pH 8.0), 1 M NaCl and incubated for 15 min at room temperature. Each column was washed extensively with at least 12 column volumes of 50 mM Tris-HCl, (pH 8.0),1 M NaCl, 10 mM EDTA, 0.5% sarkosyl followed by 10 column volumes containing only 0.05% sarkosyl to remove non-specifically bound protein. Final wash was done with 50 mM Tris-HCl (pH 8.0), 0.5 M NaCl.

Elution of the recombinant TbpB was achieved by application of 1 bed volume of 2×SDS-PAGE sample buffer under non-reducing condition and no boiling. Each eluant (supernatant) was collected after centrifuging the mixture containing the resin for 5 min at 13,000×g in a microfuge. An aliquot of each supernatant (eluant) was further submitted to SDS-PAGE and electroblotted to Immobilon PVDF (Millipore) membrane (overnight at 15V in 20 mM Tris, pH 7.5,150 mM glycine, 20% methanol and 0.1% SDS). The membrane was blocked with 0.5% skim milk in 20 mM Tris (pH 7.5), 500 mM NaCl (TBS) for 30 minutes at room temperature. A 1/1,000 dilution of the anti-TbpB serum in the blocking solution was applied to the membrane for 1 hour at 37° C. followed by two, 10-minute washes each with TBS. A 1/3000 dilution of secondary antibody (goat anti-rabbit IgG-horseradish peroxidase conjugate) was allowed to bind for 1 hour at 37° C. The conjugate was removed by three, 10-minute washes in TBS and developed using an HRP-substrate mixture (Chloro-Naphtol/$H_2O_2$).

N-terminal amino acid sequence analysis. Samples of affinity-purified and sequentially eluted TbpA and TbpB from H196 were subjected to SDS-PAGE, electroblotted onto PVDF (Immobilon-P, Millipore IPVH 00010) membrane, briefly stained with Coomassie Blue, and strips containing the individual protein bands were cut from the membrane for N-terminal amino acid sequence analysis.

Preparation of anti-TbpA and anti-TbpB monospecific rabbit sera. Approximately 500 mg of purified TbpA and TbpB from *P. haemolytica* strain H44 obtained from the appropriate fractions in the affinity procedure after dialysis and concentration was mixed with Freund's complete adjuvant and injected intramuscularly into two white female New Zealand rabbits, respectively. The rabbits were boosted twice at 3-week intervals with the same amount of antigens plus Freund's incomplete adjuvant. Two weeks after the final boost, blood was collected to determine the serum titre to the respective antigens using the dot assay in a dot-blot apparatus. The rabbits were either further boosted if titre was unsatisfactory or terminally bled, if the titre was satisfactory. The specificity of the sera against TbpA and TbpB from H44 was examined by SDS-PAGE and Western Immunoblot analysis using goat anti-rabbit IgG conjugated to HRP as secondary antibody. Expectedly, both TbpA and TbpB antisera crossreacted with TbpA and TbpB from strain H196, respectively.

Nucleotide sequence analysis. Two separate strategies for sequencing the tbp region were adopted. One approach primarily involved subdoning fragments from recombinant plasmids into the M13 vectors and then sequencing subsequently isolated single stranded DNA prepared by the dideoxy chain termination method using vector primers. In a limited number of cases, oligonucleotide primers were synthesized on the basis of the sequence results from the cloned inserts and used to complete the sequence of the cloned insert. In this analysis the nucleotide sequences were complied and analyzed by the Pustell programs (IBI).

An alternate approach primarily involved sequence determination of a succession of cloned inserts obtained by PCR amplification from chromosomal DNA. Oligonucleotide primers were synthesized on the basis of the preceeding sequence analysis. The PCR amplified products were cloned into the pCRII cloning vector (Invitrogen). Double stranded DNA sequencing wis performed using purified recombinant plasmids by the oligonucleotide primer-directed procedure using synthetic oligonucleotides, fluorescent dye-labelled dideoxynucleotide triphosphate terminators, and cycle sequencing with Taq polymerase. Sequence reaction products were analysed on a Applied Biosystems(ABI) model 373A automated fluorescent sequencer. The results from successive sequencing runs were compared and the composite sequence was determined by comparison of the chromatograms using the SeqEd program. This sequence was subsequently compared to the sequence obtained by single strand sequencing using the Mac-DNASIS program. In addition the sequence was analyzed by comparing the predicted protein sequence in all three reading frames with aligned sequences for Tbps from several different species. Any areas of uncertainty identified by this analysis were subjected to repeated runs of sequence analysis.

Results

Cloning the transferrin receptor genes. Anti-receptor antisera and N-terminal amino acid sequences were obtained in order to facilitate cloning of the *P. haemolytica* transferrin receptor genes. Monospecific antisera was obtained by immunizing rabbits with the affinity purified receptor proteins, TbpA and TbpB from a serotype A1 strain (H44) of *P. haemolytica*. Amino acid sequence analysis of an electroblotted preparation of purified native H196 TbpA yielded a readable sequence of 20 amino acids (top of FIG. 20). A similar analysis with the purified TbpB failed to provide any sequence information suggesting the N-terminus of this protein may be blocked.

The sequence of the first eight amino acids of the purified TbpA was used to design an oligonucleotide primer based on a *P. haemolytica* preferred codon usage table (tbpA primer 023, Table 4) (See also SEQ. ID. NOS.25 to 37). This primer was used in combination with either of two vector primers (RL2 and RL3, Table 4) for polymerase chain reaction (PCR) amplification of a portion of the tbpA gene from a *P. haemolytica* plasmid bank (Lo et al., 1985). An 800 bp PCR product was obtained with vector primers RL2 and 023 and its authenticity was verified by sequence analysis since the predicted amino acid sequence contained a sequence that was identical to the N-terminal amino acid sequence and exhibited homology with other TbpA proteins. The cloned PCR product was used as a hybridization probe for Southern analysis of restriction endonuclease-digested H196 *P. haemolytica* chromosomal DNA and for screening of the plasmid bank. The Southern analysis provided a restriction map of the chromosomal DNA in the tbp region for comparison to cloned inserts obtained from the plasmid bank.

TABLE 4

Oligonucleotide primers.

| Primer No. | Description (gene/region - location) | Direction* | Sequence |
| --- | --- | --- | --- |
| 023 | tbpA - 5' end, 1st 8 N-terminal aa's | 5'–3' | GGAAGCTTACTGAAAATAAAAAAATCGAAGAA |
| 088 | tbpA - 5' end, | 3'–5'* | CACTACTTTCCCCAAGCCAG |
| RL2 | pBR322 - upstream of BamH1 site | 3'–5'* | GGAATTCCCTCCTGTGGATC |
| 198 | tbpA - 3' end, | 3'–5'* | GCIGCII(G/C)IGCICGIAA(T/C)T(T/A)(T/C) |
| 190 | tbpB - 5' end, leader peptide region | 5'–3' | CAAAGCTTGCTTG(TC)TCIGGIGG |
| 352 | upstream of tbpB - 5' end | 5'–3' | AGATCTGGATTCTAAATCAGACCGCTTGTATTTTAG |

TABLE 4-continued

Oligonucleotide primers.

| Primer No. | Description (gene/region - location) | Direction* | Sequence |
|---|---|---|---|
| 192 | tbpB - conserved as sequence near 3' end | 5'–3' | GTT(T/A)(A/G/C)IGGIGGITT(C/T)TA(T/C)GG |
| 401 | tbpB - 5' end | 5'–3' | TAAATTAAAGGAGACATTATGTTTAAACT |
| 350 | tbpB - 3' end, flanking NcoI site | 3'–5'* | CGACGCCCATGGTTATTTTTCTATTTGACGTTTTCC |
| 199 | tbpB - 3' end, flanking HindIII site | 3'–5'* | GCGCAAGCTTTTATTTTTCTATTTGACG |
| 349 | tbpA - 5' end, BamH1/BglII sites upstream of rbs | 5'–3' | GGATTCAGATCTTAAAGGAGACCCTATCTAATGATAATG |
| 255 | tbpA - 5' end, NdeI site at start codon | 5'–3' | CCCTATCATATGATAATGAAATATCATC |
| 256 | tbpA - 3' end, HindIII site after stop | 3'–5'* | TAGCGCAAGCTTCTAAAACTTCATTTCAAAT |

*Direction relative to orientation of coding strand for the relevant gene.

Initially, two strongly hybridizing colonies were identified from the *E. coli* clones. Plasmid p(clone 9) contained a 9 kb insert which included most of the tbpA gene with adjacent downstream regions but was fused with DNA from another chromosomal locus (fis in FIG. 20). The second plasmid, p(clone 10), only contained a 1.2 kb insert that was primarily situated around the 5 end of the tbpA gene.

The artificial junction in plasmid pRYCL9 was reminiscent of similar artifacts observed while attempting to clone the meningococcal tbpB gene and the ensuing difficulties that were encountered (23) prompted consideration of alternative strategies for cloning the *P. haemolytica* tbpB region. One strategy was based on the observation that in other species the tbpB gene was located upstream of the tbpA gene (19, 20, 23) and that there were short stretches of amino acid identity in the predicted sequences of the respective TbpBs. A conserved amino acid sequence near the carboxy terminus of TbpBs was used to design a degenerate oligonucleotide primer (primer 192, Table 4) to obtain the remainder of the tbpA gene, the intergenic region and a portion of the 3' end of the tbpB gene. This primer was used in combination with a primer based on the sequence from the 5 end of the tbpA gene (primer 088, Table 4) to amplify a 700 bp fragment from H196 chromosomal DNA. The sequence from this insert enabled the design of an oligonucleotide primer based on the authentic sequence of the 3' end of the tbpB gene (primer 199, Table 4) which was used in combination with degenerate oligonucleotide based on a conserved amino acid sequence present in the leader peptide region of known TbpBs (oligo 190, Table 4) for PCR amplification. The resulting 2.4 kb PCR product obtained when H196 chromosomal DNA was used as a template contained the authentic 3' end of the tbpB gene. When this PCR fragment was cloned in the pCRII vector and used in expression experiments utilizing the T7 promoter, an intact recombinant TbpB was produced indicating that the ribosomal binding site and start of the tbpB gene was contained within the insert.

A second strategy utilized anchored PCR in which PstI-digested pBluescript plasmid was ligated to Pst I-digested H196 chromosomal DNA and used as template for a PCR reaction utilizing a primer from the 3' end of the tbpB gene (oligo 199, Table 4) and the M13 reverse primer from the vector. The resulting 3.5 kb product was subcloned into the PCRII vector, producing a plasmid that contained the entire tbpB gene and a considerable amount of adjacent upstream regions (ORF and RNase T in FIG. 20) and SEQ. ID. NO.21.

Further subcloning the tbp genes into expression vectors involved PCR amplification with oligonucleotide primers complementary to the 5 and 3 ends of the genes and inclusion of appropriate restriction sites. One set of primers for amplifying the tbpA gene (primer 349 and 256, Table 4) involved introduction of a BamHI and Bgl II site immediately upstream of the predicted ribosomal binding site (rbs) so that provision of an exogenous promoter should result in expression due to the presence of the native rbs. An alternate 5 primer (255, Table 4) involved the introduction of an Nde I site at the start codon so that cloning into the pT7-7 expression vector, which supplies a properly position ribosomal binding site, was possible. Since the expression experiments preceeded definitive identification of the start of the tbpB gene, the subcloned tbpB gene was obtained by PCR amplification with an upstream sequencing primer (primer 352, Table 4) and a primer containing the authentic 3 end flanked by an Nco I site (primer 350, Table 4).

Characterization of the transferrin receptor genes. As illustrated in FIG. 20, the tbp genes appear to be in an operon arrangement, with the tbpB gene located upstream of the tbpA gene. Comparative sequence analysis revealed that the tbpB gene was preceded by an open reading frame (ORF) encoding a protein whose sequence was highly identical to RNaseT from *E. coli* and *H. influenzae*. This ORF was in turn preceeded by another ORF encoding a protein with considerable identity to hypothetical proteins identified in influenzae and Vibrio parahaemolyticus. Downstream of the tbpA gene is an ORF encoding a protein whose sequence was 70% identical to factor-for-inversion stimulation (FIS protein—recombinational enhancer) proteins from *H. influenzae* and *E. coli*. This effectively demarcates the boundaries of the transferrin receptor protein gene operon and indicates that there are no immediately adjacent genes related to this iron acquisition pathway.

There is a 420 bp region between the end of the ORF encoding the RNaseT homologue and the start of the tbpB gene with potential ribosomal binding sites, promoter sites and regulatory sites all present within the last 62 base pairs (FIG. 20). The remaining 358 bp intervening region could presumably contain transcriptional termination signals for the RNaseT gene and sequences potentially involved in regulation of the tbp operon. The putative promoter region contains 5/6 and 6/6 of the consensus bases for the *E. coli* s70-35 and -10 promoter regions, respectively.

Previous studies have demonstrated that the expression of the *P.haemolytica* transferrin receptor proteins is regulated by the level of available iron in the medium (26). The identification of a putative Fur box overlapping the -10 site of the tbpB promoter (FIG. 20) suggests that regulation by iron may be at the transcriptional level via the action of a Fur homologue in *P. haemolytica*. The putative Fur box had 12/19 bases identical to the *E. coli* Fur binding site consensus sequence (Litwin and Calderwood, 1993).

Between the tbpB and tbpA genes there is a 96 bp intergenic region which contains a putative ribosomal binding site upstream of the tbpA gene but no evident promoter. In addition, there is no evident transcriptional terminators in this region. Downstream of the tbpA gene stop codon and the stop codon of the gene encoding the FIS homologue is a 98 bp region with no evident transcriptional terminators.

Sequence analysis of the tbpA gene region from serotype A1 *P. haemolytica* strain H196 revealed an ORF of 2,790 bp encoding a protein with a predicted molecular mass of 106,921 Da (FIG. 22). The putative signal peptidase cleavage site at residue 28 was confirmed by comparison with the known N-terminal amino acid sequence of the mature protein (top of FIG. 22). The predicted amino acid sequence of TbpA was compared to the sequences of TbpA from *N. meningitidis* (23), *N. gonorrhoeae* (8), *H. influenzae* (20) and *Actinobacillus pleuropneumoniae* (19). The localization of identical amino acids between these proteins (bold-underlined amino acids, FIG. 22) was compared to the proposed topology of these amino add segments based on the model predicted by Tommassen (28). It is evident that most of the identical amino acids are clustered in regions corresponding to the short transmembrane β-sheets or in the segments of the internal and external loops that are immediately adjacent to the transmembrane sections. It is interesting to note that there are conserved pairs of cysteines in proposed external loops 4, 6 and 7 and a unique cysteine pair in loop 10 of the *P. haemolytica* TbpA. These likely represent disulfide bridges that would provide structural stability to the external loops.

Analysis of the sequence in the tbpB gene from serotype A1 *P. haemolytica* strain H196 revealed an ORF of 1,752 bp encoding a protein with a predicted molecular mass of 63,419 Da (FIG. 23). This predicted protein sequence of TbpB was compared to the published sequences of TbpBs from *N. meningitidis* (23), *N. gonorrhoeae* (1), *H. influenzae* (20) and *Actinobacillus pleuropneumoniae* (14). This predicted amino acid sequence included a 18 amino acid leader peptide, a signal peptidase II recognition sequence with a cysteine as the predicted N-terminal amino acid of the mature protein. The presence of an N-terminal cysteine, which has been shown to be lipidated in other species (14, 24), may explain the inability to obtain an N-terminal amino acid sequence for this protein and may serve as the primary means of anchoring the protein to the outer membrane. Regions that aligned with the putative binding regions of the *A.pleuropneumoniae* TbpB (TfbA) recently identified by Gerlach et. al. (36) are indicated by a double underline.

It is apparent that there are several regions of homology found throughout the length of the amino acid sequence which include several short stretches of identical amino acids (FIG. 24). Upon closer inspection it is apparent that there is some homology between regions in the N-terminal and C-terminal portions of the protein suggesting there may be an underlying bilobed structure to the protein, analogous to what is observed for transferring. Thus the sequences YKGYW (aa 185–189) (SEQ. ID. NO.38) and YRGTW (aa 449–453) (SEQ. ID. NO.39), FTADFANK (aa 237–244) (SEQ. ID. NO.40) and FDVDFVNK (aa 480–487) (SEQ. ID. NO.41), GNRFSG (aa 276–281) (SEQ. ID. NO.42) and GNGFGG (aa 513–518) (SEQ. ID. NO.43), and LEGGFFG (aa 300–306) (SEQ. ID. NO.44) and FEGGFYG (aa 546–552) (SEQ. ID. NO.45) represent consecutive stretches of homologous amino acids in equivalent positions of the N-terminal and C-terminal portions of the protein.

Expression and analysis of the recombinant receptor proteins. The intact tbpB and tbpA genes were PCR amplified from H196 chromosomal DNA and subcloned into expression vectors for production of recombinant proteins. For initial attempts at expression of the tbpB gene, the subcloned tbpB gene was obtained by PCR amplification with an upstream primer (352, Table 4) and a primer containing the authentic 3 end flanked by an NcoI site (350, Table 4). When the PCR amplified fragment was subcloned into the pCRII vector, all five of the resulting clones were in the same orientation; downstream of the T7 promoter and in the opposite direction of the lac promoter. Since the lac promoter would not be tightly regulated in a high copy number vector, this result suggests that expression of the insert in *E. coli* may be selected against. Once the sequence of this region was available it became apparent that primer 352 was immediately upstream of the RNaseT gene and thus expression of either this gene or the tbpB gene could have been responsible for the selective pressure. Expression of TbpB from the T7 promoter was accomplished by infection with CE6 λ phage, which encodes the T7 RNA polymerase. Two hours after infection a protein of the anticipated molecular weight for TbpB was evident and this protein reacted with anti-TbpB antiserum after electroblotting.

There was detectable binding of labelled bovine transferrin (bTf) by immobilized intact cells expressing the TbpB protein and this level of binding did not increase significantly with prior sonication of the cells (data not shown). Although this could be interpreted as proper processing and export of the TbpB to the cell surface in the heterologous *E. coli* system, disturbance of the outer membrane integrity by overexpression of a foreign protein antigen is an equally plausible explanation. The preliminary binding studies suggested that a functional TbpB protein was being produced, indicating that further analysis might enable evaluation of the functional properties of this protein and ascertain its contribution to the previously characterized properties of the native receptor complex. Thus, crude membranes were prepared from cells expressing TbpB and used in affinity isolation experiments designed to evaluate its binding characteristics. These experiments indicated that the recombinant TbpB is capable of being affinity isolated by immobilized bTf and this isolation could be inhibited by an excess of bovine, ovine or caprine Tf, demonstrating its ability to effectively bind to all three of these ruminant Tfs. Human transferrin as well as apo-bTf did not inhibit the affinity isolation of recombinant TbpB by immobilized iron-loaded bTf. This assay also revealed that both N-lobe and C-lobe of bTf effectively blocked binding of recombinant TbpB to the immobilized bTf.

For expressing the tbpA gene, PCR amplification was performed with a set of primers (oligos 349 and 256, Table 4) that maintained the predicted ribosomal binding site (FIG. 21). After subcloning the PCR product into the pCRII vector, no recombinant TbpA was expressed after infection with CE6 phage (encoding T7 RNA polymerase). Sequence analysis of one of the clones revealed excision of several base pairs that eliminated ribosomal binding site. Other repeated attempts at subcloning the tbpA gene from PCR using 255 and 256 primers (see Table 4) into the NdeI site of the pT7–7 vector (which provides an optimally positioned ribosomal binding site) were unsuccessful.

Discussion

In the initial studies demonstrating the presence of a transferrin receptor in *Pasteurella haemolytica* (26) only a single receptor protein (TbpA) was isolated by an affinity method that yielded two receptor proteins (TbpA and TbpB) in other species (32). Thus the ability to use iron from bovine transferrin for growth (26) and the specific binding of ruminant transferrins (39) was initially presumed to be largely mediated by this receptor protein. In subsequent studies that demonstrated that the binding region of bovine transferrin was localized to the C-lobe (41), two receptor proteins (TbpA and TbpB) were isolated by a modified affinity method, although the yield of TbpA greatly exceeded that of TbpB. Thus it was not possible to conclusively attribute the observed binding characteristics of the receptor to either receptor protein, and particularly not to TbpB.

The cloning of the tbp genes and expression of recombinant TbpB has enabled specific evaluation of its binding characteristics. These studies have demonstrated that TbpB has a similar host specificity as the native receptor complex (TbpA and TbpB) as it specifically binds Tfs from several ruminant species. In contrast, unlike the native receptor complex, the recombinant TbpB was able to recognize binding determinants on the N-lobe as well as the C-lobe of bTf, suggesting that in the previous study (Yu and Schryvers, 1994) an interaction between TbpA and TbpB might have interfered in the ability of TbpB to also bind to the N-lobe of bTf.

In competitive binding assays with immobilized membranes (TbpA and TbpB) from P. haemolytica there was no evident preference for the iron-loaded or apo form of bTf (30) which is similar to what has been observed in most other bacterial species (Blanton et al., 1990; 32; Tsai et al., 1988; 32, 37), except Moraxella catarrhalis (Yu and Schryvers, 1993). In the present study recombinant TbpB clearly showed a strong preference for the iron-loaded form of bTf. This preference of TbpB may have functional relevance in increasing the efficiency of iron acquisition in vivo.

Example 4
Vaccine Potential of Recombinant Tbp2 and Authentic Tbp1

The transferrin-binding proteins Tbp1 and Tbp2 are attractive targets for a number of reasons:

a) Since acquisition of iron from transferrin is likely essential for bacterial survival, an antibody response against these antigens should be protective.

b) The genes coding for Tbp1 and Tbp2 appear to be conserved within various isolates of P. haemolytica A1.

This study deals with testing the vaccine potential of recombinant Tbp2 and authentic Tbp1, alone and in combination, in an experimental P. haemolytica challenge model.

Methods

The Tbp1 and Tbp2 proteins were affinity purified from P. haemolytica and recombinant E. coli outer membranes, respectively, by affinity chromatography using standard techniques as described herein. Vaccines were formulated using a proprietary mineral oil-based adjuvant (VSA3) such that the volume of each dose was 2 cc containing the following amount of each antigen: Tbp2-45 mg; Tbp1 -85 mg when used by itself or 100 mg when combined with Tbp2. In addition, a placebo vaccine was prepared containing sterile diluent in place of antigen. Five groups were included in the trial, including one which received a single immunization of Tbp2 ten days before challenge, and groups which received two immunizations with Tbp2, Tbp1 +Tbp2, placebo, or Tbp1. The interval between primary and secondary immunization was three weeks and all vaccinations were carried out at a farm in Southern Saskatchewan. Vaccines were delivered via the subcutaneous route. Approximately ten days prior to challenge, animals were transported to Saskatoon and housed at the VIDO research station. All groups contained ten animals with the exception of the group receiving Tbp1 in which there were six. This group was not in the original proposal and was added in order to determine the protective capacity of Tbp1 by itself. In addition, one calf which received one immunization with the Tbp2 formulation developed clinical signs of disease unrelated to vaccination and was therefore excluded from the trial. The composition of the vaccine groups is summarized in Table 5.

TABLE 5

Composition of vaccine groups.

| Vaccine Group | Antigens | Immunizations | Animals/Group |
|---|---|---|---|
| 1 | Tbp2 | One | 9 |
| 2 | Tbp2 | Two | 10 |
| 3 | Tbp1 & Tbp2 | Two | 10 |
| 4 | Placebo | Two | 10 |
| 5 | Tbp1 | Two | 6 |

Calves were challenged via the aerosol route by first exposing them to a suspension of bovine herpesvirus-1 strain 108 containing approximately $2.5 \times 10^6$ PFU/ml followed four days later by an aerosol of P. haemolytica containing approximately $5 \times 10^8$ CFU/ml. Animals were examined daily by a veterinarian and animal health technician and the following data wks recorded: weight, temperature, nasal scores, depression, strength, respiratory distress and sickness. Each of these criteria with the exception of weight and temperature were scored on a scale of 0–4.

The serological response to vaccination was measured using an enzyme-linked immunosorbent assay (ELISA). Serum samples were collected at the time of the first and second immunizations plus on the day of challenge with BHV-1. The titers are presented as the reciprocal of the serum dilution which resulted in an optical density equivalent to the background plus two standard deviations. Responses against Tbp1, Tbp2 and the P. haemolytica leukotoxin were measured. The latter was included as a diagnostic test to determine if animals had been naturally exposed to the organism.

Results a) Response to Vaccination: None of the animals showed any adverse reaction to vaccination with any of the formulations used. The serological response to vaccination was determined using an ELISA procedure which measured the serum antibody levels to Tbp1, Tbp2 and the P. haemolytica leukotoxin. The latter antigen was included in order to ensure that none of the animals had increased titers due to the natural exposure to the bacteria. The titers against each antigen are shown in Table 6 and it can be seen that the titers against leukotoxin were comparable at the time of initial vaccination (Bleed 1), the second vaccination (Bleed 2), and at challenge (Bleed 3). Animals which have a titer below 3,000 were considered to be clean. Interestingly, none of the animals seroconverted to a significant degree to the Tbp1 antigen. Based upon the inventors experience with Tbp1 from other organisms, the expected titers should be low but it was unexpected that no significant increase in antibody levels would be detectable. All groups which received Tbp2 responded well to vaccination and although the group which received Tbp1+2 had titers approximately ½ of that in the Tbp2 group, this difference is not significant.

TABLE 6

Serological response to vaccination.

| ELISA Antigen | Vaccine Group | Titer - Bleed 1 | Titer - Bleed 2 | Titer - Bleed 3 |
|---|---|---|---|---|
| Leukotoxin | Tbp2 (1 dose) | 1010 | 1350 | 2156 |
|  | Tbp2 | 1136 | 1547 | 2656 |
|  | Tbp1 & 2 | 1159 | 1239 | 1137 |
|  | Placebo | 1688 | 1834 | 2782 |
|  | Tbp1 | 980 | 1282 | 1339 |
| Tbp1 | Tbp2 (1 dose) | 113 | 364 | 229 |
|  | Tbp2 | 203 | 206 | 296 |
|  | Tbp1 & 2 | 150 | 388 | 367 |
|  | Placebo | 140 | 130 | 226 |
|  | Tbp1 | 57 | 55 | 139 |
| Tbp2 | Tbp2 (1 dose) | 408 | 639 | 9871 |
|  | Tbp2 | 397 | 12154 | 66697 |
|  | Tbp1 & 2 | 119 | 7838 | 27515 |
|  | Placebo | 360 | 269 | 378 |
|  | Tbp1 | 359 | 433433 | 478 |

ELISA titers against leukotoxin, Tbp1 and Tbp2 were determined using serum samples taken at the time of the first immunization (Bleed 1), the second immunization (Bleed 2), and the day of challenge with bovine herpesvirus-1 (Bleed 3). The numbers are expressed as the reciprocal of the dilution equaling a negative control plus two standard deviations.

b) Mortality: The experimental disease model has been calibrated to obtain 60–70% mortality under normal conditions. However, mortality was higher than usual in this trial, probably because of the extremely cold temperatures to which the animals were exposed throughout the time period after challenge. Daily low temperatures were in the −40° C. range and all animals were housed outdoors during the trial. The mortality by group is shown in Table 7 and the only group which showed significant protection was that which received both Tbp1 and Tbp2. This is compared to 50% mortality for Tbp2 by itself and 100% for Tbp1. A single immunization with Tbp1 was of no benefit.

TABLE 7

Group mortality observed during the trial.

| Vaccine Group | Mortality (%) |
|---|---|
| Tbp2 (1 dose) | 78 |
| Tbp2 | 50 |

TABLE 7-continued

Group mortality observed during the trial.

| Vaccine Group | Mortality (%) |
|---|---|
| Tbp1 & 2 | 10 |
| Placebo | 90 |
| Tbp1 | 100 | c) Clinical Signs of Disease: The clinical results are summarized by group in Table 8. It should be noted that Table 8 contains the clinical results for all days of the trial, including those prior to P. haemolytica infection on day four. Therefore, only the results from days 4 through ten have been used to determine the protective capacity of the vaccine formulations. The high rate of mortality observed during this trial had the effect of reducing the size of each group to the point where differences observed in all of the clinical parameters measured are not statistically significant. However, it is clear that the group which received both Tbp1 and Tbp2 showed lower scores in most categories between days 5 and 7. The groups which received two immunizations with Tbp2 alone also showed reduced clinical signs of disease in survivors although they did not do as well as the combination group. The contribution of Tbp1 to protection is unclear at present since there did not appear to be any antibody response to this antigen.

d) Postmortem Results: Necropsies were performed on all animals which died during the trial. In all cases, P. haemolytica was cultured from the lungs and the pathology observed was consistent with fibrinous pneumonia caused by P. haemolytica.

Conclusions

Two vaccinations with a formulation containing P. haemolytica Tbp1 and Tbp2 provided significant protection against experimental bovine pneumonic pasteurellosis. The exact contribution which Tbp1 provides to this protection is unclear since there did not appear to be any serological response to the protein. The beneficial effect may have been due to a cell-mediated immune response.

Immunization with two doses of Tbp2 provided some degree of protection and it may be possible to increase this by testing vaccine formulations containing greater quantities of antigen or a different adjuvant. It is likely that the immunological response to Tbp2 provided the bulk of the protection seen with the combination vaccine.

Vaccination with one dose of Tbp2 or two doses of Tbp1 had no beneficial effect after experimental challenge.

TABLE 8

Mean Clinical Scores by Group. Animals were challenged on day 0 with BHV-1 and day 4 with P. haemolyica.

| Group | Day 0 | Day 1 | Day 2 | Day 3 | Day 4 | Day 5 | Day 6 | Day 7 | Day 8 | Day 9 | Day 10 |
|---|---|---|---|---|---|---|---|---|---|---|---|
| Mean Weight (kg) | | | | | | | | | | | |
| Tbp2 (1 dose) | 232.4 | 231.6 | 228.1 | 225.9 | 222.9 | 223.1 | 223.6 | 225.7 | 256.0 | 256.0 | 256.0 |
| Tbp2 | 211.4 | 209.3 | 205.3 | 202.4 | 201.2 | 191.5 | 197.3 | 195.5 | 198.8 | 197.7 | 197.2 |
| Tbp1 & 2 | 217.8 | 218.1 | 216.0 | 212.9 | 211.2 | 208.8 | 207.5 | 208.3 | 207.7 | 207.8 | 208.3 |
| Placebo | 223.1 | 221.2 | 215.7 | 213.6 | 209.5 | 206.2 | 194.4 | 177.0 | 158.0 | 161.0 | 158.0 |
| Tbp1 | 225.3 | 225.8 | 219.8 | 216.7 | 212.7 | 208.2 | 200.0 | 193.0 | 191.0 | 190.0 | N/A |
| Mean Temperature | | | | | | | | | | | |
| Tbp2 (1 dose) | 39.06 | 38.96 | 39.92 | 40.21 | 40.53 | 40.00 | 39.40 | 39.50 | 39.25 | 38.85 | 39.30 |
| Tbp2 | 39.05 | 39.26 | 40.29 | 40.50 | 40.44 | 40.51 | 40.19 | 39.67 | 39.88 | 39.33 | 39.10 |
| Tbp1 & 2 | 39.19 | 39.36 | 40.10 | 40.00 | 40.21 | 40.20 | 39.48 | 39.49 | 39.14 | 39.26 | 39.48 |

TABLE 8-continued

Mean Clinical Scores by Group. Animals were challenged on day 0 with BHV-1 and day 4 with *P. haemolyica*.

| Group | Day 0 | Day 1 | Day 2 | Day 3 | Day 4 | Day 5 | Day 6 | Day 7 | Day 8 | Day 9 | Day 10 |
|---|---|---|---|---|---|---|---|---|---|---|---|
| Placebo | 39.03 | 39.10 | 40.30 | 40.41 | 40.83 | 40.24 | 39.96 | 40.35 | 39.50 | 39.10 | 40.70 |
| Tbp1 | 39.15 | 38.78 | 40.52 | 40.12 | 40.47 | 40.85 | 40.95 | 41.60 | 40.90 | 41.00 | N/A |
| *Mean Nasal Score* | | | | | | | | | | | |
| Tbp2 (1 dose) | 0.00 | 0.11 | 0.33 | 0.61 | 1.17 | 1.33 | 1.40 | 1.25 | 0.00 | 0.00 | 0.00 |
| Tbp2 | 0.00 | 0.05 | 0.30 | 0.85 | 1.20 | 1.45 | 1.56 | 1.44 | 0.83 | 0.33 | 0.20 |
| Tbp1 & 2 | 0.00 | 0.10 | 0.45 | 0.60 | 1.05 | 1.70 | 0.90 | 1.00 | 0.70 | 0.33 | 0.44 |
| Placebo | 0.00 | 0.15 | 0.35 | 0.95 | 1.10 | 1.78 | 1.40 | 1.50 | 1.00 | 0.00 | 0.00 |
| Tbp1 | 0.00 | 0.08 | 0.33 | 0.67 | 0.83 | 1.08 | 1.00 | 0.00 | 1.00 | 2.00 | N/A |
| *Mean Depression Score* | | | | | | | | | | | |
| Tbp2 (1 dose) | 0.00 | 0.00 | 0.00 | 0.11 | 0.22 | 0.67 | 1.60 | 1.75 | 0.00 | 0.00 | 0.00 |
| Tbp2 | 0.00 | 0.00 | 0.00 | 0.15 | 0.00 | 0.50 | 0.89 | 1.67 | 0.67 | 1.33 | 0.40 |
| Tbp1 & 2 | 0.00 | 0.00 | 0.00 | 0.00 | 0.00 | 0.60 | 1.20 | 1.10 | 0.60 | 0.33 | 0.56 |
| Placebo | 0.00 | 0.00 | 0.05 | 0.15 | 0.60 | 1.33 | 2.20 | 2.00 | 1.00 | 0.00 | 0.00 |
| Tbp1 | 0.00 | 0.00 | 0.00 | 0.17 | 0.50 | 1.83 | 1.50 | 2.00 | 2.00 | 3.00 | N/A |
| *Mean Strength Score* | | | | | | | | | | | |
| Tbp2 (1 dose) | 0.00 | 0.00 | 0.00 | 0.00 | 0.00 | 0.67 | 1.60 | 1.75 | 0.00 | 0.00 | 0.00 |
| Tbp2 | 0.00 | 0.00 | 0.00 | 0.00 | 0.00 | 0.40 | 0.78 | 1.67 | 0.50 | 1.00 | 0.40 |
| Tbp1 & 2 | 0.00 | 0.00 | 0.00 | 0.00 | 0.00 | 0.30 | 0.50 | 1.10 | 0.60 | 0.22 | 0.11 |
| Placebo | 0.00 | 0.00 | 0.00 | 0.00 | 0.00 | 0.67 | 1.60 | 1.50 | 1.00 | 0.00 | 0.00 |
| Tbp1 | 0.00 | 0.00 | 0.00 | 0.00 | 0.00 | 1.17 | 0.50 | 1.00 | 2.00 | 3.00 | N/A |
| *Mean Respiratory Distress Score* | | | | | | | | | | | |
| Tbp2 (1 dose) | 0.00 | 0.00 | 0.00 | 0.00 | 0.00 | 0.11 | 1.40 | 2.00 | 0.00 | 0.00 | 0.00 |
| Tbp2 | 0.00 | 0.00 | 0.00 | 0.00 | 0.00 | 0.10 | 0.44 | 1.22 | 0.33 | 0.67 | 0.00 |
| Tbp1 & 2 | 0.00 | 0.00 | 0.00 | 0.00 | 0.00 | 0.00 | 0.30 | 0.40 | 0.50 | 0.11 | 0.11 |
| Placebo | 0.00 | 0.00 | 0.00 | 0.00 | 0.00 | 0.67 | 1.00 | 1.00 | 0.00 | 0.00 | 0.00 |
| Tbp1 | 0.00 | 0.00 | 0.00 | 0.00 | 0.00 | 1.17 | 0.50 | 1.00 | 1.00 | 3.00 | N/A |
| *Mean Sick Score* | | | | | | | | | | | |
| Tbp2 (1 dose) | 0.00 | 0.00 | 0.56 | 0.78 | 0.89 | 0.89 | 2.00 | 2.25 | 0.00 | 0.00 | 0.00 |
| Tbp2 | 0.00 | 0.00 | 0.90 | 0.90 | 1.00 | 1.00 | 1.00 | 1.89 | 0.83 | 1.17 | 0.40 |
| Tbp1 & 2 | 0.00 | 0.00 | 0.60 | 0.50 | 0.90 | 1.10 | 0.90 | 1.20 | 0.70 | 0.33 | 0.44 |
| Placebo | 0.00 | 0.00 | 0.70 | 1.00 | 1.20 | 1.80 | 2.71 | 2.67 | 1.00 | 0.00 | 1.00 |
| Tbp1 | 0.00 | 0.00 | 0.83 | 0.50 | 1.00 | 2.83 | 2.75 | 3.00 | 2.00 | 4.00 | N/A |
| *Cumulative Mortality* | | | | | | | | | | | |
| Tbp2 (1 dose) | 0.00 | 0.00 | 0.00 | 0.00 | 0.00 | 0.00 | 0.44 | 0.78 | 0.78 | 0.78 | 0.78 |
| Tbp2 | 0.00 | 0.00 | 0.00 | 0.00 | 0.00 | 0.00 | 0.10 | 0.30 | 0.40 | 0.40 | 0.50 |
| Tbp1 & 2 | 0.00 | 0.00 | 0.00 | 0.00 | 0.00 | 0.00 | 0.00 | 0.00 | 0.00 | 0.10 | 0.10 |
| Placebo | 0.00 | 0.00 | 0.00 | 0.00 | 0.00 | 0.40 | 0.50 | 0.80 | 0.80 | 0.90 | 0.90 |
| Tbp1 | 0.00 | 0.00 | 0.00 | 0.00 | 0.00 | 0.33 | 0.67 | 0.67 | 0.83 | 0.83 | 1.00 |

Example 5
Comparison of the Transferrin Receptor from Various Ruminant Serotypes A collection of *Pasteurella haemolytica* and *P. trehalosi* strains of various serotypes isolated from cattle, sheep and goats were analyzed for binding of ruminant transferrins and utilization of transferrin iron for growth. Some of the goals of the study were to determine the prevalence of transferrin receptors from different host species, to evaluate their specificities for different ruminant transferrins and to determine if there is antigenic relatedness amongst the surface receptors from the different strains causing shipping fever in cattle, pneumonia in sheep and goats and septiceamia in lambs.

Materials

Bacterial strains. The bacterial strains used in this study are listed in Table 9. Clinical type A1 isolates of *P.haemolytica* (h93–h97)(9) and representative ATCC strains (h98–h107) from bovine pneumonia were provided by Dr. Andrew Potter, VIDO, Saskatoon. *P. trehalosi* strain h174, field isolate from goat with pneumonic pasteurellosis was provided by Dr. Frank Milward, Rhone Merieux, Lyon, France. *P. haemolytica* strain h44, a bovine clinical type A1 isolate from bovine pneumonia, has been described previously (26). Strain h196 was obtained from Dr. Lo, University of Guelph, Ontario, Canada.

TABLE 9

Bacterial strains, serotypes and sources.

| Species | Strain | Serotype | Source |
|---|---|---|---|
| *P. haemolytica* | h44 | A1 | cattle |
| *P. haemolytica* | h93 | A1 | cattle |
| *P. haemolytica* | h94 | A1 | cattle |
| *P. haemolytica* | h95 | A1 | cattle |
| *P. haemolytica* | h96 | A1 | cattle |
| *P. haemolytica* | h97 | A1 | cattle |
| *P. haemolytica* | h196 | A1 | cattle |
| *P. haemolytica* | h98 (ATCC33366) | A2 | sheep |
| *P. trehalosi* | h99 (ATCC33367) | T3 | sheep |
| *P. trehalosi* | h100 (ATCC33368) | T4 | sheep |
| *P. haemolytica* | h103 (ATCC33372) | A8 | sheep |
| *P. haemolytica* | h104 (ATCC33373) | A9 | sheep |
| *P. haemolytica* | h105 (ATCC33369) | A5 | sheep |
| *P. trehalosi* | h106 (ATCC33374) | T10 | sheep |
| *P. haemolytica* | h107 (ATCC33375) | A11 | goat |
| *P. trehalosi* | h174 (90020-16266) | T3 | goat |

Growth conditions. All bacterial strains were stored frozen at −70° C. in 30% glycerol. Isolates from the frozen stocks were streaked onto chocolate agar plates and incubated at 37° C. in a 5% $CO_2$ incubator. Iron-restricted growth was achieved by growing the bacteria in Brain Heart Infusion roth (BH1, Difco Laboratories) or O'Reilly-Niven broth (25) supplemented with 3.0 g/ml nicotinamide adenine dinucleotide (NAD) and containing the iron chelator ethylenediaminedihydroxyphenylacetic acid (EDDA, Sigma) at a final concentration of 100 M. Growth experiments for use of different transferrins as an iron source was performed as previously described (26).

Preparation of transferrins and derivatives. Bovine transferrin was obtained from Sigma. The preparation of ovine (sheep) and caprine (goat) transferrins (2), the iron loading of transferrins to 30% or 100% saturation (Herrington et al.1985) and conjugation of horse-radish peroxidase (HRP) to transferrin (37) was essentially as described previously. In the preparation of conjugates of bovine, ovine and caprine transferrins (HRP-bTf, HRP-oTf and HRP-gTf ), the mixture of HRP and transferrin were subjected to gel filtration after chemical conjugation. The fractions demonstrating maximal activity were pooled, dialyzed and aliquots frozen and stored at −70° C.

Transferrin binding assay. The solid phase binding assay for transferrin was essentially as described previously (32). After the membrane or concentrated eluates were spotted unto HA paper (Millipore Corporation, Bedford, Mass.) and blocked in 0.5% skim milk, the paper was exposed to blocking solution containing 450 ng/ml of the HRP-conjugated transferrin. The incubation, washing and development with HRP substrate mixture were performed essentially as previously described (32).

Affinity isolation of transferrin binding proteins. Bovine, ovine and caprine transferrins were individually coupled to CNBr-activated Sepharose 4B according to the manufacturers instructions using solutions containing 3.5 mg/ml of iron-saturated transferrin. Activated groups were blocked by addition of ethanolamine. Non coupled transferrin was removed by washing with 10 to 20 column volumes of a 50 mM TrisHCl, 1 M NaCl, pH 8.0 buffer containing 6.0 M guanidine hydrochloride and after further washing the bound transferrin was reloaded with iron using a solution containing 5 mg/ml $FeCl_3$ in 0.1 M sodium citrate/0.1 M $NaHCO_3$ pH 8.6 buffer.

Iron-deficient total membrane (200 mg protein) from *P. haemolytica* or *P.trehalosi* prepared as previously described (32) was diluted to 2 mg/ml in 50 mM Tris pH 8.0 containing 1.0 M NaCl. The diluted membrane was solubilized by addition of EDTA and sarkosyl to a final concentration of 10 mM and 0.75%, respectively followed by incubation of the mixture at room temperature for 15–30 min with gentle rocking. The solution was centrifuged at 10,000 rpm for 10 min to remove insoluble debris. The supernatant containing the solubilized membrane was applied to a 1.5×10 cm transferrin-affinity column and then washed extensively (at least 10 bed volumes) with 50 mM Tris pH 8.0 containing 1.0 M NaCl, 10 mM EDTA, 0.75% Sarksosyl to remove non-specifically bound protein. In experiments using low salt washing conditions the washing buffer contained 100 mM NaCl in lieu of 1M NaCl. In some instances, additional washing with 2–3 bed volumes of washing buffer containing 0.2 M guanidine hydrochloride was necessary to remove contaminating proteins.

Coelution of both transferrin binding proteins (TbpA and TbpB) was achieved by application of 2–3 bed volumes of 2.0 M guanidine hydrochloride in 50 mM Tris pH 8.0, containing 1.0 M NaCl, 1 mM EDTA, 0.01% sarkosyl. The eluant was collected for immediate dialysis against 50 mM Tris pH 8.0. Further treatment with higher concentrations of guanidine hydrochloride usually did not result in any further yield of receptor protein. Individual isolation of TbpA and TbpB was attained by sequential elution with 2 bed-volumes of each buffer containing 0.2, 0.5, 0.75, 1.0, 1.5, 2.0 and 3.0 guanidine hydrochloride, respectively. The eluates were dialyzed against 3 changes of 3 litres 50 mM Tris pH 8.0 over an 18-hour period and concentrated by ultrafiltration. After SDSPAGE analysis the fractions from the 0.5 and 0.75 M guanidine HCl elution buffers were found to contain TbpB only and were thus pooled for a preparation of TbpB and fractions from the 1.5 and 2 M guanidine HCl elution buffers were pooled for a preparation of TbpA.

Preparation of anti-TbpA and anti-TbpB monospecific rabbit sera. Approximately 500 μg of purified TbpA or TbpB from *P. haemolytica* strain h44 prepared as described above, was mixed with Freund's complete adjuvant and injected intramuscularly into two white female New Zealand rabbits. The rabbits were boosted twice at 3-week intervals with the same amount of antigens in Freund's incomplete adjuvant and the immune sera collected 2weeks after the final boost. The specificity of the sera against TbpA and TbpB was tested after SDS-PAGE and immunoblotting of the receptor proteins and using goat anti-rabbit IgG conjugated to HRP as secondary antibody.

Analytical methods. Protein samples were analyzed by SDS-PAGE followed by silver staining as previously described (32). For Western blot analysis, about 1–2 μg of purified receptor proteins or 40 μg of outer membrane protein from iron-limited cells were separated on 10% polyacrylamide gels. Proteins were electrophoretically transferred to nitrocellulose (Millipore, Bedford, Mass.) overnight at 15V in 20 mM Tris, pH 7.5, 150 mM glycine, 20% methanol and 0.1% SDS. The filters were blocked with 0.5% skim milk in 20 mM Tris pH 7.5, 500 mM NaCl (TBS) for 30 minutes at room temperature. The membrane was exposed to 1/1000 dilution of the appropriate antibody in blocking solution for 1 hour at room temperature,washed twice with TBS, and then exposed to a 1/3000 dilution of secondary antibody (goat anti-rabbit IgG-horse-radish peroxidase conjugate from BioRad). The conjugate was removed, washed three times with TBS and then developed using the HRP-substrate mixture. For the whole cell assay, iron-deficient or iron-sufficient (control) cells were directly spotted onto HA paper. After drying, the HA paper was treated with blocking solution and washed with TBS and then tested for reactivity with anti TbpA or anti TbpB antisera as described above. A control set of spotted cells was treated with HRP-bovine transferrin for 1 hour followed by development with HRP-substrate after washing in TBS.

PCR amplification of tbp genes and restriction endonuclease digest analysis. Amplification of tbpA and tbpB from *P. haemolytica* and *P. trehalosi* strains was performed on intact cells by the method of Saris et al.(1990). Amplification of tbpA was carried out with oligonucleotides tbpA 5' and tbpA 3' (#255 and #256, table2). Oligonucleotides #401 and # 199, (Table 10) were used to amplify tbpB. Reaction conditions consisted of 30 cycles of 94° C. for 1 min, 45° C. for 1 min, and 74° C. for 2 min. The PCR product was separated by 1% agarose gel electrophorsis in 0.5×TBE buffer (45mM Tris-borate, 1 mM EDTA, pH8.3) and stained with 0.5 mg of ethidium bromide per ml in the same buffer. For Sau3A restriction endonuclease (Gibco BRL) digestion, PCR products were subjected to phenol chloroform and ethanol precipitation and thereafter were digested with Sau3A. The digests were analysed with a 7.5% acrylamide gel run in 0.5×TBE buffer and visualised in the same way as the agarose gels described above.

RESULTS

Specificity of receptor binding. In a prior study it was demonstrated that transferrin receptors in representative isolates from pathogenic bacterial species varied in their interaction with goat, sheep and cattle transferrin (Yu and Schryvers 1996). Thus a set of representative isolates of *P. haemolytica* and *P. trehalosi* from cattle, sheep and goats (Table 9) were evaluated for their interactions with the different ruminant transferrins. All of these strains were capable of utilizing bovine, caprine or ovine transferrin as a source of iron for growth (data not shown). Immobilized, iron-deficient cells were positive for binding all three of the transferrins in a solid-phase binding assay (FIG. 25) and the three transferrins were equally effective at blocking binding to the cells in reciprocal competition binding assays (not shown). In addition, both TbpA and TbpB, molecular weights 100 Kda and 60 Kda respectively were effectively isolated by affinity resins containing immobilized bovine (FIG. 26, Panel A), caprine or ovine transferrin (not shown). These results indicate that the specificity of transferrin-binding within this group of related strains is indistinguishable.

Immunological analysis of transferrin receptor proteins. The observation that bovine, caprine and ovine transferrins compete for the same receptors suggested that there is conservation at least in the binding domain of the receptors. However, the extent of similarity between the individual receptor proteins from different serotypes was not known. To address this question, antibodies were raised against TbpA and TbpB individually and as a complex in rabbits using purified receptor proteins (TbpA and TbpB from a bovine strain h44).These antisera were then tested against receptor proteins from representative strains of different serotypes including isolates obtained from cattle, sheep and goats.

The results in FIG. 26, Panel B demonstrate that the antisera raised against purified TbpA and TbpB receptors from *P. haemolytica* serotype A1, strain h44, reacted strongly with similar purified receptors from all of the representative strains. Since there was variation in the yield of receptor proteins obtained from the various strains (FIG. 26, Panel A), this likely accounts for the slight differences observed in the reactivity of the antisera for a few of the strains (FIGS. 26, Panel B). Thus, these results suggest that both receptor proteins are conserved amongst the different serotypes of *P. haemolytica* causing pasteurellosis in cattle, sheep and goats.

Figure 26A:
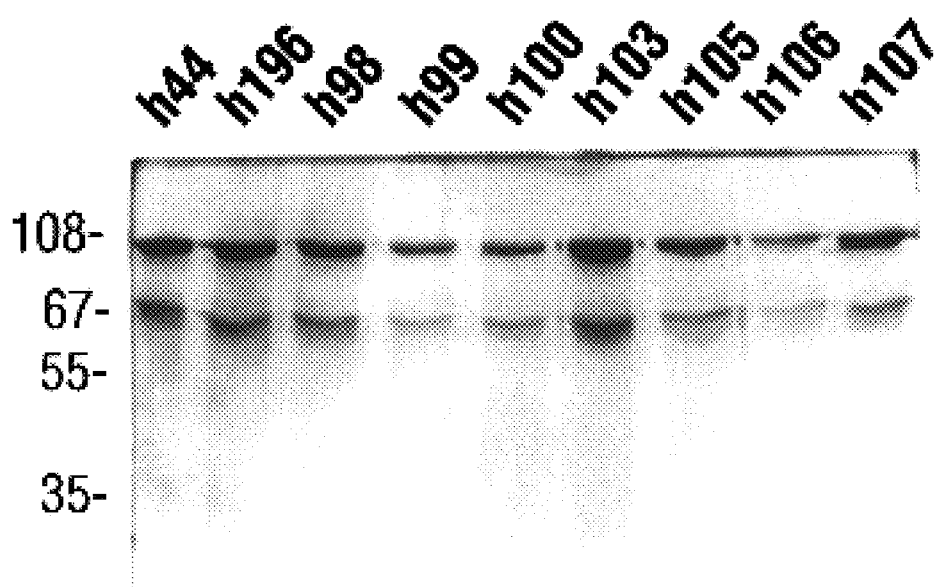
FIGS. 26A–26B are blots showing silver stain (Panel A), and western blot (Panel B) studies with anti-TbpA and anti-TbpB antisera from *P.haemolytica* serotype A1.
Figure 26B:
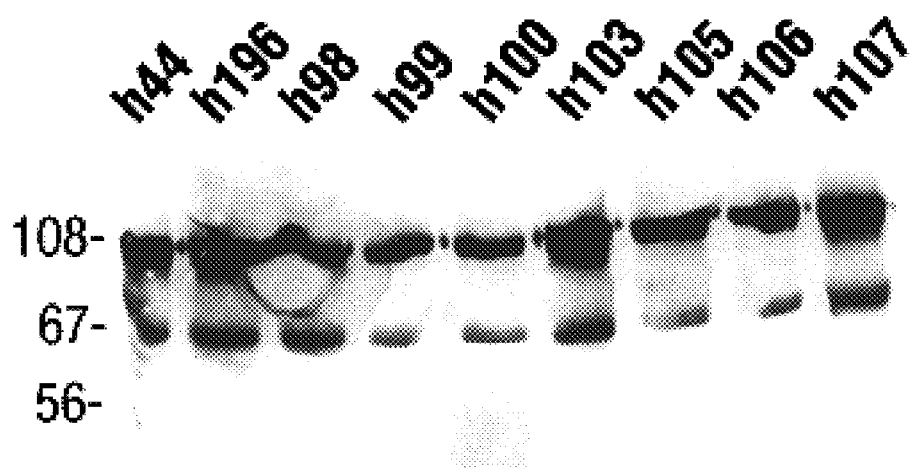
Figure 27:
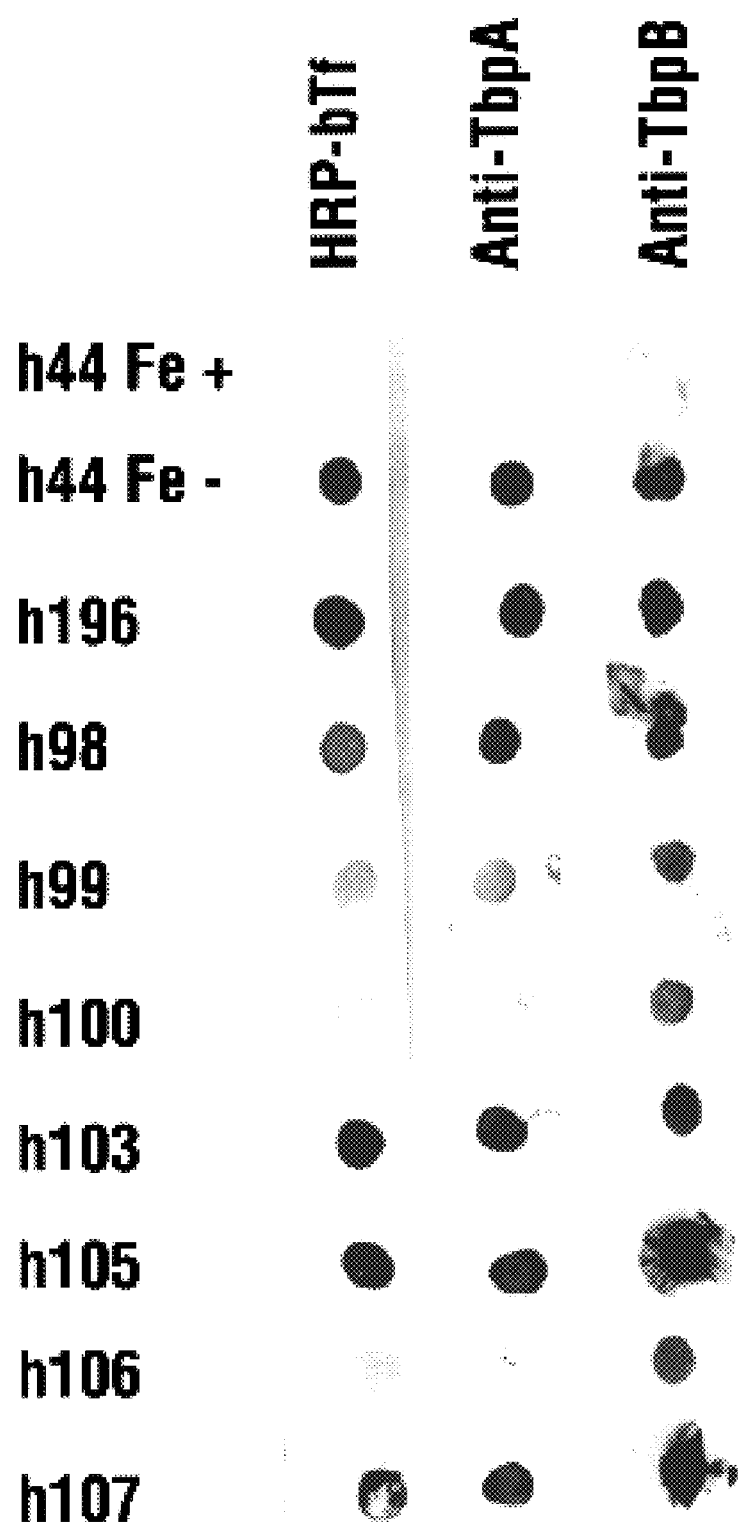
FIG. 27 is a blot showing the results of cross-reactivity studies with monospecific anti-TbpA and anti-TbpB antisera from *P. haemolytica* serotype A1 against intact cells.

Although this analysis indicates that there are crossreactive epitopes on the transferrin receptor proteins it does not provide any information as to whether there are crossreactive epitopes at the cell surface where they would be accessible to host immune effector mechanisms. As a first step in attempting to address this question the reactivity of intact iron-deficient cells from the different species to monospecific anti-receptor antisera was tested (FIG. 27). These experiments demonstrated that the monospecific antisera prepared against TbpA and TbpB from a type A1 strain of *P. haemolytica* reacted with type A1 strains (h44 and h196, FIG. 26, Panel B), several other A serotypes (h98, h103, h105, and h107), and reacted moderately with several *P. trehalosi* strains (h99, h100, h106). The monospecific antisera prepared against TbpA and TbpB from strain h44 reacted strongly with iron-limited whole cells from an extended collection of type A1 strains (data not shown), two of which (h44, h196) are illustrated in FIG. 27. There were varying degrees of reactivity with the other serotypes within *P. haemolytica* (h98, h103, h105 and h107) and *P. trehalosi* (h99, h100 and h106). The correlation between the signal obtained with the labelled bTf (FIG. 27) and with the anti-TbpA and anti-TbpB antisera (FIG. 27) in the different strains suggests that the observed reactivity in intact cells is primarily due to the receptor proteins. The absence of reactivity observed when control antiserum is utilized (data not shown) and the reduced reactivity in iron deficient cells (FIG. 26, Panel C) also supports this conclusion.

Genetic analysis of transferrin receptor protein genes. As a complement to the immunological studies the variability of the tbp genes from the various strains of *P. haemolytica* and *P. trehalosi* was evaluated. Using the sequence information obtained for the tbpA gene from a serotype A1 strain (28), specific primers were prepared for the 5 and 3 ends of the gene (primer #255 and #256, Table 10). These primers were capable of amplifying the intact tbpA genes from all the tested strains although only small yields were consistently obtained for strain h100. The intact genes (except from h100) were then subjected to digestion by the Sau3A restriction endonuclease and the resulting fragments were analyzed by electrophoresis on polyacrylamide gels. A specific pattern was observed in type A1 strains (h44 and h196, FIG. 28, Panel A) and was identical in all the seven type A1 strains that were tested (data not shown). This pattern was also present in most of the other serotypes within *P. haemolytica* (h105, h104, and h98, FIG. 28). Subtle changes in the pattern, involving one or more fragments, that is likely attributed to alteration of a single site, was observed for other type A strains (h103 and h107) and within the T strains (h106 and h99).

The restriction digestion analysis was unable to identify any differences between the tbpA genes in the A1 isolates. Thus, an alternative approach was adopted for rapidly and simply examining variation amongst the tbpA genes. This approach is based on the observation that there are segments of the TbpA (and LbpA) protein, proposed to be surface loops, which show the greatest variation in amino acid sequence among proteins from different species (21 and Legrain et al.1996). In particular, there is one large predicted loop, demonstrated to be at the surface by reactivity with a monoclonal antibody (21), in which the greatest variation in amino acid sequence was observed when aligning TbpAs from two meningococcal strains, one gonococcal strain and four *H.influenzae* strains (1; Loosemore et al.1996; Schryvers and Gonzalez 1996). An oligonucleotide primer was prepared (#450, Table 10) (SEQ. ID. NO.48; see also SEQ. ID. NOS.46 to 52) based on the known amino acid sequence (VEDTCPTLD) in this region for *P. haemolytica* typeA1 and used it in colony PCR amplification reactions in combination with a 5 specific primer (#255, Table 10) (SEQ. ID. NO.46) with the various strains. As illustrated in FIG. 29, Panel A, this oligonucleotide pair readily amplified the anticipated 800 bp PCR product under high stringency conditions from all of the strains except strain h100 where a comigrating band was barely discernable. These results suggest that there is considerable homology amongst the different serotypes of *P. haemolytica* and *P. trehalosi* even in the non-conserved amino acid regions in TbpA.

In order to evaluate the variation in the tbpB genes, a first attempt was made to amplify the intact genes from the various strains using specific primers for the 5 and 3 ends of the gene (primer#401 and #199, Table 10) (SEQ. ID. NOS.50 and 49). These primers readily amplified the intact tbpB gene from all the strains tested (Table 11). Restriction enzyme digestion analysis revealed that an identical digestion pattern was observed for all the seven A1 strains tested (see h44 and h196 in FIG. 28, Panel B) and some strains from the other groups (h105, h104 and h98). Only subtle differences in the pattern were detected in several of the other strains (h103, h107, h99, h106, FIG. 28, Panel B). Thus PCR-based approaches were used with oligonucleotide primers to variable regions to see if the variable domains found in other studies are subject to variation in *P. haemolytica*. A reverse oligonucleotide primer (#397, Table 10) (SEQ. ID. NO.51) was tested outside the reported conserved regions in tbpB (26) in combination with the 5' primer (#401, Table 10) (SEQ. ID. NO.49). Similarly, a forward primer (#400) from another variable region in combination with the 3 terminal oligonucleotide primer (#199) was used. The anticipated tbpB partial products were obtained for all the A and T strains tested except one T strain, h99 (FIG. 29B and Table 11) indicating that a considerable homology does occur not only at the 5' and 3' termini of the gene but also in a number of regions known to be variable in other species.

(biotype A) and *P. trehalosi* (biotype T) strains involved in this study includes different serotypes (Table 9), suggesting that the receptor-mediated iron acquistion mechanism is fairly widespread within these species. There was some variability in the expression of the transferrin binding activity amongst the various strains tested under the standard conditions used for the binding assay. Similar variation in the ability to bind the conjugated host transferrin (HRP-hTf) has been observed amongst *H. influenzae* strains (Robki et al.1993). This may be partly attributable to the varying growth characteristics of the different strains. However, the highly sensitive and specific nature of the binding assay enabled definitive identification of the presence of receptor activity in the strains tested.

The competitive binding experiments and the affinity isolation experiments indicate that interaction with all three ruminant transferrins is mediated by the same receptor proteins which show considerable similarity amongst the

TABLE 10

Oligonucleotide primers.

| # | Description | Direction | Sequence |
|---|---|---|---|
| 255 | tbpA - 5' end, NdeI site at start codon | forward | CCCTATCATATGATAATGAAATATCATC |
| 256 | tbpA - 3' end, HindIII site after stop | reverse | TAGCGCAAGCTTCTAAAACTTCATTTCAAAT |
| 450 | tbpA - variable region | reverse | TAATGTTGGGCAAGTATCTTCCAC |
| 401 | tbpB - 5' end | forward | TAAATTAAAGGAGACATTATGTTTAAACT |
| 199 | tbpB - 3' end, flanking HindIII site | reverse | GCGCAAGCTTTTATTTTTCTATTTGACG |
| 397 | tbpB - variable region, near 3' end | reverse | CTGTTGGCAAATCTGCCAGAG |
| 400 | tbpB - variable region, near middle | forward | AGGTAATCGCTTTTCTGGTAAAGC |

*Direction relative to orientation of coding strand for the relevant gene

TABLE 11

PCR-amplification of tbpA and tbpB gene segments from different serotypes of *Pasteurella haemolytica*.

| | Amplification of tbpA gene segments by oligo pair: Primer pair/product amplified | | Amplification of tbpB gene segments by oligo pair: Primer pair/product amplified | | |
|---|---|---|---|---|---|
| Strain | 255/256 | 255/449 | 401/399 | 401/199 | 400/199 |
| h44 | + | + | + | + | + |
| h93 | + | + | + | + | + |
| h94 | + | + | + | + | + |
| h95 | + | + | + | + | + |
| h96 | + | + | + | + | + |
| h97 | + | + | + | + | + |
| h196 | + | + | + | + | + |
| h99 | + | + | − | + | − |
| h100 | + | +/− | + | + | + |
| h103 | + | + | + | + | + |
| h104 | + | + | + | + | + |
| h105 | + | + | + | + | + |
| h106 | + | + | + | + | + |
| h107 | + | + | + | + | + |
| h174 | + | + | + | + | + |

Key:
+ = Product of anticipated size, comparable to the control (h196) obtained
+/− = Product of anticipated size but much weaker in intensity than the control
− = No product obtained.

Discussion

A collection of *P. haemolytica* and *P. trehalosi* isolates from other ruminants were found to be capable of acquiring iron from bovine, ovine and caprine transferrins (data not shown) which is presumed to be mediated by surface receptors that specifically bind ruminant transferrins (Al-Sultan and Aitken 1984). The collection of *P. haemolytica* various strains analyzed. This conclusion is further substantiated by the immunological analysis of receptor proteins prepared from a variety of *P. haemolytica* strains with monospecific sera against TbpA and TbpB (FIG. 26, Panel B). Since the immunological analysis included a variety of different serotypes within biotype A and T, it would appear that the transferrin receptor proteins are fairly conserved among *P. haemolytica* disease isolates from ruminants. Although there is considerable immunological cross-rectivity amongst the two receptor proteins in a variety of different *P. haemolytica* strains, this cross-reactivity should include epitopes present at the surface in vivo. Preliminary results with the whole cell/antibody analysis (FIG. 27) suggest the presence of such surface epitopes. The consistent pattern observed for whole cell/HRP-btf and whole cell/anti-Tbp reactivities for any given strain (FIG. 27) coupled with the greatly reduced reactivity observed for both reactions in the iron replete cells suggest that the reactivity observed is against iron regulated proteins.

An important consideration in the development of an effective vaccine against any bacterial species, is the spectrum of the vaccine against the different serotypes/biotypes of the infecting bacterial species. In *N. meningitidis* while TbpA proteins are relatively homogenous, the identification of two families in the species based upon the differences in the molecular masses and antigenic properties of their TbpB proteins (18) dictates the formulation of a heterogenous Tbp vaccine representative of the two families.

The 100 Kda transferrin receptor protein (TbpA), from bovine strain of *P.haemolytica*, serotype A1 (26) was identified by the affinity purification procedure of Schryver and Morris (32). Modification of that procedure, as described in the method section, has enabled us to identify the 60 Kda as the second transferrin binding protein in *P.haemolytica* analogous to TbpB in the other bacterial species (32 and Robki et al.1993). The affinity purification procedure isolated TbpA and TbpB of similar molecular weights from all of the strains of *P. haemolytica* and *P. trehalosi* examined (FIG. 26, Panel A). Our results in *P. haemolytica* and *P. trehalosi* showed that antisera raised against these two purified receptor proteins from a serotype A1, strain h44, specifically recognised the receptor proteins from other A1 strains (h196, FIG. 26, Panel B) and other A serotypes. These included an A11 serotype (h107) known to differ from the other A types in its reactivity with convalescent sera against the 35 Kda and 70 Kda iron regulated outer membrane proteins. The amounts of purified receptors from the T strains, h99 and h100 (FIG. 26, Panel A) and their with the antisera (FIG. 26, Panel B) appeared to be reduced compared with most of the A strains. This reduction in the antibody reactivity with the T strains was also observed in whole cell assay (FIG. 27). The reduction in the whole cell-antibody reactivity in these strains, however, was consistent with their reduced reactivity with HRP-bTf (FIG. 27). This suggests that the observed lower reactivity with the anti-TbpA and anti-TbpB antisera is likely due to differences in the expression of receptor proteins under the standard growth conditions used in these experiments.

The genes encoding TbpA and TbpB proteins, tbpA and tbpB are fairly homogeneous within serotype A1 (causing pneumonic pasteurellosis in cattle) and to a large extent, amongst the A types (causing pneumonia in sheep and goats) in general (FIG. 28). By extending the restriction enzyme digestion analysis to the *P. trehalosi* strains, we found only marginal differences (FIG. 28). The results of PCR- amplification experiments with specific 5' and 3' oligonucleotide primers and primers derived from the hypervariable regions (FIG. 29, Table 11) further supports the conclusion that the tbp genes within *P. haemolytica* species and *P. trehalosi* are relatively homogenous. These results contrast with the differences which have been observed for *H. influenzae* and *N. meningitidis* (1 and Loosemore et al.) but will need to be confirmed by sequence analysis of genes isolated from representative strains from a number of serotypes.

The lack of evident genetic hetereogeneity in the tbp genes and the apparent immunological crossreactivity of the Tbp proteins from a variety of *P. haemolytica* and *P. trehalosi* strains underscore their potential as broad-spectrum vaccine antigens for prevention of infection in ruminants.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

FULL CITATIONS FOR REFERENCES REFERRED TO IN THE SPECIFICATION

Abdullah et al., J. Bacteriol. 73:5597–5603, 1991
Adams et al., J. Am. Vet. Med. Assoc. 134:85–89, 1959
Aisen and Listowski, Annu. Rev. Biochem. 49:357:393, 1980
Al-sultan and Aitken. Res. Vet. Sci. 36:385–386,1984
Ala'Aldeen et al., Infect. Immun., 62:2984–2990, 1994
Alcantara et al., Mol. Microbiol., 8:113–1143, 1993
Archibald, FEMS Microbiol. Lett., 19:29–32, 1983.
Archibald and Devoe, Microbiol., Lett, 6:159–162, 1979
Archibald and Devoe, Infect. Immun. 27:322–334,1980
Bagg and Neilands, Biochemistry, 26:5471–5477, 1987
Bell et al., J. Bacteriol., 172:3826–3829. 1990
Benson and Silhavy, Cell., 32:1325–133, 9183
Berish et al., Mol. Microbiol. 6:2607–15, 1991
Biberstein, E. L., Microbiol. 10:253–269, 1960
Bigham et al., Am J. Vet. Res. 51:1161–1166, 1990
Birnboim et al., Nuci. Acids. Res. 7:1513–1523, 1979
Black et al., Infect. Immun. 54:710–713
Blood et al., Veterinary Medicnine. A Textbook of the Diseases of Cattle, Sheep Pigs and Horses, 5th ed. London: Bailliere Tindall. pp. 487–496, 1979
Bolin et al., Infect. Immun. 55:1239–1243, 1987
Boyd et al., Proc. Natl. Acad. Sci. USA, 81:6929–6933, 1990
Bradford, M., Anal. Biochem, 72:248–254,1976
Brewer et al, J. Mol. Biol. 216:883–895, 1990
Burnett, W. N., Anal. Biochem. 112:195–203, 1981
Burrows L. L., Molecular characterization of the RTX cytolysin determinants from Gram-negative phatogens of veterinary significance, PhD thesis. University of Guelph, Guelph, Ont.
Calder and Mekalanos, J. Bacteriol. 169:4759–4764, 1987
Carter G. R., J. Am. Med. Assoc. 169:862–864, 1973
Chen et al., Mol. Microbiol. 5:1405–13, 1993
Chenault and Earhart, Mol. Microbiol. 5:1405–13, 1991
Chengappa et al., Am. J. Vet. Res. 44:342–347, 1983
Chou and Fasman, Advances in Enz. 47:145–147,1978
Chricton et al., Eur. J. Biochem., 164:485–506, 1987
Church and Radostits, Can. Vet. 22:27–30, 1981
Cianciotto et al., Infect. Immun. 57:1255–1262, 1989
Clewell and Helinski, Biochemistry, 62:1159–1166, 1969
Coderre and Earhart, FEMS Microbiol. Lett. 25:111–116, 1984
Cohen et al., Proc. Natl. Acad. Sci. USA, 69:2110–2114, 1972
Colonna et al., J. Bacteriol. 162:307–316, 1985
Confer et al., Vet. Immun. Immunopath. 10:265–278, 1985
Confer et al, Am. J. Vet. Res., 45:2622–2624, 1984
Confer et al., Can. J. Vet. Res., 54: S48–552, 1990
Confer et al., Am. J. Vet. Res. 46:342–347, 1985
Confer et al., Am. J. Vet. Res., 48:163–168, 1987
Conlon et al., Infect. Immun., 59:587–591, 1991
Cooney and Lo, Infect. Immun. 61:4682–4688,1993
Cox et al, Proc. Natl. Acad. Sci., 78:4256–4260, 1981
Cox and Adams, Infect. Immun., 48:130–138,1985
Crosa et al., J. Bacteriol. 170:5539–5544, 1988
Davis and Hatefi, Biochemnistry, 10:2509–2512, 1971
DeLorenzo et al., J. Bacteriol., 171:2624–2630, 1987
DeLorenzo et al., Eur. J. Biochem., 173:537–546, 1988
Der Vartanian, M., Infect. Immun., 27:418–423, 1988
Donache et al. ,Vet. Immunol. Immunopathol., 11:265–279.1986
Dyer et al., Microb. Path., 3:387–395, 1987
Elikins and Earhart, J. Bacteriol., 171:5443–51, 1989
Emini et al., J. Virol., 55:856–839, 1985
Ernst et al., J. Bacteriol., 135:928–934, 1978
Evans and Williams, Biochem. J., 189:541–546, 1980
Fasano et al., Infect. Immun. 58:3717–3723, 1990
Fasman and Gilbert, Trends Biochem. Sci. 15:89–92, 1990
Feinberg and Vogelstein, Anal. Biochem., 132:6–13, 1983
Feinbert and Vogelstein, Anal. Biochem., 137:266–267, 1984
Ferrón et al., FEMS Microbiol. Left., 109:159–166, 1993

Flemming et al., Gene, 34:47–54, 1985
Flitter et al., FEBS Let. 158:310–312, 1983
Fohn et al., Infect. Immun., 55:3065–69, 1987
Frank and Tabatabai, Infect. Immun., 32:1119–1122, 1983
Frank and Smith, Am. J. Vet. Res. 44:981–985, 1983
Frank, G. H., Vet. Med. 83:1050–1064, 1988
Friend et al., Can. J. Comp. Med., 41:219–223, 1977
Frost and Rosenberg, J. Bacteriol., 124:704–12, 1975
Genco et al., FEMS Mircrobiol. Lett., 116–123–130, 1994
Gerlach et al., Mol. Microbiol., 5:892–898, 1992
Gonzales-Rayos et al., Infect. Immun., 53:505–510, 1986
Griffiths, E. Iron in biological systems. In: Iron and infection: molecular, clinical and physiological aspects (Bullen, J. J. and Griffiths E., Eds.) Wiley, Chichester. pp. 1–25.
Griffiths et al., FEMS Microbiol. Lett., 109:85–92, 1993
Guterman and Dann, J. Bacteriol., 114:1225–1230, 1973
Hancock and Carey, J. Bacteriol., 140:902–910, 1979
Hantke and Zimmerman, FEMS Microbiol. Lett., 12:32–35, 1981
Harkness et al., J. Bacteriol., 174:2425–2430, 1992
Hayashi and Wu, J. Bacteriol., 161:949–954, 1985
Hayward, G. S., Virology, 49:342–344, 1972
Higgins and Sharp, Gene, 73:237–244,1988
Higgins and Sharp, CABIOS, 5:151–153, 1989
Ho et al., J. Exp. Med., 172:795–806, 1990
Hoerlein and Marsh, J. Am. Vet. Med. Assoc., 131:12–127, 1957
Holland et al., Infect. Immun., 60:2986–2991, 1992
Hollifield and Neilands, Biochemistry, 17:1922–1929, 1978
Holt, J. G., ed. Genus Pasteurella In: The shorter Bergey's manual of determinative bacteriology. Williams and Wilins co., Baltimore, Maryland, p. 137
Isch-Horowicz and Burke, Nud. Acids. Res., 9:2989–2998, 1981
Jahnig, F., Trends. Biochem. Sci., 15:93–95, 1990
Janin et al., J. Mol. Biol., 125:357–386
Jarosik et al., Infect. Immun., 62:2470–2477, 1994
Jensen and Mackey, Shipping fever penumonia. In: Diseases of Feedlot Cattle, 3rd ed. Philadelphia: Lea and Febiger. p. 65.
Jensen et al, J. Am. Vet. Med. Assoc., 169:500–506, 1976
Jim et al., Vet. Med., 83:1084–1087, 1988
Kyte and Doolittle, J. Mol. Biol., 157:105–132, 1982
Laemmli, U. K., Cleavage of structural protens during the assembly of bacteriophage T4. Nature (London) 277:680–685, 1970
Lainson et al., J. Gen. Microbiol. 137:219–226.
Lederberg and Cohen, J. Bact., 119:1072, 1974
Lee and Bryan, J. Med. Microbiol., 28:199–205, 1989
Legrain et al.,Mol. Microbiol. 19:159–169.1996
Lillie and Thomson, Can. J. Comp. Med., 36:129–137,1972
Litwin et al., J. Bacteriol., 174:1897–1903, 1992
Liu et al., Proc. Natl. Acad. sci. USA, 90:10653–10657, 1993
Lo, R.Y.C., FEMS Microbiol. Lett., 100:125–132, 1992
Lo et al., Infect. Immun. 54:73–76,1985
Lo, R.Y.C. et al., Infect. Immun. 50:667–671, 1985
Lo et al., Infect. Immun. 55:1987–1996, 1987
Lo et al., Can. J. Biochem. Cell. Biol., 64:73–76, 1986
Lo et al., Infect. Immun., 59:3398–3406, 1991
Loosmore et al.,Mol. Microbiol. 19:575–586.1996
Luckey et al., J. Bacteriol., 111:731–735, 1972
Mandel, J., J. Mol. Biol., 53:159–162, 1970
Marmer, J., J. Mol. Biol., 3:208–218, 1961
Martin et al., Can. J. Comp. Med., 44:1–10, 1980
Mazurier, J. and G. Spik, 1989 Biochim, Biophys. Acta 629:399–408
McKenna et al., Infect. Immun., 56:785–791, 1988
Mickelsen et al., Infect. Immun., 35:915–920, 1982
Mickelsen and Sparling, Infect. Immun. 33:555–564,1981
Mietzner et al., Infect. Immun., 45:410–416, 1984
Mietzner et al, Infect. Immun., 51:60–68, 1986
Mietzner and Morse, Annu. Rev. Nutr., 14:471–493
Morck et al., J. Bacteriol., 176:4250–4259, 1994
Morck et al., Microbiol Pathogenesis, 11:373–378,1991
Morton et al., Infect. Immun. 61:4033–4037, 1993
Morton et al., J. Gen. Microbiol., 136:927–933, 1989
Mosier et al., Infect. Immun. 57:711–716, 1989
Murray et al., J. Gen. Microbiol., 138:283–288, 1992
Neilands, J. B., Annu. Rev. Microbiol., 50:715–731, 1981
Newsome and Cross, J. Am. Vet. Med. Assoc., 80:711–719, 1932
Niederhoffer et al., J. Bacteriol., 172:1930–1938, 1990
Otto et al., Crit. Rev. Microbiol., 18:217–233, 1992
Otulakowski et al., Infect. Immun., 42:2538–2537, 1983
Panciera and Corstvet, Am. J. Vet. Res., 45:238–2542, 1984
Payne, S. M., Crit. Rev. Microbiol., 16:81–111, 1988
Petterson et al., Infect. Immun. 58:3036–3041, 1990
Pidcock et al., Infect. Immun. 56:721–725, 1988
Postle et al, Mol. Microbiol., 4:2019–2025
Prince et al., Mol. Microbiol., 5:2823–2831, 1991
Rehmtella and Tomson, Can. Vet. J. 22:1–8, 1981
Rokbi et al., FEMS Microbiol. Lett., 110:51–58, 1993
Romslo and Thorstensen et al., Biochem. J., 271:1–10,1990
Russell et al., Infect. Immun., 45:143:149, 1984
Rutz et al., Science, 258:471–475, 1992
Saiki et al., Science, 239:487–491, 1988
Sanders et al., Infect. Immun., 62:4515–4525, 1994
Sanger et al., Proc. Natl. Acad. Sci. USA. 74:5463–5467, 1977
Saris et al., J.Microbiol.Methods,11:121–126.1990
Schneider and Williams, J. Cell. Sci., 3:139–149, 1985
Schryvers, A. B., J. Med. Microbiol., 29:121–130, 1989
Schryners and Lee, Infect. Immun., 35:409–415,1989
Schryvers and Gonzalez,Can. J. Microbiol. 36:145–147.1990
Schryvers, USP 5,141,743, 1992
Sharp et al., Biochemnistry, 12:3055–3063, 1973
Shea and McIntosh, Mol. Microbiol., 5:1415–28, 1991
Shewen and Wilkie, Can. J. Vet, Res, 52:30–36, 1987
Shewen and Wilkie, Vet. Med., 83:1078–1083, 1988
Shewen and Wilkie, Can. J. Vet. Med., 52:30–34, 1988
Shoji and Ozawa, J. Cell. Physiol., 127:348–356, 1986
Simonson et al., Infect. Immun., 36:107:113, 1982
Smith and Stevens, Int. J. Sys. Bacteriol., 40:148–153, 1990
Southern, E. M., J. Mol. Biol., 98:503–517, 1975
Staggs and Perry, Mol. Microbiol. 6:2507–2516, 1991
Stevenson et al., Infect. Immun., 60:2391–2396, 1989
Strathdee and Lo, J. Bacteriol., 171:5955–5962, 1989
Straus et al., Infect. Immun., 62:253–59, 1993
Struyve et al., J. Mol. Biol., 218:141–148, 1991
Tabor and Richardson, Proc. Natl. Acad. Sci. USA, 82:1074–1078, 1985
Thomas and Sparling, Mol. Microbiol., 11:725–737, 1994
Thompson et al., J. Bacteriol., 175:811–818, 1993
Thomson et al., Can. J. Comp. Med., 33:194–206,1969
Tsai et al., Infect. Immun., 56:3132–3138, 1988
Vogelstein and Gillespie, Proc. Natl. Acad. Sci. USA, 76:615–619, 1979
Von Heijne, G., Eur. J. Biochem, 133:17–21, 1983
Wahl et al., Proc. Natl. Acad. Sci. USA, 76:3688–3687, 1979
Weinberg, E. D., Quart. Rev. Biol., 64:261–290, 1989
Weinberg and Sparling, Microbiol. Rev. 42:45–66
West et al., Infect. Imnun., 47:388–394, 1985

Williams and Griffiths, Med. Microbiol. Immunol., 181:301–322, 1992

Wooldridge and Williams, FEMS Microbiol. Rev., 12:325–348, 1993

Wu, H. C., Posttranslational modification and processing of membrane proteins in bacteria. In: M. Inouye, ed., Bacterial outer membranes as model systems. New York. John Wiley and Sons. pp. 37–71.

Yanisch-Perron et al., Gene, 33:103–119, 1985

Yates, W. D. G., Can. J. Comp. Med., 46:225–263, 1982

Yu and Schryvers,j. Bacteriol. in press.1996

1. Anderson, J. A., P. F. Sparling and C. N. Cornelissen. 1994. Gonococcal transferrin-binding protein 2 facilitates but is not essential for transferrin utilization. J.Bacteriol. 176:3162–3170.
2. Arnold, R. R., J. E. Russel, W. J. Champion, M. Brewer and J. J. Gauthier. 1982. Bactericidal activity of human lactoferrin: differentiation from the stasis of iron deprivation. Infect.Immun. 35:792–797.
3. Babiuk, L. A. and S. D. Acres. 1984. Model for bovine respiratory disease p. 287–325. In R. W. Loan Bovine Respiratory Disease :a symposium. Texas A.& M. University Press, College Station,Texas,
4. Benson, M. L., R. G. Thomson and V. E. O. Valli. 1978. The bovine alveolar macrophages ii In vitro studies with *Pasteurella haemolytica*. Can.J.Comp.Med. 42:368–369.
5. Biberstein, E. L. 1978. Biotyping and serotyping of *Pasteurella haemolytica*. Methods, Microbiol. 10:253–269.
6. Biberstein, E. L., M. Gills and H. Knight. 1960. Serological types of *Pasteurella haemolytica*. Cornell Vet. 50:283–300.
7. Bullen, J. J. 1981. The significance of iron in infection. Rev.Infect.Dis. 3:1127–1138.
8. Cornelissen, C. N., G. D. Biswas, J. Tsai, D. K. Paruchuri, S. A. Thompson and P. F. Sparling. 1992. Gonococcal transferrin-binding protein 1 is required for transferrin utilization and is homologous to TonB-dependant outer membrane receptors. J.Bacteriol. 174:5788–5797.
9. Deneer, H. G. and A. A. Potter. 1989. Iron-repressible outer-membrane proteins of *Pasteurella haemolytica*. J.Gen.Microbiol. 135:435–443.
10. Donachie, W. and N. J. L. Gilmour. 1988. Sheep antibody response to cell wall antigens expressed in vivo by *Pasteurella haemolytica* serotype A2. FEMS Microbiol.Lett. 56:271–276.
11. Finkelstein, R. A., C. V. Sciortino and M. A. McIntosh. 1983. Role of iron in microbe-host interactions. Rev.Infect.Dis. 5:s759–s777.
12. Fraser, J., S. Lard and N. J. L. Gilmour. 1982. A new serotype (biotype T) of *Pasteurella haemolytica*. Res.Vet.Sci. 32:127–128.
13. Gentry, M. J., A. W. Confer and R. J. Panciera. 1985. Serum neutralization of cytotoxin from *Pasteurella haemolytica* serotype I and resistance to experimental bovine pneumonic pasteurellosis. Vet.Immunol.Immunopathol. 9:239
14. Gerlach, G.-F., S. Klashinsky, C. Anderson, A. A. Potter and P. J. Willson. 1992. Characterization of two genes encoding distinct transferrin-binding proteins in different *Actinobacillus pleuropneumoniae* isolates. Infect.Immun. 60:3253–3261.
15. Gilmour, N. J. L., W. Donachie, A. D. Sutherland, J. S. Gilmour, G. E. Jones and M. Quirie. 1991. Vaccine containing iron-regulated proteins of *Pasteurella haemolytica* A2 enhances protection against experimental pasteurellosis in lambs. Vaccine 9:137–140.
16. Gilmour, N. J. L. and J. S. Gilmour. 1989. Pasteurellosis of sheep p. 223–262. In C. Adlam and J. M. Rutter Pasteurella and Pasteurellosis. Academic Press, London,
17. Gilmour, N. J. L., W. B. Martin, J. M. Sharp, D. A. Thompson, P. W. Wells and W. Donachie. 1983. Experimental immunization of lambs against pneumonic pasteurellosis. Res.Vet.Sci. 35:80–86.
18. Gonzalez, G. C., D. L. Caamano and A. B. Schryvers. 1990. Identification and characterization of a porcine-specific transferrin receptor in *Actinobacillus pleuropneumoniae*. Mol.Microbiol. 4:1173–1179.
19. Gonzalez, G. C., R.-H. Yu, P. Rosteck and A. B. Schryvers. 1995. Characterization of the *Actinobacillus pleuropneumoniae* transferrin receptor genes and their products. Microbiol. 141:
20. Gray-Owen, S. D., S. Loosemore and A. B. Schryvers. 1995. Identification and characterization of genes encoding the human transferrin binding proteins from *Haemophilus influenzae*. Infect.Immun. 63:1201–1210.
21. Gray-Owen, S. D. and A. B. Schryvers. 1995. Bacterial transferrin and lactoferrin receptors. Trends in Microbiology in press.
22. Herrington, D. A. and P. F. Sparling. 1985. *Haemophilus influenzae* can use human transferrin as a sole source for required iron. Infect.Immun. 48 (1):248–251.
23. Legrain, M., E. Jacobs, S. W. Irwin, A. B. Schryvers and M. J. Quentin-Millet. 1993. Molecular cloning and characterization of *Neisseria meningitidis* genes encoding the transferrin binding proteins Tbp1 and Tbp2. Gene 130:73–80.
24. Lissolo, L., P. Dumas, G. Maitre and M. J. Quentin-Millet. 1994. Preliminary biochemical characterization of transferrin binding proteins from *Neisseria meningitidis* p. 399–405. In C. J. Conde-Glez, S. Morse, P. Rice, F. Sparling and E. Calderon Pathobiology and Immunobiology of Neisseriaceae.
25. O'Reilly, T. and D. F. Niven. 1985. Tryptone-yeast extract broth as a culture medium for *Haemophilus pleuropneumoniae* and *Haemophilus parasuis* to be used as challenge inocula. Can.J.Vet.Res. 50:441–443.
26. Ogunnariwo, J. A. and A. B. Schryvers. 1990. Iron acquisition in *Pasteurella haemolytica*: Expression and identification of a bovine-specific transferrin receptor. Infect.Immun. 58:2091–2097.
27. Ogunnariwo, J. A. and A. B. Schryvers. 1992. Correlation between the ability of *Haemophilus paragallinarum* to acquire ovotransferrin-bound iron and the expression of ovotransferrin-specific receptors. Avian Dis. 36:655–663.
28. Pettersson, A, V. Klarenbeek, J. van Deurzen, J. T. Poolman and J. Tommassen. 1994. Molecular characterization of the structural gene for the lactoferrin receptor of the meningococcal strain H44/76. Microbial Pathogenesis 17:395–408.
29. Schryvers, A. B. and G. C. Gonzalez. 1989. Comparison of the abilities of different protein sources of iron to enhance *Neisseria meningitidis* infection in mice. Infect.Immun. 57:2425–2429.
30. Schryvers, A. B. and S. Gray-Owen. 1992. Iron acquisition in *Haemophilus influenzae*: Receptors for human transferrin. J.Infect.Dis. 165 Suppl. 1: S103–S104.
31. Schryvers, A. B., S. W. Irwin, M. J. Middelveen, J. A. Ogunnariwo and J. Alcantara. 1991. Iron acquisition in Neisseria: Bacterial receptors for human transferrin and human lactoferrin in *Neisseria meningitidis* p. 481–486.In M. Achtman, P. Kohl, C. Marchal, G. Morelli, A. Seiler and B. Thiesen Neisseriae 1990. Walter de Gruyter, Berlin, 32. Schryvers, A. B. and L. J. Morris. 1988. Identification and characterization of the transferrin receptor from *Neisseria meningitidis*. Mol.Microbiol. 2:281–288.
33. Shewen, P. E. and B. N. Wilkie. 1983. *Pasteurella haemolytica* cytotoxin neutralizing activity in sera from Ontario beef cattle. Can.J.Comp.Med. 47:497
34. Sneath, P. H. A. and M. Stevens. 1990. *Actinobacillus rossii* sp. nov.,*Actinobacillus seminis* sp. nov., nom. rev., *Pasteurella bettii* sp. nov., *Pasteurella lymphangitidis* sp. nov., *Pasteurella mairi* sp. nov. and *Pasteurella trehalosi* sp. Int.J.Syst.Bacteriol. 40:148–153.
35. Sutherland, A. D., W. Donachie, G. E. Jones and M. Quirie. 1989. A crude cytotoxin vaccine protects sheep against experimental *Pasteurella haemolytica* serotypes A2 infection. Vet.Microbiol. 19:147–181.
36. Wilkie, B. N., R. J. F. Markham and P. E. Shewen. 1980. Response of calves to lung challenge exposure with *Pasteurella haemolytica* after parental or pulmonary immunisation. Am.J.Vet.Res. 41:1773–1778.
37. Wilson, M. B. and P. K. Nakane. 1978. Recent developments in the periodate method of conjugating horseradish peroxidase (HRPO) to antibodies p. 215–224. In W. Knapp, K. Holubar and G. Wick Immunofluorescence and Related Staining Techniques. Elsevier/North Holland Biomedical Press, Amsterdam,
38. Yu, R.-H., S. D. Gray-Owen, J. Ogunnariwo and A. B. Schryvers. 1992. Interaction of ruminant transferrin receptors in bovine isolates of *Pasteurella haemolytica* and *Haemophilus somnus*. Infect.Immun. 60:2992–2994.

DETAILED FIGURE LEGENDS

FIGS. 1A–1B. Result of PCR Analysis
a) Schematic diagram of the PCR procedure—Each circle represents a recombinant pBR322 plasmid and a possible PCR reaction. The Tbp1 primer, primer left and primer right are represented by the letters t, l and r respectively. The EcoRI site on the pBR322 plasmid is denoted by the letter, E. In the upper plasmid, the Tbp1 primer and primer left would amplify a PCR product corresponding to the heavy line. Similarly in the lower plasmid, the PCR product amplified by Tbp1 primer and primer right is represented by the heavy line.
(b) The 0.8 kb PCR product amplified by Tbp1 primer and primer left.

FIG. 2. Restriction endonuclease map of tbp plasmids 9, 10 and 482. Open box—pBR322 presented linearly. Cross-hatched box—PCRII presented linearly. The positions and the orientations of tbpA, tbpB are as shown by the dark arrows.

FIGS. 3A–3E. Preliminary nucleotide sequence of *P. haemolytica* tbpA and tbpB. Putative signal sequence cleavage sites are indicated by an arrow. The start codon (ATG) is underlined.

FIG. 4. The promoter region of *P. haemolytica* tbpB (PHTBPB). The putative Fur consensus sequence is indicated by asterisks. The Fur consensus sequences of *N. gonorrhoeae* tbpB (NGTBPB) and *N. meningitidis* tbpB (NMTBPB) are also indicated.

FIG. 5. Southern hybridization of *P. haemolytica* genomic DNA digested with ClaI and probed with the tbpA gene. Lanes 1–16 represent *P. haemolytica* serotypes 1 to 16. Lane M represents lambda DNA digested with Hind III and hybridized with lambda DNA radiolabelled separately as size markers.

FIG. 6. Southern hybridization of *P. haemolytica* genomic DNA digested with HindIII and BamHI and probed with the tbpA gene. Lanes 1–16 represent *P. haemolytica* serotypes 1–16. The molecular sizes are as indicated on the left.

FIG. 7. Southern hybridization of *A. suis* 3714, *A. pleuropneumoniae* CM5 and shope 4074 genomic DNA digested with various restriction endonucleases and probed with *P. haemolytica* tbpA. Lane M represents lambda DNA digested with Hind III and hybridized with lambda DNA radiolabelled separately as size markers.

FIG. 8. Restriction maps of the tbpA, tbpB regions in *P. haemolytica* A1, *A. pleuropneumoniae* CM5, Shope 4074 and *A. suis* 3714. Line 1 represents the tbpA probe used in FIG. 15. Line 2 represents the tbpA probe used in FIGS. 16 and 17.

FIGS. 9A–9C. Alignment of the amino acid of Tbp1 of *P. haemolytica* A1 (PHTBP) and the Tbp1 of *N. gonorrhoeae* (NGTBP1) and *N. meningitidis* (NM1). The numbers to the right indicate amino acid positions. Asterisks indicate positions of complete identity in alignment, dots indicate similar amino acid residues. Gaps were introduced to maximize sequence alignment and are indicated by dashes (–).

FIGS. 10A–10B. Alignment between *P. haemolytica* A1 Tbp1 (PHTBPI) and the *A. pleuropneumoniae* serotype 1 and 7 TfbA proteins (APL, APL7). Asterisks indicate positions of complete identity in alignment, dots indicate similar amino acid residues. Gaps were introduced to maximize sequence alignment and are indicated by dashes (–).

Figure 11:
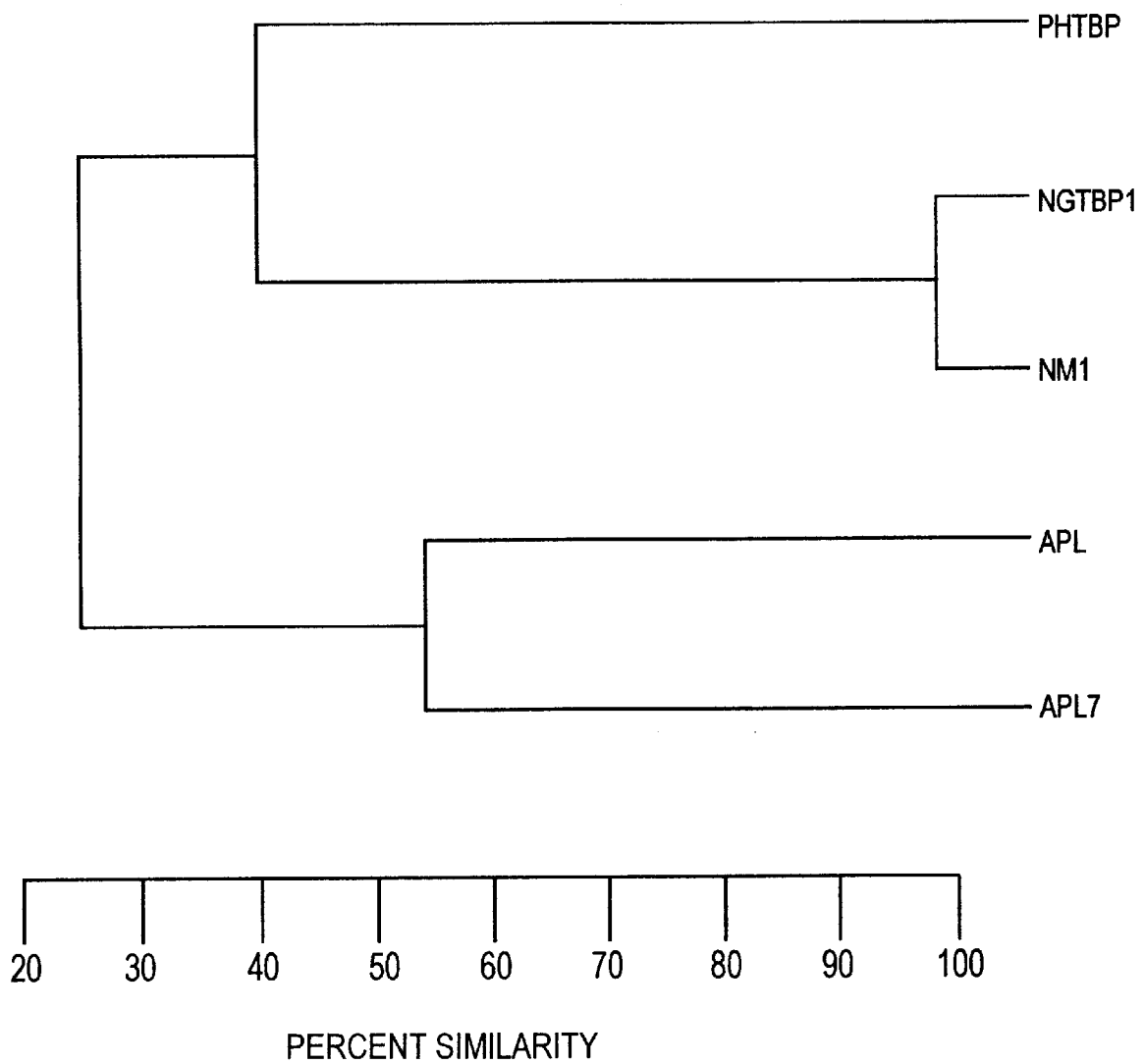
FIG. 11 is a dendogram illustrating the genetic relatedness among *P. haemolytica* A1, (PHTBP) and the Tbp1 of *N.gonorrhoeae* (NGTBP1), *N. meningitidis* (NM1) and *A. pleuropneumoniae* serotype 1 and 7 TfbA proteins (APL, APL7)

FIG. 11. Dendrogram illustrating the genetic relatedness among *P. haemolytica* Tbp1 (PHTBP), *N. gonorrhoeae* Tbp1 (NGTBP1), *N. meningitidis* Tbp1 (NM1) and the TfbA proteins from *A. pleuropneumoniae* serotype 1 and 7 (APL1, APL7).

FIG. 12. Peptide alignment between *P. haemolytica* A1 Tbp1 and TonB-dependent outer membrane receptors of *E. coli*. Asterisks show amino acids with complete identity in alignment, dots indicate similar amino acid residues. Gaps were introduced to maximize sequence alignment and are inidcated by dashes (–).

FIG. 13. T7 analysis of the *P. haemolytica* Tbp1 protein. The molecular weight marks in kDa are as indicated on the left. Lane 1—positive control recombinant plasmid. Lane 2—the recombinant plasmid containing tbpA. Lane 3—the vector plasmid pBluescript (SK)

FIG. 14. Western immunoblot of inner and outer membranes from *P. haemolytica* A1 and *E. coli* HB101. The first antibody was a rabbit antiserum raised to the soluble antigens of *P. haemolytica* A1 and the second antibody was goat anti-rabbit alkaline phosphatase conjugate. Lane M represents the molecular weight markers in kDa. Lanes 1–4 represent outer membrane fractions and lanes 5–8 are inner membrane fractions. 6 μg of protein was added to each lane. Lanes 1 and 5—*E. coli* proteins from cells grown in LT. Lanes 2 and 6—proteins from cells grown in BHIB. Lanes 3 and 7—proteins from cells grown in BHIB plus 100 μM EDDA. Lanes 4 and 8—proteins from cells grown in BHIB plus 100 μM EDDA with 1 MM FeSo$_4$ added.

FIG. 15. Western immunoblot of inner and outer membranes from *P. haemolytica* A1 and *E. coli* HB101 using sera raised in calves to soluble antigens by vaccination with Presponse®. The second antibody was goat anti-bovine alkaline phosphatase conjugate. Lane M represents the molecular weight markers in kDa. Lanes 1–4 are outer membrane fractions and lanes 5–8 are inner membrane fractions. 6 μg of protein was added to each lane. Lanes 1 and 5—*E. coli* proteins from cells grown in LT. Lanes 2 and 6—proteins from cells grown in BHIB. Lanes 3 and 7—proteins from cells grown in BHIB plus 100 μM EDDA. Lanes 4 and 8—proteins from cells grown in BHIB plus 100 μM EDDA with 1 mM FeSo$_4$ added.

FIG. 16. Binding of labelled transferrins by iron-deficient bacterial membranes. Aliquots of total membranes (4 μg protein) prepared from iron-deficient cells from the indicated bacterial strains were spotted onto strips of nitrocellulose/cellulose acetate paper and, after blocking, the papers were exposed to mixtures containing 450 ng/ml of the indicated HRP-conjugated transferrin. The filters were subsequently washed and developed with HRP substrate mixture as described in the Methods section. h173, h174, h175, h176 and h44 are representative strains of *P. haemolytica* whose serotype and source are listed in Table 1. h50—*A. equuli*. HRP-bTf,-oTf,-cTf and -eTf -HRP conjugates of bovine, ovine, caprine and equine transferrins.

Figure 17A:
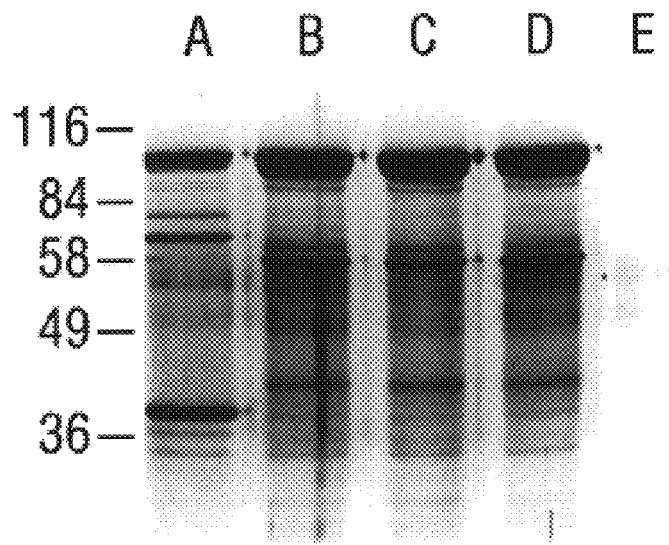
FIGS. 17A–17C is an immunoblot showing isolation of receptor proteins with transferrin affinity columns.
Figure 17B:
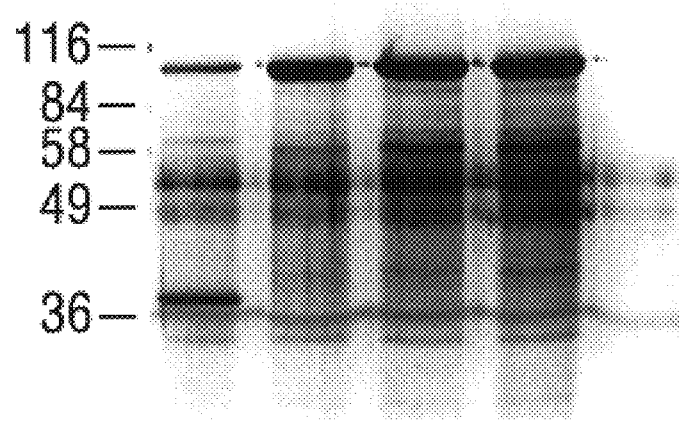
Figure 17C:
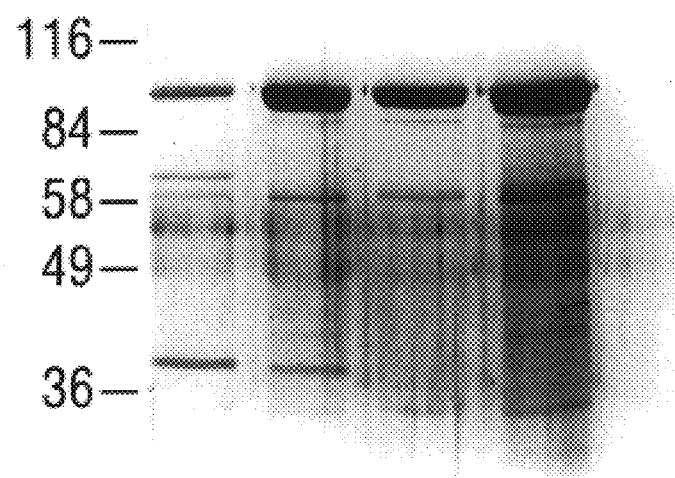

FIGS. 17A–17C. Isolation of receptor proteins with transferrin affinity columns. Affinity isolation experiments were performed with iron-deficient total membranes prepared from *P. haemolytica* strain h44 (top panel), h173 (middle panel) and h175 (bottom panel). Experiments were performed with bovine transferrin-Sepharose (lanes A and B), ovine transferrin-Sepharose (lane C), caprine transferrin-Sepharose (lane D) or equine transferrin-Sepharose (lane E) using standard washing conditions (lanes B-E) or low salt washing conditions (lane A) as outlined in the methods section. The samples eluted with buffer containing 2M guanidine HCl were dialyzed, concentrated and aliquots analyzed by SDS-PAGE and silver staining as described in the methods section.

Figure 18A:
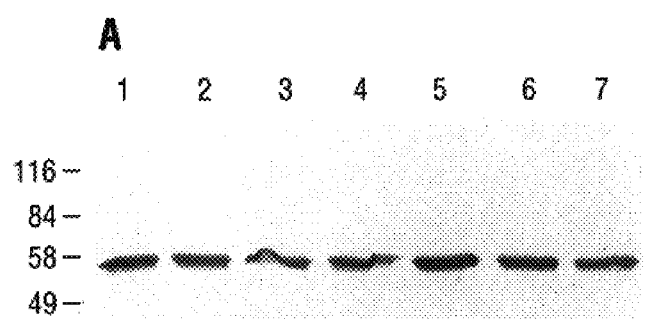
FIGS. 18A and 18B are immunoblots showing immunological analysis of receptor proteins from different serotypes of *P. haemolytica* from bovine, sheep, and goats, where Panel A is with anti-TbpB serum and Panel B is with anti-TbpA serum.
Figure 18B:
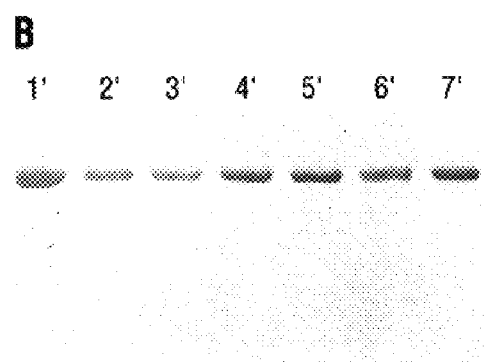

FIGS. 18A–18B. Immunological analysis of receptor proteins from different serotypes of *P. haemolytica* from bovine, sheep and goats. Aliquots of purified receptor proteins from representative serotypes of *P. haemolytica* were subjected to SDS-PAGE, electroblotted and then probed with specific anti-TbpB serum (Panel A) or with anti-TbpA serum (Panel B) as described in the methods section. The following *P. haemolytica* strains of the indicated serotype were included in the analysis; Lane 1—strain h44 (A1), Lane 2—h173 (untypable), Lane 3—h175 (A7), Lane 4—h176 (A9), Lane 5—h100 (T4), Lane 6—h106 (T10), and Lane 7—h107 (A11). The numbers on the left represent the molecular weights (×1000) of standard proteins.

FIGS. 19A–19C. Binding of labelled transferrin and antireceptor antibody by intact cells. The indicated bacterial strains were grown under iron-limiting conditions, harvested by centrifugation and resuspend to a $A_{600}$ of 1–2 in 50 mM TrisHCl, 150 mM NaCl, pH 7.5 buffer. A 5 μl aliquot of the suspensions were applied to HA membrane, the membrane was dried, blocked and then exposed to blocking solution containing labelled transferrin (HRP-bTf) or antireceptor antibody (anti-TbpA, anti-TbpB). The latter membranes were washed and subsequently exposed to labelled second antibody prior to development with substrate.

FIGS. 20A–20B. Map of the *P. haemolytica* tbp operon (Top) and regulatory sequences (Bottom). tbpA and tbpB are the genes encoding for TbpA and TbpB, respectively; p, is the putative promoter region preceding tbpB and denoted as −35 and −10 sites at the bottom. A putative Fur box is represented as two arrows in opposite directions in the sequence at the bottom; rnaseT and fis are two ORFs flanking the *P.haemolytica* tbp operon encoding for proteins highly homologous to *E. coli* and *H. influenzae* RNase transferase and factor-for-invertion stimulation proteins, respectively. Additionally, putative ribosomal binding site or Shine-Dalgarno (SD) consensus sequence, transcriptional start (Met), and stop codons (SC) are also bolded.

FIG. 21. The DNA sequence of the tbpA gene from *P. haemolytica* strain H196.

FIG. 22. Predicted amino acid sequence of the TbpA protein from *Pasteurella haemolytica* strain H196. Italicized amino acids correspond to the experimentaly determined N-terminal amino acids of the mature protein. Residues indicated by strikethrough constitute the leader peptide region. Residues that are identical in TbpAs from *Neisseria meningitidis, N. gonorrhoeae, H. influenzae* and *Actinobacillus pleuropneumoniae* are bold and underlined. Regions proposed as internal segments (dark shading), intermembrane b-strands (light shading) or external segments (no shading) based on the proposed topology model by Tommassen (28) are indicated.

FIG. 23. The DNA sequence to the tbpB gene from *P. haemolytica* strain H196.

FIG. 24. Predicted amino acid sequence of the TbpB protein from *P. haemolytica* strain H196. Italicized amino acids correspond to the predicted N-terminal amino acids of the mature protein. Residues indicated by strikethrough constitute the leader peptide region. Regions of homology are identified by shading and residues that are identical in TbpBs from *Neisseria meningitidis, N. gonorrhoeae, H. influenzae* and *Actinobacillus pleuropneumoniae* are bold and underlined.

Figure 25:
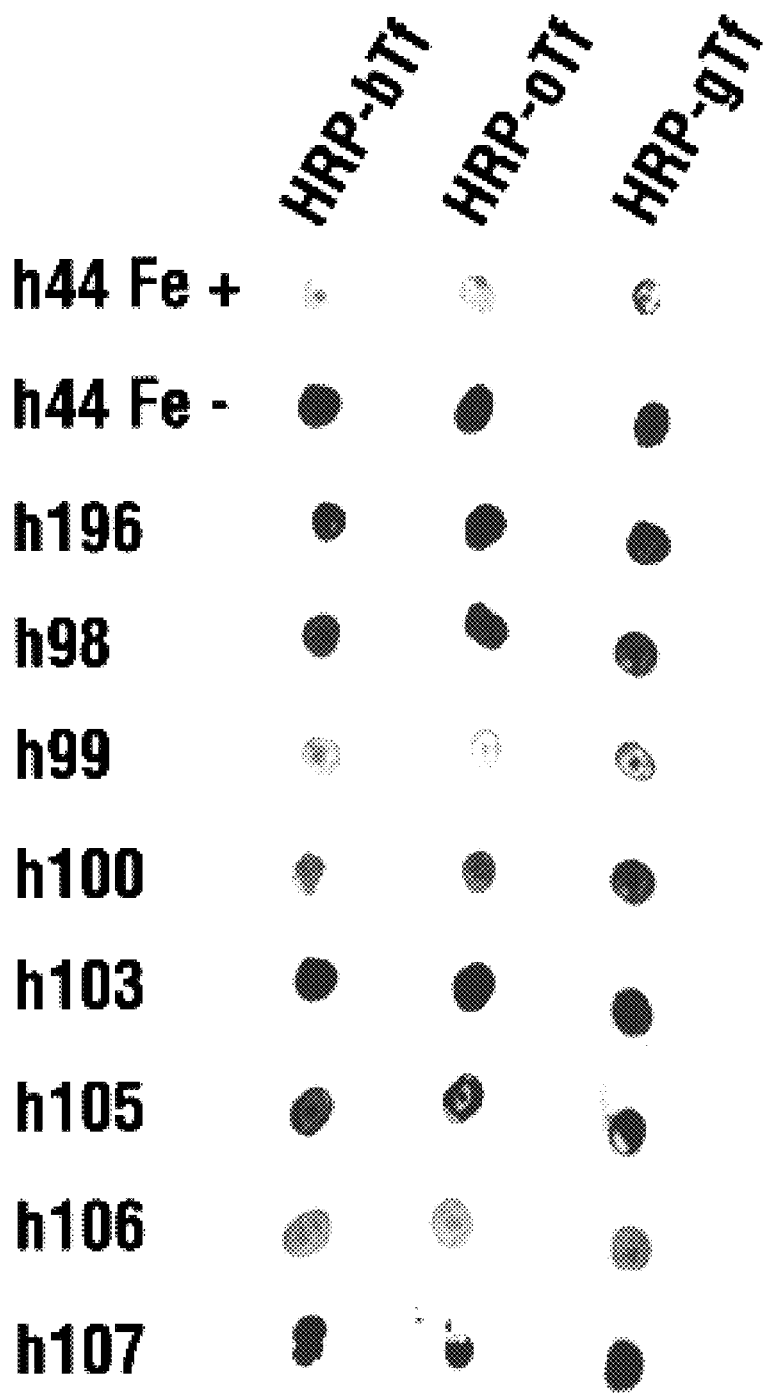
FIG. 25 is a blot showing the results of a solid-phase HRP-Tf binding assay.

FIG. 25. Solid-phase HRP-Tf binding assay. Total membrane preparations from the indicated strains of *P. haemolytica* and *P.trehalosi* were spotted onto nitrocellulose-cellulose acetate paper and blocked with skim milk prior to incubation with HRP-bTf, -oTf or -gTf. Binding was detected with chloronaphthol reagent as in the methods. The letters on the left indicate the strains while the letters on the top indicate the different HRP-labbelled ruminant transferrins FIGS. 26A–26B. Western blot cross-reactivity studies with anti-TbpA and anti-TbpB antisera from *P.haemolytica* serotype A1. Aliquots of affinity purified receptor proteins from the indicated strains of *P.haemolytica* and *P. trehalosi* were separated by SDS-PAGE and Silver stain (panel A) or subjected to Western blotting(panel B) as in Methods. Tbp proteins were identified by incubation with a mixture of anti-TbpB(1/1000) and anti-TbpA(1/1000) rabbit antisera as described in the methods section. The numbers on the left represent the molecular weights (×1000) of standard proteins in kilodaltons.

FIG. 27. Cross-reactivity studies with monospecific anti-TbpA and anti-TbpB antisera from *P. haemolytica* serotype A1 against intact cells. Aliquots of iron-limited intact cells from the indicated strains of *P. haemolytica* and *P. trehalosi* were spotted onto HA nitrocellulse paper and, after blocking, the membrane was either exposed to HRP—labelled bTf, anti-TbpA antiserum or anti-TbpB antiserum. Bound antibodies were subsequently detected by labelled goat anti-rabbit antibody as described in the methods. A preparation of intact *P. haemolytica* strain h44 (type A1) cells grown under iron-sufficient cells (indicated by h44–$Fe^+$) was spotted onto the membranes and used as a control.

Figure 28A:
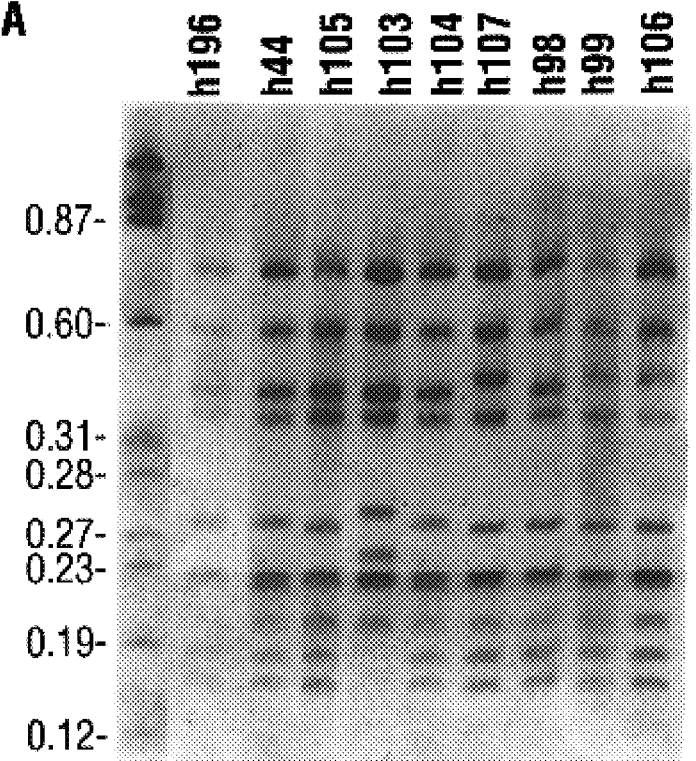
FIGS. 28A–28B shows a gel with restriction endonuclease digestion patterns of PCR-amplified tbpA (Panel A) and tbpb (Panel B) genes from *P. haemolytica* and *P. trehalosi* strains.
Figure 28B:
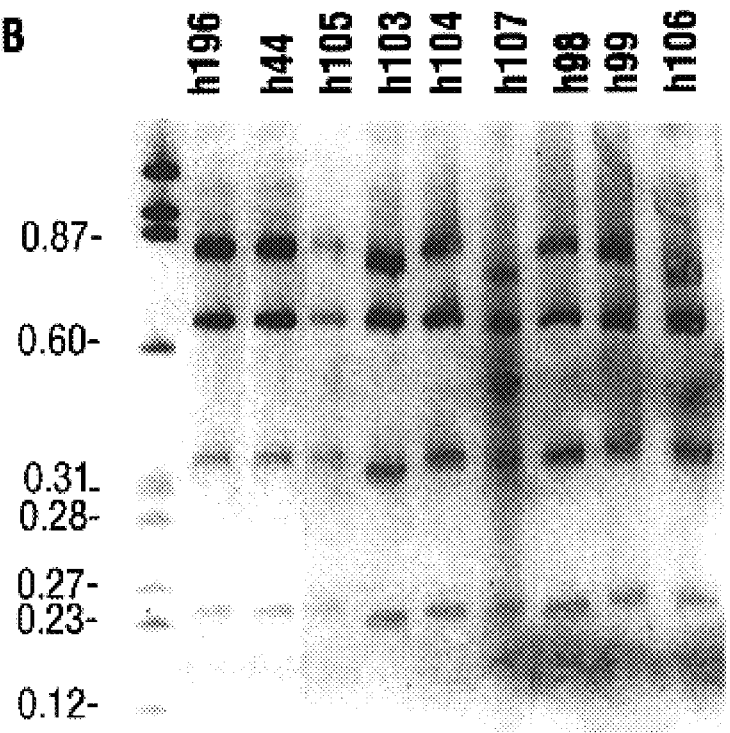

FIGS. 28A–28B. Restriction endonuclease digestion pattern of PCR-amplified tbpA (Panel A) and TbpB (Panel B) genes from *P. haemolytica* and *P. trehalosi* strains. The tbp genes were amplified by colony PCR from the indicated strains were digested with Sau3A1 restriction endonuclease. The resulting digests were electrophoresed on a 7.5% polyacrylamide gel as described in Methods. The letters above the lanes indicate the source strain template DNA used in PCR while the letters on the left indicate the molecular weight standard in kilobases. Imaging was done with a Hewlett-Parkard ScanJet IIp. In FIG. 29B, primer #s 397 and 400 from non conserved regions of *P.haemolytica* tbpB gene, were used in combination with opposing primers {#s 401(5') and 199(3')} respectively.

Figure 29A:
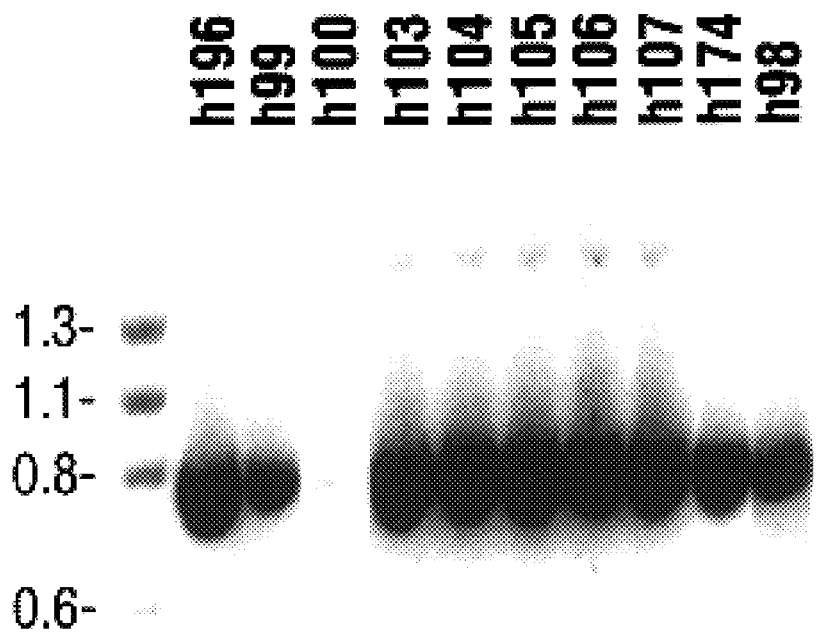
FIGS. 29A–29B is a gel showing PCR amplification of variable segments of the tbpA (Panel A) and tbpB (Panel B) genes.
Figure 29B:
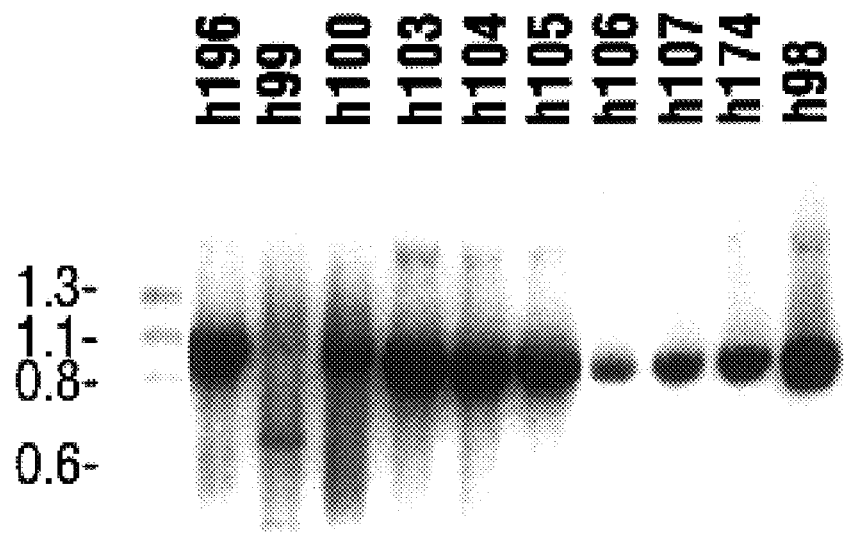

FIGS. 29A–29B. PCR amplification of variable segments of the tbpA and tbpB genes. For tbpA gene, oligonucleotide primer #450 made from the deduced amino acid sequence from a hypervariable region of tbpA was used in combination with the 5' specific primer (#255) to amplify the gene segment from the various P.haemolytica strains. The products were then analysed on 1% agarose gel followed by staining with ethidium bromide.

We claim:

1. An isolated and purified first polynucleotide, or the full complement of said first polynucleotide, wherein said first polynucleotide encodes a polypeptide that is a TbpA of *P. haemolytica* and hybridizes under stringent conditions to the complement of a second polynucleotide, wherein said second polynucleotide is selected from the group consisting of:
   (a) a polynucleotide encoding a polypeptide comprising an amino acid sequence as set forth in SEQ ID NO:2; and
   (b) a polynucleotide encoding a polypeptide comprising amino acid 29 to amino acid 930 as set forth in SEQ ID NO:2;
wherein said stringent conditions include a post hybridization wash of 2×SSC (sodium chloride/sodium citrate) at 50EC.

2. The polynucleotide of claim 1, wherein the polynucleotide is DNA.

3. The polynucleotide of claim 1, wherein the polynucleotide is RNA.

4. The polynucleotide of claim 1, wherein the polynucleotide is genomic DNA.

5. The polynucleotide of claim 1, comprising the sequence as set forth in SEQ ID NO:1 from nucleotide 1 to nucleotide 2790.

6. The polynucleotide of claim 1, comprising the sequence as set forth in SEQ ID NO:1 from nucleotide 85 to nucleotide 2790.

7. A vector comprising the DNA of claim 2.

8. A host cell comprising the vector of claim 7.

9. A process for producing a polypeptide comprising: expressing from the host cell of claim 8 the polypeptide encoded by said DNA.

10. A process for producing a cell which expresses a TbpA polypeptide comprising transfecting the cell with the vector of claim 7.

11. A method for producing a polypeptide in a host cell comprising the steps of:
    (a) incubating a host cell containing a heterologous nucleic acid molecule whose nucleotide sequence comprises the sequence of the isolated polynucleotide of claim 1, under conditions where said heterologous nucleic acid molecule is expressed to produce said polypeptide and
    (b) isolating said polypeptide.

12. Antisense nucleic acid which specifically inhibits expression of the polynucleotide of claim 1.

13. A diagnostic method for determining, in a sample derived from a host organism, the presence or absence of a nucleic acid sequence according to claim 1, said method comprising
    obtaining a sample containing nucleic acids from a host organism; and
    detecting, in said sample, said nucleic acid sequence.

14. An isolated and purified nucleic acid molecule comprising the polynucleotide of claim 1, wherein said nucleic acid molecule is produced by a process comprising the steps of:
    (a) screening a genomic DNA library using as a probe a target sequence defined by the SEQ ID NO:1, or fragments thereof;
    (b) identifying members of said library which contain sequences that hybridize to said target sequence; and
    (c) isolating an intact coding sequence from one or more of said members identified in step (b).

15. An isolated and purified DNA molecule comprising the polynccleotide of claim 1, wherein said polynucleotide is produced by a process comprising the steps of:
    (a) isolating mRNA, DNA, or cDNA produced from a *P. haemolytica* organism;
    (b) amplifying nucleic acid molecules whose nucleotide sequence is homologous to amplification primers derived from said fragment of said *P. haemolytica* genome to prime said amplification;
    (c) isolating said amplified sequences produced in step (b).

16. Antisense DNA capable of blocking expression of a polynucleotide encoding a TbpA polypeptide of *P. haemolytica* comprising the amino acid sequence as set forth in SEQ ID NO:2.

17. A host cell which has been altered to contain the polynucleotide of claim 1.

18. A kit for analyzing samples for the presence of polynucleotides encoding TbpA from *P. haemolytica*, comprising
    (a) at least one polynucleotide containing a nucleotide sequence that will hybridize to a polynucleotide of claim 1 under stringent hybridization conditions, and
    (b) reagent means for detecting said at least one polynucleotide.

*

SEQUENCE LISTING

<160> NUMBER OF SEQ ID NOS: 68

<210> SEQ ID NO 1
<211> LENGTH: 2793
<212> TYPE: DNA
<213> ORGANISM: Pasteurella haemolytica
<220> FEATURE:
<221> NAME/KEY: misc_feature
<222> LOCATION: 2544
<223> OTHER INFORMATION: a, c, g or t

<400> SEQUENCE: 1

| | | | | | |
|---|---|---|---|---|---|
| atgataatga | aatatcatca | ttttcgctat | tcacctgttg | ccttaacagt | gttatttgct | 60 |
| ctttctcatt | catacggtgc | tgcgactgaa | aataaaaaaa | tcgaagaaaa | taacgatcta | 120 |
| gctgttctgg | atgaagttat | tgtgacagag | agccattatg | ctcacgaacg | tcaaaacgaa | 180 |
| gtaactggct | tggggaaagt | agtgaaaaat | tatcacgaaa | tgagtaaaaa | tcaaattctt | 240 |
| ggtattcgtg | atttaactcg | ctatgaccct | ggtatttcgg | tggtggaaca | aggtcgcggt | 300 |
| gcaagtagtg | gctatgccat | tcgaggtgta | gataaaaacc | gtgtcagctt | acttgttgat | 360 |
| gggctaccac | aagcgcacag | ttatcatacg | ctaggttcag | atgctaatgg | tggtgcaatt | 420 |
| aatgagattg | agtatgaaaa | cattcgttca | attgagttaa | gcaaaggagc | aagttctgcg | 480 |
| gaatatggct | ctggtgcgca | tggtggtgct | attggttttc | gtactaaaga | tgcgcaggat | 540 |
| attattaaag | aggggcagca | ttggggctta | gatagtaaga | cctcttatgc | cagcaaaaat | 600 |
| agccattttt | tacagtctat | cgcagcggct | ggtgaggcgg | gtggttttga | agcacttgtt | 660 |
| attgcaactc | accgacacgg | taaagagacc | aaaattcatt | ccgaggcaaa | taattaaaa | 720 |
| cataatattc | ggcgtataac | cggctttgaa | aatcgctacg | actttaccca | aattccgcac | 780 |
| agaatgctcc | tggaggatct | ccttttaatt | gtggaagata | cttgcccaac | attagattgt | 840 |
| actcctcgtg | caagggttaa | gttgaaccgc | gataatttcc | cagtgagaac | atttccggaa | 900 |
| tatacgcctg | aagagcgcaa | acagcttgag | cagattcctt | atcgcactga | gcagctctca | 960 |
| gcccaagaat | ataccggtaa | agatcgcatt | gcaccaaacc | ctttagatta | caagagtaat | 1020 |
| tctgttttta | tgaagtttgg | ctatcacttc | aactcgtctc | attatcttgg | cgcaatctta | 1080 |
| gaagatacaa | aaacacgcta | cgatatccgt | gatatgcaaa | cgccagctta | ctatacaaaa | 1140 |
| gacgatatta | acttatcact | taggaactat | gtttatgaag | gggataatat | tttagatggc | 1200 |
| ttagtgttca | agccaaggat | cccttatggg | ttgcgctata | gccatgtgaa | gttttttgat | 1260 |
| gaacgtcacc | acaaacgtcg | tttaggattc | acctataaat | ataaaccaga | gaataatcgc | 1320 |
| tggttggata | gcattaaact | cagtgcggat | aaacaagata | ttgaactata | tagccggcta | 1380 |
| catcgcttgc | attgtagcga | ttatcctgtg | gtagataaaa | attgccgccc | gactttggat | 1440 |
| aaatcttggt | ctatgtatcg | aactgagcgt | aataattacc | aagaaaagca | tcgtgtcatt | 1500 |
| catttagaat | ttgataaagc | gctaaatgct | ggtcaaggcg | tatttaacca | aacccacaaa | 1560 |
| ctgaatttag | ggttgggctt | tgatcgattt | aattcgctta | tggatcatgg | ggatatgact | 1620 |
| gcccaatata | ccaaaggcgg | ttataccagc | taccgcggta | gagggcgttt | agataatcca | 1680 |
| tatatttatc | gccgcgatcc | acgcagtatt | gaaacggtat | ctttgtgtaa | taatacacgc | 1740 |
| ggcgacatct | taaactgtga | accgcgtaaa | attaaggcg | atagccattt | tgttagcttc | 1800 |
| cgcgatctag | tgataagcga | gtatgtggat | ttgggattag | gggtgcgttt | tgatcaacat | 1860 |
| cgatttaaat | ctgatgatcc | gtggacactt | agccgaactt | atcgaaattg | gtcttggaat | 1920 |

```
ggtgggatta cgcttaaacc aacagagttt gtatcgcttt cttatcgcat ttcaaacggt    1980
tttagagtgc ctgcattcta tgaactttat ggtaaacgtg atcatattgg gcttaaagat    2040
aacgaatatg tgcaacgcgc gcaacgtagc caccagttag agccagaaaa atcgactaat    2100
catgagattg gagttagctt taaaggtcaa tttggttacc ttgatgtgag ctatttccgt    2160
aataactata aaaatatgat tgcgacagca tgtaaaagaa taatacaaaa atcacactgt    2220
ttctataact accataatat tcaagatgta gcactaaacg ggataaattt agtcgctaaa    2280
tttgacttac acggtatttt atctatgctg ccagatggtt tttattcatc agttgcttat    2340
aaccgtgtaa aagtaaaaga gcggaaacta accgactcaa gactcgatag cgtaaacgat    2400
cctattctag atgcgattca gccagcacgc tatgtgcttg gattcggcta cgatcaccca    2460
gaagaaaaat ggggaattgg cattactacc acctattcta aagccaaaaa cgccgatgag    2520
gtggcaggca cacgtcatca cggnatacat cgcgttgatt taggtggcaa actgaccggt    2580
tcttggtaca cccatgatat taccggttac atcaattata aaaactacac cttacgtgga    2640
ggaatttata atgtgactaa tcgtaaatat tccacttggg aatcagtgcg ccaatccggt    2700
gtgaatgcag taaaccaaga ccggggtagc aattcactc gatttggcgc tccggggaga    2760
aatttcagtt tagcatttga aatgaagttt tag                                 2793
```

<210> SEQ ID NO 2
<211> LENGTH: 930
<212> TYPE: PRT
<213> ORGANISM: Pasteurella haemolytica

<400> SEQUENCE: 2

```
Met Ile Met Lys Tyr His His Phe Arg Tyr Ser Pro Val Ala Leu Thr
  1               5                  10                  15

Val Leu Phe Ala Leu Ser His Ser Tyr Gly Ala Ala Thr Glu Asn Lys
                 20                  25                  30

Lys Ile Glu Glu Asn Asn Asp Leu Ala Val Leu Asp Glu Val Ile Val
         35                  40                  45

Thr Glu Ser His Tyr Ala His Glu Arg Gln Asn Glu Val Thr Gly Leu
     50                  55                  60

Gly Lys Val Val Lys Asn Tyr His Glu Met Ser Lys Asn Gln Ile Leu
 65                  70                  75                  80

Gly Ile Arg Asp Leu Thr Arg Tyr Asp Pro Gly Ile Ser Val Val Glu
                 85                  90                  95

Gln Gly Arg Gly Ala Ser Ser Gly Tyr Ala Ile Arg Gly Val Asp Lys
            100                 105                 110

Asn Arg Val Ser Leu Leu Val Asp Gly Leu Pro Gln Ala His Ser Tyr
        115                 120                 125

His Thr Leu Gly Ser Asp Ala Asn Gly Gly Ala Ile Asn Glu Ile Glu
    130                 135                 140

Tyr Glu Asn Ile Arg Ser Ile Glu Leu Ser Lys Gly Ala Ser Ser Ala
145                 150                 155                 160

Glu Tyr Gly Ser Gly Ala His Gly Gly Ala Ile Gly Phe Arg Thr Lys
                165                 170                 175

Asp Ala Gln Asp Ile Ile Lys Gly Gln His Trp Gly Leu Asp Ser
            180                 185                 190

Lys Thr Ser Tyr Ala Ser Lys Asn Ser His Phe Leu Gln Ser Ile Ala
        195                 200                 205

Ala Ala Gly Glu Ala Gly Gly Phe Glu Ala Leu Val Ile Ala Thr His
```

-continued

```
            210                 215                 220
Arg His Gly Lys Glu Thr Lys Ile His Ser Glu Ala Asn Lys Leu Lys
225                 230                 235                 240

His Asn Ile Arg Arg Ile Thr Gly Phe Glu Asn Arg Tyr Asp Phe Thr
                    245                 250                 255

Gln Ile Pro His Arg Met Leu Leu Glu Asp Leu Leu Leu Ile Val Glu
                260                 265                 270

Asp Thr Cys Pro Thr Leu Asp Cys Thr Pro Arg Ala Arg Val Lys Leu
            275                 280                 285

Asn Arg Asp Asn Phe Pro Val Arg Thr Phe Pro Glu Tyr Thr Pro Glu
290                 295                 300

Glu Arg Lys Gln Leu Glu Gln Ile Pro Tyr Arg Thr Glu Gln Leu Ser
305                 310                 315                 320

Ala Gln Glu Tyr Thr Gly Lys Asp Arg Ile Ala Pro Asn Pro Leu Asp
                325                 330                 335

Tyr Lys Ser Asn Ser Val Phe Met Lys Phe Gly Tyr His Phe Asn Ser
                340                 345                 350

Ser His Tyr Leu Gly Ala Ile Leu Glu Asp Thr Lys Thr Arg Tyr Asp
            355                 360                 365

Ile Arg Asp Met Gln Thr Pro Ala Tyr Tyr Lys Asp Asp Ile Asn
370                 375                 380

Leu Ser Leu Arg Asn Tyr Val Tyr Glu Gly Asp Asn Ile Leu Asp Gly
385                 390                 395                 400

Leu Val Phe Lys Pro Arg Ile Pro Tyr Gly Leu Arg Tyr Ser His Val
                405                 410                 415

Lys Phe Phe Asp Glu Arg His His Lys Arg Arg Leu Gly Phe Thr Tyr
                420                 425                 430

Lys Tyr Lys Pro Glu Asn Asn Arg Trp Leu Asp Ser Ile Lys Leu Ser
                435                 440                 445

Ala Asp Lys Gln Asp Ile Glu Leu Tyr Ser Arg Leu His Arg Leu His
            450                 455                 460

Cys Ser Asp Tyr Pro Val Val Asp Lys Asn Cys Arg Pro Thr Leu Asp
465                 470                 475                 480

Lys Ser Trp Ser Met Tyr Arg Thr Glu Arg Asn Asn Tyr Gln Glu Lys
                485                 490                 495

His Arg Val Ile His Leu Glu Phe Asp Lys Ala Leu Asn Ala Gly Gln
                500                 505                 510

Gly Val Phe Asn Gln Thr His Lys Leu Asn Leu Gly Leu Gly Phe Asp
            515                 520                 525

Arg Phe Asn Ser Leu Met Asp His Gly Asp Met Thr Ala Gln Tyr Thr
            530                 535                 540

Lys Gly Gly Tyr Thr Ser Tyr Arg Gly Arg Gly Arg Leu Asp Asn Pro
545                 550                 555                 560

Tyr Ile Tyr Arg Arg Asp Pro Arg Ser Ile Glu Thr Val Ser Leu Cys
                565                 570                 575

Asn Asn Thr Arg Gly Asp Ile Leu Asn Cys Glu Pro Arg Lys Ile Lys
                580                 585                 590

Gly Asp Ser His Phe Val Ser Phe Arg Asp Leu Val Ile Ser Glu Tyr
            595                 600                 605

Val Asp Leu Gly Leu Gly Val Arg Phe Asp Gln His Arg Phe Lys Ser
            610                 615                 620

Asp Asp Pro Trp Thr Leu Ser Arg Thr Tyr Arg Asn Trp Ser Trp Asn
625                 630                 635                 640
```

-continued

```
Gly Gly Ile Thr Leu Lys Pro Thr Glu Phe Val Ser Leu Ser Tyr Arg
            645                 650                 655
Ile Ser Asn Gly Phe Arg Val Pro Ala Phe Tyr Glu Leu Tyr Gly Lys
            660                 665                 670
Arg Asp His Ile Gly Leu Lys Asp Asn Glu Tyr Val Gln Arg Ala Gln
            675                 680                 685
Arg Ser His Gln Leu Glu Pro Glu Lys Ser Thr Asn His Glu Ile Gly
            690                 695                 700
Val Ser Phe Lys Gly Gln Phe Gly Tyr Leu Asp Val Ser Tyr Phe Arg
705                 710                 715                 720
Asn Asn Tyr Lys Asn Met Ile Ala Thr Ala Cys Lys Arg Ile Ile Gln
            725                 730                 735
Lys Ser His Cys Phe Tyr Asn Tyr His Asn Ile Gln Asp Val Ala Leu
            740                 745                 750
Asn Gly Ile Asn Leu Val Ala Lys Phe Asp Leu His Gly Ile Leu Ser
            755                 760                 765
Met Leu Pro Asp Gly Phe Tyr Ser Ser Val Ala Tyr Asn Arg Val Lys
770                 775                 780
Val Lys Glu Arg Lys Leu Thr Asp Ser Arg Leu Asp Ser Val Asn Asp
785                 790                 795                 800
Pro Ile Leu Asp Ala Ile Gln Pro Ala Arg Tyr Val Leu Gly Phe Gly
            805                 810                 815
Tyr Asp His Pro Glu Glu Lys Trp Gly Ile Gly Ile Thr Thr Thr Tyr
            820                 825                 830
Ser Lys Ala Lys Asn Ala Asp Glu Val Ala Gly Thr Arg His His Gly
            835                 840                 845
Ile His Arg Val Asp Leu Gly Gly Lys Leu Thr Gly Ser Trp Tyr Thr
            850                 855                 860
His Asp Ile Thr Gly Tyr Ile Asn Tyr Lys Asn Tyr Thr Leu Arg Gly
865                 870                 875                 880
Gly Ile Tyr Asn Val Thr Asn Arg Lys Tyr Ser Thr Trp Glu Ser Val
            885                 890                 895
Arg Gln Ser Gly Val Asn Ala Val Asn Gln Asp Arg Gly Ser Asn Tyr
            900                 905                 910
Thr Arg Phe Gly Ala Pro Gly Arg Asn Phe Ser Leu Ala Phe Glu Met
            915                 920                 925
Lys Phe
    930

<210> SEQ ID NO 3
<211> LENGTH: 1755
<212> TYPE: DNA
<213> ORGANISM: Pasteurella haemolytica

<400> SEQUENCE: 3
atgtttaaac ttaaaagtag ttttgtactg cttaatgcgg cgctacttgc tgcttgttcc      60
tcaaatggtg gaagctttga tgttcaatct gccaagttg aatctcaaac gcaaactacc     120
cccaaaaagc caagtttaca agatgataat agtaacgcaa gacgtacagt aagcgcttct     180
gaaactgaag ctttattgca gccggggttt ggttttcag ccaaaattcc gcgtcgtaat      240
ctccttccgc aggggaagga agatgtagcc cctattggtg atataaaaga gattactgga    300
gatctgccaa aaattccgta tgaagaagag gttaaagcgt gcggtagtag tgctgatgga    360
tttagccata ctcatgatag aaatcataag ttgtatacaa gagattttaa ttttgttcgt    420
```

-continued

```
tccggctatg ttgtgcattc tggtccaaaa cctgaaataa agcctaaaga aatttttgaga    480 acaggtgcac atgggtatgt ttactattta ggtatagagc cgcccaaagc aatacctacc    540
caaaaactaa cttataaagg atattgggat tttactacct atgcggctaa ggggagagat    600
agtaatattt ttctaattcc cgcaggcatc aatagtggcg ccataccgga aaatagtcac    660
gatattaatg ttgatgattc tgaaaaacca atggggcata caggagaatt tacggctgat    720
tttgctaata aactttaac tggaacattg ttcgtaatg ggtatgttag tcgtagcaaa       780
gagcaaaaaa ttacaacaat ttacgatatt gatgcgaaaa ttaaaggtaa tcgcttttct    840
ggtaaagcaa acccaaaaaa accgatgatc cttattttttg ggaaaagctc cacgacactt   900
gaaggtggat tttttggtgg ggaggctcaa gaacttgccg gtaaattctt agctgatgat   960
aagtcggtat ttgttgtttt tgctggcaca cgagatgcta aaaagatga tagtgaatct   1020 gcctttgatg ctttcccaat taaacttaaa gatttaaata atctgagat ggatactttc    1080 gggaatgcga cacatttgat tattaacaat aagcagattc cacttattgc ggaagccaca   1140
aaaagctttg ccgagatgaa atttgatgat ttggttaccc gtactattga tggaaaaacg   1200
tatcgagttt cagtctgctg taataattta gattatgtca aatttgggat ttatagcgag   1260
ggaaataata gtgatactgc tctccaagaa tatttagtag gagaacgtac agctctggca   1320
gatttgccaa cagggacagt aaaatatcga ggtacttggg acggggtaat gtacagtaaa   1380
tctggctcgg caggggttga atcgccaagt aacagcgaaa gtggtactcg ttcactattc   1440
gatgtagatt ttgtcaataa aaaaattaat ggcaagctga ttgctaatga tggtgttgaa   1500
gaacgcccaa tgctgacact ggaaggcaat ctgaaaggga atggttttgg aggcacagcc   1560
aaaacgggca attctggttt taatcttgat cccaaaagta cgaatggtgg cacggtaggg   1620
catataaata ctcaatttga aggggcttt tatggcccta aggcgacgga attaggtggt   1680
attgtacaaa atacagaaac ggataaagat agagtcagta ttacattcgg cggaaaacgt   1740
caaatagaaa aataa                                                     1755
```

<210> SEQ ID NO 4
<211> LENGTH: 584
<212> TYPE: PRT
<213> ORGANISM: Pasteurella haemolytica

<400> SEQUENCE: 4

```
Met Phe Lys Leu Lys Ser Ser Phe Val Leu Leu Asn Ala Ala Leu Leu
  1               5                  10                  15

Ala Ala Cys Ser Ser Asn Gly Gly Ser Phe Asp Val Gln Ser Ala Lys
             20                  25                  30

Val Glu Ser Gln Thr Gln Thr Thr Pro Lys Lys Pro Ser Leu Gln Asp
         35                  40                  45

Asp Asn Ser Asn Ala Arg Arg Thr Val Ser Ala Ser Glu Thr Glu Ala
     50                  55                  60

Leu Leu Gln Pro Gly Phe Gly Ser Ala Lys Ile Pro Arg Arg Asn
 65                  70                  75                  80

Leu Leu Pro Gln Gly Lys Glu Asp Val Ala Pro Ile Gly Asp Ile Lys
                 85                  90                  95

Glu Ile Thr Gly Asp Leu Pro Lys Ile Pro Tyr Glu Glu Val Lys
            100                 105                 110

Ala Cys Gly Ser Ser Ala Asp Gly Phe Ser His Thr His Asp Arg Asn
        115                 120                 125
```

-continued

```
His Lys Leu Tyr Thr Arg Asp Phe Asn Phe Val Arg Ser Gly Tyr Val
    130                 135                 140
Val His Ser Gly Pro Lys Pro Glu Ile Lys Pro Lys Glu Ile Leu Arg
145                 150                 155                 160
Thr Gly Ala His Gly Tyr Val Tyr Tyr Leu Gly Ile Glu Pro Pro Lys
                165                 170                 175
Ala Ile Pro Thr Gln Lys Leu Thr Tyr Lys Gly Tyr Trp Asp Phe Thr
            180                 185                 190
Thr Tyr Ala Ala Lys Gly Arg Asp Ser Asn Ile Phe Leu Ile Pro Ala
        195                 200                 205
Gly Ile Asn Ser Gly Ala Ile Pro Glu Asn Ser His Asp Ile Asn Val
    210                 215                 220
Asp Asp Ser Glu Lys Pro Met Gly His Thr Gly Glu Phe Thr Ala Asp
225                 230                 235                 240
Phe Ala Asn Lys Thr Leu Thr Gly Thr Leu Val Arg Asn Gly Tyr Val
                245                 250                 255
Ser Arg Ser Lys Glu Gln Lys Ile Thr Thr Ile Tyr Asp Ile Asp Ala
            260                 265                 270
Lys Ile Lys Gly Asn Arg Phe Ser Gly Lys Ala Asn Pro Lys Lys Pro
        275                 280                 285
Met Ile Leu Ile Phe Gly Lys Ser Ser Thr Thr Leu Glu Gly Gly Phe
    290                 295                 300
Phe Gly Gly Glu Ala Gln Glu Leu Ala Gly Lys Phe Leu Ala Asp Asp
305                 310                 315                 320
Lys Ser Val Phe Val Val Phe Ala Gly Thr Arg Asp Ala Lys Lys Asp
                325                 330                 335
Asp Ser Glu Ser Ala Phe Asp Ala Phe Pro Ile Lys Leu Lys Asp Leu
            340                 345                 350
Asn Lys Ser Glu Met Asp Thr Phe Gly Asn Ala Thr His Leu Ile Ile
        355                 360                 365
Asn Asn Lys Gln Ile Pro Leu Ile Ala Glu Ala Thr Lys Ser Phe Ala
    370                 375                 380
Glu Met Lys Phe Asp Asp Leu Val Thr Arg Thr Ile Asp Gly Lys Thr
385                 390                 395                 400
Tyr Arg Val Ser Val Cys Cys Asn Asn Leu Asp Tyr Val Lys Phe Gly
                405                 410                 415
Ile Tyr Ser Glu Gly Asn Asn Ser Asp Thr Ala Leu Gln Glu Tyr Leu
            420                 425                 430
Val Gly Glu Arg Thr Ala Leu Ala Asp Leu Pro Thr Gly Thr Val Lys
        435                 440                 445
Tyr Arg Gly Thr Trp Asp Gly Val Met Tyr Ser Lys Ser Gly Ser Ala
    450                 455                 460
Gly Val Glu Ser Pro Ser Asn Ser Glu Ser Gly Thr Arg Ser Leu Phe
465                 470                 475                 480
Asp Val Asp Phe Val Asn Lys Lys Ile Asn Gly Lys Leu Ile Ala Asn
                485                 490                 495
Asp Gly Val Glu Glu Arg Pro Met Leu Thr Leu Glu Gly Asn Leu Lys
            500                 505                 510
Gly Asn Gly Phe Gly Gly Thr Ala Lys Thr Gly Asn Ser Gly Phe Asn
        515                 520                 525
Leu Asp Pro Lys Ser Thr Asn Gly Gly Thr Val Gly His Ile Asn Thr
    530                 535                 540
Gln Phe Glu Gly Gly Phe Tyr Gly Pro Lys Ala Thr Glu Leu Gly Gly
```

```
545                550                555                560
Ile Val Gln Asn Thr Glu Thr Asp Lys Asp Arg Val Ser Ile Thr Phe
                565                570                575
Gly Gly Lys Arg Gln Ile Glu Lys
            580

<210> SEQ ID NO 5
<211> LENGTH: 2045
<212> TYPE: DNA
<213> ORGANISM: Pasteurella haemolytica

<400> SEQUENCE: 5
cgcttgcaga tttgtaaaaa atttagctaa aatcagacct ggcttgtatt ttagggttat      60
tatggaacag acaacggaac aaatagatta taaattatta aagcatcgtt ttcgtggcta     120
tttaccgctt gtgattgatg tggaacagag gcttaaatgc ccaaactgtg ccttattgga     180
attggccgga attactttaa aattggacga gccaaggtta tcttattgcc ggattcaaca     240
atgccaattt ccaatttgcg gccattggag ggggcgattt tcaagggccg aatatttacc     300
ctcagtcatt aaaattcaac ggcattcata ttcacaaccc tctagaggaa gcggtttaga     360
gaatattgcc caattcccgg aaatgttcaa aatggttcgc aaagcaatga aggaagcaag     420
gctgccaacg ggcggtgatt gttgccccac aatgccagcg ttcgatcagg gctttttac      480 agggctgcga ttaaacggaa tgccaagcga gagatccctt tcaccctttt ggcgatgttt     540
gactaccgcc gccacccttt gcaggtttta tgttatgggc aaaccgtgtt cgttaaaagc     600
ctgccagtgc aaaatccgtt cacgtagcag cactataggg cgaattgggt accgggcccc     660
cctcgaggtc gacggtatcg ataaagcttc atatcgaatt cctgcagccc ggggatccg      720 atgcgccttg cggctcaagt tattagtggc atcggttttt tgggtgatgg tgtcattttg     780
cataagaaaa atgatgcgat ttcaggttta cccactgcgg cgattatttg ggcttctgcg     840
gggatcggta ttgctgcagg ggagggtttc gtgtttcatg cggtcatcgc cactgtcatt     900
attttggtgt ctattcgatt atgtccgttg gttcaacgtt gggttcatcg taaatcacaa     960
cgtcgtcgac gaaatattct tgtcaatgat gcggaaagca tacggaaagt tacccaattg    1020
ttattcaata atcagtatcg tattgaacat atacaagtca aagatcaaag tagtggagaa    1080
gttgccggtt acaaattcgt attgattcca caatgttcaa agatgcgtat gctttactta    1140
aagcagaaga tggcgaatac tgttcaagta gatatcatga aaaagagtgc ttatattcaa    1200
ttttttattt tttatttaat ttcttttccac aaaagatcat tttcaattat atatactgga    1260
attttgcctt acgctatctg tcatttatta tgctattcaa gcacaacaaa ctatggaaca    1320
acaatcaaaa tgtacgctta tcggctgccg atgatttcga taatgatcga tgtgcagaaa    1380
tatttgaact tacgattttc actgagcagt caaagcacgt tcgcgagtat cgactctact    1440
ttatttatcg tttgtgcact atgtataatc cacctaattc cgtgccttgg ccataaaagc    1500 cccctttcaaa ttgtatttat atcagctacc gtgccaccat tcgtactttt cggatcaaga    1560
ttaaaacaga atccctgcat gcacagcgaa atcagctgcg gtatgcgaaa cgccgcagga    1620
gcgcagtacg cgaagtgtac cgtcactatc agtgctagat ttgtcaataa aaaattagtg    1680
accaagcttg ggtgcataat gatggtgatg aaagaacgct caatgcttga cacgttgcag    1740
gctatctgta agggtatggt agttacaggc acagcccaaa cggccaattg ctggtttttt    1800
atccttgatc cgaacagtac gaatggtggt cacggtagtg catatacata ctcaattgaa    1860
gggggctttt atggccctaa ggcgacggaa ttaggtggta ttgtacatag tgcagaaacg    1920
```

-continued

```
gataaagata gagtcagtat tacattcggc ggaaaacgtc aaatagaaaa ataatcataa    1980
ttcccctttg ctggttgtag atagcagcgg gcaattttt ataaaaattt gcaaaattta    2040
aataa                                                                2045
```

<210> SEQ ID NO 6
<211> LENGTH: 3023
<212> TYPE: DNA
<213> ORGANISM: Pasteurella haemolytica

<400> SEQUENCE: 6

```
agaccctatc taatgataat gaaatatcat cattttcgct attcacctgt tgccttaaca     60
gtgttatttg ctctttctca ttcatacggt gctgcgactg aaaataaaaa aatcgaagaa    120
aataacgatc tagctgttct ggatgaagtt attgtgacag agagccatta tggtcacgaa    180
cgtcaaaacg aagtaactgg cttggggaaa gtagtgaaaa attatcacga aatgagtaaa    240
aatcaaattc ttggtattcg tgatttaact cgctatgacc ctggtatttc ggtggtggaa    300
caaggtcgcg gtgcaagtag tggctatgcc attcgaggtg tagataaaaa ccgtgtcagc    360
ttacttgttg atgggctacc accagcgcac agttatcata cgctggttca gatgctaatg    420
gtggtgcaat taatgagatt gagtatgaaa acattcgttc aattgagtta agcaaaggag    480
caagttctgc ggaatatggc tctggtgcgc atggtggtgc tattggtttt cgtactaaag    540
atcgccagga tattattaaa gaggggcagc attgggcctt acatagtaag acctcttatg    600
ccagcaaaaa tagccatttt tacagtctat cgcagcggct ggtcaggcgg gtggttttca    660
agcacttgtt attgcaactc accgacacgg taaagagacc aaaattcatt ccgaggcaaa    720
tcaattacat attattcggc gtataaccgg cttttcaaaat cgctacgact ttacccaatt    780
ccgcacagaa tgcctcctgg aggatctttt tttattgtgg aagatacttg cccaacatta    840
gattgtactc ctcgtgcaag ggttaagttg aacgcgataa tttcccagtc agaacatttc    900
cgaatatacg cctggaagag gcgaaacagc ttgagattcc ttatcgcact gagctctcag    960
cccaaagaat acaccggtaa agatcgcatt gcaccaaacc ctttagatta caagagtaat   1020 tctgtttta tgaagtttgg ctatcacttt acctcgtctc attatcttgg cgcatctcac   1080
aagatgatac aaaacaacgc acgatatccg tcatctgcaa acgccagctt actatacaaa   1140
agacgatatt tacttatcac tttggaacta tgtttatcaa ggggatatta tttagatggc   1200
ttagtgttca agccaaggat cccttatggg ttgcgcatat gccatgtgaa cgtcaccaca   1260
aacgtcgttt aggattcacc tataaatata accagagaa taatcgctgg ttggatagca   1320
ttaactcgtg cgtacgtgct ttgcgctctc gctgctgtgc tctgagtaaa caagatattg   1380
aactatatag ccggctacat cgcttgcatt gtagcgatta tcctgtggta gataaaaatt   1440
gcggcccgac tttggataaa tctggtctat gtatcgaact gagcgtaata attaccaaga   1500
aaagcatcgt gtcattcatt tagaatttga taaagcgcta aatgctggtc aaggcgtatt   1560
taagcaaacc cacaaactga atttaggctt gggctttgaa tcgattaatc gcttatgatc   1620
atggggatat gactgcccaa tataccaaag gccggttata ccagctaccg cggagagggg   1680
ctttagataa tccatatatt tatcgccgcg atccacgcag tattgaaacg gtatctttgt   1740
gtaataatac agcggcgaca cttaactgtg acgcgttaaa taaaggcata cgtttgtacc   1800
tccgctgcac ttaggaacta tagttttatga aggggataat atttagatgg cttagtgttc   1860
aagcaagcaa ggatccctta tgggttgcgc gatatgccat gtgaagtttt tgatgaacgt   1920
```

-continued

```
caccacaaac gtcgtttagg attcacacct ataaatatat aaaccagaga ataatcgctg    1980
gttggatagc attaactcgt gcgtacgtgc tttgcgctct cgctgctgtg ctgtgagtta    2040
aacaagatat tgaaacttat agccggctac atcgcttgca ttgtgagcga ttatcctgtg    2100
gtagtagtaa aaattgcggc ccgactttgg ataaatcttg gtctatgtat cgaacggagc    2160
gtaataatta ccaagaaaag catcgtgtca ttcatttaga atttgataaa gcgctaaatg    2220
ctggtcaagg cgtatttaag caaacccaca aactgaattt aggattgggc tttgaatcga    2280
ttaattcgct tatggatcat ggggatatga ctgcccaata taccaaaggc cggttatacc    2340
agctaaccgc gagagggcgt ttagataatc catatttatc gccgcgatcc acgcagtatt    2400
gaaacggtat ctttgtgtaa taatacacgc gcgacactaa ctgtgacgcg ttaaataaag    2460
gcatacgttt gtacctccgc tgctgcctaa taaatcaaaa gaataaccga gatacggttc    2520
agtgttgttc caaccagttg cgatggccca ctacgtgaac catcaccta atcaagtttt     2580 ttggggtcga ggtgccgtaa agcacttaac ccttctgtcg tctcccgtgg atgcttaaat    2640
tcgcagctag tggcaggcag gcacgtcact cctctcggtg atttcaggtg caactgaccg    2700
gttcttggta ccaccccttga tattaaccgg agtcaattat aaaaacgagt acgtggagc    2760 gcaatttata atgtcgatgt cagatactgt aaaactctat attaccgtgg gcagcaatta    2820
ggtgacaggg ccacggggca agcgaaacca gacgggtacc aattacaccg atttgccgcc    2880
cccgggagag aaatttcagt taccattcaa agaagtttag agccggccaa aagaaaatac    2940
aaaaaacgct gaaagtatat tcagcgcgtt tttgttgctc taacggatta catacgaatt    3000
caaaatgttt taacggtcgg taa                                           3023
```

<210> SEQ ID NO 7
<211> LENGTH: 65
<212> TYPE: DNA
<213> ORGANISM: Pasteurella haemolytica

<400> SEQUENCE: 7

```
cgcttgcaga tttgtaaaaa atttagctaa aatcagacct ggcttgtatt ttagggttat     60
taatg                                                                65
```

<210> SEQ ID NO 8
<211> LENGTH: 59
<212> TYPE: DNA
<213> ORGANISM: Neisseria gonorrhoeae

<400> SEQUENCE: 8

```
tttaaaaata aataaaataa taatccttat cattctttaa ttgaatcggg tttgttatg      59
```

<210> SEQ ID NO 9
<211> LENGTH: 71
<212> TYPE: DNA
<213> ORGANISM: Neisseria meningitidis

<400> SEQUENCE: 9

```
gtatttgcaa attgttaaaa ataaataaaa taataatcct tatcattctt taattgaatt     60
gggtttatat g                                                         71
```

<210> SEQ ID NO 10
<211> LENGTH: 898
<212> TYPE: PRT
<213> ORGANISM: Pasteurella haemolytica

<400> SEQUENCE: 10
```

-continued

```
Met Ile Met Lys Tyr His His Phe Arg Tyr Ser Thr Val Ala Leu Thr
 1               5                  10                 15

Val Leu Phe Ala Leu Ser His Ser Tyr Gly Ala Ala Thr Glu Asn Lys
            20                  25                  30

Lys Ile Glu Glu Asn Asn Asp Leu Ala Val Leu Asp Glu Val Ile Val
        35                  40                  45

Thr Glu Ser His Tyr Ala His Glu Arg Gln Asn Glu Val Thr Gly Leu
 50                  55                  60

Gly Lys Val Val Lys Asn Tyr His Glu Met Ser Lys Asn Gln Ile Leu
 65              70                  75                      80

Gly Ile Arg Asp Leu Thr Arg Tyr Asp Pro Gly Ile Ser Val Val Glu
                85                  90                  95

Gln Gly Arg Gly Ala Ser Ser Gly Tyr Ala Ile Arg Gly Val Asp Lys
                100                 105                 110

Asn Arg Val Ser Leu Leu Val Asp Gly Leu Pro Gln Ala His Ser Tyr
                115                 120                 125

His Thr Leu Ser Asp Gly Ala Asn Gly Gly Ala Ile Asn Glu Ile Glu
            130                 135                 140

Tyr Glu Asn Ile Arg Ser Ile Glu Leu Ser Lys Gly Ala Ser Ser Ala
145                 150                 155                 160

Glu Tyr Gly Ser Gly Ala His Gly Gly Ala Ile Gly Phe Arg Thr Lys
                165                 170                 175

Asp Ala Gln Asp Ile Ile Lys Glu Gly Gln His Trp Gly Leu Asp Ser
            180                 185                 190

Lys Thr Ser Tyr Ala Ser Lys Asn Ser His Phe Leu Gln Ile Ala Ala
            195                 200                 205

Ala Gly Glu Ala Gly Gly Phe Glu Ala Leu Val Ile Ala Thr His Arg
210                 215                 220

His Gly Lys Glu Thr Lys Ile His Ser Glu Ala Asn Lys Leu His Lys
225                 230                 235                 240

Asn Ile Arg Arg Ile Thr Gly Phe Glu Asn Arg Tyr Asp Phe Thr Gln
                245                 250                 255

Ile Pro His Arg Met Pro Pro Gly Gly Ser Phe Phe Ile Val Glu Asp
                260                 265                 270

Thr Cys Pro Thr Leu Asp Cys Thr Pro Arg Ala Arg Val Lys Leu Asn
            275                 280                 285

Arg Asp Asn Phe Pro Val Arg Thr Phe Pro Glu Tyr Thr Pro Glu Glu
290                 295                 300

Arg Asn Ala Glu Gln Ile Pro Tyr Arg Thr Glu Gln Leu Ser Ala Gln
305                 310                 315                 320

Glu Lys Thr Gly Lys Asp Arg Ile Ala Pro Asn Pro Leu Asp Tyr Lys
                325                 330                 335

Ser Asn Ser Val Phe Met Lys Phe Gly Tyr His Phe Asn Ser Ser His
                340                 345                 350

Tyr Leu Gly Ala Ile Leu Glu Asp Thr Lys Gln Arg Thr Ile Ser Val
                355                 360                 365

Ile Cys Lys Arg Gln Leu Thr Ile Gln Lys Thr Ile Leu Thr Tyr His
        370                 375                 380

Leu Gly Thr Met Phe Met Lys Gly Ile Ile Phe Arg Trp Leu Ser Val
385                 390                 395                 400

Gln Ala Lys Asp Pro Leu Trp Val Ala His Met Pro Cys Glu Val Asp
                405                 410                 415
```

-continued

```
Glu Arg His His Lys Arg Arg Leu Gly Phe Thr Tyr Lys Tyr Lys Pro
            420                 425                 430

Glu Asn Asn Arg Trp Leu Asp Ser Ile Asn Ser Cys Val Arg Ala Leu
            435                 440                 445

Arg Ser Arg Cys Cys Ala Leu Ser Lys Gln Asp Ile Glu Leu Tyr Ser
            450                 455                 460

Arg Leu His Arg Leu His Cys Ser Asp Tyr Pro Val Val Asp Lys Asn
465                 470                 475                 480

Cys Gly Pro Thr Leu Asp Lys Ser Trp Ser Met Tyr Arg Thr Glu Arg
            485                 490                 495

Asn Asn Tyr Gln Glu Lys His Arg Val Ile His Leu Glu Phe Asp Leu
            500                 505                 510

Ala Leu Asn Ala Gly Gln Gly Val Phe Leu Gln Thr His Lys Leu Asn
            515                 520                 525

Leu Gly Leu Gly Phe Glu Ser Ile Asn Ser Leu Met Asp His Gly Asp
            530                 535                 540

Met Thr Ala Gln Tyr Thr Leu Gly Arg Leu Tyr Gln Leu Pro Arg Arg
545                 550                 555                 560

Asp Pro Arg Ser Ile Trp Thr Val Ser Leu Cys Asn Asn Thr Arg Ala
                        565                 570                 575

Thr Leu Asn Cys Asp Ala Leu Asn Leu Gly Ile Arg Leu Tyr Leu Arg
                        580                 585                 590

Cys Cys Leu Ile Asn Gln Leu Asn Asn Pro Arg Tyr Gly Ser Val Leu
        595                 600                 605

Phe Gln Phe Gly Thr Arg Val His Arg Thr Trp Thr Pro Thr Ser Leu
        610                 615                 620

Gly Glu Leu Pro Ser Ile Arg Ala Met Ala His Tyr Val Asn His His
625                 630                 635                 640

Pro Asn Gln Val Phe Trp Gly Arg Gly Ala Val Lys His Leu Thr Leu
                        645                 650                 655

Leu Ser Ser Pro Trp Met Leu Lys Phe Ala Ala Ser Gly Arg His Val
                        660                 665                 670

Thr Leu Ser Val Ile Ser Gly Ala Thr Asp Arg Phe Leu Val Pro Pro
        675                 680                 685

Leu Ile Leu Thr Gly Val Asn Tyr Lys Asn Glu Ser Tyr Val Ser Ala
        690                 695                 700

Ile Tyr Asn Val Asp Val Arg Tyr Cys Lys Thr Leu Tyr Tyr Arg Gly
705                 710                 715                 720

Gln Gln Leu Gly Asp Arg Ala Thr Gly Gln Ala Lys Pro Asp Gly Tyr
                        725                 730                 735

Gln Leu His Arg Phe Ala Ala Pro Gly Arg Asn Phe Ser Tyr His Ser
                        740                 745                 750

Lys Lys Phe Arg Pro Ala Lys Glu Asn Thr Lys Asn Ala Glu Ser Ile
            755                 760                 765

Phe Ser Ala Phe Phe Val Gly Ser Asn Gly Leu His Thr Asn Ser Lys
        770                 775                 780

Ser Cys Phe Asn Gly Arg Leu His Glu Pro Ile Pro Tyr Phe Phe Asn
785                 790                 795                 800

Phe Leu Arg Asn Val Pro Arg Phe Asn Glu Tyr His Cys Cys Cys Thr
                        805                 810                 815

Ser Leu Ile Ala Ala Ser Ile Leu Leu His His Ile Tyr His Trp Val
                        820                 825                 830

Phe Asp Phe Arg Tyr Tyr Tyr Phe Val Tyr Phe Cys Trp Ile Leu His
```

-continued

```
            835                 840                 845
His Leu Ile His Ile Asn Ser Phe Leu Met Leu Ser His Tyr Arg
            850                 855                 860
Glu Val Val Tyr Leu Thr Cys Cys Ala Cys Ala Phe Asn Ile Val Thr
865                 870                 875                 880
Val Asn Gly Phe Cys Val Gly Cys Cys Ser Asn Ile Leu Ala Glu Met
                885                 890                 895
Lys Phe

<210> SEQ ID NO 11
<211> LENGTH: 917
<212> TYPE: PRT
<213> ORGANISM: Neisseria gonorrhoeae

<400> SEQUENCE: 11

Met Gln Gln Gln His Leu Phe Arg Leu Asn Ile Leu Cys Leu Ser Leu
1               5                   10                  15
Met Thr Ala Leu Pro Ala Tyr Ala Glu Asn Val Gln Ala Gly Gln Ala
            20                  25                  30
Gln Glu Lys Gln Leu Asp Thr Ile Gln Val Lys Ala Lys Lys Gln Lys
        35                  40                  45
Thr Arg Arg Asp Asn Glu Val Thr Gly Leu Gly Lys Leu Val Lys Thr
    50                  55                  60
Ala Asp Thr Leu Ser Lys Glu Gln Val Leu Asp Ile Arg Asp Leu Thr
65                  70                  75                  80
Arg Tyr Asp Pro Gly Ile Ala Val Val Glu Gln Gly Arg Gly Ala Ser
                85                  90                  95
Ser Gly Tyr Ser Ile Arg Gly Met Asp Lys Asn Arg Val Ser Leu Thr
            100                 105                 110
Val Asp Gly Leu Ala Gln Ile Gln Ser Tyr Thr Ala Gln Ala Ala Leu
        115                 120                 125
Gly Gly Thr Arg Thr Ala Gly Ser Ser Gly Ala Ile Asn Glu Ile Glu
    130                 135                 140
Tyr Glu Asn Val Lys Ala Val Glu Ile Ser Lys Gly Ser Asn Ser Val
145                 150                 155                 160
Glu Gln Gly Ser Gly Ala Leu Ala Gly Ser Val Ala Phe Gln Thr Lys
                165                 170                 175
Thr Ala Asp Asp Val Ile Gly Glu Gly Arg Gln Trp Gly Ile Gln Ser
            180                 185                 190
Lys Thr Ala Tyr Ser Gly Lys Asn Arg Gly Leu Thr Gln Ser Ile Ala
        195                 200                 205
Leu Ala Gly Arg Ile Gly Gly Ala Glu Ala Leu Leu Ile Arg Thr Gly
    210                 215                 220
Arg His Ala Gly Glu Ile Arg Ala His Glu Ala Ala Gly Arg Gly Val
225                 230                 235                 240
Gln Ser Phe Asn Arg Leu Ala Pro Val Asp Asp Gly Ser Lys Tyr Ala
                245                 250                 255
Tyr Phe Ile Val Glu Glu Cys Lys Asn Gly Gly His Glu Lys Cys
            260                 265                 270
Lys Ala Asn Pro Lys Lys Asp Val Val Gly Glu Asp Lys Arg Gln Thr
        275                 280                 285
Val Ser Thr Arg Asp Tyr Thr Gly Pro Asn Arg Phe Leu Ala Asp Pro
    290                 295                 300
Leu Ser Tyr Glu Ser Arg Ser Trp Leu Phe Arg Pro Gly Phe Arg Phe
```

-continued

```
305              310              315              320
Glu Asn Lys Arg His Tyr Ile Gly Gly Ile Leu Glu Arg Thr Gln Gln
            325              330              335
Thr Phe Asp Thr Arg Asp Met Thr Val Pro Ala Phe Leu Thr Lys Ala
            340              345              350
Val Phe Asp Ala Asn Gln Lys Gln Ala Gly Ser Leu Arg Gly Asn Gly
            355              360              365
Asn His Lys Tyr Ala Gly Asn His Lys Tyr Gly Gly Leu Phe Thr Ser
            370              375              380
Gly Glu Asn Asn Ala Pro Val Gly Ala Glu Tyr Gly Thr Gly Val Phe
385              390              395              400
Tyr Asp Glu Thr His Thr Lys Ser Arg Tyr Gly Leu Glu Tyr Val Tyr
            405              410              415
Thr Asn Ala Asp Lys Asp Thr Trp Ala Asp Tyr Ala Arg Leu Ser Tyr
            420              425              430
Asp Arg Gln Gly Ile Gly Leu Asp Asn His Phe Gln Gln Thr His Cys
            435              440              445
Ser Ala Asp Gly Ser Asp Lys Tyr Cys Arg Pro Ser Ala Asp Lys Pro
            450              455              460
Phe Ser Tyr Tyr Lys Ser Asp Arg Val Ile Tyr Gly Glu Ser His Lys
465              470              475              480
Leu Leu Gln Ala Ala Phe Lys Lys Ser Phe Asp Thr Ala Lys Ile Arg
            485              490              495
His Asn Leu Ser Val Asn Leu Gly Tyr Asp Arg Phe Gly Ser Asn Leu
            500              505              510
Arg His Gln Asp Tyr Tyr Gln Ser Ala Asn Arg Ala Tyr Ser Leu
            515              520              525
Lys Thr Pro Pro Gln Asn Asn Gly Lys Lys Thr Ser Pro Asn Gly Arg
            530              535              540
Glu Lys Asn Pro Tyr Trp Val Ser Ile Gly Arg Gly Asn Val Val Thr
545              550              555              560
Arg Gln Ile Cys Leu Phe Gly Asn Asn Thr Tyr Thr Asp Cys Thr Pro
            565              570              575
Arg Ser Ile Asn Gly Lys Ser Tyr Tyr Ala Ala Val Arg Asp Asn Val
            580              585              590
Arg Leu Gly Arg Trp Ala Asp Val Gly Ala Gly Leu Arg Tyr Asp Tyr
            595              600              605
Arg Ser Thr His Ser Asp Asp Gly Ser Val Ser Thr Gly Thr His Arg
            610              615              620
Thr Leu Ser Trp Asn Ala Gly Ile Val Leu Lys Pro Ala Asp Trp Leu
625              630              635              640
Asp Leu Thr Tyr Arg Thr Ser Thr Gly Phe Arg Leu Pro Ser Phe Ala
            645              650              655
Glu Met Tyr Gly Trp Arg Ser Gly Asp Lys Ile Lys Ala Val Lys Ile
            660              665              670
Asp Pro Glu Lys Ser Phe Asn Lys Glu Ala Gly Ile Val Phe Lys Gly
            675              680              685
Asp Phe Gly Asn Leu Glu Ala Ser Trp Phe Asn Asn Ala Tyr Arg Asp
            690              695              700
Leu Ile Val Arg Gly Tyr Glu Ala Gln Ile Lys Asp Gly Lys Glu Gln
705              710              715              720
Val Lys Gly Asn Pro Ala Tyr Leu Asn Ala Gln Ser Ala Arg Ile Thr
            725              730              735
```

```
Gly Ile Asn Ile Leu Gly Lys Ile Asp Trp Asn Gly Val Trp Asp Lys
                740                 745                 750

Leu Pro Glu Gly Trp Tyr Ser Thr Phe Ala Tyr Asn Arg Val Arg Val
            755                 760                 765

Arg Asp Ile Lys Lys Arg Ala Asp Arg Thr Asp Ile Gln Ser His Leu
        770                 775                 780

Phe Asp Ala Ile Gln Pro Ser Arg Tyr Val Val Gly Ser Gly Tyr Asp
785                 790                 795                 800

Gln Pro Glu Gly Lys Trp Gly Val Asn Gly Met Leu Thr Tyr Ser Lys
                805                 810                 815

Ala Lys Glu Ile Thr Glu Leu Leu Gly Ser Arg Ala Leu Leu Asn Gly
            820                 825                 830

Asn Ser Arg Asn Thr Lys Ala Thr Ala Arg Arg Thr Arg Pro Trp Tyr
        835                 840                 845

Ile Val Asp Val Ser Gly Tyr Tyr Thr Val Lys Lys His Phe Thr Leu
            850                 855                 860

Arg Ala Gly Val Tyr Asn Leu Leu Asn His Arg Tyr Val Thr Trp Glu
865                 870                 875                 880

Asn Val Arg Gln Thr Ala Ala Gly Ala Val Asn Gln His Lys Asn Val
                885                 890                 895

Gly Val Tyr Asn Arg Tyr Ala Ala Pro Gly Arg Asn Tyr Thr Phe Ser
                900                 905                 910

Leu Glu Met Lys Phe
        915

<210> SEQ ID NO 12
<211> LENGTH: 908
<212> TYPE: PRT
<213> ORGANISM: Neisseria meningitidis

<400> SEQUENCE: 12

Met Gln Gln Gln His Leu Phe Arg Leu Asn Ile Leu Cys Leu Ser Leu
1               5                   10                  15

Met Thr Ala Leu Pro Val Tyr Ala Glu Asn Val Gln Ala Glu Gln Ala
            20                  25                  30

Gln Glu Lys Gln Leu Asp Thr Ile Gln Val Lys Ala Lys Lys Gln Lys
        35                  40                  45

Thr Arg Arg Asp Asn Glu Val Thr Gly Leu Gly Lys Leu Val Lys Ser
    50                  55                  60

Ser Asp Thr Leu Ser Lys Glu Gln Val Leu Asn Ile Arg Asp Leu Thr
65                  70                  75                  80

Arg Tyr Asp Pro Gly Ile Ala Val Val Glu Gln Gly Arg Gly Ala Ser
                85                  90                  95

Ser Gly Tyr Ser Ile Arg Gly Met Asp Lys Asn Arg Val Ser Leu Thr
            100                 105                 110

Val Asp Gly Val Ser Gln Ile Gln Ser Tyr Thr Ala Gln Ala Ala Leu
        115                 120                 125

Gly Gly Thr Arg Thr Ala Gly Ser Ser Gly Ala Ile Asn Glu Ile Glu
    130                 135                 140

Tyr Glu Asn Val Lys Ala Val Glu Ile Ser Lys Gly Ser Asn Ser Ser
145                 150                 155                 160

Glu Tyr Gly Asn Gly Ala Leu Ala Gly Ser Val Ala Phe Gln Thr Lys
                165                 170                 175

Thr Ala Ala Asp Ile Ile Gly Glu Gly Lys Gln Trp Gly Ile Gln Ser
```

-continued

```
                180                 185                 190
Lys Thr Ala Tyr Ser Gly Lys Asp His Ala Leu Thr Gln Ser Leu Ala
            195                 200                 205
Leu Ala Gly Arg Ser Gly Gly Ala Glu Ala Leu Leu Ile Tyr Thr Lys
        210                 215                 220
Arg Arg Gly Arg Glu Ile His Ala His Lys Asp Ala Gly Lys Gly Val
225                 230                 235                 240
Gln Ser Phe Asn Arg Leu Val Leu Asp Glu Asp Lys Lys Glu Gly Gly
                245                 250                 255
Ser Gln Tyr Arg Tyr Phe Ile Val Glu Glu Cys His Asn Gly Tyr
            260                 265                 270
Ala Ala Cys Lys Asn Lys Leu Lys Glu Asp Ala Ser Val Lys Asp Glu
        275                 280                 285
Arg Lys Thr Val Ser Thr Gln Asp Tyr Thr Gly Ser Asn Arg Leu Leu
290                 295                 300
Ala Asn Pro Leu Glu Tyr Gly Ser Gln Ser Trp Leu Phe Arg Pro Gly
305                 310                 315                 320
Trp His Leu Asp Asn Arg His Tyr Val Gly Ala Val Leu Glu Arg Thr
                325                 330                 335
Gln Gln Thr Phe Asp Thr Arg Asp Met Thr Val Pro Ala Tyr Phe Thr
            340                 345                 350
Ser Glu Asp Tyr Val Pro Gly Ser Leu Lys Gly Leu Gly Lys Tyr Ser
        355                 360                 365
Gly Asp Asn Lys Ala Glu Arg Leu Phe Val Gln Gly Glu Gly Ser Thr
        370                 375                 380
Leu Gln Gly Ile Gly Tyr Gly Thr Gly Val Phe Tyr Asp Glu Arg His
385                 390                 395                 400
Thr Lys Asn Arg Tyr Gly Val Glu Tyr Val Tyr His Asn Ala Asp Lys
                405                 410                 415
Asp Thr Trp Ala Asp Tyr Ala Arg Leu Ser Tyr Asp Arg Gln Gly Ile
            420                 425                 430
Asp Leu Asp Asn Arg Leu Gln Gln Thr His Cys Ser His Asp Gly Ser
        435                 440                 445
Asp Lys Asn Cys Arg Pro Asp Gly Asn Lys Pro Tyr Ser Phe Tyr Lys
        450                 455                 460
Ser Asp Arg Met Ile Tyr Glu Glu Ser Arg Asn Leu Phe Gln Ala Val
465                 470                 475                 480
Phe Lys Lys Ala Phe Asp Thr Ala Lys Ile Arg His Asn Leu Ser Ile
                485                 490                 495
Asn Leu Gly Tyr Asp Arg Phe Lys Ser Gln Leu Ser His Ser Asp Tyr
            500                 505                 510
Tyr Leu Gln Asn Ala Val Gln Ala Tyr Asp Leu Ile Thr Pro Lys Lys
        515                 520                 525
Pro Pro Phe Pro Asn Gly Ser Lys Asp Asn Pro Tyr Arg Val Ser Ile
        530                 535                 540
Gly Lys Thr Thr Val Asn Thr Ser Pro Ile Cys Arg Phe Gly Asn Asn
545                 550                 555                 560
Thr Tyr Thr Asp Cys Thr Pro Arg Asn Ile Gly Gly Asn Gly Tyr Tyr
                565                 570                 575
Ala Ala Val Gln Asp Asn Val Arg Leu Gly Arg Trp Ala Asp Val Gly
            580                 585                 590
Ala Gly Ile Arg Tyr Asp Tyr Arg Ser Thr His Ser Glu Asp Lys Ser
        595                 600                 605
```

```
Val Ser Thr Gly Thr His Arg Asn Leu Ser Trp Asn Ala Gly Val Val
    610                 615                 620

Leu Lys Pro Phe Thr Trp Met Asp Leu Thr Tyr Arg Ala Ser Thr Gly
625                 630                 635                 640

Phe Arg Leu Pro Ser Phe Ala Glu Met Tyr Gly Trp Arg Ala Gly Glu
                645                 650                 655

Ser Leu Lys Thr Leu Asp Leu Lys Pro Glu Lys Ser Phe Asn Arg Glu
            660                 665                 670

Ala Gly Ile Val Phe Lys Gly Asp Phe Gly Asn Leu Glu Ala Ser Tyr
        675                 680                 685

Phe Asn Asn Ala Tyr Arg Asp Leu Ile Ala Phe Gly Tyr Glu Thr Arg
    690                 695                 700

Thr Gln Asn Gly Gln Thr Ser Ala Ser Gly Asp Pro Gly Tyr Arg Asn
705                 710                 715                 720

Ala Gln Asn Ala Arg Ile Ala Gly Ile Asn Ile Leu Gly Lys Ile Asp
                725                 730                 735

Trp His Gly Val Trp Gly Gly Leu Pro Asp Gly Leu Tyr Ser Thr Leu
            740                 745                 750

Ala Tyr Asn Arg Ile Lys Val Lys Asp Ala Asp Ile Arg Ala Asp Arg
        755                 760                 765

Thr Phe Val Thr Ser Tyr Leu Phe Asp Ala Val Gln Pro Ser Arg Tyr
    770                 775                 780

Val Leu Gly Leu Gly Tyr Asp His Pro Asp Gly Ile Trp Gly Ile Asn
785                 790                 795                 800

Thr Met Phe Thr Tyr Ser Lys Ala Lys Ser Val Asp Glu Leu Leu Gly
                805                 810                 815

Ser Gln Ala Leu Leu Asn Gly Asn Ala Asn Ala Lys Lys Ala Ala Ser
            820                 825                 830

Arg Arg Thr Arg Pro Trp Tyr Val Thr Asp Val Ser Gly Tyr Tyr Asn
        835                 840                 845

Ile Lys Lys His Leu Thr Leu Arg Ala Gly Val Tyr Asn Leu Leu Asn
    850                 855                 860

Tyr Arg Tyr Val Thr Trp Glu Asn Val Arg Gln Thr Ala Gly Gly Ala
865                 870                 875                 880

Val Asn Gln His Lys Asn Val Gly Val Tyr Asn Arg Tyr Ala Ala Pro
                885                 890                 895

Gly Arg Asn Tyr Thr Phe Ser Leu Glu Met Lys Phe
            900                 905

<210> SEQ ID NO 13
<211> LENGTH: 604
<212> TYPE: PRT
<213> ORGANISM: Pasteurella haemolytica

<400> SEQUENCE: 13

Met Ile Met Lys Tyr His His Phe Arg Tyr Ser Thr Val Ala Leu Thr
1               5                   10                  15

Val Leu Phe Ala Leu Ser His Ser Tyr Gly Ala Ala Thr Glu Asn Lys
            20                  25                  30

Lys Ile Glu Glu Asn Asn Asp Leu Ala Val Leu Asp Val Ile Val
        35                  40                  45

Thr Glu Ser His Tyr Ala His Glu Arg Gln Asn Glu Val Thr Gly Leu
    50                  55                  60

Gly Lys Val Val Lys Asn Tyr His Glu Met Ser Lys Asn Gln Ile Leu
```

```
65                  70                  75                  80
Gly Ile Arg Asp Leu Thr Arg Tyr Asp Pro Gly Ile Ser Val Val Glu
                85                  90                  95
Gln Gly Arg Gly Ala Ser Ser Gly Tyr Ala Ile Arg Gly Val Asp Lys
            100                 105                 110
Asn Arg Val Ser Leu Leu Val Asp Gly Leu Pro Gln Ala His Ser Tyr
        115                 120                 125
His Thr Leu Ser Gly Asp Ala Asn Gly Ala Ile Asn Glu Ile Glu
    130                 135                 140
Tyr Glu Asn Ile Arg Ser Ile Glu Leu Ser Lys Gly Ala Ser Ser Ala
145                 150                 155                 160
Glu Tyr Gly Ser Gly Ala His Gly Gly Ala Ile Gly Phe Arg Thr Lys
            165                 170                 175
Asp Ala Gln Asp Ile Ile Lys Glu Gly Gln His Trp Gly Leu Asp Ser
        180                 185                 190
Lys Thr Ser Tyr Ala Ser Lys Asn Ser His Phe Leu Gln Ile Ala Ala
    195                 200                 205
Ala Gly Glu Ala Gly Gly Phe Glu Ala Leu Val Ile Ala Thr His Arg
    210                 215                 220
His Gly Lys Glu Thr Lys Ile His Ser Glu Ala Asn Lys Leu Lys His
225                 230                 235                 240
Asn Ile Arg Arg Ile Thr Gly Phe Glu Asn Arg Tyr Asp Phe Thr Gln
            245                 250                 255
Ile Pro His Arg Met Pro Pro Gly Gly Ser Phe Phe Ile Val Glu Asp
            260                 265                 270
Thr Cys Pro Thr Leu Asp Cys Thr Pro Arg Ala Arg Val Lys Leu Asn
        275                 280                 285
Arg Asp Asn Phe Pro Val Arg Thr Phe Pro Glu Tyr Thr Pro Glu Glu
290                 295                 300
Arg Asn Ala Glu Gln Ile Pro Tyr Arg Thr Glu Gln Leu Ser Ala Gln
305                 310                 315                 320
Glu Lys Thr Gly Lys Asp Arg Ile Ala Pro Asn Pro Leu Asp Tyr Lys
            325                 330                 335
Ser Asn Ser Val Phe Met Lys Phe Gly Tyr His Phe Asn Ser Ser His
        340                 345                 350
Tyr Leu Gly Ala Ile Leu Glu Asp Thr Lys Gln Arg Thr Ile Ser Val
    355                 360                 365
Ile Cys Lys Arg Gln Leu Thr Ile Gln Lys Thr Ile Leu Thr Tyr His
    370                 375                 380
Leu Gly Thr Met Phe Met Lys Gly Ile Ile Phe Arg Trp Leu Ser Val
385                 390                 395                 400
Gln Ala Lys Asp Pro Leu Met Val Ala His Met Pro Cys Glu Val Asp
            405                 410                 415
Glu Arg His His Lys Arg Arg Leu Gly Phe Thr Tyr Lys Tyr Lys Pro
            420                 425                 430
Glu Asn Asn Arg Trp Leu Asp Ser Ile Asn Ser Cys Val Arg Ala Leu
        435                 440                 445
Arg Ser Arg Cys Cys Ala Leu Ser Lys Gln Asp Ile Glu Leu Tyr Ser
    450                 455                 460
Arg Leu His Arg Leu His Cys Ser Asp Tyr Pro Val Val Asp Lys Asn
465                 470                 475                 480
Cys Gly Pro Thr Leu Asp Lys Ser Trp Ser Met Tyr Arg Thr Glu Arg
            485                 490                 495
```

```
Asn Asn Tyr Gln Glu Lys Ala Thr Cys His Ser Phe Cys Ile Leu Lys
            500                 505                 510

Ala Leu Asn Ala Gly Gln Gly Val Phe Lys Gln Thr His Lys Leu Asn
            515                 520                 525

Leu Gly Leu Gly Phe Glu Ser Asn Leu Ile Arg Leu Thr Ile Ile Gly
            530                 535                 540

Ile Ile Leu Pro Asn Ile Pro Lys Ala Gly Tyr Thr Ser Tyr Arg Gly
545                 550                 555                 560

Arg Gly Arg Leu Asp Asn Pro Tyr Ile Tyr Arg Arg Asp Pro Arg Ser
            565                 570                 575

Ile Glu Thr Val Ser Leu Cys Asn Asn Thr Arg Ala Thr Leu Leu Leu
            580                 585                 590

Leu Arg Val Asn Lys Gly Ile Arg Leu Leu Leu Arg
            595                 600
```

<210> SEQ ID NO 14
<211> LENGTH: 593
<212> TYPE: PRT
<213> ORGANISM: Actinobacillus pleuropneumoniae

<400> SEQUENCE: 14

```
Met His Phe Lys Leu Asn Pro Tyr Ala Leu Ala Phe Thr Ser Leu Phe
  1               5                  10                  15

Leu Val Ala Cys Ser Gly Gly Lys Gly Ser Phe Asp Leu Glu Asp Val
             20                  25                  30

Arg Pro Asn Gln Thr Ala Lys Ala Glu Lys Ala Thr Thr Ser Tyr Gln
             35                  40                  45

Asp Glu Glu Thr Lys Lys Thr Lys Glu Glu Leu Asp Lys Leu Met
 50                  55                  60

Glu Pro Ala Leu Gly Tyr Glu Thr Gln Ile Leu Arg Arg Asn Lys Ala
 65                  70                  75                  80

Pro Lys Thr Glu Thr Gly Glu Lys Arg Asn Glu Arg Val Val Glu Leu
             85                  90                  95

Ser Glu Asp Lys Ile Thr Lys Leu Tyr Gln Glu Ser Val Glu Ile Ile
            100                 105                 110

Pro His Leu Asp Glu Leu Asn Gly Lys Thr Thr Ser Asn Asp Val Tyr
            115                 120                 125

His Ser His Asp Ser Lys Arg Leu Asp Lys Asn Arg Asp Leu Lys Tyr
            130                 135                 140

Val Arg Ser Gly Tyr Val Tyr Asp Gly Ser Phe Asn Glu Ile Arg Arg
145                 150                 155                 160

Asn Asp Ser Gly Phe His Val Phe Lys Gln Gly Ile Asp Gly Tyr Val
            165                 170                 175

Tyr Tyr Leu Gly Val Thr Pro Ser Lys Glu Leu Pro Lys Gly Lys Val
            180                 185                 190

Ile Ser Tyr Lys Gly Thr Trp Asp Phe Val Ser Asn Ile Asn Leu Glu
            195                 200                 205

Arg Glu Ile Asp Gly Phe Asp Thr Ser Gly Asp Gly Lys Asn Val Ser
            210                 215                 220

Ala Thr Ser Ile Thr Glu Thr Val Asn Arg Asp His Lys Val Gly Glu
225                 230                 235                 240

Lys Leu Gly Asp Asn Glu Val Lys Gly Val Ala His Ser Ser Glu Phe
            245                 250                 255

Ala Val Asp Phe Asp Asn Lys Lys Leu Thr Gly Ser Leu Tyr Arg Asn
```

-continued

```
            260                 265                 270

Gly Tyr Ile Asn Arg Asn Lys Ala Gln Glu Val Thr Lys Arg Tyr Ser
        275                 280                 285

Ile Glu Ala Asp Ile Ala Gly Asn Arg Phe Arg Gly Lys Ala Lys Ala
    290                 295                 300

Glu Lys Ala Gly Asp Pro Ile Phe Thr Asp Ser Asn Tyr Leu Glu Gly
305                 310                 315                 320

Gly Phe Tyr Gly Pro Lys Ala Glu Glu Met Ala Gly Lys Phe Phe Thr
                325                 330                 335

Asn Asn Lys Ser Leu Phe Ala Val Phe Ala Ala Lys Ser Glu Asn Gly
            340                 345                 350

Glu Thr Thr Thr Glu Arg Ile Ile Asp Ala Thr Lys Ile Asp Leu Thr
        355                 360                 365

Gln Phe Asn Ala Lys Glu Leu Asn Asn Phe Gly Asp Ala Ser Val Leu
    370                 375                 380

Ile Ile Asp Gly Gln Lys Ile Asp Leu Ala Gly Val Asn Phe Lys Asn
385                 390                 395                 400

Ser Lys Thr Val Glu Ile Asn Gly Lys Thr Met Val Ala Val Ala Cys
                405                 410                 415

Cys Ser Asn Leu Glu Tyr Met Lys Phe Gly Gln Leu Trp Gln Lys Glu
            420                 425                 430

Gly Lys Gln Gln Val Lys Asp Asn Ser Leu Phe Leu Gln Gly Glu Arg
        435                 440                 445

Thr Ala Thr Asp Lys Met Pro Ala Gly Gly Asn Tyr Lys Tyr Val Gly
    450                 455                 460

Thr Trp Asp Ala Leu Val Ser Lys Gly Thr Asn Trp Ile Ala Glu Ala
465                 470                 475                 480

Asp Asn Asn Arg Glu Ser Gly Tyr Arg Thr Glu Phe Asp Val Asn Phe
                485                 490                 495

Ser Asp Lys Lys Val Asn Gly Lys Leu Phe Asp Lys Gly Gly Val Asn
            500                 505                 510

Pro Val Phe Thr Val Asp Ala Thr Ile Asn Gly Asn Gly Phe Ile Gly
        515                 520                 525

Ser Ala Lys Thr Ser Asp Ser Gly Phe Ala Leu Asp Ala Gly Ser Ser
    530                 535                 540

Gln His Gly Asn Ala Val Phe Ser Asp Ile Lys Val Asn Gly Gly Phe
545                 550                 555                 560

Tyr Gly Pro Thr Ala Gly Glu Leu Gly Gly Gln Phe His His Lys Ser
                565                 570                 575

Asp Asn Gly Ser Val Gly Ala Val Phe Gly Ala Lys Arg Gln Ile Glu
            580                 585                 590

Lys

<210> SEQ ID NO 15
<211> LENGTH: 547
<212> TYPE: PRT
<213> ORGANISM: Actinobacillus pleuropneumoniae

<400> SEQUENCE: 15

Met His Phe Lys Leu Asn Pro Tyr Ala Leu Ala Phe Thr Ser Leu Phe
 1               5                  10                  15

Leu Val Ala Cys Ser Gly Gly Lys Gly Ser Phe Asp Leu Glu Asp Val
            20                  25                  30

Arg Pro Asn Lys Thr Thr Gly Val Ser Lys Glu Glu Tyr Lys Asp Val
```

-continued

```
                35                      40                      45
Glu Thr Ala Lys Lys Glu Lys Glu Gln Leu Gly Glu Leu Met Glu Pro
             50                      55                      60
Ala Leu Gly Tyr Val Val Lys Val Pro Val Ser Ser Phe Glu Asn Lys
 65                      70                      75                      80
Lys Val Asp Ile Ser Asp Ile Glu Val Ile Thr Asn Gly Asn Leu Asp
                     85                      90                      95
Asp Val Pro Tyr Lys Ala Asn Ser Ser Lys Tyr Asn Tyr Pro Asp Ile
                    100                     105                     110
Lys Thr Lys Asp Ser Ser Leu Gln Tyr Val Arg Ser Gly Tyr Val Ile
                115                     120                     125
Asp Gly Glu His Ser Gly Ser Asn Glu Lys Gly Tyr Val Tyr Tyr Lys
            130                     135                     140
Gly Asn Ser Pro Ala Lys Glu Leu Pro Val Asn Gln Leu Leu Thr Tyr
145                     150                     155                     160
Thr Gly Ser Trp Asp Phe Thr Ser Asn Ala Asn Leu Asn Asn Glu Glu
                        165                     170                     175
Gly Arg Pro Asn Tyr Leu Asn Asp Asp Tyr Tyr Thr Lys Phe Ile Gly
                    180                     185                     190
Lys Arg Val Gly Leu Val Ser Gly Asp Ala Lys Pro Ala Lys His Lys
                195                     200                     205
Tyr Thr Ser Gln Phe Glu Val Asp Phe Ala Thr Lys Lys Met Thr Gly
            210                     215                     220
Lys Leu Ser Asp Lys Glu Lys Thr Ile Tyr Thr Val Asn Ala Asp Ile
225                     230                     235                     240
Arg Gly Asn Arg Phe Thr Gly Ala Ala Thr Ala Ser Asp Lys Asn Lys
                        245                     250                     255
Gly Lys Gly Glu Ser Tyr Asn Phe Phe Ser Ala Asp Ser Gln Ser Leu
                    260                     265                     270
Glu Gly Gly Phe Tyr Gly Pro Lys Ala Glu Glu Met Ala Gly Lys Phe
                275                     280                     285
Val Ala Asn Asp Lys Ser Leu Phe Ala Val Phe Ser Ala Lys His Asn
            290                     295                     300
Gly Ser Asn Val Asn Thr Val Arg Ile Ile Asp Ala Ser Lys Ile Asp
305                     310                     315                     320
Leu Thr Asn Phe Ser Ile Ser Glu Leu Asn Asn Phe Gly Asp Ala Ser
                        325                     330                     335
Val Leu Ile Ile Asp Gly Lys Lys Ile Lys Leu Ala Gly Ser Gly Phe
                    340                     345                     350
Thr Asn Lys His Thr Ile Glu Ile Asn Gly Lys Thr Met Val Ala Val
                355                     360                     365
Ala Cys Cys Ser Asn Leu Glu Tyr Met Lys Phe Gly Gln Leu Trp Gln
            370                     375                     380
Gln Ala Glu Gly Gly Lys Pro Glu Asn Asn Ser Leu Phe Leu Gln Gly
385                     390                     395                     400
Glu Arg Thr Ala Thr Asp Lys Met Pro Lys Gly Gly Asn Tyr Lys Tyr
                        405                     410                     415
Ile Gly Thr Trp Asp Ala Gln Val Ser Lys Glu Asn Asn Trp Val Ala
                    420                     425                     430
Thr Ala Asp Asp Arg Lys Ala Gly Tyr Arg Thr Glu Phe Asp Val
                435                     440                     445
Asp Phe Gly Asn Lys Asn Leu Ser Gly Lys Leu Phe Asp Lys Asn Gly
450                     455                     460
```

```
Val Asn Pro Val Phe Thr Val Asp Ala Lys Ile Asp Gly Asn Gly Phe
465                 470                 475                 480

Thr Gly Lys Ala Lys Thr Ser Asp Glu Gly Phe Ala Leu Asp Ser Gly
                485                 490                 495

Ser Ser Arg Tyr Glu Asn Val Lys Phe Asn Asp Val Ala Val Ser Gly
            500                 505                 510

Gly Phe Tyr Gly Pro Thr Ala Ala Glu Leu Gly Gly Gln Phe His His
            515                 520                 525

Lys Ser Glu Asn Gly Ser Val Gly Ala Val Phe Gly Ala Lys Gln Gln
            530                 535                 540

Val Lys Lys
545

<210> SEQ ID NO 16
<211> LENGTH: 7
<212> TYPE: PRT
<213> ORGANISM: Pasteurella haemolytica

<400> SEQUENCE: 16

Asp Glu Val Ile Val Thr Glu
1               5

<210> SEQ ID NO 17
<211> LENGTH: 7
<212> TYPE: PRT
<213> ORGANISM: Escherichia coli

<400> SEQUENCE: 17

Glu Thr Met Val Val Thr Ala
1               5

<210> SEQ ID NO 18
<211> LENGTH: 7
<212> TYPE: PRT
<213> ORGANISM: Escherichia coli

<400> SEQUENCE: 18

Asp Thr Ile Val Val Thr Ala
1               5

<210> SEQ ID NO 19
<211> LENGTH: 7
<212> TYPE: PRT
<213> ORGANISM: Escherichia coli

<400> SEQUENCE: 19

Asp Thr Ile Thr Val Thr Ala
1               5

<210> SEQ ID NO 20
<211> LENGTH: 7
<212> TYPE: PRT
<213> ORGANISM: Escherichia coli

<400> SEQUENCE: 20

Phe Thr Leu Ser Val Asp Ala
1               5

<210> SEQ ID NO 21
<211> LENGTH: 330
<212> TYPE: DNA
<213> ORGANISM: Pasteurella haemolytica
```

<400> SEQUENCE: 21

```
atttttatc taatctaaaa acaagcgttt ccaccttgga aatgattaac atgatcctga      60
aactaataaa gttcaaacct ttacattaag tttatattat aaattataat gattattatt    120
ttataaatta aaggagacat tatgtttaaa cttaaaagta gttttgtact ggaaaaataa    180
tcataattcc cctttgctgg ttgtagatag caagcgggca atttttata aaatttgca      240
aaatttaaat aaaggagacc ctatctaatg ataatgaaat atcatcattt tcgcagaaat    300
ttcagtttag catttgaaat gaagttttag                                     330
```

<210> SEQ ID NO 22
<211> LENGTH: 32
<212> TYPE: DNA
<213> ORGANISM: Artificial Sequence
<220> FEATURE:
<223> OTHER INFORMATION: Oligonucleotide primer

<400> SEQUENCE: 22

```
ggaagcttac tgaaataaa aaaatcgaag aa                                    32
```

<210> SEQ ID NO 23
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 23

```
ggaattcccg tcctgtggat c                                               21
```

<210> SEQ ID NO 24
<211> LENGTH: 22
<212> TYPE: DNA
<213> ORGANISM: Artificial Sequence
<220> FEATURE:
<223> OTHER INFORMATION: Oligonucleotide primer

<400> SEQUENCE: 24

```
gtgaattccg gcgtagagga tc                                              22
```

<210> SEQ ID NO 25
<211> LENGTH: 32
<212> TYPE: DNA
<213> ORGANISM: Artificial Sequence
<220> FEATURE:
<223> OTHER INFORMATION: Oligonucleotide primer

<400> SEQUENCE: 25

```
ggaagcttac tgaaataaa aaaatcgaag aa                                    32
```

<210> SEQ ID NO 26
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 26

```
cactactttc cccaagccag                                                 20
```

<210> SEQ ID NO 27
<211> LENGTH: 20
<212> TYPE: DNA

```
<213> ORGANISM: Artificial Sequence
<220> FEATURE:
<223> OTHER INFORMATION: Oligonucleotide primer

<400> SEQUENCE: 27
ggaattccct cctgtggatc                                              20

<210> SEQ ID NO 28
<211> LENGTH: 21
<212> TYPE: DNA
<213> ORGANISM: Artificial Sequence
<220> FEATURE:
<221> NAME/KEY: misc_feature
<222> LOCATION: 3
<223> OTHER INFORMATION: modified nucleotide "i" or inosine
<220> FEATURE:
<221> NAME/KEY: misc_feature
<222> LOCATION: 6
<223> OTHER INFORMATION: modified nucleotide "i" or inosine
<220> FEATURE:
<221> NAME/KEY: misc_feature
<222> LOCATION: 7
<223> OTHER INFORMATION: modified nucleotide "i" or inosine
<220> FEATURE:
<221> NAME/KEY: misc_feature
<222> LOCATION: 9
<223> OTHER INFORMATION: modified nucleotide "i" or inosine
<220> FEATURE:
<221> NAME/KEY: misc_feature
<222> LOCATION: 12
<223> OTHER INFORMATION: modified nucleotide "i" or inosine
<221> NAME/KEY: misc_feature
<222> LOCATION: 15
<223> OTHER INFORMATION: modified nucleotide "i" or inosine
<220> FEATURE:
<223> OTHER INFORMATION: Oligonucleotide primer

<400> SEQUENCE: 28
gcngcnnsng cncgnaaytw y                                            21

<210> SEQ ID NO 29
<211> LENGTH: 22
<212> TYPE: DNA
<213> ORGANISM: Pasteurella haemolytica
<220> FEATURE:
<221> NAME/KEY: misc_feature
<222> LOCATION: 11
<223> OTHER INFORMATION: modified nucleotide "i" or inosine
<220> FEATURE:
<221> NAME/KEY: misc_feature
<222> LOCATION: 17
<223> OTHER INFORMATION: modified nucleotide "i" or inosine
<221> NAME/KEY: misc_feature
<222> LOCATION: 20
<223> OTHER INFORMATION: modified nucleotide "i" or inosine
<223> OTHER INFORMATION: Oligonucleotide primer

<400> SEQUENCE: 29
caaagcttgc ntgytcnggn gg                                           22

<210> SEQ ID NO 30
<211> LENGTH: 36
<212> TYPE: DNA
<213> ORGANISM: Artificial Sequence
<220> FEATURE:
<223> OTHER INFORMATION: Oligonucleotide primer

<400> SEQUENCE: 30
agatctggat tctaaatcag accgcttgta ttttag                            36

<210> SEQ ID NO 31
```

```
<211> LENGTH: 20
<212> TYPE: DNA
<213> ORGANISM: Artificial Sequence
<220> FEATURE:
<221> NAME/KEY: misc_feature
<222> LOCATION: 3
<223> OTHER INFORMATION: modified nucleotide "i" or inosine
<220> FEATURE:
<221> NAME/KEY: misc_feature
<222> LOCATION: 6
<223> OTHER INFORMATION: modified nucleotide "i" or inosine
<220> FEATURE:
<221> NAME/KEY: misc_feature
<222> LOCATION: 9
<223> OTHER INFORMATION: modified nucleotide "i" or inosine
<221> NAME/KEY: misc_feature
<222> LOCATION: 12
<223> OTHER INFORMATION: modified nucleotide "i" or inosine
<220> FEATURE:
<223> OTHER INFORMATION: Oligonucleotide primer

<400> SEQUENCE: 31
gtnwvnggng gnttytaygg                                         20

<210> SEQ ID NO 32
<211> LENGTH: 29
<212> TYPE: DNA
<213> ORGANISM: Artificial Sequence
<220> FEATURE:
<223> OTHER INFORMATION: Oligonucleotide primer

<400> SEQUENCE: 32
taaattaaag gagacattat gtttaaact                               29

<210> SEQ ID NO 33
<211> LENGTH: 36
<212> TYPE: DNA
<213> ORGANISM: Artificial Sequence
<220> FEATURE:
<223> OTHER INFORMATION: Oligonucleotide primer

<400> SEQUENCE: 33
cgacgcccat ggttatttttt ctatttgacg ttttcc                      36

<210> SEQ ID NO 34
<211> LENGTH: 28
<212> TYPE: DNA
<213> ORGANISM: Artificial Sequence
<220> FEATURE:
<223> OTHER INFORMATION: Oligonucleotide primer

<400> SEQUENCE: 34
gcgcaagctt ttatttttct atttgacg                                28

<210> SEQ ID NO 35
<211> LENGTH: 39
<212> TYPE: DNA
<213> ORGANISM: Artificial Sequence
<220> FEATURE:
<223> OTHER INFORMATION: Oligonucleotide primer

<400> SEQUENCE: 35
ggattcagat cttaaaggag accctatcta atgataatg                    39

<210> SEQ ID NO 36
<211> LENGTH: 28
<212> TYPE: DNA
<213> ORGANISM: Artificial Sequence
<220> FEATURE:
```

```
<223> OTHER INFORMATION: Oligonucleotide primer

<400> SEQUENCE: 36
ccctatcata tgataatgaa atatcatc                                    28

<210> SEQ ID NO 37
<211> LENGTH: 31
<212> TYPE: DNA
<213> ORGANISM: Artificial Sequence
<220> FEATURE:
<223> OTHER INFORMATION: Oligonucleotide primer

<400> SEQUENCE: 37
tagcgcaagc ttctaaaact tcatttcaaa t                                31

<210> SEQ ID NO 38
<211> LENGTH: 5
<212> TYPE: PRT
<213> ORGANISM: Pasteurella haemolytica

<400> SEQUENCE: 38

Tyr Lys Gly Tyr Trp
 1               5

<210> SEQ ID NO 39
<211> LENGTH: 5
<212> TYPE: PRT
<213> ORGANISM: Pasteurella haemolytica

<400> SEQUENCE: 39

Tyr Arg Gly Thr Trp
 1               5

<210> SEQ ID NO 40
<211> LENGTH: 8
<212> TYPE: PRT
<213> ORGANISM: Pasteurella haemolytica

<400> SEQUENCE: 40

Phe Thr Ala Asp Phe Ala Asn Lys
 1               5

<210> SEQ ID NO 41
<211> LENGTH: 8
<212> TYPE: PRT
<213> ORGANISM: Pasteurella haemolytica

<400> SEQUENCE: 41

Phe Asp Val Asp Phe Val Asn Lys
 1               5

<210> SEQ ID NO 42
<211> LENGTH: 6
<212> TYPE: PRT
<213> ORGANISM: Pasteurella haemolytica

<400> SEQUENCE: 42

Gly Asn Arg Phe Ser Gly
 1               5

<210> SEQ ID NO 43
<211> LENGTH: 6
<212> TYPE: PRT
<213> ORGANISM: Pasteurella haemolytica
```

```
<400> SEQUENCE: 43

Gly Asn Gly Phe Gly Gly
 1               5

<210> SEQ ID NO 44
<211> LENGTH: 7
<212> TYPE: PRT
<213> ORGANISM: Pasteurella haemolytica

<400> SEQUENCE: 44

Leu Glu Gly Gly Phe Phe Gly
 1               5

<210> SEQ ID NO 45
<211> LENGTH: 7
<212> TYPE: PRT
<213> ORGANISM: Pasteurella haemolytica

<400> SEQUENCE: 45

Phe Glu Gly Gly Phe Tyr Gly
 1               5

<210> SEQ ID NO 46
<211> LENGTH: 28
<212> TYPE: DNA
<213> ORGANISM: Artificial Sequence
<220> FEATURE:
<223> OTHER INFORMATION: Oligonucleotide primer

<400> SEQUENCE: 46
ccctatcata tgataatgaa atatcatc                                        28

<210> SEQ ID NO 47
<211> LENGTH: 31
<212> TYPE: DNA
<213> ORGANISM: Artificial Sequence
<220> FEATURE:
<223> OTHER INFORMATION: Oligonucleotide primer

<400> SEQUENCE: 47
tagcgcaagc ttctaaaact tcatttcaaa t                                    31

<210> SEQ ID NO 48
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 48
taatgttggg caagtatctt ccac                                            24

<210> SEQ ID NO 49
<211> LENGTH: 29
<212> TYPE: DNA
<213> ORGANISM: Artificial Sequence
<220> FEATURE:
<223> OTHER INFORMATION: Oligonucleotide primer

<400> SEQUENCE: 49
taaattaaag gagacattat gtttaaact                                       29

<210> SEQ ID NO 50
<211> LENGTH: 28
<212> TYPE: DNA
```

```
<213> ORGANISM: Artificial Sequence
<220> FEATURE:
<223> OTHER INFORMATION: Oligonucleotide primer

<400> SEQUENCE: 50
gcgcaagctt ttatttttct atttgacg                                          28

<210> SEQ ID NO 51
<211> LENGTH: 21
<212> TYPE: DNA
<213> ORGANISM: Artificial Sequence
<220> FEATURE:
<223> OTHER INFORMATION: Oligonucleotide primer

<400> SEQUENCE: 51
ctgttggcaa atctgccaga g                                                 21

<210> SEQ ID NO 52
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 52
aggtaatcgc ttttctggta aagc                                              24

<210> SEQ ID NO 53
<211> LENGTH: 17
<212> TYPE: PRT
<213> ORGANISM: Pasterurella haemolytica

<400> SEQUENCE: 53

Tyr Ala Ile Arg Gly Val Asp Lys Asn Arg Val Ser Leu Leu Val Asp
 1               5                  10                  15
Gly

<210> SEQ ID NO 54
<211> LENGTH: 17
<212> TYPE: PRT
<213> ORGANISM: Escherichia coli

<400> SEQUENCE: 54

Val Ser Ile Arg Gly Leu Asp Ser Ser Tyr Thr Leu Ile Leu Val Asp
 1               5                  10                  15
Gly

<210> SEQ ID NO 55
<211> LENGTH: 17
<212> TYPE: PRT
<213> ORGANISM: Escherichia coli

<400> SEQUENCE: 55

Ile Asp Ile Arg Gly Met Gly Pro Glu Asn Thr Leu Ile Leu Ile Asp
 1               5                  10                  15
Gly

<210> SEQ ID NO 56
<211> LENGTH: 19
<212> TYPE: PRT
<213> ORGANISM: Escherichia coli

<400> SEQUENCE: 56
```

```
Leu Ile Ile Arg Gly Phe Ala Ala Glu Gly Gln Ser Gln Asn Asn Tyr
  1               5                  10                  15

Leu Asn Gly
```

<210> SEQ ID NO 57
<211> LENGTH: 20
<212> TYPE: PRT
<213> ORGANISM: Escherichia coli

<400> SEQUENCE: 57

```
Phe Gly Ile Arg Gly Leu Asn Pro Arg Leu Thr Ser Arg Ser Thr Val
  1               5                  10                  15

Leu Met Asp Gly
             20
```

<210> SEQ ID NO 58
<211> LENGTH: 27
<212> TYPE: PRT
<213> ORGANISM: Pasterurella haemolytica

<400> SEQUENCE: 58

```
Ile Glu Leu Ser Lys Gly Ala Ser Ser Ala Glu Tyr Gly Ser Gly Ala
  1               5                  10                  15

His Gly Gly Ala Ile Gly Phe Arg Thr Lys Asp
             20                  25
```

<210> SEQ ID NO 59
<211> LENGTH: 27
<212> TYPE: PRT
<213> ORGANISM: Escherichia coli

<400> SEQUENCE: 59

```
Ile Glu Val Val Arg Gly Pro Met Ser Ser Leu Tyr Gly Ser Asp Ala
  1               5                  10                  15

Leu Gly Gly Val Val Asn Ile Ile Thr Lys Lys
             20                  25
```

<210> SEQ ID NO 60
<211> LENGTH: 27
<212> TYPE: PRT
<213> ORGANISM: Escherichia coli

<400> SEQUENCE: 60

```
Ile Glu Val Leu Arg Gly Pro Ala Arg Ala Arg Tyr Gly Asn Gly Ala
  1               5                  10                  15

Ala Gly Gly Val Val Asn Ile Ile Thr Lys Lys
             20                  25
```

<210> SEQ ID NO 61
<211> LENGTH: 27
<212> TYPE: PRT
<213> ORGANISM: Escherichia coli

<400> SEQUENCE: 61

```
Ala Glu Ile Met Arg Gly Pro Val Ser Val Leu Tyr Gly Lys Ser Ser
  1               5                  10                  15

Pro Gly Gly Leu Leu Asn Met Val Ser Lys Arg
             20                  25
```

<210> SEQ ID NO 62
<211> LENGTH: 27
<212> TYPE: PRT

```
<213> ORGANISM: Escherichia coli

<400> SEQUENCE: 62

Ile Asp Val Val Arg Gly Gly Ala Val Arg Tyr Gly Pro Gln Ser
1               5                   10                  15

Val Gly Gly Val Val Asn Phe Val Thr Arg Ala
            20                  25

<210> SEQ ID NO 63
<211> LENGTH: 13
<212> TYPE: PRT
<213> ORGANISM: Pasterurella haemolytica

<400> SEQUENCE: 63

Phe Lys Gln Thr His Lys Leu Asn Leu Gly Leu Gly Phe
1               5                   10

<210> SEQ ID NO 64
<211> LENGTH: 13
<212> TYPE: PRT
<213> ORGANISM: Escherichia coli

<400> SEQUENCE: 64

Pro Glu Thr Ser Glu Ser Trp Glu Leu Gly Leu Tyr Tyr
1               5                   10

<210> SEQ ID NO 65
<211> LENGTH: 13
<212> TYPE: PRT
<213> ORGANISM: Escherichia coli

<400> SEQUENCE: 65

Ala Glu Thr Ser Ile Asn Lys Glu Ile Gly Leu Glu Phe
1               5                   10

<210> SEQ ID NO 66
<211> LENGTH: 13
<212> TYPE: PRT
<213> ORGANISM: Escherichia coli

<400> SEQUENCE: 66

Pro Ser Lys Gly Lys Gln Tyr Glu Val Gly Val Lys Tyr
1               5                   10

<210> SEQ ID NO 67
<211> LENGTH: 13
<212> TYPE: PRT
<213> ORGANISM: Escherichia coli

<400> SEQUENCE: 67

Pro Glu Lys Ala Arg Thr Trp Glu Leu Gly Thr Arg Tyr
1               5                   10

<210> SEQ ID NO 68
<211> LENGTH: 8
<212> TYPE: PRT
<213> ORGANISM: Pasteurella haemolytica

<400> SEQUENCE: 68

Thr Glu Asn Lys Lys Ile Glu Glu
1               5
```